(12) United States Patent (10) Patent No.: US 8,257,943 B2
Hashimoto et al. (45) Date of Patent: Sep. 4, 2012

(54) PROCESS FOR PRODUCING DIPEPTIDES OR DIPEPTIDE DERIVATIVES

(75) Inventors: Shin-ichi Hashimoto, Hofu (JP); Hajime Ikeda, Hofu (JP); Makoto Yagasaki, Machida (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 99 days.

(21) Appl. No.: 11/165,226

(22) Filed: Jun. 24, 2005

(65) Prior Publication Data

US 2005/0287627 A1 Dec. 29, 2005

(30) Foreign Application Priority Data

Jun. 25, 2004 (JP) ................................ 2004-189007

(51) Int. Cl.
*C12P 1/00* (2006.01)
*C12P 21/04* (2006.01)
*C12P 13/00* (2006.01)
*C12P 1/04* (2006.01)

(52) U.S. Cl. ........ 435/41; 435/71.1; 435/71.2; 435/128; 435/170

(58) Field of Classification Search .................... 435/41, 435/68.1, 71.1, 71.2, 106–116, 128
See application file for complete search history.

(56) References Cited

U.S. PATENT DOCUMENTS

| | | | |
|---|---|---|---|
| 7,514,242 B2 * | 4/2009 | Hashimoto et al. ............ | 435/128 |
| 7,514,243 B2 * | 4/2009 | Hashimoto et al. ............ | 435/128 |
| 2004/0171106 A1 * | 9/2004 | Hashimoto et al. ........... | 435/68.1 |

FOREIGN PATENT DOCUMENTS

| | | |
|---|---|---|
| EP | 1 096 011 | 5/2001 |
| EP | 1 433 791 | 6/2004 |
| EP | 1 529 837 | 5/2005 |
| EP | 1 548 122 | 6/2005 |
| WO | WO 2004/076477 | 9/2004 |

OTHER PUBLICATIONS

Henrich et al., 1990, J. Bacteriol., 172, 4641-51.*
Olson et al., 1991, J. Bacteriol., 173, 234-44.*
Hilton et al., 1988, J. Bacteriol., 170, 482-4.*
Zhang et al., 2002, Proceedings of the National Academy of Sciences, 99, 16678-16683.*
Kameda, et al., 2001, Journal of Bioscience and Bioengineering, vol. 91, Issue 6, pp. 557-563.*
Noguchi et al, Biosci. Biotechnol. Biochem., 1998, 62(8), 1594-1596.

(Continued)

*Primary Examiner* — Ruth Davis
*Assistant Examiner* — Sheridan Macauley
(74) *Attorney, Agent, or Firm* — Fitzpatrick, Cella, Harper & Scinto

(57) ABSTRACT

The present invention provides a process for producing a dipeptide or a dipeptide derivative using a phosphate donor, a substance selected from the group consisting of adenosine-5'-monophosphate, adenosine-5'-diphosphate and adenosine-5'-triphosphate, one or more kinds of amino acids or amino acid derivatives, and as enzyme sources, a protein having polyphosphate kinase activity, or a culture of cells having the ability to produce the protein or a treated matter of the culture, and a protein having the activity to ATP-dependently form the dipeptide or dipeptide derivative from one or more kinds of amino acids or amino acid derivatives, or a culture of cells having the ability to produce the protein or a treated matter of the culture.

11 Claims, 4 Drawing Sheets

OTHER PUBLICATIONS

Nakajima et al, Int. J. Peptide Protein Res., 1986, vol. 28, 179-185.
Dieckmann et al, FEBS Letters, 2001, vol. 498, No. 1, 42-45.
Sakajoh et al, Journal of Industrial Microbiology, 1987, vol. 2, No. 4, 201-208.
Lautru et al, Chemistry & Biology, Dec. 2002, vol. 9, 1355-1364.
Murata et al, Agric. Biol. Chem., 1988, 52(6), 1471-1477.
Hoffman et al, Biotechnology and Applied Biochemistry, 1988, vol. 10, 107-117.
Haeusler et al, Biotechnology and Applied Biochemistry, 1992, vol. 15, 125-133.
Akiyama et al, The Journal of Biological Chemistry, 1992, vol. 267, No. 31, pp. 22556-22561.
Bloch et al, The Journal of Biological Chemistry, 1959, vol. 234, No. 10, 2595-2604.
Henning et al, Archives of Biochemistry and Biophysics, 1959, vol. 83, pp. 259-267.
Skilleter et al, Biochem. J. 1971, vol. 124, pp. 407-417.
Levy et al, Biochem. J. 1960, vol. 75, 417-428.
Yazgan et al, Bacilysin biosynthesis by a partially-purified enzyme fraction from *Bacillus subtilis*, Enzyme and Microbial Technology 29 (2001), pp. 400-406.
Sakajoh et al, Cell-free synthesis of the dipeptide antibiotic bacilysin, Journal of Industrial Microbiology, 2 (1987), pp. 201-208.
Kunst et al, The complete genome sequence of the Gram-positive bacterium *Bacillus subtilis*, Nature, 1997, vol. 390, 249-256.
Database UniProt, Feb. 1, 1995, XP002314261, Database Accession No. P39641.
Database UniProt, Oct. 1, 2002, XP002314262, Database Accession No. Q8KWT3.
Khumtaveeporn et al, Tetrahedron Asymmetry, vol. 10 (1999), pp. 2563-2572.
European Search Report dated Apr. 21, 2006 issued in connection with EP 05 01 3733.
Inaoka et al, The Journal of Biological Chemistry, 2003, vol. 278, No. 4, pp. 2169-2176.
Database Protein [Online] Aug. 2, 2002, Steinborn & Hofemeister: XP002362028, retrieved from NCBI, Database Accession No. AAM90571.
Database Protein [Online] Aug. 2, 2002, Steinborn & Hofemeister: XP002362029, retrieved from NCBI, Database Accession No. AAM90576.
Sequence comparison between SEQ ID Nos. 1 (ywfE), 9, 10, 11, 12, 13, AAM90571 and AAM90576, XP002362036, May 31, 2006.
Kameda et al, Journal of Bioscience and Bioengineering, 2001, vol. 91, No. 6, pp. 557-563.
Doekel et al, Chemistry and Biology, 2000, vol. 7, No. 6, pp. 373-384.
Tuzun et al, Enzyme and Microbial Technology, 2003, vol. 33, No. 5, pp. 725-728.

* cited by examiner

SEQUENCE LISTING

<160> NUMBER OF SEQ ID NOS: 131

<210> SEQ ID NO 1
<211> LENGTH: 472
<212> TYPE: PRT
<213> ORGANISM: Bacillus subtilis 168

<400> SEQUENCE: 1

```
Met Glu Arg Lys Thr Val Leu Val Ile Ala Asp Leu Gly Gly Cys Pro
 1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
    65                  70                  75                  80

His Asn Lys Pro Glu Glu Glu Val Val Glu Gln Ile Val Lys Val Ala
                    85                  90                  95

Glu Met Phe Gly Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
        130                 135                 140

Phe Asn Lys Ala Gly Val Lys Ser Ile Lys Asn Lys Arg Val Thr Thr
    145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240
```

```
Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln His Ala Lys Leu
    450                 455                 460

Thr Ala Lys Tyr Val Leu Pro Val
465                 470

<210> SEQ ID NO 2
<211> LENGTH: 472
<212> TYPE: PRT
<213> ORGANISM: Bacillus subtilis ATCC6633

<400> SEQUENCE: 2

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Gln Ser
    50                  55                  60

Leu Ala Asp Phe Glu His Pro Asp Ser Ile Tyr Trp Ala His Glu Asp
65                  70                  75                  80

His Asp Lys Pro Glu Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140
```

```
Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
            165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
            195                 200                 205

Lys Ser Ile Asn Val Pro Lys Ala Val Thr Phe Glu Ala Pro Phe Ile
            210                 215                 220

Ala Glu Glu Phe Leu Gln Gly Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Ala Lys Lys
            275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys His Leu Tyr Pro Gln His Phe
            370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
            405                 410                 415

Thr Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
            450                 455                 460

Thr Ala Lys Tyr Val Leu Pro Val
465                 470

<210> SEQ ID NO 3
<211> LENGTH: 472
<212> TYPE: PRT
<213> ORGANISM: Bacillus subtilis IAM1213

<400> SEQUENCE: 3

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45
```

-continued

```
Glu Lys Tyr Ser Val Ala Val Ile Lys Asp Lys Asp Tyr Phe Lys Ser
 50                  55                  60
Leu Ala Asp Phe Glu His Pro Asp Ser Ile Tyr Trp Ala His Glu Asp
 65                  70                  75                  80
His Asn Lys Pro Glu Glu Val Val Glu Gln Ile Val Lys Val Ala
                 85                  90                  95
Glu Met Phe Gly Ala Asp Ala Ile Thr Thr Asn Asn Glu Leu Phe Ile
                100                 105                 110
Ala Pro Met Ala Lys Ala Cys Glu Arg Leu Gly Leu Arg Gly Ala Gly
             115                 120                 125
Val Gln Ala Ala Glu Asn Ala Arg Asp Lys Asn Lys Met Arg Asp Ala
130                 135                 140
Phe Asn Lys Ala Gly Val Lys Ser Ile Lys Asn Lys Arg Val Thr Thr
145                 150                 155                 160
Leu Glu Asp Phe Arg Ala Ala Leu Glu Glu Ile Gly Thr Pro Leu Ile
                165                 170                 175
Leu Lys Pro Thr Tyr Leu Ala Ser Ser Ile Gly Val Thr Leu Ile Thr
             180                 185                 190
Asp Thr Glu Thr Ala Glu Asp Glu Phe Asn Arg Val Asn Asp Tyr Leu
             195                 200                 205
Lys Ser Ile Asn Val Pro Lys Ala Val Thr Phe Glu Ala Pro Phe Ile
210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
                245                 250                 255
Tyr Phe Pro Ile Ala Ile His Asp Lys Thr Pro Gln Ile Gly Phe Thr
             260                 265                 270
Glu Thr Ser His Ile Thr Pro Ser Ile Leu Asp Glu Glu Ala Lys Lys
             275                 280                 285
Lys Ile Val Glu Ala Ala Lys Lys Ala Asn Glu Gly Leu Gly Leu Gln
290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Leu Asp Met Ala Gln Leu Leu Leu Asp
             340                 345                 350
Val Leu Cys Phe Gly Lys Asp Ala Asp Leu Pro Asp Gly Leu Leu Asp
             355                 360                 365
Gln Glu Pro Tyr Val Ala Asp Cys His Leu Tyr Pro Gln His Phe
370                 375                 380
Lys Gln Asn Gly Gln Ile Pro Glu Thr Ala Asp Leu Val Ile Glu
385                 390                 395                 400
Ala Ile Asp Leu Pro Asp Gly Leu Leu Lys Gly Asp Thr Glu Ile Val
                405                 410                 415
Ser Phe Ser Ala Ala Pro Gly Thr Ser Val Asp Leu Thr Leu Phe
             420                 425                 430
Glu Ala Phe Asn Ser Ile Ala Ala Phe Glu Leu Lys Gly Ser Asn Ser
             435                 440                 445
Gln Asp Val Ala Glu Ser Ile Arg Gln Ile Gln Gln His Ala Lys Leu
450                 455                 460
Thr Ala Lys Tyr Val Leu Pro Val
465                 470
```

<210> SEQ ID NO 4
<211> LENGTH: 472
<212> TYPE: PRT
<213> ORGANISM: Bacillus subtilis IAM1107

<400> SEQUENCE: 4

```
Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
             20                  25                  30

Phe Ile Pro Arg Pro Phe Ala Ile Thr Ala Ser His Ala Ala Leu Ile
         35                  40                  45

Glu Lys Tyr Ser Val Ala Val Val Lys Asp Lys Asp Tyr Phe Lys Ser
     50                  55                  60

Leu Ala Asp Phe Glu His Pro Asp Ser Ile Tyr Trp Ala His Glu Asp
 65                  70                  75                  80

His Asn Lys Pro Glu Glu Val Val Glu Gln Ile Val Lys Val Ala
                 85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Lys Lys Ala Asn Glu Gly Leu Gly Leu Gln
    290                 295                 300

Asn Cys Ala Thr His Thr Glu Val Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380
```

```
Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Phe
            405                 410                 415

Ser Phe Ser Ala Ala Pro Gly Thr Ser Val Asp Leu Thr Leu Phe
        420                 425                 430

Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 5
<211> LENGTH: 472
<212> TYPE: PRT
<213> ORGANISM: Bacillus subtilis IAM1214

<400> SEQUENCE: 5

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Gln Ser
    50                  55                  60

Leu Ala Asp Phe Glu His Pro Asp Ser Ile Tyr Trp Ala His Glu Asp
65                  70                  75                  80

His Asp Lys Pro Glu Glu Val Val Glu Gln Ile Val Lys Val Ala
                85                  90                  95

Gln Met Phe Glu Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205

Lys Ser Ile Asn Val Pro Lys Ala Val Thr Phe Glu Ala Pro Phe Ile
    210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285
```

```
Lys Ile Val Glu Ala Ala Lys Lys Ala Asn Glu Gly Leu Gly Leu Gln
        290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Ala Gln Leu Leu Leu Asp
            340                 345                 350

Val Leu Cys Phe Gly Lys Asp Ala Asp Leu Pro Asp Gly Leu Leu Asp
        355                 360                 365

Gln Glu Pro Tyr Tyr Val Ala Asp Cys His Leu Tyr Pro Gln His Phe
    370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Thr Phe Ser Ala Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 6
<211> LENGTH: 472
<212> TYPE: PRT
<213> ORGANISM: Bacillus subtilis ATCC21555

<400> SEQUENCE: 6

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Ile Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asp Lys Pro Glu Glu Glu Val Val Glu Glu Ile Val Lys Val Ala
                85                  90                  95

Asp Met Phe Gly Val Asp Ala Ile Thr Thr Asn Asn Glu Leu Phe Ile
            100                 105                 110

Ala Pro Met Ala Lys Ala Cys Lys Arg Leu Gly Leu Arg Gly Ala Gly
        115                 120                 125

Val Gln Ala Ala Glu Asn Ala Arg Asp Lys Asn Lys Met Arg Ala Ala
    130                 135                 140

Phe Asn Arg Ala Gly Val Lys Ser Ile Lys Asn Lys Arg Val Thr Thr
145                 150                 155                 160

Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190
```

-continued

Glu Met Glu Thr Ala Glu Ala Glu Phe Asn Arg Val Asn Glu Tyr Leu
            195                 200                 205

Lys Ser Ile Asn Val Pro Lys Ala Val Thr Phe Glu Ala Pro Phe Ile
            210                 215                 220

Ala Glu Glu Phe Leu Gln Gly Tyr Asp Asp Trp Tyr Glu Thr Ser
225                 230                 235                 240

Gly Tyr Ser Asp Tyr Ile Ser Ile Glu Gly Ile Met Ala Asp Gly Glu
            245                 250                 255

Tyr Phe Pro Val Ala Ile His Asp Lys Thr Pro Gln Ile Gly Phe Thr
            260                 265                 270

Glu Thr Ala His Ile Thr Pro Ser Ile Leu Asp Asp Ala Lys Arg
            275                 280                 285

Lys Ile Val Glu Ala Ala Lys Ala Asn Glu Gly Leu Gly Leu Glu
            290                 295                 300

Asn Cys Ala Thr His Thr Glu Ile Lys Leu Met Lys Asn Arg Glu Ala
305                 310                 315                 320

Gly Leu Ile Glu Ser Ala Ala Arg Phe Ala Gly Trp Asn Met Ile Pro
            325                 330                 335

Asn Ile Lys Lys Val Phe Gly Val Asp Met Ala Gln Leu Leu Leu Asp
            340                 345                 350

Val Leu Cys Tyr Gly Lys Glu Ala Asp Leu Pro Lys Gly Leu Leu Glu
            355                 360                 365

Gln Glu Pro Cys Tyr Val Ala Asp Cys His Leu Tyr Pro Gln His Phe
            370                 375                 380

Lys Glu Asn Gly Gln Leu Pro Glu Thr Val Val Asp Phe Val Ile Glu
385                 390                 395                 400

Ser Ile Glu Ile Pro Asp Gly Val Leu Lys Gly Asp Thr Glu Leu Val
            405                 410                 415

Ser Phe Ser Ala Ala Glu Ala Gly Thr Ser Val Asp Leu Arg Leu Phe
            420                 425                 430

Glu Ala Phe Asn Ser Ile Ala Ala Phe Glu Leu Lys Gly Ser Asn Ser
            435                 440                 445

Asn Asp Val Ala Glu Ser Ile Lys Gln Ile Gln Gln Ala Lys Leu
            450                 455                 460

Thr Ala Lys Tyr Ala Leu Ser Val
465                 470

<210> SEQ ID NO 7
<211> LENGTH: 472
<212> TYPE: PRT
<213> ORGANISM: Bacillus amyloliquefaciens IFO3022

<400> SEQUENCE: 7

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Ser Ile Tyr Trp Ala His Glu Asp
65                  70                  75                  80

His Asp Lys Pro Glu Glu Glu Val Val Glu Ile Val Lys Val Ala
            85                  90                  95

Gly Met Phe Ala Val Asp Ala Ile Thr Thr Asn Asn Glu Leu Phe Ile
             100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Ala Ala
130                 135                 140

Phe Asn Arg Ala Gly Val Lys Ser Ile Lys Asn Arg Arg Val Thr Thr
145                 150                 155                 160

Leu Glu Asp Phe Arg Ala Ala Leu Gln Glu Ile Gly Thr Pro Leu Ile
                165                 170                 175

Leu Lys Pro Thr Tyr Leu Ala Ser Ser Ile Gly Val Thr Leu Ile Lys
            180                 185                 190

Glu Arg Glu Thr Ala Glu Ala Glu Phe Asn Arg Val Asn Glu Tyr Leu
            195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Asp Asp Trp Tyr Glu Thr Ser
225                 230                 235                 240

Gly Tyr Ser Asp Tyr Ile Ser Ile Glu Gly Ile Met Ala Asp Gly Glu
                245                 250                 255

Tyr Phe Pro Val Ala Ile His Asp Lys Thr Pro Gln Ile Gly Phe Thr
            260                 265                 270

Glu Thr Ser His Ile Thr Pro Ser Ile Leu Asp Asp Ala Lys Arg
            275                 280                 285

Lys Ile Val Glu Ala Lys Lys Ala Asn Glu Gly Leu Gly Leu Glu
290                 295                 300

Asn Cys Ala Thr His Thr Glu Ile Lys Leu Met Lys Asn Arg Glu Ala
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Val Asp Met Ala Gln Leu Leu Leu Asp
            340                 345                 350

Val Leu Cys Phe Gly Lys Glu Ala Asp Leu Pro Lys Gly Leu Leu Glu
            355                 360                 365

Gln Glu Pro Cys Tyr Val Ala Asp Cys His Leu Tyr Pro Gln His Phe
370                 375                 380

Lys Glu Asn Gly Gln Leu Pro Glu Thr Ala Val Asp Phe Val Ile Glu
385                 390                 395                 400

Ser Ile Asp Ile Pro Asp Gly Val Leu Lys Gly Asp Thr Glu Ile Val
                405                 410                 415

Ser Phe Ser Ala Ala Glu Ala Gly Thr Ser Val Asp Leu Arg Leu Phe
            420                 425                 430

Glu Ala Phe Asn Ser Ile Ala Ala Phe Glu Leu Lys Gly Ser Asn Ser
            435                 440                 445

Gly Asp Val Ala Glu Ser Ile Lys Gln Ile Gln Gln Ala Lys Leu
450                 455                 460

Thr Ala Lys Tyr Ala Leu Pro Val
465                 470

<210> SEQ ID NO 8
<211> LENGTH: 476
<212> TYPE: PRT
<213> ORGANISM: Bacillus pumilus NRRL B-12025

<400> SEQUENCE: 8

-continued

```
Val Leu Ser Leu Ser Lys Lys Thr Val Leu Ile Ala Asp Leu Gly
 1               5                   10                  15

Gly Cys Pro Pro His Met Phe Tyr Glu Ser Val Ala Ala Ser Tyr His
            20                  25                  30

Ile Val Ser Tyr Ile Pro Arg Pro Phe Ala Ile Thr Lys Gly His Ala
             35                  40                  45

Glu Leu Ile Glu Lys Tyr Ser Ile Ala Val Ile Lys Asp Arg Asp Tyr
         50                  55                  60

Phe Glu Thr His Pro Ser Phe Glu His Pro Asp Ser Ile Tyr Trp Ala
 65                  70                  75                  80

His Asp Asp Tyr Pro Lys Ser Glu Glu Val Val Glu Asp Phe Ile
                 85                  90                  95

Arg Val Ala Ser Phe Phe Lys Ala Asp Ala Ile Thr Thr Asn Asn Glu
                100                 105                 110

Leu Phe Ile Ala Pro Met Ala Lys Ala Ala Glu Arg Leu Gly Leu Arg
            115                 120                 125

Gly Ala Gly Val Lys Ala Ala Glu Met Ala Arg Asp Lys Ser Gln Met
        130                 135                 140

Arg Ala Ala Phe Asn Ala Ser Gly Val Lys Ala Val Lys Thr Gln Pro
145                 150                 155                 160

Val Thr Thr Leu Ser Asp Phe Gln Gln Ala Ile Glu Ser Ile Gly Thr
                165                 170                 175

Pro Leu Ile Leu Lys Pro Thr Tyr Leu Ala Ser Ser Ile Gly Val Thr
            180                 185                 190

Leu Phe His Asp Lys Ala Gly Ser Asp Asp Leu Phe Leu Gln Val Gln
        195                 200                 205

Ser Tyr Leu Glu Thr Ile Pro Val Pro Asp Ala Val Thr Tyr Glu Ala
210                 215                 220

Pro Phe Val Ala Glu Thr Tyr Leu Glu Gly Ala Tyr Glu Asp Trp Tyr
225                 230                 235                 240

Glu Asp Glu Gly Tyr Ala Asp Tyr Val Ser Val Glu Gly Leu Val Val
                245                 250                 255

Glu Gly Glu Tyr Leu Pro Phe Val Ile His Asp Lys Thr Pro Gln Ile
            260                 265                 270

Gly Phe Thr Glu Thr Ala His Ile Thr Pro Thr Ile Leu Asp Asn Glu
        275                 280                 285

Ala Lys Gln Ile Ile Ile Glu Ala Ala Arg Lys Ala Asn Glu Gly Leu
    290                 295                 300

Gly Leu Glu His Cys Ala Thr His Thr Glu Ile Lys Leu Met Lys Asn
305                 310                 315                 320

Arg Glu Thr Gly Leu Ile Glu Ala Ala Arg Phe Ala Gly Trp Asn
                325                 330                 335

Met Ile Pro Asn Ile Lys Lys Val Phe Gly Val Asp Met Ala Lys Leu
            340                 345                 350

Leu Ile Asp Val Leu Val Asp Gly Lys Lys Ala Val Leu Pro Lys Gln
        355                 360                 365

Leu Leu Ser Gly His Thr Phe Tyr Val Ala Asp Cys His Leu Tyr Pro
    370                 375                 380

Gln His Phe Lys Glu Ser Gly Leu Ile Pro Pro Glu Ala Thr His Ile
385                 390                 395                 400

Thr Ile Asp His Val Ser Ile Pro Gln Glu Ala Phe Val Gly Asp Thr
                405                 410                 415

Ala Ile Val Ser Gln Ser Phe Pro Ala Lys Gly Thr Ile Val Asp Leu
```

```
                    420                 425                 430
Glu Leu Phe Glu Ala Phe Asn Gly Ile Val Ser Leu Glu Leu Lys Gly
                435                 440                 445

Ser Ser Ser Gln Asp Val Ala Ala Ser Ile Arg Asn Ile Gln Lys Gln
            450                 455                 460

Ala Thr Ile Gln Leu Met Asp Glu Leu Val Lys Gly
465                 470                 475

<210> SEQ ID NO 9
<211> LENGTH: 472
<212> TYPE: PRT
<213> ORGANISM: Artificial Sequence
<220> FEATURE:
<223> OTHER INFORMATION: Description of Artificial Sequence: Mutant PRT

<400> SEQUENCE: 9

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
                 20                  25                  30

Phe Ile Pro Arg Pro Phe Ala Ile Thr Ala Ser His Ala Ala Leu Ile
             35                  40                  45

Glu Lys Tyr Ser Val Ala Val Ile Lys Asp Lys Asp Tyr Phe Lys Ser
         50                  55                  60

Leu Ala Asp Phe Glu His Pro Asp Pro Ile Tyr Trp Ala His Glu Asp
 65                  70                  75                  80

His Asn Lys Pro Glu Glu Val Val Glu Gln Ile Val Lys Val Ala
                 85                  90                  95

Glu Met Phe Gly Ala Asp Ala Ile Thr Thr Asn Asn Glu Leu Phe Ile
                100                 105                 110

Ala Pro Met Ala Lys Ala Cys Glu Arg Leu Gly Leu Arg Gly Ala Gly
            115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Phe Asn Arg Val Asn Asp Tyr Leu
            195                 200                 205

Lys Ser Ile Asn Val Pro Lys Ala Val Thr Phe Val Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320
```

```
Gly Leu Ile Glu Ser Ala Ala Arg Phe Ala Gly Trp Asn Met Ile Pro
            325                 330                 335

Asn Ile Lys Lys Val Phe Gly Leu Asp Met Val Gln Leu Leu Leu Asp
        340                 345                 350

Val Leu Cys Phe Gly Lys Asp Ala Asp Leu Pro Asp Gly Leu Leu Asp
    355                 360                 365

Gln Glu Pro Tyr Tyr Val Ala Asp Cys Arg Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
        435                 440                 445

Gln Asp Val Ala Glu Ser Ile Arg Gln Ile Gln Gln His Ala Lys Leu
    450                 455                 460

Thr Ala Lys Tyr Val Leu Pro Val
465                 470

<210> SEQ ID NO 10
<211> LENGTH: 472
<212> TYPE: PRT
<213> ORGANISM: Artificial Sequence
<220> FEATURE:
<223> OTHER INFORMATION: Description of Artificial Sequence: Mutant PRT

<400> SEQUENCE: 10

Met Glu Arg Lys Thr Val Leu Val Ile Ala Asp Leu Gly Gly Cys Pro
1               5                   10                  15

Pro His Met Phe Tyr Lys Ser Ala Ala Glu Lys Tyr Asn Leu Val Ser
            20                  25                  30

Phe Ile Pro Arg Pro Phe Ala Ile Thr Ala Ser His Ala Ala Leu Ile
        35                  40                  45

Glu Lys Tyr Ser Val Ala Val Ile Lys Asp Lys Asp Tyr Phe Lys Ser
    50                  55                  60

Leu Ala Asp Phe Glu His Pro Asp Pro Ile Tyr Trp Ala His Glu Asp
65                  70                  75                  80

His Asn Lys Pro Glu Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
    130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Thr Tyr Leu Ala Ser Ser Ile Gly Val Thr Leu Ile Thr
            180                 185                 190

Asp Thr Glu Thr Ala Glu Asp Glu Phe Asn Arg Val Asn Asp Tyr Leu
        195                 200                 205
```

```
Lys Ser Ile Asn Val Pro Lys Ala Val Thr Phe Glu Ala Pro Phe Ile
        210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Ala Lys Lys Ala Asn Gly Leu Gly Leu Gln
290                 295                 300

Asn Cys Ala Thr His Thr Glu Ile Lys Leu Met Lys Asn Arg Glu Pro
305                 310                 315                 320

Gly Leu Ile Glu Ser Ala Ala Arg Phe Ala Gly Trp Asn Met Ile Pro
                325                 330                 335

Asn Ile Lys Lys Val Phe Gly Leu Asp Met Val Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys Arg Leu Tyr Pro Gln His Phe
370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Asn Ser
            435                 440                 445

Gln Asp Val Val Glu Ser Ile Arg Gln Ile Gln Gln His Ala Lys Leu
        450                 455                 460

Thr Ala Lys Tyr Val Leu Pro Val
465                 470

<210> SEQ ID NO 11
<211> LENGTH: 472
<212> TYPE: PRT
<213> ORGANISM: Artificial Sequence
<220> FEATURE:
<223> OTHER INFORMATION: Description of Artificial Sequence: Mutant PRT

<400> SEQUENCE: 11

Met Glu Arg Lys Thr Val Leu Val Ile Ala Asp Leu Gly Gly Cys Pro
  1               5                  10                  15

Pro His Met Phe Tyr Lys Ser Ala Ala Glu Lys Tyr Asn Leu Val Ser
             20                  25                  30

Phe Ile Pro Arg Pro Phe Ala Ile Thr Ala Ser His Ala Ala Leu Ile
         35                  40                  45

Glu Lys Tyr Ser Val Ala Val Ile Lys Asp Lys Asp Tyr Phe Lys Ser
     50                  55                  60

Leu Ala Asp Phe Glu His Pro Asp Pro Ile Tyr Trp Ala His Glu Asp
 65                  70                  75                  80

His Asn Lys Pro Glu Glu Glu Val Val Glu Gln Ile Val Lys Val Ala
                 85                  90                  95

Glu Met Phe Gly Ala Asp Ala Ile Thr Thr Asn Asn Glu Leu Phe Ile
```

Ala Pro Met Ala Lys Ala Cys Glu Arg Leu Gly Leu Arg Gly Ala Gly
            115                 120                 125
Val Gln Ala Ala Glu Asn Ala Arg Asp Lys Asn Lys Met Arg Asp Ala
        130                 135                 140
Phe Asn Lys Ala Gly Val Lys Ser Ile Lys Asn Lys Arg Val Thr Thr
145                 150                 155                 160
Leu Glu Asp Phe Arg Ala Ala Leu Glu Glu Ile Gly Thr Pro Leu Ile
                165                 170                 175
Leu Lys Pro Thr Tyr Leu Ala Ser Ser Ile Gly Val Thr Leu Ile Thr
            180                 185                 190
Asp Thr Glu Thr Ala Glu Asp Glu Phe Asn Arg Val Asn Asp Tyr Leu
        195                 200                 205
Lys Ser Ile Asn Val Pro Lys Ala Val Thr Phe Glu Ala Pro Phe Ile
    210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
                245                 250                 255
Tyr Phe Pro Ile Ala Ile His Asp Lys Thr Pro Gln Ile Gly Phe Thr
            260                 265                 270
Glu Thr Ser His Ile Thr Pro Ser Ile Leu Asp Glu Ala Lys Lys
        275                 280                 285
Lys Ile Val Glu Ala Ala Lys Lys Ala Asn Glu Gly Leu Gly Leu Gln
    290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Leu Asp Met Val Gln Leu Leu Leu Asp
            340                 345                 350
Val Leu Cys Phe Gly Lys Asp Ala Asp Leu Pro Asp Gly Leu Leu Asp
        355                 360                 365
Gln Glu Pro Tyr Tyr Val Ala Asp Cys Arg Leu Tyr Pro Gln His Phe
    370                 375                 380
Lys Gln Asn Gly Gln Ile Pro Glu Thr Ala Glu Asp Leu Val Ile Glu
385                 390                 395                 400
Ala Ile Asp Ile Pro Asp Gly Leu Leu Lys Gly Asp Thr Glu Ile Val
                405                 410                 415
Ser Phe Ser Ala Ala Pro Gly Thr Ser Val Asp Leu Thr Leu Phe
            420                 425                 430
Glu Ala Phe Asn Pro Ile Ala Ala Phe Glu Leu Lys Gly Ser Asn Ser
        435                 440                 445
Gln Asp Val Ala Glu Ser Ile Arg Gln Ile Gln Gln His Ala Lys Leu
    450                 455                 460
Thr Ala Lys Tyr Val Leu Pro Val
465                 470

<210> SEQ ID NO 12
<211> LENGTH: 472
<212> TYPE: PRT
<213> ORGANISM: Artificial Sequence
<220> FEATURE:
<223> OTHER INFORMATION: Description of Artificial Sequence: Mutant PRT

<400> SEQUENCE: 12

-continued

```
Met Glu Arg Lys Thr Val Leu Val Ile Ala Asp Leu Gly Gly Cys Pro
 1               5                  10                  15
Pro His Met Phe Tyr Lys Ser Ala Ala Glu Lys Tyr Asn Leu Val Ser
             20                  25                  30
Phe Ile Pro Arg Pro Phe Ala Ile Thr Ala Ser His Ala Ala Leu Ile
         35                  40                  45
Glu Lys Tyr Ser Val Ala Val Ile Lys Asp Lys Asp Tyr Phe Lys Ser
     50                  55                  60
Leu Ala Asp Phe Glu His Pro Asp Pro Ile Tyr Trp Ala His Glu Asp
 65                  70                  75                  80
His Asn Lys Pro Glu Glu Val Val Glu Gln Ile Val Lys Val Ala
                 85                  90                  95
Glu Met Phe Gly Ala Asp Ala Ile Thr Thr Asn Asn Glu Leu Phe Ile
                100                 105                 110
Ala Pro Met Ala Lys Ala Cys Glu Arg Leu Gly Leu Arg Gly Ala Gly
             115                 120                 125
Val Gln Ala Ala Glu Asn Ala Arg Asp Lys Asn Lys Met Arg Asp Ala
    130                 135                 140
Phe Asn Lys Ala Gly Val Lys Ser Ile Lys Asn Lys Arg Val Thr Thr
145                 150                 155                 160
Leu Glu Asp Phe Arg Ala Ala Leu Glu Glu Ile Gly Thr Pro Leu Ile
                165                 170                 175
Leu Lys Pro Ala Tyr Leu Ala Ser Ser Ile Gly Val Thr Leu Ile Thr
            180                 185                 190
Asp Thr Glu Thr Ala Glu Asp Glu Phe Asn Arg Val Asn Asp Tyr Leu
        195                 200                 205
Lys Ser Ile Asn Val Pro Lys Ala Val Thr Phe Glu Ala Pro Phe Ile
    210                 215                 220
Ala Glu Glu Phe Leu Gln Gly Glu Tyr Gly Asp Trp Tyr Gln Thr Glu
225                 230                 235                 240
Gly Tyr Ser Asp Tyr Ile Ser Ile Glu Gly Ile Met Ala Asp Gly Glu
                245                 250                 255
Tyr Phe Pro Ile Ala Ile His Asp Lys Thr Pro Gln Ile Gly Phe Thr
            260                 265                 270
Glu Thr Ser His Ile Thr Pro Ser Ile Leu Asp Glu Glu Ala Lys Lys
        275                 280                 285
Lys Ile Val Glu Ala Ala Lys Lys Ala Asn Glu Gly Leu Gly Leu Gln
    290                 295                 300
Asn Cys Ala Thr His Thr Glu Ile Lys Leu Met Lys Asn Arg Glu Pro
305                 310                 315                 320
Gly Leu Ile Glu Ser Ala Ala Arg Phe Ala Gly Trp Asn Met Ile Pro
                325                 330                 335
Asn Ile Lys Lys Val Phe Gly Leu Asp Met Val Gln Leu Leu Leu Asp
            340                 345                 350
Val Leu Cys Phe Gly Lys Asp Ala Asp Leu Pro Asp Gly Leu Leu Asp
        355                 360                 365
Gln Glu Pro Tyr Tyr Val Ala Asp Cys Arg Leu Tyr Pro Gln His Phe
    370                 375                 380
Lys Gln Asn Gly Gln Ile Pro Glu Thr Ala Glu Asp Leu Val Ile Glu
385                 390                 395                 400
Ala Ile Asp Ile Pro Asp Gly Leu Leu Lys Gly Asp Thr Glu Ile Val
                405                 410                 415
Ser Phe Ser Ala Ala Ala Pro Gly Thr Ser Val Asp Leu Thr Leu Phe
```

-continued

```
                420                 425                 430
Glu Ala Phe Asn Ser Ile Ala Ala Phe Glu Leu Lys Gly Ser Asn Ser
            435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 13
<211> LENGTH: 472
<212> TYPE: PRT
<213> ORGANISM: Artificial Sequence
<220> FEATURE:
<223> OTHER INFORMATION: Description of Artificial Sequence: Mutant PRT

<400> SEQUENCE: 13

Met Glu Arg Lys Thr Val Leu Val Ile Ala Asp Leu Gly Gly Cys Pro
1               5                  10                  15

Pro His Met Phe Tyr Lys Ser Ala Ala Glu Lys Tyr Asn Leu Val Ser
                20                  25                  30

Phe Ile Pro Arg Pro Phe Ala Ile Thr Ala Ser His Ala Ala Leu Ile
            35                  40                  45

Glu Lys Tyr Ser Val Ala Val Ile Lys Asp Lys Asp Tyr Phe Lys Ser
        50                  55                  60

Leu Ala Asp Phe Glu His Pro Asp Pro Ile Tyr Trp Ala His Glu Asp
65                  70                  75                  80

His Asn Lys Pro Glu Glu Val Val Glu Gln Ile Val Lys Val Ala
                85                  90                  95

Glu Met Phe Gly Ala Asp Ala Ile Thr Thr Asn Asn Glu Leu Phe Ile
            100                 105                 110

Ala Pro Met Ala Lys Ala Cys Glu Arg Leu Gly Leu Arg Gly Ala Gly
        115                 120                 125

Val Gln Ala Ala Glu Asn Ala Arg Asp Lys Asn Lys Met Arg Asp Ala
130                 135                 140

Phe Asn Lys Ala Gly Val Lys Ser Ile Lys Asn Lys Arg Val Thr Thr
145                 150                 155                 160

Leu Glu Asp Phe Arg Ala Ala Leu Glu Glu Ile Gly Thr Pro Leu Ile
                165                 170                 175

Leu Lys Pro Ala Tyr Leu Ala Ser Ser Ile Gly Val Thr Leu Ile Thr
            180                 185                 190

Asp Thr Glu Thr Ala Glu Asp Phe Asn Arg Val Asn Asp Tyr Leu
        195                 200                 205

Lys Ser Ile Asn Val Pro Lys Ala Val Thr Phe Glu Ala Pro Phe Ile
210                 215                 220

Ala Glu Glu Phe Leu Gln Gly Glu Tyr Gly Asp Trp Tyr Gln Thr Glu
225                 230                 235                 240

Gly Tyr Ser Asp Tyr Ile Ser Ile Glu Gly Ile Met Ala Asp Gly Glu
                245                 250                 255

Tyr Phe Pro Ile Ala Ile His Asp Lys Thr Pro Gln Ile Gly Phe Thr
            260                 265                 270

Glu Thr Ser His Ile Thr Pro Ser Ile Leu Asp Glu Glu Ala Lys Lys
        275                 280                 285

Lys Ile Val Glu Ala Lys Lys Ala Asn Glu Gly Leu Gly Leu Gln
290                 295                 300

Asn Cys Ala Thr His Thr Glu Ile Lys Leu Met Lys Asn Arg Glu Pro
305                 310                 315                 320
```

```
Gly Leu Ile Glu Ser Ala Ala Arg Phe Ala Gly Trp Asn Met Ile Pro
            325                 330                 335

Asn Ile Lys Lys Val Phe Gly Leu Asp Met Val Gln Leu Leu Leu Asp
            340                 345                 350

Val Leu Cys Phe Gly Lys Asp Ala Asp Leu Pro Asp Gly Leu Leu Asp
            355                 360                 365

Gln Glu Pro Tyr Tyr Val Ala Asp Cys Arg Leu Tyr Pro Gln His Phe
        370                 375                 380

Lys Gln Asn Gly Gln Ile Pro Glu Thr Ala Glu Asp Leu Val Ile Glu
385                 390                 395                 400

Ala Ile Asp Ile Pro Asp Gly Leu Leu Lys Gly Asp Thr Glu Ile Val
                405                 410                 415

Ser Phe Ser Ala Ala Pro Gly Thr Ser Val Asp Leu Thr Leu Phe
            420                 425                 430

Glu Ala Phe Asn Ser Ile Ala Ala Phe Glu Leu Lys Gly Ser Ile Ser
            435                 440                 445

Gln Asp Val Ala Glu Ser Ile Arg Gln Ile Gln Gln His Ala Lys Leu
        450                 455                 460

Thr Ala Lys Tyr Val Leu Pro Val
465                 470

<210> SEQ ID NO 14
<211> LENGTH: 1416
<212> TYPE: DNA
<213> ORGANISM: Bacillus subtilis 168

<400> SEQUENCE: 14 atg gag aga aaa aca gta ttg gtc atc gct gat ctt gga ggc tgc ccg      48
Met Glu Arg Lys Thr Val Leu Val Ile Ala Asp Leu Gly Gly Cys Pro
 1               5                  10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
             20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
         35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
     50                  55                  60 tta gct gat ttt gaa cac cct gat tcc att tat tgg gcg cat gaa gat     240
Leu Ala Asp Phe Glu His Pro Asp Ser Ile Tyr Trp Ala His Glu Asp
 65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc     384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc     528
```

-continued

| | | |
|---|---|---|
| Leu Glu Asp Phe Arg Ala Ala Leu Glu Glu Ile Gly Thr Pro Leu Ile<br>165                170                175 | | |
| tta aag cct aca tac tta gcg agt tct atc ggt gta acg ctg att acg<br>Leu Lys Pro Thr Tyr Leu Ala Ser Ser Ile Gly Val Thr Leu Ile Thr<br>        180                185                190 | 576 | |
| gac act gag acg gca gaa gat gaa ttt aac aga gtc aat gac tat ctg<br>Asp Thr Glu Thr Ala Glu Asp Glu Phe Asn Arg Val Asn Asp Tyr Leu<br>195                200                205 | 624 | |
| aaa tca att aac gtg cca aag gcg gtt acg ttt gaa gcg ccg ttt atc<br>Lys Ser Ile Asn Val Pro Lys Ala Val Thr Phe Glu Ala Pro Phe Ile<br>    210                215                220 | 672 | |
| gct gaa gaa ttt tta cag ggt gag tac gga gac tgg tat caa aca gaa<br>Ala Glu Glu Phe Leu Gln Gly Glu Tyr Gly Asp Trp Tyr Gln Thr Glu<br>225                230                235                240 | 720 | |
| ggg tac tcc gac tat atc agt ata gaa ggc atc atg gct gac ggt gag<br>Gly Tyr Ser Asp Tyr Ile Ser Ile Glu Gly Ile Met Ala Asp Gly Glu<br>                245                250                255 | 768 | |
| tat ttc ccg atc gcc att cat gat aaa acg ccg caa atc ggg ttt aca<br>Tyr Phe Pro Ile Ala Ile His Asp Lys Thr Pro Gln Ile Gly Phe Thr<br>        260                265                270 | 816 | |
| gag aca tcc cac att acg ccg tcc att ctg gat gaa gag gca aaa aag<br>Glu Thr Ser His Ile Thr Pro Ser Ile Leu Asp Glu Glu Ala Lys Lys<br>275                280                285 | 864 | |
| aaa att gtc gaa gct gcc aaa aag gca aat gaa ggg ctt gga ctg caa<br>Lys Ile Val Glu Ala Ala Lys Lys Ala Asn Glu Gly Leu Gly Leu Gln<br>    290                295                300 | 912 | |
| aat tgc gca aca cat aca gag atc aag cta atg aaa aac aga gaa ccg<br>Asn Cys Ala Thr His Thr Glu Ile Lys Leu Met Lys Asn Arg Glu Pro<br>305                310                315                320 | 960 | |
| ggt tta ata gag tcg gca gcc aga ttt gcc ggc tgg aat atg atc ccc<br>Gly Leu Ile Glu Ser Ala Ala Arg Phe Ala Gly Trp Asn Met Ile Pro<br>                325                330                335 | 1008 | |
| aat att aaa aag gtc ttt ggc ctt gat atg gcg caa tta tta tta gat<br>Asn Ile Lys Lys Val Phe Gly Leu Asp Met Ala Gln Leu Leu Leu Asp<br>        340                345                350 | 1056 | |
| gtc ctc tgt ttc gga aaa gac gcc gat ctg ccg gac gga tta ttg gat<br>Val Leu Cys Phe Gly Lys Asp Ala Asp Leu Pro Asp Gly Leu Leu Asp<br>355                360                365 | 1104 | |
| caa gag cct tat tat gtt gcc gac tgc cat ttg tac ccg cag cat ttc<br>Gln Glu Pro Tyr Tyr Val Ala Asp Cys His Leu Tyr Pro Gln His Phe<br>    370                375                380 | 1152 | |
| aaa caa aat ggc caa att cct gaa act gct gag gat ttg gtc att gaa<br>Lys Gln Asn Gly Gln Ile Pro Glu Thr Ala Glu Asp Leu Val Ile Glu<br>385                390                395                400 | 1200 | |
| gcg atc gat att ccg gac ggg ctt tta aaa ggg gat act gaa atc gtt<br>Ala Ile Asp Ile Pro Asp Gly Leu Leu Lys Gly Asp Thr Glu Ile Val<br>                405                410                415 | 1248 | |
| tct ttt tcg gcc gca gca cca ggc act tca gtt gat ttg aca ttg ttt<br>Ser Phe Ser Ala Ala Ala Pro Gly Thr Ser Val Asp Leu Thr Leu Phe<br>        420                425                430 | 1296 | |
| gaa gct ttc aat tcc att gct gca ttt gaa ctg aaa ggc agt aat tca<br>Glu Ala Phe Asn Ser Ile Ala Ala Phe Glu Leu Lys Gly Ser Asn Ser<br>435                440                445 | 1344 | |
| cag gat gtg gct gaa tca atc aga caa att cag cag cat gcg aag ctg<br>Gln Asp Val Ala Glu Ser Ile Arg Gln Ile Gln Gln His Ala Lys Leu<br>    450                455                460 | 1392 | |
| acg gca aag tat gtg ctg cca gta<br>Thr Ala Lys Tyr Val Leu Pro Val<br>465                470 | 1416 | |

<210> SEQ ID NO 15
<211> LENGTH: 1416
<212> TYPE: DNA
<213> ORGANISM: Bacillus subtilis ATCC6633

<400> SEQUENCE: 15

| | | | | | | | | | | | | | | | | |
|---|---|---|---|---|---|---|---|---|---|---|---|---|---|---|---|---|
| atg | gag | aga | aaa | aca | gta | ttg | gtc | atc | gct | gat | ctt | gga | ggc | tgc | ccg | 48 |
| Met | Glu | Arg | Lys | Thr | Val | Leu | Val | Ile | Ala | Asp | Leu | Gly | Gly | Cys | Pro | |
| 1 | | | | 5 | | | | | 10 | | | | | 15 | | |
| ccg | cac | atg | ttt | tat | aaa | agc | gct | gct | gaa | aaa | tat | aac | ctg | gtt | agc | 96 |
| Pro | His | Met | Phe | Tyr | Lys | Ser | Ala | Ala | Glu | Lys | Tyr | Asn | Leu | Val | Ser | |
| | | | 20 | | | | | 25 | | | | | 30 | | | |
| ttt | att | ccg | aga | cct | ttt | gca | ata | aca | gcc | tcc | cat | gca | gca | ctg | att | 144 |
| Phe | Ile | Pro | Arg | Pro | Phe | Ala | Ile | Thr | Ala | Ser | His | Ala | Ala | Leu | Ile | |
| | | 35 | | | | | 40 | | | | | 45 | | | | |
| gaa | aaa | tac | tcg | gtc | gcg | gtc | ata | aaa | gat | aaa | gac | tat | ttt | cag | agc | 192 |
| Glu | Lys | Tyr | Ser | Val | Ala | Val | Ile | Lys | Asp | Lys | Asp | Tyr | Phe | Gln | Ser | |
| | 50 | | | | | 55 | | | | | 60 | | | | | |
| tta | gct | gat | ttt | gag | cat | ccc | gat | tca | att | tat | tgg | gcg | cat | gag | gat | 240 |
| Leu | Ala | Asp | Phe | Glu | His | Pro | Asp | Ser | Ile | Tyr | Trp | Ala | His | Glu | Asp | |
| 65 | | | | | 70 | | | | | 75 | | | | | 80 | |
| cat | gac | aag | cct | gaa | gaa | gag | gtt | gtc | gag | caa | atc | gtc | aag | gtt | gcc | 288 |
| His | Asp | Lys | Pro | Glu | Glu | Glu | Val | Val | Glu | Gln | Ile | Val | Lys | Val | Ala | |
| | | | | 85 | | | | | 90 | | | | | 95 | | |
| caa | atg | ttt | gag | gcg | gac | gcc | atc | aca | aca | aac | aat | gaa | tta | ttc | att | 336 |
| Gln | Met | Phe | Glu | Ala | Asp | Ala | Ile | Thr | Thr | Asn | Asn | Glu | Leu | Phe | Ile | |
| | | | 100 | | | | | 105 | | | | | 110 | | | |
| gcc | ccg | atg | gcg | aaa | gcc | tgt | gaa | cgc | ctt | ggc | ctg | agg | ggc | gcc | gga | 384 |
| Ala | Pro | Met | Ala | Lys | Ala | Cys | Glu | Arg | Leu | Gly | Leu | Arg | Gly | Ala | Gly | |
| | | 115 | | | | | 120 | | | | | 125 | | | | |
| gtg | cag | gca | gcg | gaa | aat | gcc | aga | gat | aaa | aat | aaa | atg | agg | gac | gct | 432 |
| Val | Gln | Ala | Ala | Glu | Asn | Ala | Arg | Asp | Lys | Asn | Lys | Met | Arg | Asp | Ala | |
| | 130 | | | | | 135 | | | | | 140 | | | | | |
| ttt | aat | aag | gcg | gga | gtc | aaa | tcg | atc | aaa | aac | aaa | cga | gtc | aca | act | 480 |
| Phe | Asn | Lys | Ala | Gly | Val | Lys | Ser | Ile | Lys | Asn | Lys | Arg | Val | Thr | Thr | |
| 145 | | | | | 150 | | | | | 155 | | | | | 160 | |
| ctt | gag | gat | ttt | cgt | gct | gca | ctt | gaa | gag | atc | ggc | aca | cct | cta | atc | 528 |
| Leu | Glu | Asp | Phe | Arg | Ala | Ala | Leu | Glu | Glu | Ile | Gly | Thr | Pro | Leu | Ile | |
| | | | | 165 | | | | | 170 | | | | | 175 | | |
| tta | aag | cct | aca | tac | tta | gcg | agt | tca | atc | ggc | gta | acg | ctg | att | acc | 576 |
| Leu | Lys | Pro | Thr | Tyr | Leu | Ala | Ser | Ser | Ile | Gly | Val | Thr | Leu | Ile | Thr | |
| | | | 180 | | | | | 185 | | | | | 190 | | | |
| gac | acg | gag | acg | gca | gaa | gat | gaa | ttt | aac | aga | gtc | aat | gac | tac | ctg | 624 |
| Asp | Thr | Glu | Thr | Ala | Glu | Asp | Glu | Phe | Asn | Arg | Val | Asn | Asp | Tyr | Leu | |
| | | 195 | | | | | 200 | | | | | 205 | | | | |
| aaa | tcg | att | aac | gtg | ccg | aag | gcg | gtc | aca | ttt | gaa | gca | ccg | ttt | att | 672 |
| Lys | Ser | Ile | Asn | Val | Pro | Lys | Ala | Val | Thr | Phe | Glu | Ala | Pro | Phe | Ile | |
| | 210 | | | | | 215 | | | | | 220 | | | | | |
| gct | gag | gaa | ttt | tta | cag | ggt | gag | tac | gga | gac | tgg | tat | caa | aca | gaa | 720 |
| Ala | Glu | Glu | Phe | Leu | Gln | Gly | Glu | Tyr | Gly | Asp | Trp | Tyr | Gln | Thr | Glu | |
| 225 | | | | | 230 | | | | | 235 | | | | | 240 | |
| ggg | tac | tcc | gac | tat | atc | agc | ata | gaa | ggc | att | atg | gca | gat | ggt | gag | 768 |
| Gly | Tyr | Ser | Asp | Tyr | Ile | Ser | Ile | Glu | Gly | Ile | Met | Ala | Asp | Gly | Glu | |
| | | | | 245 | | | | | 250 | | | | | 255 | | |
| tat | ttt | ccg | atc | gcc | att | cat | gac | aaa | acg | ccg | caa | att | gga | ttt | aca | 816 |
| Tyr | Phe | Pro | Ile | Ala | Ile | His | Asp | Lys | Thr | Pro | Gln | Ile | Gly | Phe | Thr | |
| | | | 260 | | | | | 265 | | | | | 270 | | | |
| gag | aca | tca | cat | att | acg | cca | tcc | att | ctg | gat | gaa | gag | gcg | aaa | aag | 864 |
| Glu | Thr | Ser | His | Ile | Thr | Pro | Ser | Ile | Leu | Asp | Glu | Glu | Ala | Lys | Lys | |
| | | 275 | | | | | 280 | | | | | 285 | | | | |
| aaa | att | gtc | gaa | gcg | gct | aaa | aag | gca | aat | gaa | ggg | ctt | gga | ctg | caa | 912 |

| | | | | | | | | | | | | | |
|---|---|---|---|---|---|---|---|---|---|---|---|---|---|
|Lys|Ile|Val|Glu|Ala|Ala|Lys|Lys|Ala|Asn|Glu|Gly|Leu|Gly Leu Gln|
| |290| | | |295| | | |300| | | | |

```
aat tgc gca aca cat aca gaa atc aag cta atg aaa aac aga gaa ccg      960
Asn Cys Ala Thr His Thr Glu Ile Lys Leu Met Lys Asn Arg Glu Pro
305             310                 315                 320 ggt tta ata gag tcg gct gcc aga ttc gca ggc tgg aat atg att cct     1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat     1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat     1104
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc     1152
Gln Glu Pro Tyr Tyr Val Ala Asp Cys His Leu Tyr Pro Gln His Phe
    370                 375                 380 aaa caa aat ggc cag atc cct gaa act gcc gag gat ttg gta atc gaa     1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt     1248
Ala Ile Asp Ile Pro Asp Gly Leu Leu Lys Gly Asp Thr Glu Ile Val
                405                 410                 415 act ttt tcg gct gcg gca cca gga aca tca gtt gat ttg aca ctg ttt     1296
Thr Phe Ser Ala Ala Ala Pro Gly Thr Ser Val Asp Leu Thr Leu Phe
            420                 425                 430 gaa gcc ttc aac tcc att gct gca ttt gaa ctg aaa ggc agc aat tca     1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                     1416
Thr Ala Lys Tyr Val Leu Pro Val
465                 470

<210> SEQ ID NO 16
<211> LENGTH: 1416
<212> TYPE: DNA
<213> ORGANISM: Bacillus subtilis IAM1213

<400> SEQUENCE: 16 atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc       96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att      144
Phe Ile Pro Arg Pro Phe Ala Ile Thr Ala Ser His Ala Ala Leu Ile
            35                  40                  45 gaa aaa tac tcg gtc gcg gtc ata aaa gat aaa gac tat ttt aag agt      192
Glu Lys Tyr Ser Val Ala Val Ile Lys Asp Lys Asp Tyr Phe Lys Ser
        50                  55                  60 tta gct gat ttt gag cat cct gac tcc att tat tgg gcg cat gag gat      240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc      288
His Asn Lys Pro Glu Glu Glu Val Val Glu Gln Ile Val Lys Val Ala
                85                  90                  95 gaa atg ttt ggg gcg gat gcc atc aca aca aac aat gaa tta ttc att      336
Glu Met Phe Gly Ala Asp Ala Ile Thr Thr Asn Asn Glu Leu Phe Ile
```

```
                Glu Met Phe Gly Ala Asp Ala Ile Thr Thr Asn Asn Glu Leu Phe Ile
                            100                 105                 110 gct ccg atg gcg aaa gcc tgt gaa cgt ctg ggc ctg aga ggt gcc ggc        384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct        432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act        480
Phe Asn Lys Ala Gly Val Lys Ser Ile Lys Asn Lys Arg Val Thr Thr
145                 150                 155                 160 ctc gaa gat ttc cgt gct gct ctt gaa gag atc ggc aca cct ctt atc        528
Leu Glu Asp Phe Arg Ala Ala Leu Glu Glu Ile Gly Thr Pro Leu Ile
                165                 170                 175 tta aag cct aca tac tta gcg agt tca atc ggt gta acg ctg att acg        576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg        624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc        672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa        720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag        768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca        816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag        864
Glu Thr Ser His Ile Thr Pro Ser Ile Leu Asp Glu Glu Ala Lys Lys
        275                 280                 285 aaa att gtc gaa gct gcc aaa aag gca aat gaa ggt ctt ggc ctg caa        912
Lys Ile Val Glu Ala Ala Lys Lys Ala Asn Glu Gly Leu Gly Leu Gln
290                 295                 300 aat tgc gca aca cat aca gag atc aag cta atg aaa aat aga gaa ccg        960
Asn Cys Ala Thr His Thr Glu Ile Lys Leu Met Lys Asn Arg Glu Pro
305                 310                 315                 320 ggt tta att gaa tcg gca gcc aga ttc gcc ggc tgg aat atg atc ccc       1008
Gly Leu Ile Glu Ser Ala Ala Arg Phe Ala Gly Trp Asn Met Ile Pro
                325                 330                 335 aat att aaa aag gtc ttt ggc ctt gat atg gcg caa tta tta tta gat       1056
Asn Ile Lys Lys Val Phe Gly Leu Asp Met Ala Gln Leu Leu Leu Asp
            340                 345                 350 gtc ctt tgt ttc gga aaa gac gcc gat ctg ccg gac gga tta ttg gat       1104
Val Leu Cys Phe Gly Lys Asp Ala Asp Leu Pro Asp Gly Leu Leu Asp
        355                 360                 365 caa gag cct tat tat gtt gcc gac tgc cat ttg tac ccg caa cat ttc       1152
Gln Glu Pro Tyr Tyr Val Ala Asp Cys His Leu Tyr Pro Gln His Phe
370                 375                 380 aaa caa aat ggc cag att cca gaa act gct gag gat ttg gtc att gaa       1200
Lys Gln Asn Gly Gln Ile Pro Glu Thr Ala Glu Asp Leu Val Ile Glu
385                 390                 395                 400 gcg atc gat ctg cct gac ggg ctt tta aaa ggg gat act gag atc gtt       1248
Ala Ile Asp Leu Pro Asp Gly Leu Leu Lys Gly Asp Thr Glu Ile Val
                405                 410                 415 tct ttt tcg gcc gca gca cca gga act tca gtt gat ttg aca ttg ttt       1296
```

```
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca    1344
Glu Ala Phe Asn Ser Ile Ala Ala Phe Glu Leu Lys Gly Ser Asn Ser
435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
    450                 455                 460 acg gca aag tat gtg ctg cca gta                                    1416
Thr Ala Lys Tyr Val Leu Pro Val
465                 470

<210> SEQ ID NO 17
<211> LENGTH: 1416
<212> TYPE: DNA
<213> ORGANISM: Bacillus subtilis IAM1107

<400> SEQUENCE: 17 atg gag aga aaa aca gta ttg gtc atc gct gat ctt gga ggc tgc ccg     48
Met Glu Arg Lys Thr Val Leu Val Ile Ala Asp Leu Gly Gly Cys Pro
1               5                  10                  15 ccg cac atg ttt tat aaa agc gct gct gaa aaa tat aac ctg gtc agc     96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att    144
Phe Ile Pro Arg Pro Phe Ala Ile Thr Ala Ser His Ala Ala Leu Ile
            35                  40                  45 gaa aaa tac tcg gtc gcg gtc gta aaa gat aaa gac tat ttt aag agt    192
Glu Lys Tyr Ser Val Ala Val Val Lys Asp Lys Asp Tyr Phe Lys Ser
    50                  55                  60 tta gct gat ttt gag cat cct gac tcc att tat tgg gcg cat gag gat    240
Leu Ala Asp Phe Glu His Pro Asp Ser Ile Tyr Trp Ala His Glu Asp
65                  70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                85                  90                  95 gaa atg ttc ggg gcg gat gcc atc aca aca aac aat gaa tta ttc att    336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc    384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg    576
Leu Lys Pro Thr Tyr Leu Ala Ser Ser Ile Gly Val Thr Leu Ile Thr
                180                 185                 190 gac act gag acg gca gaa gat gaa ttt aac aga gtc aat gac tat ctg    624
Asp Thr Glu Thr Ala Glu Asp Glu Phe Asn Arg Val Asn Asp Tyr Leu
            195                 200                 205 aaa tca att aac gtg cca aag gcg gtt acg ttt gaa gcg ccg ttt atc    672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa    720
Ala Glu Glu Phe Leu Gln Gly Glu Tyr Gly Asp Trp Tyr Gln Thr Glu
```

```
                                       -continued
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag    768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca    816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag    864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt ggc ctg caa    912
Lys Ile Val Glu Ala Ala Lys Lys Ala Asn Glu Gly Leu Gly Leu Gln
    290                 295                 300 aat tgc gca aca cat aca gag gtc aag cta atg aaa aac aga gaa ccg    960
Asn Cys Ala Thr His Thr Glu Val Lys Leu Met Lys Asn Arg Glu Pro
305                 310                 315                 320 ggt tta att gaa tcg gca gcc aga ttt gcc ggc tgg aat atg atc cct   1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat   1056
Asn Ile Lys Lys Val Phe Gly Leu Asp Met Ala Gln Leu Leu Leu Asp
            340                 345                 350 gtc ctc tgt ttc gga aaa gat gcc gat ctg ccg gac gga tta ttg gat   1104
Val Leu Cys Phe Gly Lys Asp Ala Asp Leu Pro Asp Gly Leu Leu Asp
        355                 360                 365 caa gag cct tac tat gtc gcc gac tgc cat ttg tac ccg cag cat ttc   1152
Gln Glu Pro Tyr Tyr Val Ala Asp Cys His Leu Tyr Pro Gln His Phe
    370                 375                 380 aaa caa aat ggc cag att cca gaa acc gct gag gat ttg gtc att gaa   1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc ttt   1248
Ala Ile Asp Ile Pro Asp Gly Leu Leu Lys Gly Asp Thr Glu Ile Phe
                405                 410                 415 tct ttt tcg gcc gca gca cca ggc act tca gtt gat ttg aca ttg ttt   1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca   1344
Glu Ala Phe Asn Ser Ile Ala Ala Phe Glu Leu Lys Gly Ser Asn Ser
        435                 440                 445 cag gat gtg gct gaa tca atc aga caa att cag cag cat gcg aag ctg   1392
Gln Asp Val Ala Glu Ser Ile Arg Gln Ile Gln Gln His Ala Lys Leu
    450                 455                 460 acg gca aag tat gtg ctg cca gta                                    1416
Thr Ala Lys Tyr Val Leu Pro Val
465                 470

<210> SEQ ID NO 18
<211> LENGTH: 1416
<212> TYPE: DNA
<213> ORGANISM: Bacillus subtilis IAM1214

<400> SEQUENCE: 18 atg gag aga aaa aca gta ttg gtc atc gct gat ctt gga ggc tgc ccg     48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtt agc     96
Pro His Met Phe Tyr Lys Ser Ala Ala Glu Lys Tyr Asn Leu Val Ser
                20                  25                  30 ttt att ccg aga cct ttt gca ata aca gcc tcc cat gca gca ctg att    144
```

-continued

```
                Phe Ile Pro Arg Pro Phe Ala Ile Thr Ala Ser His Ala Ala Leu Ile
                                 35                  40                  45 gaa aaa tac tcg gtc gcg gtc ata aaa gat aaa gac tat ttt cag agc              192
Glu Lys Tyr Ser Val Ala Val Ile Lys Asp Lys Asp Tyr Phe Gln Ser
 50                  55                  60 tta gct gat ttt gag cat ccc gat tca att tat tgg gcg cat gag gat              240
Leu Ala Asp Phe Glu His Pro Asp Ser Ile Tyr Trp Ala His Glu Asp
 65                  70                  75                  80 cat gac aag cct gaa gaa gag gtt gtc gag caa atc gtc aag gtt gcc              288
His Asp Lys Pro Glu Glu Glu Val Val Glu Gln Ile Val Lys Val Ala
                 85                  90                  95 caa atg ttt gag gcg gac gcc atc aca aca aac aat gaa tta ttc att              336
Gln Met Phe Glu Ala Asp Ala Ile Thr Thr Asn Asn Glu Leu Phe Ile
            100                 105                 110 gcc ccg atg gca aaa gcc tgt gaa cgc ctt ggc ctg agg ggc gcc gga              384
Ala Pro Met Ala Lys Ala Cys Glu Arg Leu Gly Leu Arg Gly Ala Gly
        115                 120                 125 gtg cag gca gcg gaa aat gcc aga gat aaa aat aaa atg agg gac gct              432
Val Gln Ala Ala Glu Asn Ala Arg Asp Lys Asn Lys Met Arg Asp Ala
130                 135                 140 ttt aat aag gcg gga gtc aaa tcg atc aaa aac aaa cga gtc aca act              480
Phe Asn Lys Ala Gly Val Lys Ser Ile Lys Asn Lys Arg Val Thr Thr
145                 150                 155                 160 ctt gag gat ttt cgt gct gca ctt gaa gag atc ggc aca cct cta atc              528
Leu Glu Asp Phe Arg Ala Ala Leu Glu Glu Ile Gly Thr Pro Leu Ile
                165                 170                 175 tta aag cct aca tac tta gcg agt tca atc ggc gta acg ctg att acc              576
Leu Lys Pro Thr Tyr Leu Ala Ser Ser Ile Gly Val Thr Leu Ile Thr
            180                 185                 190 gac acg gag acg gca gaa gat gaa ttt aac aga gtc aat gac tac ctg              624
Asp Thr Glu Thr Ala Glu Asp Glu Phe Asn Arg Val Asn Asp Tyr Leu
        195                 200                 205 aaa tcg att aac gtg ccg aag gcg gtc aca ttt gaa gca ccg ttt att              672
Lys Ser Ile Asn Val Pro Lys Ala Val Thr Phe Glu Ala Pro Phe Ile
210                 215                 220 gct gag gaa ttt tta cag ggt gag tac gga gac tgg tat caa aca gaa              720
Ala Glu Glu Phe Leu Gln Gly Glu Tyr Gly Asp Trp Tyr Gln Thr Glu
225                 230                 235                 240 ggg tac tcc gac tat atc agc ata gaa ggc att atg gca gat ggt gag              768
Gly Tyr Ser Asp Tyr Ile Ser Ile Glu Gly Ile Met Ala Asp Gly Glu
                245                 250                 255 tat ttt ccg atc gcc att cat gac aaa acg ccg caa att gga ttt aca              816
Tyr Phe Pro Ile Ala Ile His Asp Lys Thr Pro Gln Ile Gly Phe Thr
            260                 265                 270 gag aca tca cat att acg cca tcc att ctg gat gaa gag gcg aaa aag              864
Glu Thr Ser His Ile Thr Pro Ser Ile Leu Asp Glu Glu Ala Lys Lys
        275                 280                 285 aaa att gtc gaa gcg gct aaa aag gca aat gaa ggg ctt gga ctg caa              912
Lys Ile Val Glu Ala Ala Lys Lys Ala Asn Glu Gly Leu Gly Leu Gln
290                 295                 300 aat tgc gca aca cat aca gaa atc aag cta atg aaa aac aga gaa ccg              960
Asn Cys Ala Thr His Thr Glu Ile Lys Leu Met Lys Asn Arg Glu Pro
305                 310                 315                 320 ggt tta ata gag tcg gct gcc aga ttc gca ggc tgg aat atg att cct             1008
Gly Leu Ile Glu Ser Ala Ala Arg Phe Ala Gly Trp Asn Met Ile Pro
                325                 330                 335 aac att aaa aag gtt ttc ggc ctt gat atg gcg caa tta tta tta gat             1056
Asn Ile Lys Lys Val Phe Gly Leu Asp Met Ala Gln Leu Leu Leu Asp
            340                 345                 350 gtt ctc tgt ttc gga aaa gat gct gat ctg ccg gac ggg tta ttg gat             1104
Val Leu Cys Phe Gly Lys Asp Ala Asp Leu Pro Asp Gly Leu Leu Asp
```

```
Val Leu Cys Phe Gly Lys Asp Ala Asp Leu Pro Asp Gly Leu Leu Asp
        355                 360                 365 caa gag cct tac tat gtt gct gac tgc cat ctg tac cct cag cat ttc    1152
Gln Glu Pro Tyr Tyr Val Ala Asp Cys His Leu Tyr Pro Gln His Phe
370                 375                 380 aaa caa aat ggc cag atc cct gaa act gcc gag gat ttg gta atc gaa    1200
Lys Gln Asn Gly Gln Ile Pro Glu Thr Ala Glu Asp Leu Val Ile Glu
385                 390                 395                 400 gcg atc gat att ccg gat ggg ctt ttg aag ggt gat aca gaa atc gtt    1248
Ala Ile Asp Ile Pro Asp Gly Leu Leu Lys Gly Asp Thr Glu Ile Val
            405                 410                 415 act ttt tcg gct gcg gca cca gga aca tca gtt gat ttg aca ctg ttt    1296
Thr Phe Ser Ala Ala Ala Pro Gly Thr Ser Val Asp Leu Thr Leu Phe
        420                 425                 430 gaa gcc ttc aac tcc att gct gca ttt gaa ctg aaa ggc agc aat tca    1344
Glu Ala Phe Asn Ser Ile Ala Ala Phe Glu Leu Lys Gly Ser Asn Ser
    435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
450                 455                 460 acg gca aag tat gtg ctg cca gta                                    1416
Thr Ala Lys Tyr Val Leu Pro Val
465                 470

<210> SEQ ID NO 19
<211> LENGTH: 1416
<212> TYPE: DNA
<213> ORGANISM: Bacillus subtilis ATCC21555

<400> SEQUENCE: 19 atg gag aga aaa aca gta ttg gtt atc gct gat ctt ggg ggc tgc ccg      48
Met Glu Arg Lys Thr Val Leu Val Ile Ala Asp Leu Gly Gly Cys Pro
1               5                  10                  15 ccg cat atg ttt tac aaa agc gca gcc gaa aaa tac aac ctc gtc agc      96
Pro His Met Phe Tyr Lys Ser Ala Ala Glu Lys Tyr Asn Leu Val Ser
            20                  25                  30 ttt att ccg aga ccc ttt gca att aca gcc tct cat gcg gcc tta att     144
Phe Ile Pro Arg Pro Phe Ala Ile Thr Ala Ser His Ala Ala Leu Ile
        35                  40                  45 gaa aaa tac tcg att gcg gtc att aaa gat aaa gac tat ttt aag agt     192
Glu Lys Tyr Ser Ile Ala Val Ile Lys Asp Lys Asp Tyr Phe Lys Ser
    50                  55                  60 ctg gct gat ttt gaa cat ccc gat tcg att tat tgg gct cat gaa gat     240
Leu Ala Asp Phe Glu His Pro Asp Ser Ile Tyr Trp Ala His Glu Asp
65                  70                  75                  80 cat gac aaa cct gag gaa gaa gtc gtc gaa gaa atc gtg aaa gtg gcc     288
His Asp Lys Pro Glu Glu Glu Val Val Glu Glu Ile Val Lys Val Ala
                85                  90                  95 gac atg ttt ggg gtt gac gcc att acg acc aac aat gaa ctg ttt atc     336
Asp Met Phe Gly Val Asp Ala Ile Thr Thr Asn Asn Glu Leu Phe Ile
            100                 105                 110 gct ccg atg gca aaa gcg tgt aaa cgt ctc ggc ctg cgg gga gcg ggc     384
Ala Pro Met Ala Lys Ala Cys Lys Arg Leu Gly Leu Arg Gly Ala Gly
        115                 120                 125 gta cag gcc gct gaa aac gcc aga gat aaa aat aaa atg aga gcc gcc     432
Val Gln Ala Ala Glu Asn Ala Arg Asp Lys Asn Lys Met Arg Ala Ala
130                 135                 140 ttc aac cgg gcc ggc gtc aaa tcc atc aaa aac aaa cgg gtg acg acc     480
Phe Asn Arg Ala Gly Val Lys Ser Ile Lys Asn Lys Arg Val Thr Thr
145                 150                 155                 160 ctg gaa gat ttc cgc gcc gcg ctt cag gaa atc gga acg ccg ctt att     528
```

```
                Leu Glu Asp Phe Arg Ala Ala Leu Gln Glu Ile Gly Thr Pro Leu Ile
                                165                 170                 175 ctg aag cct aca tat ctg gca agc tcg atc ggc gtg acg ctt att aaa        576
Leu Lys Pro Thr Tyr Leu Ala Ser Ser Ile Gly Val Thr Leu Ile Lys
            180                 185                 190 gag atg gaa acg gcc gaa gct gaa ttc aac aga gtc aat gag tac ttg        624
Glu Met Glu Thr Ala Glu Ala Glu Phe Asn Arg Val Asn Glu Tyr Leu
        195                 200                 205 aaa tcg att aat gta ccg aaa gcg gtg acg ttt gaa gcg ccg ttt atc        672
Lys Ser Ile Asn Val Pro Lys Ala Val Thr Phe Glu Ala Pro Phe Ile
    210                 215                 220 gcg gaa gaa ttc ttg cag ggc gag tat gat gac tgg tac gaa aca agc        720
Ala Glu Glu Phe Leu Gln Gly Glu Tyr Asp Asp Trp Tyr Glu Thr Ser
225                 230                 235                 240 ggt tat tcc gac tat atc agc atc gaa ggc atc atg gcc gac gga gaa        768
Gly Tyr Ser Asp Tyr Ile Ser Ile Glu Gly Ile Met Ala Asp Gly Glu
                245                 250                 255 tac ttc ccc gtt gcg atc cat gat aaa aca ccg caa atc gga ttc acg        816
Tyr Phe Pro Val Ala Ile His Asp Lys Thr Pro Gln Ile Gly Phe Thr
            260                 265                 270 gag aca gcg cat att acg ccg tcc atc ctg gat gat gac gcc aag cgg        864
Glu Thr Ala His Ile Thr Pro Ser Ile Leu Asp Asp Asp Ala Lys Arg
        275                 280                 285 aaa atc gtc gaa gct gcc aag aag gcg aat gaa gga ctc ggc ctc gaa        912
Lys Ile Val Glu Ala Ala Lys Lys Ala Asn Glu Gly Leu Gly Leu Glu
    290                 295                 300 aac tgt gca acg cat aca gaa ata aaa tta atg aaa aac cgg gaa gcc        960
Asn Cys Ala Thr His Thr Glu Ile Lys Leu Met Lys Asn Arg Glu Ala
305                 310                 315                 320 gga ctg att gag tca gcg gcc aga ttc gcg gga tgg aat atg att ccg       1008
Gly Leu Ile Glu Ser Ala Ala Arg Phe Ala Gly Trp Asn Met Ile Pro
                325                 330                 335 aat att aaa aag gtc ttc ggc gtt gat atg gcg cag cta tta ttg gat       1056
Asn Ile Lys Lys Val Phe Gly Val Asp Met Ala Gln Leu Leu Leu Asp
            340                 345                 350 gtt ctc tgt tac gga aaa gaa gct gat ctg ccg aaa gga tta ttg gag       1104
Val Leu Cys Tyr Gly Lys Glu Ala Asp Leu Pro Lys Gly Leu Leu Glu
        355                 360                 365 cag gag cca tgc tat gtc gca gac tgc cac ttg tat cct cag cat ttc       1152
Gln Glu Pro Cys Tyr Val Ala Asp Cys His Leu Tyr Pro Gln His Phe
    370                 375                 380 aaa gag aac ggc cag ctg cct gag acg gtt gtc gat ttc gtc att gaa       1200
Lys Glu Asn Gly Gln Leu Pro Glu Thr Val Val Asp Phe Val Ile Glu
385                 390                 395                 400 agc att gaa att cct gac ggc gtc tta aag gga gac act gaa ctc gtt       1248
Ser Ile Glu Ile Pro Asp Gly Val Leu Lys Gly Asp Thr Glu Leu Val
                405                 410                 415 tct ttc tca gcg gct gag gcg ggt acg tca gtg gat ctg cgg ctg ttc       1296
Ser Phe Ser Ala Ala Glu Ala Gly Thr Ser Val Asp Leu Arg Leu Phe
            420                 425                 430 gaa gcg ttc aac agc att gcg gcg ttt gag ctg aaa gga agc aat tcg       1344
Glu Ala Phe Asn Ser Ile Ala Ala Phe Glu Leu Lys Gly Ser Asn Ser
        435                 440                 445 aac gac gtg gcc gaa tca atc aaa caa att cag cag cag gcg aag ctg       1392
Asn Asp Val Ala Glu Ser Ile Lys Gln Ile Gln Gln Gln Ala Lys Leu
    450                 455                 460 act gca aag tat gcg tta tcg gta                                       1416
Thr Ala Lys Tyr Ala Leu Ser Val

<210> SEQ ID NO 20
```

<211> LENGTH: 1416
<212> TYPE: DNA
<213> ORGANISM: Bacillus amyloliquefaciens IFO3022

<400> SEQUENCE: 20

```
atg gag aga aaa aca gta ttg gtt atc gct gac ctt ggg gga tgc ccg      48
Met Glu Arg Lys Thr Val Leu Val Ile Ala Asp Leu Gly Gly Cys Pro
1               5                   10                  15 ccg cat atg ttt tac aaa agc gca gcc gaa aaa tac aac ctc gtc agc      96
Pro His Met Phe Tyr Lys Ser Ala Ala Glu Lys Tyr Asn Leu Val Ser
            20                  25                  30 ttt att ccg aga cct ttt gca att aca gcc tct cat gcg gca tta att     144
Phe Ile Pro Arg Pro Phe Ala Ile Thr Ala Ser His Ala Ala Leu Ile
        35                  40                  45 gaa aaa tac tcg gtc gcg gta ata aaa gat aaa gac tat ttt aag agt     192
Glu Lys Tyr Ser Val Ala Val Ile Lys Asp Lys Asp Tyr Phe Lys Ser
50                  55                  60 ctg gct gat ttt gag cat ccc gat tcg att tac tgg gct cat gaa gat     240
Leu Ala Asp Phe Glu His Pro Asp Ser Ile Tyr Trp Ala His Glu Asp
65                  70                  75                  80 cat gac aaa cct gag gaa gaa gta gtc gaa gaa atc gtc aag gtg gcc     288
His Asp Lys Pro Glu Glu Glu Val Val Glu Glu Ile Val Lys Val Ala
                85                  90                  95 ggc atg ttc gcg gtt gac gcc att acg acc aac aat gaa ctg ttt atc     336
Gly Met Phe Ala Val Asp Ala Ile Thr Thr Asn Asn Glu Leu Phe Ile
            100                 105                 110 gct ccg atg gca aaa gcg tgt gaa cgt ctc ggc ctg cgg gga gcg ggc     384
Ala Pro Met Ala Lys Ala Cys Glu Arg Leu Gly Leu Arg Gly Ala Gly
        115                 120                 125 gta cag gcc gct gaa aat gcc aga gat aaa aac aaa atg aga gcc gct     432
Val Gln Ala Ala Glu Asn Ala Arg Asp Lys Asn Lys Met Arg Ala Ala
    130                 135                 140 ttc aac cgg gcc ggc gtc aag tct atc aaa aac aga cgg gtg acg acg     480
Phe Asn Arg Ala Gly Val Lys Ser Ile Lys Asn Arg Arg Val Thr Thr
145                 150                 155                 160 ctg gaa gat ttc cgc gcc gcg ctt cag gaa atc gga acg ccg ctc att     528
Leu Glu Asp Phe Arg Ala Ala Leu Gln Glu Ile Gly Thr Pro Leu Ile
                165                 170                 175 ctg aag cct aca tat ctg gcg agc tcc atc ggc gtg acg ctc atc aaa     576
Leu Lys Pro Thr Tyr Leu Ala Ser Ser Ile Gly Val Thr Leu Ile Lys
            180                 185                 190 gag agg gaa acg gcc gaa gcc gaa ttt aac aga gtc aat gaa tac ctg     624
Glu Arg Glu Thr Ala Glu Ala Glu Phe Asn Arg Val Asn Glu Tyr Leu
        195                 200                 205 aag tcg atc aac gta ccg aaa gcg gtc acg ttt gaa gcg ccg ttt atc     672
Lys Ser Ile Asn Val Pro Lys Ala Val Thr Phe Glu Ala Pro Phe Ile
    210                 215                 220 gcg gaa gaa ttt ttg cag ggc gag tat gac gac tgg tac gaa aca agc     720
Ala Glu Glu Phe Leu Gln Gly Glu Tyr Asp Asp Trp Tyr Glu Thr Ser
225                 230                 235                 240 ggt tat tcc gac tat atc agc ata gaa ggc atc atg gcc gac gga gaa     768
Gly Tyr Ser Asp Tyr Ile Ser Ile Glu Gly Ile Met Ala Asp Gly Glu
                245                 250                 255 tac ttc cct gtc gca att cat gat aaa aca ccg caa atc gga ttc acg     816
Tyr Phe Pro Val Ala Ile His Asp Lys Thr Pro Gln Ile Gly Phe Thr
            260                 265                 270 gag aca tcg cat att acg ccg tcc atc ctg gat gat gac gcg aag cgg     864
Glu Thr Ser His Ile Thr Pro Ser Ile Leu Asp Asp Asp Ala Lys Arg
        275                 280                 285 aaa atc gtc gaa gca gcc aaa aag gcg aat gaa gga ctc ggc ctc gaa     912
Lys Ile Val Glu Ala Ala Lys Lys Ala Asn Glu Gly Leu Gly Leu Glu
```

```
                290                 295                 300
aac tgc gca acc cat aca gag att aaa tta atg aaa aac cgg gaa gcc     960
Asn Cys Ala Thr His Thr Glu Ile Lys Leu Met Lys Asn Arg Glu Ala
305                 310                 315                 320 gga ctg att gaa tca gcg gca cga ttt gcg ggc tgg aac atg att ccg    1008
Gly Leu Ile Glu Ser Ala Ala Arg Phe Ala Gly Trp Asn Met Ile Pro
                325                 330                 335 aat att aaa aag gtc ttc ggc gtc gat atg gcg cag ctg tta ttg gat    1056
Asn Ile Lys Lys Val Phe Gly Val Asp Met Ala Gln Leu Leu Leu Asp
            340                 345                 350 gtt ctc tgt ttc gga aaa gaa gcc gat ctg ccg aaa gga tta ttg gag    1104
Val Leu Cys Phe Gly Lys Glu Ala Asp Leu Pro Lys Gly Leu Leu Glu
        355                 360                 365 cag gag ccg tgc tat gtc gcc gac tgc cac ttg tat cct cag cat ttc    1152
Gln Glu Pro Cys Tyr Val Ala Asp Cys His Leu Tyr Pro Gln His Phe
    370                 375                 380 aaa gag aac ggc cag ctg cct gag acg gct gtc gat ttc gtc att gaa    1200
Lys Glu Asn Gly Gln Leu Pro Glu Thr Ala Val Asp Phe Val Ile Glu
385                 390                 395                 400 agc att gac att ccc gac ggc gtc tta aag gga gac acc gaa atc gtt    1248
Ser Ile Asp Ile Pro Asp Gly Val Leu Lys Gly Asp Thr Glu Ile Val
                405                 410                 415 tct ttc tcg gcg gcc gag gcg ggt aca tcc gtg gat ctg cgg ctg ttc    1296
Ser Phe Ser Ala Ala Glu Ala Gly Thr Ser Val Asp Leu Arg Leu Phe
            420                 425                 430 gaa gcg ttc aac agc att gcg gcg ttc gag ctg aaa gga agc aat tcg    1344
Glu Ala Phe Asn Ser Ile Ala Ala Phe Glu Leu Lys Gly Ser Asn Ser
        435                 440                 445 ggt gac gtg gcc gaa tca atc aaa caa att cag cag cag gcg aag ctg    1392
Gly Asp Val Ala Glu Ser Ile Lys Gln Ile Gln Gln Gln Ala Lys Leu
    450                 455                 460 act gca aag tat gcg tta ccg gta                                     1416
Thr Ala Lys Tyr Ala Leu Pro Val <210> SEQ ID NO 21
<211> LENGTH: 1428
<212> TYPE: DNA
<213> ORGANISM: Bacillus pumilus NRRL B-12025

<400> SEQUENCE: 21 gtg ctt tca ttg agt aaa aaa act gta ctt gtc att gct gac tta gga      48
Val Leu Ser Leu Ser Lys Lys Thr Val Leu Val Ile Ala Asp Leu Gly
1               5                   10                  15 ggg tgc ccg ccc cat atg ttt tat gaa agc gtg gcg gca tca tac cat      96
Gly Cys Pro Pro His Met Phe Tyr Glu Ser Val Ala Ala Ser Tyr His
                20                  25                  30 atc gtt tct tat atc cca aga ccc ttt gcg att aca aag gga cat gcc     144
Ile Val Ser Tyr Ile Pro Arg Pro Phe Ala Ile Thr Lys Gly His Ala
            35                  40                  45 gag cta atc gaa aaa tac tcc att gcc gtc atc aaa gac cgt gat tat     192
Glu Leu Ile Glu Lys Tyr Ser Ile Ala Val Ile Lys Asp Arg Asp Tyr
        50                  55                  60 ttt gag aca cac cct tct ttt gaa cac cct gat tct att tac tgg gca     240
Phe Glu Thr His Pro Ser Phe Glu His Pro Asp Ser Ile Tyr Trp Ala
65                  70                  75                  80 cat gat gat tat cca aaa tca gaa gaa gaa gtt gtg gaa gac ttc att     288
His Asp Asp Tyr Pro Lys Ser Glu Glu Glu Val Val Glu Asp Phe Ile
                85                  90                  95 cga gta gct tcc ttt ttc aaa gca gat gca atc acg acc aat aat gaa     336
Arg Val Ala Ser Phe Phe Lys Ala Asp Ala Ile Thr Thr Asn Asn Glu
            100                 105                 110
```

|   |   |
|---|---:|
| tta ttc att gca ccg atg gca aag gcc gct gaa cgt ctt ggg cta cga<br>Leu Phe Ile Ala Pro Met Ala Lys Ala Ala Glu Arg Leu Gly Leu Arg<br>              115                    120                    125 | 384 |
| ggt gcc ggt gtc aag gca gcc gaa atg gcg cgt gat aaa agc caa atg<br>Gly Ala Gly Val Lys Ala Ala Glu Met Ala Arg Asp Lys Ser Gln Met<br>130                    135                    140 | 432 |
| agg gct gca ttc aat gcc tct ggc gtc aaa gcg gtg aaa act cag cct<br>Arg Ala Ala Phe Asn Ala Ser Gly Val Lys Ala Val Lys Thr Gln Pro<br>145                    150                    155                    160 | 480 |
| gtc acg act tta tct gat ttc caa caa gcc att gag tct atc gga aca<br>Val Thr Thr Leu Ser Asp Phe Gln Gln Ala Ile Glu Ser Ile Gly Thr<br>              165                    170                    175 | 528 |
| ccg ctc att tta aag cct aca tat tta gcc agt tct att ggc gtc acc<br>Pro Leu Ile Leu Lys Pro Thr Tyr Leu Ala Ser Ser Ile Gly Val Thr<br>                  180                    185                    190 | 576 |
| ttg ttt cat gac aaa gcc gga agt gat gac ttg ttt tta caa gta caa<br>Leu Phe His Asp Lys Ala Gly Ser Asp Asp Leu Phe Leu Gln Val Gln<br>              195                    200                    205 | 624 |
| tcg tat ttg gaa acc ata cca gtc cca gac gct gtc acg tat gaa gca<br>Ser Tyr Leu Glu Thr Ile Pro Val Pro Asp Ala Val Thr Tyr Glu Ala<br>          210                    215                    220 | 672 |
| ccg ttt gtc gct gaa aca tat tta gag ggt gct tac gaa gat tgg tat<br>Pro Phe Val Ala Glu Thr Tyr Leu Glu Gly Ala Tyr Glu Asp Trp Tyr<br>225                    230                    235                    240 | 720 |
| gaa gac gaa gga tat gct gat tat gtc agt gta gaa ggg ctg gtc gta<br>Glu Asp Glu Gly Tyr Ala Asp Tyr Val Ser Val Glu Gly Leu Val Val<br>                  245                    250                    255 | 768 |
| gag ggc gaa tat ctc cct ttt gtc ata cat gat aaa acc cct caa atc<br>Glu Gly Glu Tyr Leu Pro Phe Val Ile His Asp Lys Thr Pro Gln Ile<br>              260                    265                    270 | 816 |
| ggc ttt aca gaa acg gct cat atc act ccg acg atc tta gac aat gaa<br>Gly Phe Thr Glu Thr Ala His Ile Thr Pro Thr Ile Leu Asp Asn Glu<br>              275                    280                    285 | 864 |
| gcc aag caa atc atc att gaa gca gca agg aag gca aat gaa ggg cta<br>Ala Lys Gln Ile Ile Ile Glu Ala Ala Arg Lys Ala Asn Glu Gly Leu<br>          290                    295                    300 | 912 |
| ggt ctt gaa cat tgt gca acc cat aca gaa atc aaa ctc atg aaa aat<br>Gly Leu Glu His Cys Ala Thr His Thr Glu Ile Lys Leu Met Lys Asn<br>305                    310                    315                    320 | 960 |
| cga gaa act gga ctg atc gag gca gcg gct cga ttc gct ggc tgg aat<br>Arg Glu Thr Gly Leu Ile Glu Ala Ala Ala Arg Phe Ala Gly Trp Asn<br>                  325                    330                    335 | 1008 |
| atg atc ccg aat att aaa aaa gtc ttt ggc gtc gat atg gcg aag cta<br>Met Ile Pro Asn Ile Lys Lys Val Phe Gly Val Asp Met Ala Lys Leu<br>              340                    345                    350 | 1056 |
| ttg att gat gta tta gtt gat ggt aaa aag gct gta ctg cca aaa cag<br>Leu Ile Asp Val Leu Val Asp Gly Lys Lys Ala Val Leu Pro Lys Gln<br>          355                    360                    365 | 1104 |
| ctg ctt tct gga cat aca ttt tat gta gcg gac tgc cac ctg tac cct<br>Leu Leu Ser Gly His Thr Phe Tyr Val Ala Asp Cys His Leu Tyr Pro<br>370                    375                    380 | 1152 |
| cag cat ttt aaa gag agt ggg ctt atc ccg cct gaa gcc aca cat att<br>Gln His Phe Lys Glu Ser Gly Leu Ile Pro Pro Glu Ala Thr His Ile<br>385                    390                    395                    400 | 1200 |
| acc att gat cat gtg tct att ccg cag gaa gca ttc gtt gga gat act<br>Thr Ile Asp His Val Ser Ile Pro Gln Glu Ala Phe Val Gly Asp Thr<br>                  405                    410                    415 | 1248 |
| gcg att gtc agt caa tca ttc cct gcc aaa ggg act att gtg gat ctt<br>Ala Ile Val Ser Gln Ser Phe Pro Ala Lys Gly Thr Ile Val Asp Leu<br>          420                    425                    430 | 1296 |

```
gaa tta ttt gaa gct ttt aat gga atc gta tct ctt gaa tta aaa gga      1344
Glu Leu Phe Glu Ala Phe Asn Gly Ile Val Ser Leu Glu Leu Lys Gly
        435                 440                 445 tca tcc tca caa gat gtt gcc gcg tcc atc cgc aac att cag aaa cag      1392
Ser Ser Ser Gln Asp Val Ala Ala Ser Ile Arg Asn Ile Gln Lys Gln
450                 455                 460 gca acg att cag tta atg gat gaa tta gtg aag gga                      1428
Ala Thr Ile Gln Leu Met Asp Glu Leu Val Lys Gly
465                 470                 475

<210> SEQ ID NO 22
<211> LENGTH: 1416
<212> TYPE: DNA
<213> ORGANISM: Artificial Sequence
<220> FEATURE:
<223> OTHER INFORMATION: Description of Artificial Sequence: Mutant DNA

<400> SEQUENCE: 22 atg gag aga aaa aca gta ttg gtc atc gct gat ctt gga ggc tgc ccg       48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc       96
Pro His Met Phe Tyr Lys Ser Ala Ala Glu Lys Tyr Asn Leu Val Ser
                20                  25                  30 ttt att cca aga cct ttt gca att aca gcc tcc cat gca gca ttg att      144
Phe Ile Pro Arg Pro Phe Ala Ile Thr Ala Ser His Ala Ala Leu Ile
            35                  40                  45 gaa aaa tac tcg gtc gcg gta ata aaa gat aaa gac tat ttt aag agt      192
Glu Lys Tyr Ser Val Ala Val Ile Lys Asp Lys Asp Tyr Phe Lys Ser
        50                  55                  60 tta gct gat ttt gaa cac cct gat ccc att tat tgg gcg cat gaa gat      240
Leu Ala Asp Phe Glu His Pro Asp Pro Ile Tyr Trp Ala His Glu Asp
65                  70                  75                  80 cat aac aag cct gag gaa gag gtc gtc gag caa atc gtc aag gtt gcc      288
His Asn Lys Pro Glu Glu Glu Val Val Glu Gln Ile Val Lys Val Ala
                85                  90                  95 gaa atg ttt ggg gcg gat gcc atc aca aca aac aac gaa tta ttc att      336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ttg aga ggt gcc ggc      384
Ala Pro Met Ala Lys Ala Cys Glu Arg Leu Gly Leu Arg Gly Ala Gly
            115                 120                 125 gtg cag gca gcc gaa aat gcc aga gat aaa aat aaa atg agg gac gct      432
Val Gln Ala Ala Glu Asn Ala Arg Asp Lys Asn Lys Met Arg Asp Ala
        130                 135                 140 ttt aat aag gcc gga gtc aaa tcg atc aaa aac aaa cga gtc aca act      480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg      576
Leu Lys Pro Thr Tyr Leu Ala Ser Ser Ile Gly Val Thr Leu Ile Thr
                180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
            195                 200                 205 aaa tca att aac gtg cca aag gcg gtt acg ttt gta gcg ccg ttt atc      672
Lys Ser Ile Asn Val Pro Lys Ala Val Thr Phe Val Ala Pro Phe Ile
        210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
```

```
                Ala Glu Glu Phe Leu Gln Gly Glu Tyr Gly Asp Trp Tyr Gln Thr Glu
                225                 230                 235                 240 ggg tac tcc gac tat atc agt ata gaa ggc atc atg gct gac ggt gag       768
Gly Tyr Ser Asp Tyr Ile Ser Ile Glu Gly Ile Met Ala Asp Gly Glu
            245                 250                 255 tat ttc ccg atc gcc att cat gat aaa acg ccg caa atc ggg ttt aca       816
Tyr Phe Pro Ile Ala Ile His Asp Lys Thr Pro Gln Ile Gly Phe Thr
        260                 265                 270 gag aca tcc cac att acg ccg tcc att ctg gat gaa gag gca aaa aag       864
Glu Thr Ser His Ile Thr Pro Ser Ile Leu Asp Glu Glu Ala Lys Lys
    275                 280                 285 aaa att gtc gaa gct gcc aaa aag gca aat gaa ggg ctt gga ctg caa       912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg       960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc      1008
Gly Leu Ile Glu Ser Ala Ala Arg Phe Ala Gly Trp Asn Met Ile Pro
            325                 330                 335 aat att aaa aag gtc ttt ggc ctt gat atg gtg caa tta tta tta gat      1056
Asn Ile Lys Lys Val Phe Gly Leu Asp Met Val Gln Leu Leu Leu Asp
        340                 345                 350 gtc ctc tgc ttc gga aaa gac gcc gat ctg ccg gac gga tta ttg gat      1104
Val Leu Cys Phe Gly Lys Asp Ala Asp Leu Pro Asp Gly Leu Leu Asp
    355                 360                 365 caa gag cct tat tat gtt gcc gac tgc cgt ttg tac ccg cag cat ttc      1152
Gln Glu Pro Tyr Tyr Val Ala Asp Cys Arg Leu Tyr Pro Gln His Phe
370                 375                 380 aaa caa aat ggc caa att cct gaa act gct gag gat ttg gtc att gaa      1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt      1248
Ala Ile Asp Ile Pro Asp Gly Leu Leu Lys Gly Asp Thr Glu Ile Val
            405                 410                 415 tct ttt tcg gcc gca gca cca ggc act tca gtt gat ttg aca ttg ttt      1296
Ser Phe Ser Ala Ala Ala Pro Gly Thr Ser Val Asp Leu Thr Leu Phe
        420                 425                 430 gaa gct ttc aat tcc att gct gca ttt gaa ctg aaa ggc agt aat tca      1344
Glu Ala Phe Asn Ser Ile Ala Ala Phe Glu Leu Lys Gly Ser Asn Ser
    435                 440                 445 cag gat gtg gct gaa tca atc aga caa att cag cag cat gcg aag ctg      1392
Gln Asp Val Ala Glu Ser Ile Arg Gln Ile Gln Gln His Ala Lys Leu
450                 455                 460 acg gca aag tat gtg ctg cca gta                                      1416
Thr Ala Lys Tyr Val Leu Pro Val
465                 470

<210> SEQ ID NO 23
<211> LENGTH: 1416
<212> TYPE: DNA
<213> ORGANISM: Artificial Sequence
<220> FEATURE:
<223> OTHER INFORMATION: Description of Artificial Sequence: Mutant DNA

<400> SEQUENCE: 23 atg gag aga aaa aca gta ttg gtc atc gct gat ctt gga ggc tgc ccg        48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc        96
Pro His Met Phe Tyr Lys Ser Ala Ala Glu Lys Tyr Asn Leu Val Ser
            20                  25                  30
```

```
ttt att cca aga cct ttt gca att aca gcc tcc cat gca gca ttg att    144
Phe Ile Pro Arg Pro Phe Ala Ile Thr Ala Ser His Ala Ala Leu Ile
         35                  40                  45 gaa aaa tac tcg gtc gcg gta ata aaa gat aaa gac tat ttt aag agt    192
Glu Lys Tyr Ser Val Ala Val Ile Lys Asp Lys Asp Tyr Phe Lys Ser
 50                  55                  60 tta gct gat ttt gaa cac cct gat ccc att tat tgg gcg cat gaa gat    240
Leu Ala Asp Phe Glu His Pro Asp Pro Ile Tyr Trp Ala His Glu Asp
 65                  70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                 85                  90                  95 gaa atg ttt ggg gcg gat gcc atc aca aca aac aac gaa tta ttc att    336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc    384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
130                 135                 140 ttt aat aag gcc gga gtc aaa tcg atc aaa aac aaa cga gtc aca act    480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc    528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg    576
Leu Lys Pro Thr Tyr Leu Ala Ser Ser Ile Gly Val Thr Leu Ile Thr
            180                 185                 190 gac act gag acg gca gaa gat gaa ttt aac aga gtc aat gac tat ctg    624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc    672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa    720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag    768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca    816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag    864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa    912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg    960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc   1008
Gly Leu Ile Glu Ser Ala Ala Arg Phe Ala Gly Trp Asn Met Ile Pro
                325                 330                 335 aat att aaa aag gtc ttt ggc ctt gat atg gtg caa tta tta tta gat   1056
Asn Ile Lys Lys Val Phe Gly Leu Asp Met Val Gln Leu Leu Leu Asp
            340                 345                 350
```

```
gtc ctc tgc ttc gga aaa gac gcc gat ctg ccg gac gga tta ttg gat    1104
Val Leu Cys Phe Gly Lys Asp Ala Asp Leu Pro Asp Gly Leu Leu Asp
            355                 360                 365 caa gag cct tat tat gtt gcc gac tgc cgt ttg tac ccg cag cat ttc    1152
Gln Glu Pro Tyr Tyr Val Ala Asp Cys Arg Leu Tyr Pro Gln His Phe
370                 375                 380 aaa caa aat ggc caa att cct gaa act gct gag gat ttg gtc att gaa    1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt    1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt    1296
Ser Phe Ser Ala Ala Ala Pro Gly Thr Ser Val Asp Leu Thr Leu Phe
            420                 425                 430 gaa gct ttc aat tcc att gct gca ttt gaa ctg aaa ggc agt aat tca    1344
Glu Ala Phe Asn Ser Ile Ala Ala Phe Glu Leu Lys Gly Ser Asn Ser
            435                 440                 445 cag gat gtg gtt gaa tca atc aga caa att cag cag cat gcg aag ctg    1392
Gln Asp Val Val Glu Ser Ile Arg Gln Ile Gln Gln His Ala Lys Leu
450                 455                 460 acg gca aag tat gtg ctg cca gta                                    1416
Thr Ala Lys Tyr Val Leu Pro Val
465                 470

<210> SEQ ID NO 24
<211> LENGTH: 1416
<212> TYPE: DNA
<213> ORGANISM: Artificial Sequence
<220> FEATURE:
<223> OTHER INFORMATION: Description of Artificial Sequence: Mutant DNA

<400> SEQUENCE: 24 atg gag aga aaa aca gta ttg gtc atc gct gat ctt gga ggc tgc ccg    48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc    96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att    144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt aag agt    192
Glu Lys Tyr Ser Val Ala Val Ile Lys Asp Lys Asp Tyr Phe Lys Ser
    50                  55                  60 tta gct gat ttt gaa cac cct gat ccc att tat tgg gcg cat gaa gat    240
Leu Ala Asp Phe Glu His Pro Asp Pro Ile Tyr Trp Ala His Glu Asp
65                  70                  75                  80 cat aac aag cct gag gaa gag gtc gtc gag caa atc gtc aag gtt gcc    288
His Asn Lys Pro Glu Glu Glu Val Val Glu Gln Ile Val Lys Val Ala
                85                  90                  95 gaa atg ttt ggg gcg gat gcc atc aca aca aac aac gaa tta ttc att    336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc    384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct    432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act    480
```

-continued

| | | |
|---|---|---|
| Phe Asn Lys Ala Gly Val Lys Ser Ile Lys Asn Lys Arg Val Thr Thr<br>145                                150                            155                            160 | |

```
ctt gaa gat ttc cgt gct gct ctt gaa gag atc ggc aca cct ctt atc      528
Leu Glu Asp Phe Arg Ala Ala Leu Glu Glu Ile Gly Thr Pro Leu Ile
                165                 170                 175 tta aag cct aca tac tta gcg agt tct atc ggt gta acg ctg att acg      576
Leu Lys Pro Thr Tyr Leu Ala Ser Ser Ile Gly Val Thr Leu Ile Thr
        180                 185                 190 gac act gag acg gca gaa gat gaa ttt aac aga gtc aat gac tat ctg      624
Asp Thr Glu Thr Ala Glu Asp Glu Phe Asn Arg Val Asn Asp Tyr Leu
    195                 200                 205 aaa tca att aac gtg cca aag gcg gtt acg ttt gaa gcg ccg ttt atc      672
Lys Ser Ile Asn Val Pro Lys Ala Val Thr Phe Glu Ala Pro Phe Ile
210                 215                 220 gct gaa gaa ttt tta cag ggt gag tac gga gac tgg tat caa aca gaa      720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag      768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca      816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa      912
Lys Ile Val Glu Ala Ala Lys Lys Ala Asn Glu Gly Leu Gly Leu Gln
    290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc     1008
Gly Leu Ile Glu Ser Ala Ala Arg Phe Ala Gly Trp Asn Met Ile Pro
                325                 330                 335 aat att aaa aag gtc ttt ggc ctt gat atg gtg caa tta tta tta gat     1056
Asn Ile Lys Lys Val Phe Gly Leu Asp Met Val Gln Leu Leu Leu Asp
            340                 345                 350 gtc ctc tgc ttc gga aaa gac gcc gat ctg ccg gac gga tta ttg gat     1104
Val Leu Cys Phe Gly Lys Asp Ala Asp Leu Pro Asp Gly Leu Leu Asp
        355                 360                 365 caa gag cct tat tat gtt gcc gac tgc cgt ttg tac ccg cag cat ttc     1152
Gln Glu Pro Tyr Tyr Val Ala Asp Cys Arg Leu Tyr Pro Gln His Phe
    370                 375                 380 aaa caa aat ggc caa att cct gaa act gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
            420                 425                 430 gaa gct ttc aat ccc att gct gca ttt gaa ctg aaa ggc agt aat tca     1344
Glu Ala Phe Asn Pro Ile Ala Ala Phe Glu Leu Lys Gly Ser Asn Ser
        435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
    450                 455                 460 acg gca aag tat gtg ctg cca gta                                     1416
```

-continued

```
Thr Ala Lys Tyr Val Leu Pro Val
465                 470

<210> SEQ ID NO 25
<211> LENGTH: 1416
<212> TYPE: DNA
<213> ORGANISM: Artificial Sequence
<220> FEATURE:
<223> OTHER INFORMATION: Description of Artificial Sequence: Mutant DNA

<400> SEQUENCE: 25 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
    50                  55                  60 tta gct gat ttt gaa cac cct gat ccc att tat tgg gcg cat gaa gat     240
Leu Ala Asp Phe Glu His Pro Asp Pro Ile Tyr Trp Ala His Glu Asp
65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                85                  90                  95 gaa atg ttt ggg gcg gat gcc atc aca aca aac aac gaa tta ttc att     336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc     384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct     432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act     480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc     528
Leu Glu Asp Phe Arg Ala Ala Leu Glu Glu Ile Gly Thr Pro Leu Ile
                165                 170                 175 tta aag cct gca tac tta gcg agt tct atc ggt gta acg ctg att acg     576
Leu Lys Pro Ala Tyr Leu Ala Ser Ser Ile Gly Val Thr Leu Ile Thr
            180                 185                 190 gac act gag acg gca gaa gat gaa ttt aac aga gtc aat gac tat ctg     624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc     672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa     720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag     768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca     816
Tyr Phe Pro Ile Ala Ile His Asp Lys Thr Pro Gln Ile Gly Phe Thr
            260                 265                 270
```

```
gag aca tcc cac att acg ccg tcc att ctg gat gaa gag gca aaa aag      864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa      912
Lys Ile Val Glu Ala Ala Lys Lys Ala Asn Glu Gly Leu Gly Leu Gln
290                 295                 300 aat tgc gca aca cat aca gag atc aag cta atg aaa aac aga gaa ccg      960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc     1008
Gly Leu Ile Glu Ser Ala Ala Arg Phe Ala Gly Trp Asn Met Ile Pro
            325                 330                 335 aat att aaa aag gtc ttt ggc ctt gat atg gtg caa tta tta tta gat     1056
Asn Ile Lys Lys Val Phe Gly Leu Asp Met Val Gln Leu Leu Leu Asp
        340                 345                 350 gtc ctc tgc ttc gga aaa gac gcc gat ctg ccg gac gga tta ttg gat     1104
Val Leu Cys Phe Gly Lys Asp Ala Asp Leu Pro Asp Gly Leu Leu Asp
    355                 360                 365 caa gag cct tat tat gtt gcc gac tgc cgt ttg tac ccg cag cat ttc     1152
Gln Glu Pro Tyr Tyr Val Ala Asp Cys Arg Leu Tyr Pro Gln His Phe
370                 375                 380 aaa caa aat ggc caa att cct gaa act gct gag gat ttg gtc att gaa     1200
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt     1248
Ala Ile Asp Ile Pro Asp Gly Leu Leu Lys Gly Asp Thr Glu Ile Val
            405                 410                 415 tct ttt tcg gcc gca gca cca ggc act tca gtt gat ttg aca ttg ttt     1296
Ser Phe Ser Ala Ala Ala Pro Gly Thr Ser Val Asp Leu Thr Leu Phe
        420                 425                 430 gaa gct ttc aat tcc att gct gca ttt gaa ctg aaa ggc agt aat tca     1344
Glu Ala Phe Asn Ser Ile Ala Ala Phe Glu Leu Lys Gly Ser Asn Ser
    435                 440                 445 cag gat gtg gct gaa tca atc aga caa att cag cag cat gcg aag ctg     1392
Gln Asp Val Ala Glu Ser Ile Arg Gln Ile Gln Gln His Ala Lys Leu
450                 455                 460 acg gca aag tat gtg ctg cca gta                                     1416
Thr Ala Lys Tyr Val Leu Pro Val
465                 470

<210> SEQ ID NO 26
<211> LENGTH: 1416
<212> TYPE: DNA
<213> ORGANISM: Artificial Sequence
<220> FEATURE:
<223> OTHER INFORMATION: Description of Artificial Sequence: Mutant DNA

<400> SEQUENCE: 26 atg gag aga aaa aca gta ttg gtc atc gct gat ctt gga ggc tgc ccg      48
Met Glu Arg Lys Thr Val Leu Val Ile Ala Asp Leu Gly Gly Cys Pro
1               5                   10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
            20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
        35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
    50                  55                  60 tta gct gat ttt gaa cac cct gat ccc att tat tgg gcg cat gaa gat     240
```

```
Leu Ala Asp Phe Glu His Pro Asp Pro Ile Tyr Trp Ala His Glu Asp
 65                  70                  75                  80 cat aac aag cct gag gaa gag gtc gtc gag caa atc gtc aag gtt gcc        288
His Asn Lys Pro Glu Glu Glu Val Val Glu Gln Ile Val Lys Val Ala
                 85                  90                  95 gaa atg ttt ggg gcg gat gcc atc aca aca aac aac gaa tta ttc att        336
Glu Met Phe Gly Ala Asp Ala Ile Thr Thr Asn Asn Glu Leu Phe Ile
            100                 105                 110 gct ccg atg gcg aaa gcc tgt gaa cgt ctg ggc ttg aga ggt gcc ggc        384
Ala Pro Met Ala Lys Ala Cys Glu Arg Leu Gly Leu Arg Gly Ala Gly
        115                 120                 125 gtg cag gca gcc gaa aat gcc aga gat aaa aat aaa atg agg gac gct        432
Val Gln Ala Ala Glu Asn Ala Arg Asp Lys Asn Lys Met Arg Asp Ala
    130                 135                 140 ttt aat aag gcc gga gtc aaa tcg atc aaa aac aaa cga gtc aca act        480
Phe Asn Lys Ala Gly Val Lys Ser Ile Lys Asn Lys Arg Val Thr Thr
145                 150                 155                 160 ctt gaa gat ttc cgt gct gct ctt gaa gag atc ggc aca cct ctt atc        528
Leu Glu Asp Phe Arg Ala Ala Leu Glu Glu Ile Gly Thr Pro Leu Ile
                165                 170                 175 tta aag cct gca tac tta gcg agt tct atc ggt gta acg ctg att acg        576
Leu Lys Pro Ala Tyr Leu Ala Ser Ser Ile Gly Val Thr Leu Ile Thr
            180                 185                 190 gac act gag acg gca gaa gat gaa ttt aac aga gtc aat gac tat ctg        624
Asp Thr Glu Thr Ala Glu Asp Glu Phe Asn Arg Val Asn Asp Tyr Leu
        195                 200                 205 aaa tca att aac gtg cca aag gcg gtt acg ttt gaa gcg ccg ttt atc        672
Lys Ser Ile Asn Val Pro Lys Ala Val Thr Phe Glu Ala Pro Phe Ile
    210                 215                 220 gct gaa gaa ttt tta cag ggt gag tac gga gac tgg tat caa aca gaa        720
Ala Glu Glu Phe Leu Gln Gly Glu Tyr Gly Asp Trp Tyr Gln Thr Glu
225                 230                 235                 240 ggg tac tcc gac tat atc agt ata gaa ggc atc atg gct gac ggt gag        768
Gly Tyr Ser Asp Tyr Ile Ser Ile Glu Gly Ile Met Ala Asp Gly Glu
                245                 250                 255 tat ttc ccg atc gcc att cat gat aaa acg ccg caa atc ggg ttt aca        816
Tyr Phe Pro Ile Ala Ile His Asp Lys Thr Pro Gln Ile Gly Phe Thr
            260                 265                 270 gag aca tcc cac att acg ccg tcc att ctg gat gaa gag gca aaa aag        864
Glu Thr Ser His Ile Thr Pro Ser Ile Leu Asp Glu Glu Ala Lys Lys
        275                 280                 285 aaa att gtc gaa gct gcc aaa aag gca aat gaa ggg ctt gga ctg caa        912
Lys Ile Val Glu Ala Ala Lys Lys Ala Asn Glu Gly Leu Gly Leu Gln
    290                 295                 300 aat tgc gca aca cat aca gag atc aag cta atg aaa aac aga gaa ccg        960
Asn Cys Ala Thr His Thr Glu Ile Lys Leu Met Lys Asn Arg Glu Pro
305                 310                 315                 320 ggt tta ata gag tcg gca gcc aga ttt gcc ggc tgg aat atg atc ccc       1008
Gly Leu Ile Glu Ser Ala Ala Arg Phe Ala Gly Trp Asn Met Ile Pro
                325                 330                 335 aat att aaa aag gtc ttt ggc ctt gat atg gtg caa tta tta tta gat       1056
Asn Ile Lys Lys Val Phe Gly Leu Asp Met Val Gln Leu Leu Leu Asp
            340                 345                 350 gtc ctc tgc ttc gga aaa gac gcc gat ctg ccg gac gga tta ttg gat       1104
Val Leu Cys Phe Gly Lys Asp Ala Asp Leu Pro Asp Gly Leu Leu Asp
        355                 360                 365 caa gag cct tat tat gtt gcc gac tgc cgt ttg tac ccg cag cat ttc       1152
Gln Glu Pro Tyr Tyr Val Ala Asp Cys Arg Leu Tyr Pro Gln His Phe
    370                 375                 380 aaa caa aat ggc caa att cct gaa act gct gag gat ttg gtc att gaa       1200
```

```
Lys Gln Asn Gly Gln Ile Pro Glu Thr Ala Glu Asp Leu Val Ile Glu
385                 390                 395                 400 gcg atc gat att ccg gac ggg ctt tta aaa ggg gat act gaa atc gtt    1248
Ala Ile Asp Ile Pro Asp Gly Leu Leu Lys Gly Asp Thr Glu Ile Val
                405                 410                 415 tct ttt tcg gcc gca gca cca ggc act tca gtt gat ttg aca ttg ttt    1296
Ser Phe Ser Ala Ala Ala Pro Gly Thr Ser Val Asp Leu Thr Leu Phe
                420                 425                 430 gaa gct ttc aat tcc att gct gca ttt gaa ctg aaa ggc agt att tca    1344
Glu Ala Phe Asn Ser Ile Ala Ala Phe Glu Leu Lys Gly Ser Ile Ser
                435                 440                 445 cag gat gtg gct gaa tca atc aga caa att cag cag cat gcg aag ctg    1392
Gln Asp Val Ala Glu Ser Ile Arg Gln Ile Gln Gln His Ala Lys Leu
        450                 455                 460 acg gca aag tat gtg ctg cca gta                                    1416
Thr Ala Lys Tyr Val Leu Pro Val
465                 470

<210> SEQ ID NO 27
<211> LENGTH: 93
<212> TYPE: PRT
<213> ORGANISM: Bacillus subtilis 168

<400> SEQUENCE: 27

Gly Ala Gly Val Gln Ala Ala Glu Asn Ala Arg Asp Lys Asn Lys Met
1               5                   10                  15

Arg Asp Ala Phe Asn Lys Ala Gly Val Lys Ser Ile Lys Asn Lys Arg
            20                  25                  30

Val Thr Thr Leu Glu Asp Phe Arg Ala Ala Leu Glu Glu Ile Gly Thr
        35                  40                  45

Pro Leu Ile Leu Lys Pro Thr Tyr Leu Ala Ser Ser Ile Gly Val Thr
    50                  55                  60

Leu Ile Thr Asp Thr Glu Thr Ala Glu Asp Glu Phe Asn Arg Val Asn
65                  70                  75                  80

Asp Tyr Leu Lys Ser Ile Asn Val Pro Lys Ala Val Thr
                85                  90

<210> SEQ ID NO 28
<211> LENGTH: 279
<212> TYPE: DNA
<213> ORGANISM: Bacillus subtilis 168

<400> SEQUENCE: 28 ggt gcc ggc gtg cag gca gcc gaa aat gcc aga gat aaa aat aaa atg    48
Gly Ala Gly Val Gln Ala Ala Glu Asn Ala Arg Asp Lys Asn Lys Met
1               5                   10                  15 agg gac gct ttt aat aag gcc gga gtc aaa tcg atc aaa aac aaa cga    96
Arg Asp Ala Phe Asn Lys Ala Gly Val Lys Ser Ile Lys Asn Lys Arg
            20                  25                  30 gtc aca act ctt gaa gat ttc cgt gct gct ctt gaa gag atc ggc aca    144
Val Thr Thr Leu Glu Asp Phe Arg Ala Ala Leu Glu Glu Ile Gly Thr
        35                  40                  45 cct ctt atc tta aag cct aca tac tta gcg agt tct atc ggt gta acg    192
Pro Leu Ile Leu Lys Pro Thr Tyr Leu Ala Ser Ser Ile Gly Val Thr
    50                  55                  60 ctg att acg gac act gag acg gca gaa gat gaa ttt aac aga gtc aat    240
Leu Ile Thr Asp Thr Glu Thr Ala Glu Asp Glu Phe Asn Arg Val Asn
65                  70                  75                  80 gac tat ctg aaa tca att aac gtg cca aag gcg gtt acg                279
Asp Tyr Leu Lys Ser Ile Asn Val Pro Lys Ala Val Thr
                85                  90
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
attctcgagt agagaaggag tgttttacat                                       30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
ttaggatcct catactggca gcacatactt                                       30

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
caagaattct catgtttgac agct                                             24

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
taactcgaga ttccctttt acgtgaac                                          28

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
ttaaccatgg agagaaaaac agtattg                                          27

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
atatggatcc tactggcagc acatactttg                                       30

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
caccgcagac ggaggataca c                                              21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
cggacgtcac ccaataatcg tg                                             22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
ccgatggcra aagcstgtra acg                                            23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
cggcagatcr gcdtcttttc c                                              21

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
gctaggtctt gaacattgtg caaccc                                         26

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
ggtgttccga tagactcaat ggc                                            23

<210> SEQ ID NO 41
<211> LENGTH: 44

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
catgccatgg agaaaaaaac tgtacttgtc attgctgact tagg                       44

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
cgcggatccc ttcactaatt catccattaa ctgaatcg                              38

<210> SEQ ID NO 43
<211> LENGTH: 12
<212> TYPE: PRT
<213> ORGANISM: Artificial Sequence
<220> FEATURE:
<221> NAME/KEY: UNSURE
<222> LOCATION: (3)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (4)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (9)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (10)
<223> OTHER INFORMATION: Xaa represents any amino acid selected from
      Leu, Ile, Val, Met and Ala
<220> FEATURE:
<221> NAME/KEY: UNSURE
<222> LOCATION: (11)
<223> OTHER INFORMATION: Xaa represents Glu, Ser or Ala
<220> FEATURE:
<221> NAME/KEY: UNSURE
<222> LOCATION: (12)
<223> OTHER INFORMATION: Xaa represents Gly, Ser or Ala
<220> FEATURE:
<223> OTHER INFORMATION: Description of Artificial Sequence: Amino
      acid sequence used for data base search

<400> SEQUENCE: 43

His Gly Xaa Xaa Gly Gln Asp Gly Xaa Xaa Xaa Xaa
                5                   10

<210> SEQ ID NO 44
<211> LENGTH: 28
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa represents Leu Ile or Val
<220> FEATURE:
<221> NAME/KEY: UNSURE
<222> LOCATION: (2)
```

```
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (3)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (4)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (5)
<223> OTHER INFORMATION: Xaa represents Gly or Ala
<220> FEATURE:
<221> NAME/KEY: UNSURE
<222> LOCATION: (6)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (7)
<223> OTHER INFORMATION: Xaa represents any amino acid selected from
     Gly, Ser, Ala, Ile and Val
<220> FEATURE:
<221> NAME/KEY: UNSURE
<222> LOCATION: (9)
<223> OTHER INFORMATION: Xaa represents any amino acid selected from
     Leu, Ile, Val, Met, Cys and Ala
<220> FEATURE:
<221> NAME/KEY: UNSURE
<222> LOCATION: (11)
<223> OTHER INFORMATION: Xaa represents any amino acid selected from
     Leu, Ile, Val, Met, Phe and Ala
<220> FEATURE:
<221> NAME/KEY: UNSURE
<222> LOCATION: (12)
<223> OTHER INFORMATION: Xaa represents any amino acid selected from
     Leu, Ile, Val, Met, Phe and Ala
<220> FEATURE:
<221> NAME/KEY: UNSURE
<222> LOCATION: (13)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (14)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (15)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (16)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (17)
<223> OTHER INFORMATION: Xaa represents any amino acid selected from
     Ala, Arg, Asn, Asp, Cys, Glu, Gln, Gly, His, Ile, Leu, Ly
     s, Met, Phe, Pro, Ser, Thr, Trp, Tyr and Val
<220> FEATURE:
<221> NAME/KEY: UNSURE
<222> LOCATION: (18)
<223> OTHER INFORMATION: Xaa represents any amino acid selected from
     Ala, Arg, Asn, Asp, Cys, Glu, Gln, Gly, His, Ile, Leu, Ly
```

-continued

```
      s, Met, Phe, Pro, Ser, Thr, Trp, Tyr and Val
<220> FEATURE:
<221> NAME/KEY: UNSURE
<222> LOCATION: (19)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (20)
<223> OTHER INFORMATION: Xaa represents Leu, Ile or Val
<220> FEATURE:
<221> NAME/KEY: UNSURE
<222> LOCATION: (21)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (23)
<223> OTHER INFORMATION: Xaa represents any amino acid selected from
      Leu, Ile, Val, Ala and Pro
<220> FEATURE:
<221> NAME/KEY: UNSURE
<222> LOCATION: (25)
<223> OTHER INFORMATION: Xaa represents Ser, Thr or Pro
<220> FEATURE:
<221> NAME/KEY: UNSURE
<222> LOCATION: (26)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (28)
<223> OTHER INFORMATION: Xaa represents Gly or Ala
<220> FEATURE:
<223> OTHER INFORMATION: Description of Artificial Sequence: Amino
      acid sequence used for data base search

<400> SEQUENCE: 44

Xaa Xaa Xaa Xaa Xaa Xaa Xaa Arg Xaa Asp Xaa Xaa Xaa Xaa Xaa Xaa
                 5                  10                  15

Xaa Xaa Xaa Xaa Xaa Gln Xaa Asn Xaa Xaa Pro Xaa
             20                  25

<210> SEQ ID NO 45
<211> LENGTH: 30
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa represents Leu Ile or Val
<220> FEATURE:
<221> NAME/KEY: UNSURE
<222> LOCATION: (2)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (3)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (4)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (5)
<223> OTHER INFORMATION: Xaa represents Gly or Ala
<220> FEATURE:
```

```
<221> NAME/KEY: UNSURE
<222> LOCATION: (6)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (7)
<223> OTHER INFORMATION: Xaa represents any amino acid selected from
      Gly, Ser, Ala, Ile and Val
<220> FEATURE:
<221> NAME/KEY: UNSURE
<222> LOCATION: (9)
<223> OTHER INFORMATION: Xaa represents any amino acid selected from
      Leu, Ile, Val, Met, Cys and Ala
<220> FEATURE:
<221> NAME/KEY: UNSURE
<222> LOCATION: (11)
<223> OTHER INFORMATION: Xaa represents any amino acid selected from
      Leu, Ile, Val, Met, Phe and Ala
<220> FEATURE:
<221> NAME/KEY: UNSURE
<222> LOCATION: (12)
<223> OTHER INFORMATION: Xaa represents any amino acid selected from
      Leu, Ile, Val, Met, Phe and Ala
<220> FEATURE:
<221> NAME/KEY: UNSURE
<222> LOCATION: (13)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (14)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (15)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (16)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (17)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (18)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (19)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (20)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (21)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
```

```
<221> NAME/KEY: UNSURE
<222> LOCATION: (22)
<223> OTHER INFORMATION: Xaa represents Leu, Ile or Val
<220> FEATURE:
<221> NAME/KEY: UNSURE
<222> LOCATION: (23)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (25)
<223> OTHER INFORMATION: Xaa represents any amino acid selected from
      Leu, Ile, Val, Ala and Pro
<220> FEATURE:
<221> NAME/KEY: UNSURE
<222> LOCATION: (27)
<223> OTHER INFORMATION: Xaa represents Ser, Thr or Pro
<220> FEATURE:
<221> NAME/KEY: UNSURE
<222> LOCATION: (28)
<223> OTHER INFORMATION: Xaa represents any amino acid selected from
      Ala, Arg, Asn, Asp, Cys, Glu, Gln, Gly, His, Ile, Leu, Ly
      s, Met, Phe, Pro, Ser, Thr, Trp, Tyr and Val
<220> FEATURE:
<221> NAME/KEY: UNSURE
<222> LOCATION: (30)
<223> OTHER INFORMATION: Xaa represents Gly or Ala
<220> FEATURE:
<223> OTHER INFORMATION: Description of Artificial Sequence: Amino
      acid sequence used for data base search

<400> SEQUENCE: 45

Xaa Xaa Xaa Xaa Xaa Xaa Xaa Arg Xaa Asp Xaa Xaa Xaa Xaa Xaa
                 5                  10                  15

Xaa Xaa Xaa Xaa Xaa Xaa Xaa Gln Xaa Asn Xaa Xaa Pro Xaa
             20                  25                  30

<210> SEQ ID NO 46
<211> LENGTH: 1416
<212> TYPE: DNA
<213> ORGANISM: Bacillus subtilis ATCC 15245 and Bacillus subtilis
      IAM 1033

<400> SEQUENCE: 46 atg gag aga aaa aca gta ttg gtc atc gct gat ctt gga ggc tgc ccg      48
Met Glu Arg Lys Thr Val Leu Val Ile Ala Asp Leu Gly Gly Cys Pro
 1               5                  10                  15 ccg cac atg ttt tat aaa agc gct gct gaa aaa tat aac ctg gtc agc      96
Pro His Met Phe Tyr Lys Ser Ala Ala Glu Lys Tyr Asn Leu Val Ser
                 20                  25                  30 ttt att cca aga cct ttt gca att aca gcc tcc cat gca gca ttg att     144
Phe Ile Pro Arg Pro Phe Ala Ile Thr Ala Ser His Ala Ala Leu Ile
             35                  40                  45 gaa aaa tac tcg gtc gcg gtc ata aaa gat aaa gac tat ttt aag agt     192
Glu Lys Tyr Ser Val Ala Val Ile Lys Asp Lys Asp Tyr Phe Lys Ser
 50                  55                  60 tta gct gat ttt gag cat cct gat tcc att tat tgg gcg cat gag gat     240
Leu Ala Asp Phe Glu His Pro Asp Ser Ile Tyr Trp Ala His Glu Asp
 65                  70                  75                  80 cat aac aag cct gag gaa gag gtc gtc gag caa atc gtc aag gtt gcc     288
His Asn Lys Pro Glu Glu Glu Val Val Glu Gln Ile Val Lys Val Ala
                 85                  90                  95 gaa atg ttt ggg gcg gat gcc atc aca aca aac aat gaa tta ttc att     336
Glu Met Phe Gly Ala Asp Ala Ile Thr Thr Asn Asn Glu Leu Phe Ile
                100                 105                 110 gct ccg atg gcg aaa gcc tgt gaa cgt ctg ggc ctg aga ggt gcc ggc     384
Ala Pro Met Ala Lys Ala Cys Glu Arg Leu Gly Leu Arg Gly Ala Gly
            115                 120                 125
```

| | | |
|---|---|---|
| gtg cag gca gcc gaa aat gcc aga gat aaa aat aaa atg agg gac gct<br>Val Gln Ala Ala Glu Asn Ala Arg Asp Lys Asn Lys Met Arg Asp Ala<br>130                               135                           140 | 432 |
| ttt aat aag gcc gga gtc aaa tcg atc aaa aac aaa cga gtc aca act<br>Phe Asn Lys Ala Gly Val Lys Ser Ile Lys Asn Lys Arg Val Thr Thr<br>145                              150                          155                        160 | 480 |
| ctt gaa gat ttc cgt gct gct ctt gaa gag atc ggc aca cct ctt atc<br>Leu Glu Asp Phe Arg Ala Ala Leu Glu Glu Ile Gly Thr Pro Leu Ile<br>                  165                           170                          175 | 528 |
| tta aag cct aca tac tta gcg agt tca atc ggt gta acg ctg att acg<br>Leu Lys Pro Thr Tyr Leu Ala Ser Ser Ile Gly Val Thr Leu Ile Thr<br>                180                           185                          190 | 576 |
| gac act gag acg gca gaa gat gaa ttt aac aga gtc aat gac tat ctg<br>Asp Thr Glu Thr Ala Glu Asp Glu Phe Asn Arg Val Asn Asp Tyr Leu<br>     195                           200                          205 | 624 |
| aaa tca att aac gtg cca aag gcg gtt acg ttt gaa gcg ccg ttt atc<br>Lys Ser Ile Asn Val Pro Lys Ala Val Thr Phe Glu Ala Pro Phe Ile<br>210                               215                          220 | 672 |
| gct gaa gaa ttt tta cag ggt gag tac gga gac tgg tat caa aca gaa<br>Ala Glu Glu Phe Leu Gln Gly Glu Tyr Gly Asp Trp Tyr Gln Thr Glu<br>225                               230                          235                        240 | 720 |
| ggg tac tcc gac tat atc agt ata gaa ggc atc atg gct gac ggt gag<br>Gly Tyr Ser Asp Tyr Ile Ser Ile Glu Gly Ile Met Ala Asp Gly Glu<br>                  245                           250                          255 | 768 |
| tat ttc ccg atc gcc att cat gat aaa acg ccg caa atc ggg ttt aca<br>Tyr Phe Pro Ile Ala Ile His Asp Lys Thr Pro Gln Ile Gly Phe Thr<br>                260                           265                          270 | 816 |
| gag aca tcc cac att acg ccg tcc att ctg gat gaa gag gca aaa aag<br>Glu Thr Ser His Ile Thr Pro Ser Ile Leu Asp Glu Glu Ala Lys Lys<br>     275                           280                          285 | 864 |
| aaa att gtc gaa gct gcc aaa aag gca aat gaa ggg ctt ggc ctg caa<br>Lys Ile Val Glu Ala Ala Lys Lys Ala Asn Glu Gly Leu Gly Leu Gln<br>290                               295                          300 | 912 |
| aat tgc gca aca cat aca gag atc aag cta atg aaa aac aga gaa ccg<br>Asn Cys Ala Thr His Thr Glu Ile Lys Leu Met Lys Asn Arg Glu Pro<br>305                               310                          315                        320 | 960 |
| ggt tta ata gag tcg gca gcc aga ttc gca ggc tgg aat atg att cct<br>Gly Leu Ile Glu Ser Ala Ala Arg Phe Ala Gly Trp Asn Met Ile Pro<br>                  325                           330                          335 | 1008 |
| aat att aaa aag gtc ttt ggc ctt gat atg gcg caa tta tta tta gat<br>Asn Ile Lys Lys Val Phe Gly Leu Asp Met Ala Gln Leu Leu Leu Asp<br>                340                           345                          350 | 1056 |
| gtc ctc tgt ttc gga aaa gac gcc gat ctg ccg gac gga tta ttg gat<br>Val Leu Cys Phe Gly Lys Asp Ala Asp Leu Pro Asp Gly Leu Leu Asp<br>                  355                           360                          365 | 1104 |
| caa gag cct tat tat gtt gcc gac tgc cat ttg tac ccg cag cat ttc<br>Gln Glu Pro Tyr Tyr Val Ala Asp Cys His Leu Tyr Pro Gln His Phe<br>370                               375                          380 | 1152 |
| aaa caa aat ggc cag att cca gaa acc gct gag gat ttg gtc att gaa<br>Lys Gln Asn Gly Gln Ile Pro Glu Thr Ala Glu Asp Leu Val Ile Glu<br>385                               390                          395                        400 | 1200 |
| gcg atc gat att ccg gac ggg ctt tta aaa ggg gat act gaa atc gtt<br>Ala Ile Asp Ile Pro Asp Gly Leu Leu Lys Gly Asp Thr Glu Ile Val<br>                           405                           410                          415 | 1248 |
| tca ttt tca gcc gca gca cca ggc act tca gtt gat ttg aca ttg ttt<br>Ser Phe Ser Ala Ala Ala Pro Gly Thr Ser Val Asp Leu Thr Leu Phe<br>                      420                           425                          430 | 1296 |
| gaa gct ttc aat tcc att gct gca ttt gaa ctg aaa ggc agt aat tca<br>Glu Ala Phe Asn Ser Ile Ala Ala Phe Glu Leu Lys Gly Ser Asn Ser<br>                435                           440                          445 | 1344 |

-continued

```
cag gat gtg gct gaa tca atc aga caa att cag cag cat gca aag ctg      1392
Gln Asp Val Ala Glu Ser Ile Arg Gln Ile Gln Gln His Ala Lys Leu
    450                 455                 460 acg gca aag tat gtg ctg cca gta                                      1416
Thr Ala Lys Tyr Val Leu Pro Val
465                 470
```

<210> SEQ ID NO 47
<211> LENGTH: 239
<212> TYPE: PRT
<213> ORGANISM: Streptomyces noursei IFO15452

<400> SEQUENCE: 47

Met Leu Ala Gly Leu Val Pro Ala Pro Asp His Gly Met Arg Glu Glu
 1               5                  10                  15

Ile Leu Gly Asp Arg Ser Arg Leu Ile Arg Gln Arg Gly Glu His Ala
                20                  25                  30

Leu Ile Gly Ile Ser Ala Gly Asn Ser Tyr Phe Ser Gln Lys Asn Thr
            35                  40                  45

Val Met Leu Leu Gln Trp Ala Gly Gln Arg Phe Glu Arg Thr Asp Val
        50                  55                  60

Val Tyr Val Asp Thr His Ile Asp Glu Met Leu Ile Ala Asp Gly Arg
    65                  70                  75                  80

Ser Ala Gln Glu Ala Glu Arg Ser Val Lys Arg Thr Leu Lys Asp Leu
                85                  90                  95

Arg Arg Arg Leu Arg Arg Ser Leu Glu Ser Val Gly Asp His Ala Glu
            100                 105                 110

Arg Phe Arg Val Arg Ser Leu Ser Glu Leu Gln Glu Thr Pro Glu Tyr
        115                 120                 125

Arg Ala Val Arg Glu Arg Thr Asp Arg Ala Phe Glu Glu Asp Ala Glu
    130                 135                 140

Phe Ala Thr Ala Cys Glu Asp Met Val Arg Ala Val Val Met Asn Arg
145                 150                 155                 160

Pro Gly Asp Gly Val Gly Ile Ser Ala Glu His Leu Arg Ala Gly Leu
                165                 170                 175

Asn Tyr Val Leu Ala Glu Ala Pro Leu Phe Ala Asp Ser Pro Gly Val
            180                 185                 190

Phe Ser Val Pro Ser Ser Val Leu Cys Tyr His Ile Asp Thr Pro Ile
        195                 200                 205

Thr Ala Phe Leu Ser Arg Arg Glu Thr Gly Phe Arg Ala Ala Glu Gly
    210                 215                 220

Gln Ala Tyr Val Val Val Arg Pro Gln Glu Leu Ala Asp Ala Ala
225                 230                 235

<210> SEQ ID NO 48
<211> LENGTH: 239
<212> TYPE: PRT
<213> ORGANISM: Streptomyces alborus IFO15452

<400> SEQUENCE: 48

Met Leu Ala Gly Leu Val Pro Ala Leu Asp His Ser Met Arg Glu Glu
 1               5                  10                  15

Ile Leu Gly Asn Arg Gly Arg Lys Ile Arg Gln Arg Gly Glu His Ala
                20                  25                  30

Leu Ile Gly Ile Ser Ala Gly Asn Ser Tyr Phe Ser Gln Lys Asn Val
            35                  40                  45

Thr Met Leu Leu Gln Trp Ala Gly Gln His Phe Glu Arg Thr Asp Val

```
                50                  55                  60
Val Tyr Val Asp Thr His Ile Asp Asp Met Leu Met Ala Asp Gly Arg
 65                  70                  75                  80

Ser Ala Gln Glu Ala Glu Lys Ser Val Lys Arg Thr Leu Lys Asp Leu
                 85                  90                  95

Arg Arg Arg Leu Arg Arg Ser Leu Glu Ser Val Gly Asp His Ser Glu
            100                 105                 110

Arg Phe Arg Val Arg Ser Leu Ser Glu Ile Gln Glu Thr Pro Glu Tyr
        115                 120                 125

Arg Ala Ala Arg Glu Ser Thr Asp Arg Ala Phe Arg Glu Asp Gly Glu
    130                 135                 140

Phe Ala Thr Val Cys Glu Glu Met Val Arg Ala Val Val Met Asn Arg
145                 150                 155                 160

Pro Gly Asp Gly Val Asp Ile Ser Glu Glu His Leu Arg Ala Gly Leu
                165                 170                 175

Asn Tyr Val Leu Ala Glu Ala Pro Leu Phe Ala Asp Ser Pro Gly Val
            180                 185                 190

Phe Ser Val Pro Ser Ser Val Leu Cys Tyr His Ile Pro Thr Pro Val
        195                 200                 205

Ser Thr Phe Leu Ala His Arg Glu Thr Gly Phe Gln Ala Ala Gln Gly
    210                 215                 220

Gln Ala Tyr Val Val Arg Pro Gln Glu Leu Ala Asp Ala Ala
225                 230                 235

<210> SEQ ID NO 49
<211> LENGTH: 717
<212> TYPE: DNA
<213> ORGANISM: Streptomyces noursei IFO15452

<400> SEQUENCE: 49 atg ctt gca ggc tta gtt ccc gcg ccg gac cac gga atg cgg gaa gaa    48
Met Leu Ala Gly Leu Val Pro Ala Pro Asp His Gly Met Arg Glu Glu
 1               5                  10                  15 ata ctt ggc gac cgc agc cga ttg atc cgg caa cgc ggt gag cac gcc    96
Ile Leu Gly Asp Arg Ser Arg Leu Ile Arg Gln Arg Gly Glu His Ala
             20                  25                  30 ctc atc gga atc agt gcg ggc aac agt tat ttc agc cag aag aac acc   144
Leu Ile Gly Ile Ser Ala Gly Asn Ser Tyr Phe Ser Gln Lys Asn Thr
         35                  40                  45 gtc atg ctg ctg caa tgg gcc ggg cag cgt ttc gag cgc acc gat gtc   192
Val Met Leu Leu Gln Trp Ala Gly Gln Arg Phe Glu Arg Thr Asp Val
     50                  55                  60 gtc tat gtc gac acc cac atc gac gag atg ctg atc gcc gac ggc cgc   240
Val Tyr Val Asp Thr His Ile Asp Glu Met Leu Ile Ala Asp Gly Arg
 65                  70                  75                  80 agc gcg cag gag gcc gag cgg tcg gtc aaa cgc acg ctc aag gat ctg   288
Ser Ala Gln Glu Ala Glu Arg Ser Val Lys Arg Thr Leu Lys Asp Leu
                 85                  90                  95 cgg cgc aga ctc cgg cgc tcg ctg gag agc gtg ggc gac cac gcc gag   336
Arg Arg Arg Leu Arg Arg Ser Leu Glu Ser Val Gly Asp His Ala Glu
            100                 105                 110 cgg ttc cgt gtc cgg tcc ctg tcc gag ctc cag gag acc cct gag tac   384
Arg Phe Arg Val Arg Ser Leu Ser Glu Leu Gln Glu Thr Pro Glu Tyr
        115                 120                 125 cgg gcc gta cgc gag cgc acc gac cgg gcc ttc gag gag gac gcc gaa   432
Arg Ala Val Arg Glu Arg Thr Asp Arg Ala Phe Glu Glu Asp Ala Glu
    130                 135                 140 ttc gcc acc gcc tgc gag gac atg gtg cgg gcc gtg gtg atg aac cgg   480
```

```
                  Phe Ala Thr Ala Cys Glu Asp Met Val Arg Ala Val Val Met Asn Arg
                  145                 150                 155                 160 ccc ggt gac ggc gtc ggc atc tcc gcg gaa cac ctg cgg gcc ggt ctg        528
Pro Gly Asp Gly Val Gly Ile Ser Ala Glu His Leu Arg Ala Gly Leu
                165                 170                 175 aac tac gtg ctg gcc gag gcc ccg ctc ttc gcg gac tcg ccc gga gtc        576
Asn Tyr Val Leu Ala Glu Ala Pro Leu Phe Ala Asp Ser Pro Gly Val
            180                 185                 190 ttc tcc gtc ccc tcc tcg gtg ctc tgc tac cac atc gac acc ccg atc        624
Phe Ser Val Pro Ser Ser Val Leu Cys Tyr His Ile Asp Thr Pro Ile
        195                 200                 205 acg gcg ttc ctg tcc cgg cgc gag acc ggt ttc cgg gcg gcc gag gga        672
Thr Ala Phe Leu Ser Arg Arg Glu Thr Gly Phe Arg Ala Ala Glu Gly
    210                 215                 220 cag gcg tac gtc gtc gtc agg ccc cag gag ctg gcc gac gcg gcc            717
Gln Ala Tyr Val Val Val Arg Pro Gln Glu Leu Ala Asp Ala Ala
225                 230                 235

<210> SEQ ID NO 50
<211> LENGTH: 717
<212> TYPE: DNA
<213> ORGANISM: Streptomyces alborus IFO15452

<400> SEQUENCE: 50 atg ctt gca ggc tta gtt ccc gcg ctg gac cac agc atg cgg gaa gaa         48
Met Leu Ala Gly Leu Val Pro Ala Leu Asp His Ser Met Arg Glu Glu
1               5                   10                  15 ata ctt ggc aat cgc ggc cga aag atc cgg caa cgc ggt gag cac gct         96
Ile Leu Gly Asn Arg Gly Arg Lys Ile Arg Gln Arg Gly Glu His Ala
                20                  25                  30 ctc att gga atc agt gcg ggc aac agt tat ttc agc cag aag aac gtc        144
Leu Ile Gly Ile Ser Ala Gly Asn Ser Tyr Phe Ser Gln Lys Asn Val
            35                  40                  45 acc atg ctg ctg caa tgg gcc ggg cag cat ttc gag cgc acg gat gtc        192
Thr Met Leu Leu Gln Trp Ala Gly Gln His Phe Glu Arg Thr Asp Val
        50                  55                  60 gtc tac gtg gac acg cac atc gac gac atg ctg atg gcg gac ggc cgc        240
Val Tyr Val Asp Thr His Ile Asp Asp Met Leu Met Ala Asp Gly Arg
65                  70                  75                  80 agc gcg cag gaa gcc gag aag tcg gtc aag cgc acg ctc aag gat ctg        288
Ser Ala Gln Glu Ala Glu Lys Ser Val Lys Arg Thr Leu Lys Asp Leu
                85                  90                  95 cgc cgc agg ctg cgg cgc tcg ttg gaa agc gtg ggc gac cac agc gag        336
Arg Arg Arg Leu Arg Arg Ser Leu Glu Ser Val Gly Asp His Ser Glu
                100                 105                 110 cgg ttc cgc gtc cgg tcc ctg tcc gag atc cag gag acc cct gag tac        384
Arg Phe Arg Val Arg Ser Leu Ser Glu Ile Gln Glu Thr Pro Glu Tyr
            115                 120                 125 cgg gcc gca cgc gag tcc acc gac cgg gcc ttc cgc gag gac ggc gag        432
Arg Ala Ala Arg Glu Ser Thr Asp Arg Ala Phe Arg Glu Asp Gly Glu
        130                 135                 140 ttc gcc acc gtc tgc gag gag atg gtg cgc gcc gtg gtg atg aac cgg        480
Phe Ala Thr Val Cys Glu Glu Met Val Arg Ala Val Val Met Asn Arg
145                 150                 155                 160 ccc ggt gac ggc gtc gac atc tcg gag gaa cac ctg cgg gcc ggt ctg        528
Pro Gly Asp Gly Val Asp Ile Ser Glu Glu His Leu Arg Ala Gly Leu
                165                 170                 175 aac tac gtg ctc gcc gag gcc ccg ctc ttc gcg gac tcg ccc ggc gtg        576
Asn Tyr Val Leu Ala Glu Ala Pro Leu Phe Ala Asp Ser Pro Gly Val
            180                 185                 190 ttc tcc gtc ccc tcg tcg gtg ctc tgc tac cac atc ccc acc ccg gta        624
```

-continued

```
            Phe Ser Val Pro Ser Ser Val Leu Cys Tyr His Ile Pro Thr Pro Val
                195                 200                 205 tcg acg ttc ctg gcc cat cgc gag acc ggt ttc cag gcg gct cag ggt       672
Ser Thr Phe Leu Ala His Arg Glu Thr Gly Phe Gln Ala Ala Gln Gly
    210                 215                 220 cag gca tac gtc gtc gtc agg ccg cag gag ctg gcc gac gcg gcc           717
Gln Ala Tyr Val Val Val Arg Pro Gln Glu Leu Ala Asp Ala Ala
225                 230                 235

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
agagccatgg gacttgcagg cttagttccc gc                                    32

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
agagagatct ggccgcgtcg gccagctcc                                        29

<210> SEQ ID NO 53
<211> LENGTH: 1078
<212> TYPE: PRT
<213> ORGANISM: Brevibacillus brevis

<400> SEQUENCE: 53

Met Leu Asn Ser Ser Lys Ser Ile Leu Ile His Ala Gln Asn Lys Asn
  1               5                  10                  15

Gly Thr His Glu Glu Glu Gln Tyr Leu Phe Ala Val Asn Asn Thr Lys
             20                  25                  30

Ala Glu Tyr Pro Arg Asp Lys Thr Ile His Gln Leu Phe Glu Glu Gln
         35                  40                  45

Val Ser Lys Arg Pro Asn Asn Val Ala Ile Val Cys Glu Asn Glu Gln
     50                  55                  60

Leu Thr Tyr His Glu Leu Asn Val Lys Ala Asn Gln Leu Ala Arg Ile
 65                  70                  75                  80

Phe Ile Glu Lys Gly Ile Gly Lys Asp Thr Leu Val Gly Ile Met Met
                 85                  90                  95

Glu Lys Ser Ile Asp Leu Phe Ile Gly Ile Leu Ala Val Leu Lys Ala
            100                 105                 110

Gly Gly Ala Tyr Val Pro Ile Asp Ile Glu Tyr Pro Lys Glu Val His
        115                 120                 125

Leu Ile His Asn Ile Gln Phe Asn Gly Gln Val Glu Ile Phe Glu Glu
    130                 135                 140

Asp Thr Ile Lys Ile Arg Glu Gly Thr Asn Leu His Val Pro Ser Lys
145                 150                 155                 160

Ser Thr Asp Leu Ala Tyr Val Ile Tyr Thr Ser Gly Thr Thr Gly Asn
                165                 170                 175

Pro Lys Gly Thr Met Leu Glu His Lys Gly Ile Ser Asn Leu Lys Val
            180                 185                 190
```

```
Phe Phe Glu Asn Ser Leu Asn Val Thr Glu Lys Asp Arg Ile Gly Gln
        195                 200                 205

Phe Ala Ser Ile Ser Phe Asp Ala Ser Val Trp Glu Met Phe Met Ala
        210                 215                 220

Leu Leu Thr Gly Ala Ser Leu Tyr Ile Ile Leu Lys Asp Thr Ile Asn
225                 230                 235                 240

Asp Phe Val Lys Phe Glu Gln Tyr Ile Asn Gln Lys Glu Ile Thr Val
            245                 250                 255

Ile Thr Leu Pro Pro Thr Tyr Val Val His Leu Asp Pro Glu Arg Ile
            260                 265                 270

Leu Ser Ile Gln Thr Leu Ile Thr Ala Gly Ser Ala Thr Ser Pro Ser
            275                 280                 285

Leu Val Asn Lys Trp Lys Glu Lys Val Thr Tyr Ile Asn Ala Tyr Gly
            290                 295                 300

Pro Thr Glu Thr Thr Ile Cys Ala Thr Thr Cys Val Ala Thr Lys Glu
305                 310                 315                 320

Thr Ile Gly His Ser Val Pro Ile Gly Ala Pro Ile Gln Asn Thr Gln
                325                 330                 335

Ile Tyr Ile Val Asp Glu Asn Leu Gln Leu Lys Ser Val Gly Glu Ala
            340                 345                 350

Gly Glu Leu Cys Ile Gly Gly Glu Gly Leu Ala Arg Gly Tyr Trp Lys
            355                 360                 365

Arg Pro Glu Leu Thr Ser Gln Lys Phe Val Asp Asn Pro Phe Val Pro
        370                 375                 380

Gly Glu Lys Leu Tyr Lys Thr Gly Asp Gln Ala Arg Trp Leu Ser Asp
385                 390                 395                 400

Gly Asn Ile Glu Tyr Leu Gly Arg Ile Asp Asn Gln Val Lys Ile Arg
            405                 410                 415

Gly His Arg Val Glu Leu Glu Glu Val Glu Ser Ile Leu Leu Lys His
            420                 425                 430

Met Tyr Ile Ser Glu Thr Ala Val Ser Val His Lys Asp His Gln Glu
        435                 440                 445

Gln Pro Tyr Leu Cys Ala Tyr Phe Val Ser Glu Lys His Ile Pro Leu
        450                 455                 460

Glu Gln Leu Arg Gln Phe Ser Ser Glu Leu Pro Thr Tyr Met Ile
465                 470                 475                 480

Pro Ser Tyr Phe Ile Gln Leu Asp Lys Met Pro Leu Thr Ser Asn Gly
            485                 490                 495

Lys Ile Asp Arg Lys Gln Leu Pro Glu Pro Asp Leu Thr Phe Gly Met
            500                 505                 510

Arg Val Asp Tyr Glu Ala Pro Arg Asn Glu Ile Glu Thr Leu Val
        515                 520                 525

Thr Ile Trp Gln Asp Val Leu Gly Ile Glu Lys Ile Gly Ile Lys Asp
        530                 535                 540

Asn Phe Tyr Ala Leu Gly Gly Asp Ser Ile Lys Ala Ile Gln Val Ala
545                 550                 555                 560

Ala Arg Leu His Ser Tyr Gln Leu Lys Leu Glu Thr Lys Asp Leu Leu
                565                 570                 575

Lys Tyr Pro Thr Ile Asp Gln Leu Val His Tyr Ile Lys Asp Ser Lys
            580                 585                 590

Arg Arg Ser Glu Gln Gly Ile Val Glu Gly Ile Gly Leu Thr Pro
        595                 600                 605

Ile Gln His Trp Phe Phe Glu Gln Gln Phe Thr Asn Met His His Trp
```

-continued

```
                610                 615                 620
Asn Gln Ser Tyr Met Leu Tyr Arg Pro Asn Gly Phe Asp Lys Glu Ile
625                 630                 635                 640

Leu Leu Arg Val Phe Asn Lys Ile Val Glu His His Asp Ala Leu Arg
                645                 650                 655

Met Ile Tyr Lys His His Asn Gly Lys Ile Val Gln Ile Asn Arg Gly
                660                 665                 670

Leu Glu Gly Thr Leu Phe Asp Phe Tyr Thr Phe Asp Leu Thr Ala Asn
                675                 680                 685

Asp Asn Glu Gln Gln Val Ile Cys Glu Glu Ser Ala Arg Leu Gln Asn
690                 695                 700

Ser Ile Asn Leu Glu Val Gly Pro Leu Val Lys Ile Ala Leu Phe His
705                 710                 715                 720

Thr Gln Asn Gly Asp His Leu Phe Met Ala Ile His Leu Val Val
                725                 730                 735

Asp Gly Ile Ser Trp Arg Ile Leu Phe Glu Asp Leu Ala Thr Ala Tyr
                740                 745                 750

Glu Gln Ala Met His Gln Gln Thr Ile Ala Leu Pro Glu Lys Thr Asp
                755                 760                 765

Ser Phe Lys Asp Trp Ser Ile Glu Leu Glu Lys Tyr Ala Asn Ser Glu
770                 775                 780

Leu Phe Leu Glu Glu Ala Glu Tyr Trp His His Leu Asn Tyr Tyr Thr
785                 790                 795                 800

Glu Asn Val Gln Ile Lys Lys Asp Tyr Val Thr Met Asn Asn Lys Gln
                805                 810                 815

Lys Asn Ile Arg Tyr Val Gly Met Glu Leu Thr Ile Glu Glu Thr Glu
                820                 825                 830

Lys Leu Leu Lys Asn Val Asn Lys Ala Tyr Arg Thr Glu Ile Asn Asp
835                 840                 845

Ile Leu Leu Thr Ala Leu Gly Phe Ala Leu Lys Glu Trp Ala Asp Ile
850                 855                 860

Asp Lys Ile Val Ile Asn Leu Glu Gly His Gly Arg Glu Glu Ile Leu
865                 870                 875                 880

Glu Gln Met Asn Ile Ala Arg Thr Val Gly Trp Phe Thr Ser Gln Tyr
                885                 890                 895

Pro Val Val Leu Asp Met Gln Lys Ser Asp Asp Leu Ser Tyr Gln Ile
                900                 905                 910

Lys Leu Met Lys Glu Asn Leu Arg Arg Ile Pro Asn Lys Gly Ile Gly
                915                 920                 925

Tyr Glu Ile Phe Lys Tyr Leu Thr Thr Glu Tyr Leu Arg Pro Val Leu
                930                 935                 940

Pro Phe Thr Leu Lys Pro Glu Ile Asn Phe Asn Tyr Leu Gly Gln Phe
945                 950                 955                 960

Asp Thr Asp Val Lys Thr Glu Leu Phe Thr Arg Ser Pro Tyr Ser Met
                965                 970                 975

Gly Asn Ser Leu Gly Pro Asp Gly Lys Asn Asn Leu Ser Pro Glu Gly
                980                 985                 990

Glu Ser Tyr Phe Val Leu Asn Ile Asn Gly Phe Ile Glu Glu Gly Lys
                995                 1000                1005

Leu His Ile Thr Phe Ser Tyr Asn Glu Gln Gln Tyr Lys Glu Asp Thr
                1010                1015                1020

Ile Gln Gln Leu Ser Arg Ser Tyr Lys Gln His Leu Leu Ala Ile Ile
1025                1030                1035                1040
```

```
Glu His Cys Val Gln Lys Glu Asp Thr Glu Leu Thr Pro Ser Asp Phe
            1045                1050                1055

Ser Phe Lys Glu Leu Glu Leu Glu Glu Met Asp Asp Ile Phe Asp Leu
        1060                1065                1070

Leu Ala Asp Ser Leu Thr
        1075

<210> SEQ ID NO 54
<211> LENGTH: 3234
<212> TYPE: DNA
<213> ORGANISM: Brevibacillus brevis

<400> SEQUENCE: 54
```

| | | | | | | | | | | | | | | | | |
|---|---|---|---|---|---|---|---|---|---|---|---|---|---|---|---|---|
| atg | tta | aac | agt | tct | aaa | agt | ata | ttg | att | cat | gct | caa | aat | aaa | aat | 48 |
| Met | Leu | Asn | Ser | Ser | Lys | Ser | Ile | Leu | Ile | His | Ala | Gln | Asn | Lys | Asn | |
| 1 | | | | 5 | | | | | 10 | | | | | 15 | | |
| gga | acg | cat | gaa | gag | gag | cag | tat | ctc | ttt | gct | gtg | aac | aac | acc | aaa | 96 |
| Gly | Thr | His | Glu | Glu | Glu | Gln | Tyr | Leu | Phe | Ala | Val | Asn | Asn | Thr | Lys | |
| | | | 20 | | | | | 25 | | | | | 30 | | | |
| gcg | gag | tat | cca | cgt | gat | aag | acg | atc | cat | cag | tta | ttt | gaa | gag | cag | 144 |
| Ala | Glu | Tyr | Pro | Arg | Asp | Lys | Thr | Ile | His | Gln | Leu | Phe | Glu | Glu | Gln | |
| | 35 | | | | | 40 | | | | | 45 | | | | | |
| gtt | agt | aag | aga | cca | aac | aat | gta | gcc | att | gta | tgt | gaa | aat | gag | caa | 192 |
| Val | Ser | Lys | Arg | Pro | Asn | Asn | Val | Ala | Ile | Val | Cys | Glu | Asn | Glu | Gln | |
| 50 | | | | | 55 | | | | | 60 | | | | | | |
| ctt | acc | tac | cat | gag | ctt | aat | gtg | aaa | gcc | aat | caa | cta | gca | cgg | att | 240 |
| Leu | Thr | Tyr | His | Glu | Leu | Asn | Val | Lys | Ala | Asn | Gln | Leu | Ala | Arg | Ile | |
| 65 | | | | | 70 | | | | | 75 | | | | | 80 | |
| ttt | ata | gaa | aaa | ggg | att | gga | aaa | gac | act | ctt | gtt | gga | att | atg | atg | 288 |
| Phe | Ile | Glu | Lys | Gly | Ile | Gly | Lys | Asp | Thr | Leu | Val | Gly | Ile | Met | Met | |
| | | | | 85 | | | | | 90 | | | | | 95 | | |
| gag | aaa | tct | atc | gat | tta | ttt | ata | ggc | ata | tta | gcc | gtt | tta | aaa | gca | 336 |
| Glu | Lys | Ser | Ile | Asp | Leu | Phe | Ile | Gly | Ile | Leu | Ala | Val | Leu | Lys | Ala | |
| | | | 100 | | | | | 105 | | | | | 110 | | | |
| ggt | gga | gca | tat | gtt | ccg | att | gat | att | gaa | tat | cct | aag | gaa | gtt | cat | 384 |
| Gly | Gly | Ala | Tyr | Val | Pro | Ile | Asp | Ile | Glu | Tyr | Pro | Lys | Glu | Val | His | |
| | 115 | | | | | 120 | | | | | 125 | | | | | |
| tta | att | cat | aat | att | caa | ttt | aat | ggg | caa | gtg | gaa | att | ttt | gaa | gaa | 432 |
| Leu | Ile | His | Asn | Ile | Gln | Phe | Asn | Gly | Gln | Val | Glu | Ile | Phe | Glu | Glu | |
| 130 | | | | | 135 | | | | | 140 | | | | | | |
| gat | act | atc | aaa | att | aga | gaa | gga | act | aat | cta | cat | gta | cca | agt | aaa | 480 |
| Asp | Thr | Ile | Lys | Ile | Arg | Glu | Gly | Thr | Asn | Leu | His | Val | Pro | Ser | Lys | |
| 145 | | | | | 150 | | | | | 155 | | | | | 160 | |
| tca | acc | gat | ctt | gct | tat | gtt | att | tat | act | tct | ggt | aca | aca | ggc | aat | 528 |
| Ser | Thr | Asp | Leu | Ala | Tyr | Val | Ile | Tyr | Thr | Ser | Gly | Thr | Thr | Gly | Asn | |
| | | | | 165 | | | | | 170 | | | | | 175 | | |
| cca | aaa | ggt | aca | atg | ctg | gag | cat | aaa | gga | ata | agt | aat | cta | aag | gta | 576 |
| Pro | Lys | Gly | Thr | Met | Leu | Glu | His | Lys | Gly | Ile | Ser | Asn | Leu | Lys | Val | |
| | | | 180 | | | | | 185 | | | | | 190 | | | |
| ttt | ttc | gaa | aat | agt | ctt | aac | gtg | act | gaa | aag | gat | aga | att | ggt | caa | 624 |
| Phe | Phe | Glu | Asn | Ser | Leu | Asn | Val | Thr | Glu | Lys | Asp | Arg | Ile | Gly | Gln | |
| | 195 | | | | | 200 | | | | | 205 | | | | | |
| ttt | gcc | agc | atc | tct | ttt | gat | gca | tct | gta | tgg | gag | atg | ttt | atg | gct | 672 |
| Phe | Ala | Ser | Ile | Ser | Phe | Asp | Ala | Ser | Val | Trp | Glu | Met | Phe | Met | Ala | |
| 210 | | | | | 215 | | | | | 220 | | | | | | |
| ttg | tta | acg | ggg | gct | agc | ctg | tat | att | atc | ctg | aag | gat | aca | atc | aat | 720 |
| Leu | Leu | Thr | Gly | Ala | Ser | Leu | Tyr | Ile | Ile | Leu | Lys | Asp | Thr | Ile | Asn | |
| 225 | | | | | 230 | | | | | 235 | | | | | 240 | |
| gat | ttt | gtg | aag | ttt | gaa | caa | tac | att | aac | caa | aag | gaa | atc | act | gtt | 768 |
| Asp | Phe | Val | Lys | Phe | Glu | Gln | Tyr | Ile | Asn | Gln | Lys | Glu | Ile | Thr | Val | |
| | | | | 245 | | | | | 250 | | | | | 255 | | |

```
att acg tta cca cct acc tat gta gtt cat ctt gat cca gaa cgt att      816
Ile Thr Leu Pro Pro Thr Tyr Val Val His Leu Asp Pro Glu Arg Ile
        260                 265                 270 tta tcg ata caa acg tta att aca gca ggc tca gct acc tcg cct tcc      864
Leu Ser Ile Gln Thr Leu Ile Thr Ala Gly Ser Ala Thr Ser Pro Ser
            275                 280                 285 tta gta aac aag tgg aag gag aaa gta act tac ata aat gcc tat ggc      912
Leu Val Asn Lys Trp Lys Glu Lys Val Thr Tyr Ile Asn Ala Tyr Gly
    290                 295                 300 cct acg gaa aca act att tgt gcg act aca tgc gta gcc acc aaa gaa      960
Pro Thr Glu Thr Thr Ile Cys Ala Thr Thr Cys Val Ala Thr Lys Glu
305                 310                 315                 320 aca ata ggt cat tca gtt cca atc gga gca cca att caa aat aca caa     1008
Thr Ile Gly His Ser Val Pro Ile Gly Ala Pro Ile Gln Asn Thr Gln
                325                 330                 335 att tat att gtc gat gaa aat ctt caa tta aaa tcg gtt ggt gaa gct     1056
Ile Tyr Ile Val Asp Glu Asn Leu Gln Leu Lys Ser Val Gly Glu Ala
            340                 345                 350 ggt gaa ttg tgt att ggt gga gaa ggg tta gca agg gga tat tgg aag     1104
Gly Glu Leu Cys Ile Gly Gly Glu Gly Leu Ala Arg Gly Tyr Trp Lys
        355                 360                 365 cga ccg gaa tta act tcc cag aag ttc gtt gat aac ccg ttt gtt cca     1152
Arg Pro Glu Leu Thr Ser Gln Lys Phe Val Asp Asn Pro Phe Val Pro
370                 375                 380 gga gag aag ttg tat aaa aca gga gat cag gca aga tgg cta tct gat     1200
Gly Glu Lys Leu Tyr Lys Thr Gly Asp Gln Ala Arg Trp Leu Ser Asp
385                 390                 395                 400 gga aat att gaa tat ctc gga aga ata gat aac cag gta aag att aga     1248
Gly Asn Ile Glu Tyr Leu Gly Arg Ile Asp Asn Gln Val Lys Ile Arg
                405                 410                 415 ggt cac cga gtt gaa cta gaa gaa gtt gag tct att ctt cta aag cat     1296
Gly His Arg Val Glu Leu Glu Glu Val Glu Ser Ile Leu Leu Lys His
            420                 425                 430 atg tat att agc gaa act gca gta agt gtg cat aaa gat cac caa gaa     1344
Met Tyr Ile Ser Glu Thr Ala Val Ser Val His Lys Asp His Gln Glu
        435                 440                 445 cag ccg tat ttg tgc gct tat ttt gta tcg gaa aag cat ata cca cta     1392
Gln Pro Tyr Leu Cys Ala Tyr Phe Val Ser Glu Lys His Ile Pro Leu
    450                 455                 460 gaa cag tta aga caa ttc tca tca gaa gaa ctg cca acg tat atg atc     1440
Glu Gln Leu Arg Gln Phe Ser Ser Glu Glu Leu Pro Thr Tyr Met Ile
465                 470                 475                 480 cct tct tat ttt atc cag tta gac aaa atg ccg ctt aca tca aat ggg     1488
Pro Ser Tyr Phe Ile Gln Leu Asp Lys Met Pro Leu Thr Ser Asn Gly
                485                 490                 495 aag att gat cga aag cag ttg ccg gaa cct gat tta act ttc ggg atg     1536
Lys Ile Asp Arg Lys Gln Leu Pro Glu Pro Asp Leu Thr Phe Gly Met
            500                 505                 510 agg gta gac tat gaa gcg ccg cga aat gaa atc gag gaa acg ctt gtt     1584
Arg Val Asp Tyr Glu Ala Pro Arg Asn Glu Ile Glu Glu Thr Leu Val
        515                 520                 525 act atc tgg cag gat gta tta ggt att gag aaa atc ggt att aaa gat     1632
Thr Ile Trp Gln Asp Val Leu Gly Ile Glu Lys Ile Gly Ile Lys Asp
    530                 535                 540 aat ttc tat gca tta ggt gga gat tct att aaa gca ata cag gtt gct     1680
Asn Phe Tyr Ala Leu Gly Gly Asp Ser Ile Lys Ala Ile Gln Val Ala
545                 550                 555                 560 gct cgc ctg cat tcc tac caa tta aag cta gaa aca aaa gat tta tta     1728
Ala Arg Leu His Ser Tyr Gln Leu Lys Leu Glu Thr Lys Asp Leu Leu
                565                 570                 575
```

```
aag tat cca aca atc gat caa ctc gtt cat tat ata aaa gat agt aaa    1776
Lys Tyr Pro Thr Ile Asp Gln Leu Val His Tyr Ile Lys Asp Ser Lys
        580                 585                 590 aga aga agt gag caa ggt att gtg gaa ggt gag att gga ctt aca cct    1824
Arg Arg Ser Glu Gln Gly Ile Val Glu Gly Glu Ile Gly Leu Thr Pro
595                 600                 605 att cag cat tgg ttc ttt gaa caa caa ttt aca aat atg cac cat tgg    1872
Ile Gln His Trp Phe Phe Glu Gln Gln Phe Thr Asn Met His His Trp
    610                 615                 620 aac caa tcg tat atg ttg tat aga cca aat ggg ttt gat aaa gag atc    1920
Asn Gln Ser Tyr Met Leu Tyr Arg Pro Asn Gly Phe Asp Lys Glu Ile
625                 630                 635                 640 ttg cta agg gta ttt aat aaa att gtt gag cat cat gat gca tta cgt    1968
Leu Leu Arg Val Phe Asn Lys Ile Val Glu His His Asp Ala Leu Arg
                645                 650                 655 atg ata tac aaa cat cat aac gga aag atc gtg cag ata aat cgg ggg    2016
Met Ile Tyr Lys His His Asn Gly Lys Ile Val Gln Ile Asn Arg Gly
            660                 665                 670 ctt gaa ggt acg ttg ttt gat ttt tat acc ttt gat tta act gca aat    2064
Leu Glu Gly Thr Leu Phe Asp Phe Tyr Thr Phe Asp Leu Thr Ala Asn
        675                 680                 685 gat aat gag caa cag gtg att tgt gaa gaa tct gct cga tta caa aat    2112
Asp Asn Glu Gln Gln Val Ile Cys Glu Glu Ser Ala Arg Leu Gln Asn
690                 695                 700 agt ata aac ttg gaa gta ggc cct cta gta aag ata gcg ctg ttt cat    2160
Ser Ile Asn Leu Glu Val Gly Pro Leu Val Lys Ile Ala Leu Phe His
705                 710                 715                 720 act cag aat gga gat cac ctg ttt atg gct att cat cat ttg gtt gtg    2208
Thr Gln Asn Gly Asp His Leu Phe Met Ala Ile His His Leu Val Val
                725                 730                 735 gat ggt att tct tgg agg att ttg ttt gag gat ttg gcc aca gct tat    2256
Asp Gly Ile Ser Trp Arg Ile Leu Phe Glu Asp Leu Ala Thr Ala Tyr
            740                 745                 750 gaa caa gca atg cat cag caa acg att gct tta cca gag aaa aca gat    2304
Glu Gln Ala Met His Gln Gln Thr Ile Ala Leu Pro Glu Lys Thr Asp
        755                 760                 765 tca ttt aag gac tgg tct att gaa tta gaa aaa tat gcg aac agc gaa    2352
Ser Phe Lys Asp Trp Ser Ile Glu Leu Glu Lys Tyr Ala Asn Ser Glu
770                 775                 780 tta ttc cta gaa gaa gct gaa tat tgg cat cat ttg aat tat tat acc    2400
Leu Phe Leu Glu Glu Ala Glu Tyr Trp His His Leu Asn Tyr Tyr Thr
785                 790                 795                 800 gag aac gtt caa att aag aaa gat tat gtc acc atg aac aat aaa caa    2448
Glu Asn Val Gln Ile Lys Lys Asp Tyr Val Thr Met Asn Asn Lys Gln
                805                 810                 815 aag aat ata cgt tat gta gga atg gag tta aca ata gaa gag aca gaa    2496
Lys Asn Ile Arg Tyr Val Gly Met Glu Leu Thr Ile Glu Glu Thr Glu
            820                 825                 830 aaa tta ttg aaa aat gta aat aaa gcg tat cga aca gaa att aat gat    2544
Lys Leu Leu Lys Asn Val Asn Lys Ala Tyr Arg Thr Glu Ile Asn Asp
        835                 840                 845 att tta tta acg gca ctt ggc ttt gca ctc aaa gaa tgg gcc gat att    2592
Ile Leu Leu Thr Ala Leu Gly Phe Ala Leu Lys Glu Trp Ala Asp Ile
850                 855                 860 gat aaa att gta att aac tta gag gga cac gga cgg gaa gaa ata ctg    2640
Asp Lys Ile Val Ile Asn Leu Glu Gly His Gly Arg Glu Glu Ile Leu
865                 870                 875                 880 gaa cag atg aac att gca agg acg gta ggc tgg ttt act tcc cag tat    2688
Glu Gln Met Asn Ile Ala Arg Thr Val Gly Trp Phe Thr Ser Gln Tyr
                885                 890                 895
```

```
cct gtt gta ctt gat atg caa aaa tcg gat gat ttg tct tat caa atc    2736
Pro Val Val Leu Asp Met Gln Lys Ser Asp Asp Leu Ser Tyr Gln Ile
        900                 905                 910 aaa tta atg aaa gaa aat tta cgc aga ata cct aac aaa gga atc gga    2784
Lys Leu Met Lys Glu Asn Leu Arg Arg Ile Pro Asn Lys Gly Ile Gly
        915                 920                 925 tat gaa att ttt aag tat tta aca act gaa tat tta cgg cct gtt tta    2832
Tyr Glu Ile Phe Lys Tyr Leu Thr Thr Glu Tyr Leu Arg Pro Val Leu
    930                 935                 940 ccc ttt aca tta aag ccg gaa att aac ttt aac tac tta gga cag ttc    2880
Pro Phe Thr Leu Lys Pro Glu Ile Asn Phe Asn Tyr Leu Gly Gln Phe
945                 950                 955                 960 gat acg gac gtg aag act gaa ttg ttt act cgt tct cct tat agc atg    2928
Asp Thr Asp Val Lys Thr Glu Leu Phe Thr Arg Ser Pro Tyr Ser Met
        965                 970                 975 ggt aat tca tta gga cca gat gga aaa aat aat tta agc cca gaa ggg    2976
Gly Asn Ser Leu Gly Pro Asp Gly Lys Asn Asn Leu Ser Pro Glu Gly
        980                 985                 990 gaa agt tat ttt gta ctc aat att aat ggt ttt att gaa gaa ggt aag    3024
Glu Ser Tyr Phe Val Leu Asn Ile Asn Gly Phe Ile Glu Glu Gly Lys
        995                 1000                1005 ctt cac atc acc ttt tct tat aat gaa cag cag tat aag gag gat acc    3072
Leu His Ile Thr Phe Ser Tyr Asn Glu Gln Gln Tyr Lys Glu Asp Thr
        1010                1015                1020 att cag caa ttg agc cgg agc tat aag caa cat ctt ttg gcc atc att    3120
Ile Gln Gln Leu Ser Arg Ser Tyr Lys Gln His Leu Leu Ala Ile Ile
1025                1030                1035                1040 gaa cat tgt gta cag aag gaa gat act gag tta act cca agt gat ttc    3168
Glu His Cys Val Gln Lys Glu Asp Thr Glu Leu Thr Pro Ser Asp Phe
                1045                1050                1055 agt ttc aag gaa ctt gaa tta gaa gag atg gat gat att ttc gat ttg    3216
Ser Phe Lys Glu Leu Glu Leu Glu Glu Met Asp Asp Ile Phe Asp Leu
        1060                1065                1070 ttg gcc gat tca tta acg                                             3234
Leu Ala Asp Ser Leu Thr
        1075

<210> SEQ ID NO 55
<211> LENGTH: 503
<212> TYPE: PRT
<213> ORGANISM: Escherichia coli

<400> SEQUENCE: 55

Met Glu Phe Ser Val Lys Ser Gly Ser Pro Glu Lys Gln Arg Ser Ala
  1               5                  10                  15

Cys Ile Val Val Gly Val Phe Glu Pro Arg Arg Leu Ser Pro Ile Ala
                 20                  25                  30

Glu Gln Leu Asp Lys Ile Ser Asp Gly Tyr Ile Ser Ala Leu Leu Arg
             35                  40                  45

Arg Gly Glu Leu Glu Gly Lys Pro Gly Gln Thr Leu Leu His His
         50                  55                  60

Val Pro Asn Val Leu Ser Glu Arg Ile Leu Ile Gly Cys Gly Lys
 65                  70                  75                  80

Glu Arg Glu Leu Asp Glu Arg Gln Tyr Lys Gln Val Ile Gln Lys Thr
                 85                  90                  95

Ile Asn Thr Leu Asn Asp Thr Gly Ser Met Glu Ala Val Cys Phe Leu
            100                 105                 110

Thr Glu Leu His Val Lys Gly Arg Asn Asn Tyr Trp Lys Val Arg Gln
        115                 120                 125
```

```
Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160

Val Pro Thr Arg Arg Glu Leu Thr Ser Gly Glu Arg Ala Ile Gln His
                165                 170                 175

Gly Leu Ala Ile Ala Ala Gly Ile Lys Ala Lys Asp Leu Gly Asn
            180                 185                 190

Met Pro Pro Asn Ile Cys Asn Ala Ala Tyr Leu Ala Ser Gln Ala Arg
        195                 200                 205

Gln Leu Ala Asp Ser Tyr Ser Lys Asn Val Ile Thr Arg Val Ile Gly
    210                 215                 220

Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
                245                 250                 255

Asn Ala Ser Glu Asp Ala Arg Pro Ile Val Leu Val Gly Lys Gly Leu
            260                 265                 270

Thr Phe Asp Ser Gly Gly Ile Ser Ile Lys Pro Ser Glu Gly Met Asp
        275                 280                 285

Glu Met Lys Tyr Asp Met Cys Gly Ala Ala Val Tyr Gly Val Met
290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
            325                 330                 335

Val Leu Thr Thr Met Ser Gly Gln Thr Val Glu Val Leu Asn Thr Asp
        340                 345                 350

Ala Glu Gly Arg Leu Val Leu Cys Asp Val Leu Thr Tyr Val Glu Arg
            355                 360                 365

Phe Glu Pro Glu Ala Val Ile Asp Val Ala Thr Leu Thr Gly Ala Cys
        370                 375                 380

Val Ile Ala Leu Gly His His Ile Thr Gly Leu Met Ala Asn His Asn
385                 390                 395                 400

Pro Leu Ala His Glu Leu Ile Ala Ser Glu Gln Ser Gly Asp Arg
                405                 410                 415

Ala Trp Arg Leu Pro Leu Gly Asp Glu Tyr Gln Glu Gln Leu Glu Ser
            420                 425                 430

Asn Phe Ala Asp Met Ala Asn Ile Gly Gly Arg Pro Gly Gly Ala Ile
        435                 440                 445

Thr Ala Gly Cys Phe Leu Ser Arg Phe Thr Arg Lys Tyr Asn Trp Ala
    450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
                485                 490                 495

Ala Gly Phe Asn Gly Glu Glu
            500

<210> SEQ ID NO 56
<211> LENGTH: 427
<212> TYPE: PRT
<213> ORGANISM: Escherichia coli

<400> SEQUENCE: 56
```

```
Met Thr Glu Ala Met Lys Ile Thr Leu Ser Thr Gln Pro Ala Asp Ala
 1               5                  10                  15

Arg Trp Gly Glu Lys Ala Thr Tyr Ser Ile Asn Asn Asp Gly Ile Thr
            20                  25                  30

Leu His Leu Asn Gly Ala Asp Asp Leu Gly Leu Ile Gln Arg Ala Ala
        35                  40                  45

Arg Lys Ile Asp Gly Leu Gly Ile Lys His Val Gln Leu Ser Gly Glu
    50                  55                  60

Gly Trp Asp Ala Asp Arg Cys Trp Ala Phe Trp Gln Gly Tyr Lys Ala
65                  70                  75                  80

Pro Lys Gly Thr Arg Lys Val Val Trp Pro Asp Leu Asp Asp Ala Gln
            85                  90                  95

Arg Gln Glu Leu Asp Asn Arg Leu Met Ile Ile Asp Trp Val Arg Asp
            100                 105                 110

Thr Ile Asn Ala Pro Ala Glu Glu Leu Gly Pro Ser Gln Leu Ala Gln
        115                 120                 125

Arg Ala Val Asp Leu Ile Ser Asn Val Ala Gly Asp Arg Val Thr Tyr
    130                 135                 140

Arg Ile Thr Lys Gly Glu Asp Leu Arg Glu Gln Gly Tyr Met Gly Leu
145                 150                 155                 160

His Thr Val Gly Arg Gly Ser Glu Arg Ser Pro Val Leu Leu Ala Leu
                165                 170                 175

Asp Tyr Asn Pro Thr Gly Asp Lys Glu Ala Pro Val Tyr Ala Cys Leu
            180                 185                 190

Val Gly Lys Gly Ile Thr Phe Asp Ser Gly Gly Tyr Ser Ile Lys Gln
        195                 200                 205

Thr Ala Phe Met Asp Ser Met Lys Ser Asp Met Gly Gly Ala Ala Thr
    210                 215                 220

Val Thr Gly Ala Leu Ala Phe Ala Ile Thr Arg Gly Leu Asn Lys Arg
225                 230                 235                 240

Val Lys Leu Phe Leu Cys Cys Ala Asp Asn Leu Ile Ser Gly Asn Ala
                245                 250                 255

Phe Lys Leu Gly Asp Ile Ile Thr Tyr Arg Asn Gly Lys Lys Val Glu
            260                 265                 270

Val Met Asn Thr Asp Ala Glu Gly Arg Leu Val Leu Ala Asp Gly Leu
        275                 280                 285

Ile Asp Ala Ser Ala Gln Lys Pro Glu Met Ile Ile Asp Ala Ala Thr
    290                 295                 300

Leu Thr Gly Ala Ala Lys Thr Ala Leu Gly Asn Asp Tyr His Ala Leu
305                 310                 315                 320

Phe Ser Phe Asp Asp Ala Leu Ala Gly Arg Leu Leu Ala Ser Ala Ala
                325                 330                 335

Gln Glu Asn Glu Pro Phe Trp Arg Leu Pro Leu Ala Glu Phe His Arg
            340                 345                 350

Ser Gln Leu Pro Ser Asn Phe Ala Glu Leu Asn Asn Thr Gly Ser Ala
        355                 360                 365

Ala Tyr Pro Ala Gly Ala Ser Thr Ala Ala Gly Phe Leu Ser His Phe
    370                 375                 380

Val Glu Asn Tyr Gln Gln Gly Trp Leu His Ile Asp Cys Ser Ala Thr
385                 390                 395                 400

Tyr Arg Lys Ala Pro Val Glu Gln Trp Ser Ala Gly Ala Thr Gly Leu
                405                 410                 415

Gly Val Arg Thr Ile Ala Asn Leu Leu Thr Ala
```

<210> SEQ ID NO 57
<211> LENGTH: 485
<212> TYPE: PRT
<213> ORGANISM: Escherichia coli

<400> SEQUENCE: 57

Met Ser Glu Leu Ser Gln Leu Ser Pro Gln Pro Leu Trp Asp Ile Phe
 1               5                  10                  15

Ala Lys Ile Cys Ser Ile Pro His Pro Ser Tyr His Glu Glu Gln Leu
                20                  25                  30

Ala Glu Tyr Ile Val Gly Trp Ala Lys Glu Lys Gly Phe His Val Glu
            35                  40                  45

Arg Asp Gln Val Gly Asn Ile Leu Ile Arg Lys Pro Ala Thr Ala Gly
        50                  55                  60

Met Glu Asn Arg Lys Pro Val Val Leu Gln Ala His Leu Asp Met Val
 65                  70                  75                  80

Pro Gln Lys Asn Asn Asp Thr Val His Asp Phe Thr Lys Asp Pro Ile
                85                  90                  95

Gln Pro Tyr Ile Asp Gly Glu Trp Val Lys Ala Arg Gly Thr Thr Leu
                100                 105                 110

Gly Ala Asp Asn Gly Ile Gly Met Ala Ser Ala Leu Ala Val Leu Ala
            115                 120                 125

Asp Glu Asn Val Val His Gly Pro Leu Glu Val Leu Leu Thr Met Thr
        130                 135                 140

Glu Glu Ala Gly Met Asp Gly Ala Phe Gly Leu Gln Gly Asn Trp Leu
145                 150                 155                 160

Gln Ala Asp Ile Leu Ile Asn Thr Asp Ser Glu Glu Gly Glu Ile
                165                 170                 175

Tyr Met Gly Cys Ala Gly Gly Ile Asp Phe Thr Ser Asn Leu His Leu
            180                 185                 190

Asp Arg Glu Ala Val Pro Ala Gly Phe Glu Thr Phe Lys Leu Thr Leu
        195                 200                 205

Lys Gly Leu Lys Gly Gly His Ser Gly Gly Glu Ile His Val Gly Leu
    210                 215                 220

Gly Asn Ala Asn Lys Leu Leu Val Arg Phe Leu Ala Gly His Ala Glu
225                 230                 235                 240

Glu Leu Asp Leu Arg Leu Ile Asp Phe Asn Gly Gly Thr Leu Arg Asn
                245                 250                 255

Ala Ile Pro Arg Glu Ala Phe Ala Thr Ile Ala Val Ala Ala Asp Lys
            260                 265                 270

Val Asp Val Leu Lys Ser Leu Val Asn Thr Tyr Gln Glu Ile Leu Lys
        275                 280                 285

Asn Glu Leu Ala Glu Lys Glu Lys Asn Leu Ala Leu Leu Leu Asp Ser
    290                 295                 300

Val Ala Asn Asp Lys Ala Ala Leu Ile Ala Lys Ser Arg Asp Thr Phe
305                 310                 315                 320

Ile Arg Leu Leu Asn Ala Thr Pro Asn Gly Val Ile Arg Asn Ser Asp
                325                 330                 335

Val Ala Lys Gly Val Val Glu Thr Ser Leu Asn Val Gly Val Val Thr
            340                 345                 350

Met Thr Asp Asn Asn Val Glu Ile His Cys Leu Ile Arg Ser Leu Ile
        355                 360                 365

Asp Ser Gly Lys Asp Tyr Val Val Ser Met Leu Asp Ser Leu Gly Lys

```
                    370               375               380
Leu Ala Gly Ala Lys Thr Glu Ala Lys Gly Ala Tyr Pro Gly Trp Gln
385                 390               395               400

Pro Asp Ala Asn Ser Pro Val Met His Leu Val Arg Glu Thr Tyr Gln
                405               410               415

Arg Leu Phe Asn Lys Thr Pro Asn Ile Gln Ile Ile His Ala Gly Leu
            420               425               430

Glu Cys Gly Leu Phe Lys Lys Pro Tyr Pro Glu Met Asp Met Val Ser
                435               440               445

Ile Gly Pro Thr Ile Thr Gly Pro His Ser Pro Asp Glu Gln Val His
450                 455               460

Ile Glu Ser Val Gly His Tyr Trp Thr Leu Leu Thr Glu Leu Leu Lys
465                 470               475               480

Glu Ile Pro Ala Lys
                485

<210> SEQ ID NO 58
<211> LENGTH: 870
<212> TYPE: PRT
<213> ORGANISM: Escherichia coli

<400> SEQUENCE: 58

Met Thr Gln Gln Pro Gln Ala Lys Tyr Arg His Asp Tyr Arg Ala Pro
  1               5                  10                  15

Asp Tyr Gln Ile Thr Asp Ile Asp Leu Thr Phe Asp Leu Asp Ala Gln
                20                  25                  30

Lys Thr Val Val Thr Ala Val Ser Gln Ala Val Arg His Gly Ala Ser
            35                  40                  45

Asp Ala Pro Leu Arg Leu Asn Gly Glu Asp Leu Lys Leu Val Ser Val
         50                 55                  60

His Ile Asn Asp Glu Pro Trp Thr Ala Trp Lys Glu Glu Gly Ala
 65                 70                  75                  80

Leu Val Ile Ser Asn Leu Pro Glu Arg Phe Thr Leu Lys Ile Ile Asn
                85                  90                  95

Glu Ile Ser Pro Ala Ala Asn Thr Ala Leu Glu Gly Leu Tyr Gln Ser
               100                 105                 110

Gly Asp Ala Leu Cys Thr Gln Cys Glu Ala Glu Gly Phe Arg His Ile
            115                 120                 125

Thr Tyr Tyr Leu Asp Arg Pro Asp Val Leu Ala Arg Phe Thr Thr Lys
        130                 135                 140

Ile Ile Ala Asp Lys Ile Lys Tyr Pro Phe Leu Leu Ser Asn Gly Asn
145                 150                 155                 160

Arg Val Ala Gln Gly Glu Leu Glu Asn Gly Arg His Trp Val Gln Trp
                165                 170                 175

Gln Asp Pro Phe Pro Lys Pro Cys Tyr Leu Phe Ala Leu Val Ala Gly
            180                 185                 190

Asp Phe Asp Val Leu Arg Asp Thr Phe Thr Thr Arg Ser Gly Arg Glu
        195                 200                 205

Val Ala Leu Glu Leu Tyr Val Asp Arg Gly Asn Leu Asp Arg Ala Pro
    210                 215                 220

Trp Ala Met Thr Ser Leu Lys Asn Ser Met Lys Trp Asp Glu Glu Arg
225                 230                 235                 240

Phe Gly Leu Glu Tyr Asp Leu Asp Ile Tyr Met Ile Val Ala Val Asp
                245                 250                 255

Phe Phe Asn Met Gly Ala Met Glu Asn Lys Gly Leu Asn Ile Phe Asn
```

-continued

```
            260                 265                 270
Ser Lys Tyr Val Leu Ala Arg Thr Asp Thr Ala Thr Asp Lys Asp Tyr
        275                 280                 285
Leu Asp Ile Glu Arg Val Ile Gly His Glu Tyr Phe His Asn Trp Thr
        290                 295                 300
Gly Asn Arg Val Thr Cys Arg Asp Trp Phe Gln Leu Ser Leu Lys Glu
305                 310                 315                 320
Gly Leu Thr Val Phe Arg Asp Gln Glu Phe Ser Ser Asp Leu Gly Ser
                325                 330                 335
Arg Ala Val Asn Arg Ile Asn Asn Val Arg Thr Met Arg Gly Leu Gln
                340                 345                 350
Phe Ala Glu Asp Ala Ser Pro Met Ala His Pro Ile Arg Pro Asp Met
                355                 360                 365
Val Ile Glu Met Asn Asn Phe Tyr Thr Leu Thr Val Tyr Glu Lys Gly
        370                 375                 380
Ala Glu Val Ile Arg Met Ile His Thr Leu Leu Gly Glu Glu Asn Phe
385                 390                 395                 400
Gln Lys Gly Met Gln Leu Tyr Phe Glu Arg His Asp Gly Ser Ala Ala
                405                 410                 415
Thr Cys Asp Asp Phe Val Gln Ala Met Glu Asp Ala Ser Asn Val Asp
                420                 425                 430
Leu Ser His Phe Arg Arg Trp Tyr Ser Gln Ser Gly Thr Pro Ile Val
                435                 440                 445
Thr Val Lys Asp Asp Tyr Asn Pro Glu Thr Glu Gln Tyr Thr Leu Thr
        450                 455                 460
Ile Ser Gln Arg Thr Pro Ala Thr Pro Asp Gln Ala Glu Lys Gln Pro
465                 470                 475                 480
Leu His Ile Pro Phe Ala Ile Glu Leu Tyr Asp Asn Glu Gly Lys Val
                485                 490                 495
Ile Pro Leu Gln Lys Gly Gly His Pro Val Asn Ser Val Leu Asn Val
                500                 505                 510
Thr Gln Ala Glu Gln Thr Phe Val Phe Asp Asn Val Tyr Phe Gln Pro
        515                 520                 525
Val Pro Ala Leu Leu Cys Glu Phe Ser Ala Pro Val Lys Leu Glu Tyr
        530                 535                 540
Lys Trp Ser Asp Gln Gln Leu Thr Phe Leu Met Arg His Ala Arg Asn
545                 550                 555                 560
Asp Phe Ser Arg Trp Asp Ala Ala Gln Ser Leu Leu Ala Thr Tyr Ile
                565                 570                 575
Lys Leu Asn Val Ala Arg His Gln Gln Gly Gln Pro Leu Ser Leu Pro
                580                 585                 590
Val His Val Ala Asp Ala Phe Arg Ala Val Leu Leu Asp Glu Lys Ile
        595                 600                 605
Asp Pro Ala Leu Ala Ala Glu Ile Leu Thr Leu Pro Ser Val Asn Glu
        610                 615                 620
Met Ala Glu Leu Phe Asp Ile Ile Asp Pro Ile Ala Ile Ala Glu Val
625                 630                 635                 640
Arg Glu Ala Leu Thr Arg Thr Leu Ala Thr Glu Leu Ala Asp Glu Leu
                645                 650                 655
Leu Ala Ile Tyr Asn Ala Asn Tyr Gln Ser Glu Tyr Arg Val Glu His
                660                 665                 670
Glu Asp Ile Ala Lys Arg Thr Leu Arg Asn Ala Cys Leu Arg Phe Leu
                675                 680                 685
```

```
Ala Phe Gly Glu Thr His Leu Ala Asp Val Leu Val Ser Lys Gln Phe
        690                 695                 700

His Glu Ala Asn Asn Met Thr Asp Ala Leu Ala Leu Ser Ala Ala
705                 710                 715                 720

Val Ala Ala Gln Leu Pro Cys Arg Asp Ala Leu Met Gln Glu Tyr Asp
                    725                 730                 735

Asp Lys Trp His Gln Asn Gly Leu Val Met Asp Lys Trp Phe Ile Leu
                740                 745                 750

Gln Ala Thr Ser Pro Ala Ala Asn Val Leu Glu Thr Val Arg Gly Leu
                755                 760                 765

Leu Gln His Arg Ser Phe Thr Met Ser Asn Pro Asn Arg Ile Arg Ser
770                 775                 780

Leu Ile Gly Ala Phe Ala Gly Ser Asn Pro Ala Ala Phe His Ala Glu
785                 790                 795                 800

Asp Gly Ser Gly Tyr Leu Phe Leu Val Glu Met Leu Thr Asp Leu Asn
                805                 810                 815

Ser Arg Asn Pro Gln Val Ala Ser Arg Leu Ile Glu Pro Leu Ile Arg
                820                 825                 830

Leu Lys Arg Tyr Asp Ala Lys Arg Gln Glu Lys Met Arg Ala Ala Leu
                835                 840                 845

Glu Gln Leu Lys Gly Leu Glu Asn Leu Ser Gly Asp Leu Tyr Glu Lys
850                 855                 860

Ile Thr Lys Ala Leu Ala
865                 870

<210> SEQ ID NO 59
<211> LENGTH: 535
<212> TYPE: PRT
<213> ORGANISM: Escherichia coli

<400> SEQUENCE: 59

Met Arg Ile Ser Leu Lys Lys Ser Gly Met Leu Lys Leu Gly Leu Ser
  1                 5                  10                  15

Leu Val Ala Met Thr Val Ala Ala Ser Val Gln Ala Lys Thr Leu Val
                 20                  25                  30

Tyr Cys Ser Glu Gly Ser Pro Glu Gly Phe Asn Pro Gln Leu Phe Thr
             35                  40                  45

Ser Gly Thr Thr Tyr Asp Ala Ser Ser Val Pro Leu Tyr Asn Arg Leu
         50                  55                  60

Val Glu Phe Lys Ile Gly Thr Thr Glu Val Ile Pro Gly Leu Ala Glu
 65                  70                  75                  80

Lys Trp Glu Val Ser Glu Asp Gly Lys Thr Tyr Thr Phe His Leu Arg
                 85                  90                  95

Lys Gly Val Lys Trp His Asp Asn Lys Glu Phe Lys Pro Thr Arg Glu
                100                 105                 110

Leu Asn Ala Asp Asp Val Val Phe Ser Phe Asp Arg Gln Lys Asn Ala
            115                 120                 125

Gln Asn Pro Tyr His Lys Val Ser Gly Gly Ser Tyr Glu Tyr Phe Glu
        130                 135                 140

Gly Met Gly Leu Pro Glu Leu Ile Ser Glu Val Lys Lys Val Asp Asp
145                 150                 155                 160

Asn Thr Val Gln Phe Val Leu Thr Arg Pro Glu Ala Pro Phe Leu Ala
                165                 170                 175

Asp Leu Ala Met Asp Phe Ala Ser Ile Leu Ser Lys Glu Tyr Ala Asp
            180                 185                 190
```

Ala Met Met Lys Ala Gly Thr Pro Glu Lys Leu Asp Leu Asn Pro Ile
    195                 200                 205

Gly Thr Gly Pro Phe Gln Leu Gln Gln Tyr Gln Lys Asp Ser Arg Ile
210                 215                 220

Arg Tyr Lys Ala Phe Asp Gly Tyr Trp Gly Thr Lys Pro Gln Ile Asp
225                 230                 235                 240

Thr Leu Val Phe Ser Ile Thr Pro Asp Ala Ser Val Arg Tyr Ala Lys
                245                 250                 255

Leu Gln Lys Asn Glu Cys Gln Val Met Pro Tyr Pro Asn Pro Ala Asp
            260                 265                 270

Ile Ala Arg Met Lys Gln Asp Lys Ser Ile Asn Leu Met Glu Met Pro
        275                 280                 285

Gly Leu Asn Val Gly Tyr Leu Ser Tyr Asn Val Gln Lys Lys Pro Leu
    290                 295                 300

Asp Asp Val Lys Val Arg Gln Ala Leu Thr Tyr Ala Val Asn Lys Asp
305                 310                 315                 320

Ala Ile Ile Lys Ala Val Tyr Gln Gly Ala Gly Val Ser Ala Lys Asn
                325                 330                 335

Leu Ile Pro Pro Thr Met Trp Gly Tyr Asn Asp Asp Val Gln Asp Tyr
            340                 345                 350

Thr Tyr Asp Pro Glu Lys Ala Lys Ala Leu Leu Lys Glu Ala Gly Leu
        355                 360                 365

Glu Lys Gly Phe Ser Ile Asp Leu Trp Ala Met Pro Val Gln Arg Pro
    370                 375                 380

Tyr Asn Pro Asn Ala Arg Arg Met Ala Glu Met Ile Gln Ala Asp Trp
385                 390                 395                 400

Ala Lys Val Gly Val Gln Ala Lys Ile Val Thr Tyr Glu Trp Gly Glu
                405                 410                 415

Tyr Leu Lys Arg Ala Lys Asp Gly Glu His Gln Thr Val Met Met Gly
            420                 425                 430

Trp Thr Gly Asp Asn Gly Asp Pro Asp Asn Phe Phe Ala Thr Leu Phe
        435                 440                 445

Ser Cys Ala Ala Ser Glu Gln Gly Ser Asn Tyr Ser Lys Trp Cys Tyr
    450                 455                 460

Lys Pro Phe Glu Asp Leu Ile Gln Pro Ala Arg Ala Thr Asp Asp His
465                 470                 475                 480

Asn Lys Arg Val Glu Leu Tyr Lys Gln Ala Gln Val Val Met His Asp
                485                 490                 495

Gln Ala Pro Ala Leu Ile Ile Ala His Ser Thr Val Phe Glu Pro Val
            500                 505                 510

Arg Lys Glu Val Lys Gly Tyr Val Val Asp Pro Leu Gly Lys His His
        515                 520                 525

Phe Glu Asn Val Ser Ile Glu
    530                 535

<210> SEQ ID NO 60
<211> LENGTH: 339
<212> TYPE: PRT
<213> ORGANISM: Escherichia coli

<400> SEQUENCE: 60

Met Leu Gln Phe Ile Leu Arg Arg Leu Gly Leu Val Ile Pro Thr Phe
1               5                   10                  15

Ile Gly Ile Thr Leu Leu Thr Phe Ala Phe Val His Met Ile Pro Gly
            20                  25                  30

```
Asp Pro Val Met Ile Met Ala Gly Glu Arg Gly Ile Ser Pro Glu Arg
        35                  40                  45

His Ala Gln Leu Leu Ala Glu Leu Gly Leu Asp Lys Pro Met Trp Gln
 50                  55                  60

Gln Tyr Leu His Tyr Ile Trp Gly Val Met His Gly Asp Leu Gly Ile
 65                  70                  75                  80

Ser Met Lys Ser Arg Ile Pro Val Trp Glu Glu Phe Val Pro Arg Phe
                 85                  90                  95

Gln Ala Thr Leu Glu Leu Gly Val Cys Ala Met Ile Phe Ala Thr Ala
            100                 105                 110

Val Gly Ile Pro Val Gly Val Leu Ala Ala Val Lys Arg Gly Ser Ile
        115                 120                 125

Phe Asp His Thr Ala Val Gly Leu Ala Leu Thr Gly Tyr Ser Met Pro
130                 135                 140

Ile Phe Trp Trp Gly Met Met Leu Ile Met Leu Val Ser Val His Trp
145                 150                 155                 160

Asn Leu Thr Pro Val Ser Gly Arg Val Ser Asp Met Val Phe Leu Asp
                165                 170                 175

Asp Ser Asn Pro Leu Thr Gly Phe Met Leu Ile Asp Thr Ala Ile Trp
            180                 185                 190

Gly Glu Asp Gly Asn Phe Ile Asp Ala Val Ala His Met Ile Leu Pro
        195                 200                 205

Ala Ile Val Leu Gly Thr Ile Pro Leu Ala Val Ile Val Arg Met Thr
210                 215                 220

Arg Ser Ser Met Leu Glu Val Leu Gly Glu Asp Tyr Ile Arg Thr Ala
225                 230                 235                 240

Arg Ala Lys Gly Leu Thr Arg Met Arg Val Ile Ile Val His Ala Leu
                245                 250                 255

Arg Asn Ala Met Leu Pro Val Val Thr Val Ile Gly Leu Gln Val Gly
            260                 265                 270

Thr Leu Leu Ala Gly Ala Ile Leu Thr Glu Thr Ile Phe Ser Trp Pro
        275                 280                 285

Gly Leu Gly Arg Trp Leu Ile Asp Ala Leu Gln Arg Arg Asp Tyr Pro
290                 295                 300

Val Val Gln Gly Gly Val Leu Leu Val Ala Thr Met Ile Ile Leu Val
305                 310                 315                 320

Asn Leu Leu Val Asp Leu Leu Tyr Gly Val Val Asn Pro Arg Ile Arg
                325                 330                 335

His Lys Lys

<210> SEQ ID NO 61
<211> LENGTH: 300
<212> TYPE: PRT
<213> ORGANISM: Escherichia coli

<400> SEQUENCE: 61

Met Ser Gln Val Thr Glu Asn Lys Val Ile Ser Ala Pro Val Pro Met
 1               5                  10                  15

Thr Pro Leu Gln Glu Phe Trp His Tyr Phe Lys Arg Asn Lys Gly Ala
            20                  25                  30

Val Val Gly Leu Val Tyr Val Val Ile Val Leu Phe Ile Ala Ile Phe
        35                  40                  45

Ala Asn Trp Ile Ala Pro Tyr Asn Pro Ala Glu Gln Phe Arg Asp Ala
 50                  55                  60

Leu Leu Ala Pro Pro Ala Trp Gln Glu Gly Gly Ser Met Ala His Leu
```

```
                65                  70                  75                  80
Leu Gly Thr Asp Asp Val Gly Arg Asp Val Leu Ser Arg Leu Met Tyr
                        85                  90                  95
Gly Ala Arg Leu Ser Leu Leu Val Gly Cys Leu Val Val Val Leu Ser
                       100                 105                 110
Leu Ile Met Gly Val Ile Leu Gly Leu Ile Ala Gly Tyr Phe Gly Gly
                       115                 120                 125
Leu Val Asp Asn Ile Ile Met Arg Val Val Asp Ile Met Leu Ala Leu
                       130                 135                 140
Pro Ser Leu Leu Leu Ala Leu Val Leu Ala Ile Phe Gly Pro Ser
145                    150                 155                 160
Ile Gly Asn Ala Ala Leu Ala Leu Thr Phe Val Ala Leu Pro His Tyr
                       165                 170                 175
Val Arg Leu Thr Arg Ala Ala Val Leu Val Glu Val Asn Arg Asp Tyr
                       180                 185                 190
Val Thr Ala Ser Arg Val Ala Gly Ala Gly Ala Met Arg Gln Met Phe
                       195                 200                 205
Ile Asn Ile Phe Pro Asn Cys Leu Ala Pro Leu Ile Val Gln Ala Ser
                       210                 215                 220
Leu Gly Phe Ser Asn Ala Ile Leu Asp Met Ala Ala Leu Gly Phe Leu
225                    230                 235                 240
Gly Met Gly Ala Gln Pro Pro Thr Pro Glu Trp Gly Thr Met Leu Ser
                       245                 250                 255
Asp Val Leu Gln Phe Ala Gln Ser Ala Trp Trp Val Val Thr Phe Pro
                       260                 265                 270
Gly Leu Ala Ile Leu Leu Thr Val Leu Ala Phe Asn Leu Met Gly Asp
                       275                 280                 285
Gly Leu Arg Asp Ala Leu Asp Pro Lys Leu Lys Gln
                       290                 295                 300

<210> SEQ ID NO 62
<211> LENGTH: 327
<212> TYPE: PRT
<213> ORGANISM: Escherichia coli

<400> SEQUENCE: 62

Met Ala Leu Leu Asn Val Asp Lys Leu Ser Val His Phe Gly Asp Glu
  1                   5                  10                  15
Ser Ala Pro Phe Arg Ala Val Asp Arg Ile Ser Tyr Ser Val Lys Gln
                       20                  25                  30
Gly Glu Val Val Gly Ile Val Gly Glu Ser Gly Ser Gly Lys Ser Val
                       35                  40                  45
Ser Ser Leu Ala Ile Met Gly Leu Ile Asp Tyr Pro Gly Arg Val Met
                       50                  55                  60
Ala Glu Lys Leu Glu Phe Asn Gly Gln Asp Leu Gln Arg Ile Ser Glu
 65                    70                  75                  80
Lys Glu Arg Arg Asn Leu Val Gly Ala Glu Val Ala Met Ile Phe Gln
                       85                  90                  95
Asp Pro Met Thr Ser Leu Asn Pro Cys Tyr Thr Val Gly Phe Gln Ile
                      100                 105                 110
Met Glu Ala Ile Lys Val His Gln Gly Gly Asn Lys Ser Thr Arg Arg
                      115                 120                 125
Gln Arg Ala Ile Asp Leu Leu Asn Gln Val Gly Ile Pro Asp Pro Ala
                      130                 135                 140
Ser Arg Leu Asp Val Tyr Pro His Gln Leu Ser Gly Gly Met Ser Gln
```

```
                145                 150                 155                 160
Arg Val Met Ile Ala Met Ala Ile Ala Cys Arg Pro Lys Leu Leu Ile
                165                 170                 175

Ala Asp Glu Pro Thr Thr Ala Leu Asp Val Thr Ile Gln Ala Gln Ile
                180                 185                 190

Ile Glu Leu Leu Leu Glu Leu Gln Gln Lys Glu Asn Met Ala Leu Val
                195                 200                 205

Leu Ile Thr His Asp Leu Ala Leu Val Ala Glu Ala His Lys Ile
            210                 215                 220

Ile Val Met Tyr Ala Gly Gln Val Val Glu Thr Gly Asp Ala His Ala
225                 230                 235                 240

Ile Phe His Ala Pro Arg His Pro Tyr Thr Gln Ala Leu Leu Arg Ala
                245                 250                 255

Leu Pro Glu Phe Ala Gln Asp Lys Glu Arg Leu Ala Ser Leu Pro Gly
                260                 265                 270

Val Val Pro Gly Lys Tyr Asp Arg Pro Asn Gly Cys Leu Leu Asn Pro
                275                 280                 285

Arg Cys Pro Tyr Ala Thr Asp Arg Cys Arg Ala Glu Glu Pro Ala Leu
                290                 295                 300

Asn Met Leu Ala Asp Gly Arg Gln Ser Lys Cys His Tyr Pro Leu Asp
305                 310                 315                 320

Asp Ala Gly Arg Pro Thr Leu
                325

<210> SEQ ID NO 63
<211> LENGTH: 334
<212> TYPE: PRT
<213> ORGANISM: Escherichia coli

<400> SEQUENCE: 63

Met Ser Thr Gln Glu Ala Thr Leu Gln Gln Pro Leu Leu Gln Ala Ile
1               5                   10                  15

Asp Leu Lys Lys His Tyr Pro Val Lys Lys Gly Met Phe Ala Pro Glu
                20                  25                  30

Arg Leu Val Lys Ala Leu Asp Gly Val Ser Phe Asn Leu Glu Arg Gly
            35                  40                  45

Lys Thr Leu Ala Val Val Gly Glu Ser Gly Cys Gly Lys Ser Thr Leu
    50                  55                  60

Gly Arg Leu Leu Thr Met Ile Glu Met Pro Thr Gly Gly Glu Leu Tyr
65                  70                  75                  80

Tyr Gln Gly Gln Asp Leu Leu Lys His Asp Pro Gln Ala Gln Lys Leu
                85                  90                  95

Arg Arg Gln Lys Ile Gln Ile Val Phe Gln Asn Pro Tyr Gly Ser Leu
                100                 105                 110

Asn Pro Arg Lys Lys Val Gly Gln Ile Leu Glu Glu Pro Leu Leu Ile
                115                 120                 125

Asn Thr Ser Leu Ser Lys Glu Gln Arg Arg Glu Lys Ala Leu Ser Met
            130                 135                 140

Met Ala Lys Val Gly Leu Lys Thr Glu His Tyr Asp Arg Tyr Pro His
145                 150                 155                 160

Met Phe Ser Gly Gly Gln Arg Gln Arg Ile Ala Ile Ala Arg Gly Leu
                165                 170                 175

Met Leu Asp Pro Asp Val Val Ile Ala Asp Glu Pro Val Ser Ala Leu
                180                 185                 190

Asp Val Ser Val Arg Ala Gln Val Leu Asn Leu Met Met Asp Leu Gln
```

```
          195                 200                 205
Gln Glu Leu Gly Leu Ser Tyr Val Phe Ile Ser His Asp Leu Ser Val
    210                 215                 220

Val Glu His Ile Ala Asp Glu Val Met Val Met Tyr Leu Gly Arg Cys
225                 230                 235                 240

Val Glu Lys Gly Thr Lys Asp Gln Ile Phe Asn Asn Pro Arg His Pro
                245                 250                 255

Tyr Thr Gln Ala Leu Leu Ser Ala Thr Pro Arg Leu Asn Pro Asp Asp
                260                 265                 270

Arg Arg Glu Arg Ile Lys Leu Ser Gly Glu Leu Pro Ser Pro Leu Asn
                275                 280                 285

Pro Pro Gly Cys Ala Phe Asn Ala Arg Cys Arg Arg Phe Gly
    290                 295                 300

Pro Cys Thr Gln Leu Gln Pro Gln Leu Lys Asp Tyr Gly Gly Gln Leu
305                 310                 315                 320

Val Ala Cys Phe Ala Val Asp Gln Asp Glu Asn Pro Gln Arg
                325                 330
```

<210> SEQ ID NO 64
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
gaagttccta tactttctag agaataggaa cttc                              34

<210> SEQ ID NO 65
<211> LENGTH: 1509
<212> TYPE: DNA
<213> ORGANISM: Escherichia coli

<400> SEQUENCE: 65

```
atg gag ttt agt gta aaa agc ggt agc ccg gag aaa cag cgg agt gcc    48
Met Glu Phe Ser Val Lys Ser Gly Ser Pro Glu Lys Gln Arg Ser Ala
1               5                   10                  15 tgc atc gtc gtg ggc gtc ttc gaa cca cgt cgc ctt tct ccg att gca    96
Cys Ile Val Val Gly Val Phe Glu Pro Arg Arg Leu Ser Pro Ile Ala
                20                  25                  30 gaa cag ctc gat aaa atc agc gat ggg tac atc agc gcc ctg cta cgt   144
Glu Gln Leu Asp Lys Ile Ser Asp Gly Tyr Ile Ser Ala Leu Leu Arg
            35                  40                  45 cgg ggc gaa ctg gaa gga aaa ccg ggg cag aca ttg ttg ctg cac cat   192
Arg Gly Glu Leu Glu Gly Lys Pro Gly Gln Thr Leu Leu Leu His His
        50                  55                  60 gtt ccg aat gta ctt tcc gag cga att ctc ctt att ggt tgc ggc aaa   240
Val Pro Asn Val Leu Ser Glu Arg Ile Leu Leu Ile Gly Cys Gly Lys
65                  70                  75                  80 gaa cgt gag ctg gat gag cgt cag tac aag cag gtt att cag aaa acc   288
Glu Arg Glu Leu Asp Glu Arg Gln Tyr Lys Gln Val Ile Gln Lys Thr
                85                  90                  95 att aat acg ctg aat gat act ggc tca atg gaa gcg tcg tgc ttt ctg   336
Ile Asn Thr Leu Asn Asp Thr Gly Ser Met Glu Ala Val Cys Phe Leu
            100                 105                 110 act gag ctg cac gtt aaa ggc cgt aac aac tac tgg aaa gtg cgt cag   384
Thr Glu Leu His Val Lys Gly Arg Asn Asn Tyr Trp Lys Val Arg Gln
        115                 120                 125 gct gtc gag acg gca aaa gag acg ctc tac agt ttc gat cag ctg aaa   432
```

```
                Ala Val Glu Thr Ala Lys Glu Thr Leu Tyr Ser Phe Asp Gln Leu Lys
                    130                 135                 140 acg aac aag agc gaa ccg cgt cgt ccg ctg cgt aag atg gtg ttc aac       480
Thr Asn Lys Ser Glu Pro Arg Arg Pro Leu Arg Lys Met Val Phe Asn
145                 150                 155                 160 gtg ccg acc cgc cgt gaa ctg acc agc ggt gag cgc gcg atc cag cac       528
Val Pro Thr Arg Arg Glu Leu Thr Ser Gly Glu Arg Ala Ile Gln His
                165                 170                 175 ggt ctg gcg att gcc gcc ggg att aaa gca gca aaa gat ctc ggc aat       576
Gly Leu Ala Ile Ala Ala Gly Ile Lys Ala Ala Lys Asp Leu Gly Asn
            180                 185                 190 atg ccg ccg aat atc tgt aac gcc gct tac ctc gct tca caa gcg cgc       624
Met Pro Pro Asn Ile Cys Asn Ala Ala Tyr Leu Ala Ser Gln Ala Arg
        195                 200                 205 cag ctg gct gac agc tac agc aag aat gtc atc acc cgc gtt atc ggc       672
Gln Leu Ala Asp Ser Tyr Ser Lys Asn Val Ile Thr Arg Val Ile Gly
    210                 215                 220 gaa cag cag atg aaa gag ctg ggg atg cat tcc tat ctg gcg gtc ggt       720
Glu Gln Gln Met Lys Glu Leu Gly Met His Ser Tyr Leu Ala Val Gly
225                 230                 235                 240 cag ggt tcg caa aac gaa tcg ctg atg tcg gtg att gag tac aaa ggc       768
Gln Gly Ser Gln Asn Glu Ser Leu Met Ser Val Ile Glu Tyr Lys Gly
                245                 250                 255 aac gcg tcg gaa gat gca cgc cca atc gtg ctg gtg ggt aaa ggt tta       816
Asn Ala Ser Glu Asp Ala Arg Pro Ile Val Leu Val Gly Lys Gly Leu
                260                 265                 270 acc ttc gac tcc ggc ggt atc tcg atc aag cct tca gaa ggc atg gat       864
Thr Phe Asp Ser Gly Gly Ile Ser Ile Lys Pro Ser Glu Gly Met Asp
            275                 280                 285 gag atg aag tac gat atg tgc ggt gcg gca gcg gtt tac ggc gtg atg       912
Glu Met Lys Tyr Asp Met Cys Gly Ala Ala Ala Val Tyr Gly Val Met
        290                 295                 300 cgg atg gtc gcg gag cta caa ctg ccg att aac gtt atc ggc gtg ttg       960
Arg Met Val Ala Glu Leu Gln Leu Pro Ile Asn Val Ile Gly Val Leu
305                 310                 315                 320 gca ggc tgc gaa aac atg cct ggc gga cga gcc tat cgt ccg ggc gat      1008
Ala Gly Cys Glu Asn Met Pro Gly Gly Arg Ala Tyr Arg Pro Gly Asp
                325                 330                 335 gtg tta acc acc atg tcc ggt caa acc gtt gaa gtg ctg aac acc gac      1056
Val Leu Thr Thr Met Ser Gly Gln Thr Val Glu Val Leu Asn Thr Asp
                340                 345                 350 gct gaa ggc cgc ctg gta ctg tgc gac gtg tta act tac gtt gag cgt      1104
Ala Glu Gly Arg Leu Val Leu Cys Asp Val Leu Thr Tyr Val Glu Arg
            355                 360                 365 ttt gag ccg gaa gcg gtg att gac gtg gcg acg ctg acc ggt gcc tgc      1152
Phe Glu Pro Glu Ala Val Ile Asp Val Ala Thr Leu Thr Gly Ala Cys
        370                 375                 380 gtg atc gcg ctg ggt cat cat att act ggt ctg atg gcg aac cat aat      1200
Val Ile Ala Leu Gly His His Ile Thr Gly Leu Met Ala Asn His Asn
385                 390                 395                 400 ccg ctg gcc cat gaa ctg att gcc gcg tct gaa caa tcc ggt gac cgc      1248
Pro Leu Ala His Glu Leu Ile Ala Ala Ser Glu Gln Ser Gly Asp Arg
                405                 410                 415 gca tgg cgc tta ccg ctg ggt gac gag tat cag gaa caa ctg gag tcc      1296
Ala Trp Arg Leu Pro Leu Gly Asp Glu Tyr Gln Glu Gln Leu Glu Ser
                420                 425                 430 aat ttt gcc gat atg gcg aac att ggc ggt cgt cct ggt ggg gcg att      1344
Asn Phe Ala Asp Met Ala Asn Ile Gly Gly Arg Pro Gly Gly Ala Ile
            435                 440                 445 acc gca ggt tgc ttc ctg tca cgc ttt acc cgt aag tac aac tgg gcg      1392
```

```
                              Thr Ala Gly Cys Phe Leu Ser Arg Phe Thr Arg Lys Tyr Asn Trp Ala
                                  450                 455                 460 cac ctg gat atc gcc ggt acc gcc tgg cgt tct ggt aaa gca aaa ggc                   1440
His Leu Asp Ile Ala Gly Thr Ala Trp Arg Ser Gly Lys Ala Lys Gly
465                 470                 475                 480 gcc acc ggt cgt ccg gta gcg ttg ctg gca cag ttc ctg tta aac cgc                   1488
Ala Thr Gly Arg Pro Val Ala Leu Leu Ala Gln Phe Leu Leu Asn Arg
                485                 490                 495 gct ggg ttt aac ggc gaa gag                                                       1509
Ala Gly Phe Asn Gly Glu Glu
                500

<210> SEQ ID NO 66
<211> LENGTH: 1281
<212> TYPE: DNA
<213> ORGANISM: Escherichia coli

<400> SEQUENCE: 66 atg aca gaa gcg atg aag att acc ctc tct acc caa cct gcc gac gcg                    48
Met Thr Glu Ala Met Lys Ile Thr Leu Ser Thr Gln Pro Ala Asp Ala
1               5                   10                  15 cgc tgg gga gaa aaa gca act tac agc att aat aat gac ggc att acc                    96
Arg Trp Gly Glu Lys Ala Thr Tyr Ser Ile Asn Asn Asp Gly Ile Thr
                20                  25                  30 ctg cat ttg aac ggg gca gac gat ctg ggg ctg atc cag cgt gcg gcg                   144
Leu His Leu Asn Gly Ala Asp Asp Leu Gly Leu Ile Gln Arg Ala Ala
            35                  40                  45 cgc aag att gac ggt ctg ggc atc aag cat gtt cag tta agc ggt gaa                   192
Arg Lys Ile Asp Gly Leu Gly Ile Lys His Val Gln Leu Ser Gly Glu
        50                  55                  60 ggc tgg gat gcg gat cgc tgc tgg gca ttc tgg caa ggt tac aaa gcc                   240
Gly Trp Asp Ala Asp Arg Cys Trp Ala Phe Trp Gln Gly Tyr Lys Ala
65                  70                  75                  80 ccg aaa ggc acg cgt aaa gtg gtg tgg ccg gat ctg gac gat gcc cag                   288
Pro Lys Gly Thr Arg Lys Val Val Trp Pro Asp Leu Asp Asp Ala Gln
                85                  90                  95 cgc cag gaa ctg gat aac cgc ctg atg atc atc gac tgg gtg cgt gac                   336
Arg Gln Glu Leu Asp Asn Arg Leu Met Ile Ile Asp Trp Val Arg Asp
                100                 105                 110 acc atc aac gca ccg gca gaa gaa ttg gga cca tcg caa ctg gca cag                   384
Thr Ile Asn Ala Pro Ala Glu Glu Leu Gly Pro Ser Gln Leu Ala Gln
            115                 120                 125 cgt gct gtt gat ctg atc agc aac gtc gcg ggc gat cgt gtg act tat                   432
Arg Ala Val Asp Leu Ile Ser Asn Val Ala Gly Asp Arg Val Thr Tyr
        130                 135                 140 cgg atc acc aaa ggc gaa gat ctg cgt gag caa ggt tat atg ggg ctg                   480
Arg Ile Thr Lys Gly Glu Asp Leu Arg Glu Gln Gly Tyr Met Gly Leu
145                 150                 155                 160 cac aca gtc gga cgc ggt tca gaa cgt tct ccg gta ttg ctg gcg ctg                   528
His Thr Val Gly Arg Gly Ser Glu Arg Ser Pro Val Leu Leu Ala Leu
                165                 170                 175 gat tac aac cca act ggc gat aaa gaa gcg cca gtg tac gcg tgc ctg                   576
Asp Tyr Asn Pro Thr Gly Asp Lys Glu Ala Pro Val Tyr Ala Cys Leu
                180                 185                 190 gta ggt aaa ggt atc act ttt gac tcc ggc ggc tac agc atc aaa cag                   624
Val Gly Lys Gly Ile Thr Phe Asp Ser Gly Gly Tyr Ser Ile Lys Gln
            195                 200                 205 act gcg ttt atg gac tcg atg aag tcg gac atg ggc ggc gcg gca acg                   672
Thr Ala Phe Met Asp Ser Met Lys Ser Asp Met Gly Gly Ala Ala Thr
        210                 215                 220 gtt acc ggg gcg ctg gca ttt gcc att acg cgc gga ctg aac aag cgc                   720
```

-continued

```
Val Thr Gly Ala Leu Ala Phe Ala Ile Thr Arg Gly Leu Asn Lys Arg
225                 230                 235                 240 gtg aag ctg ttc ctc tgc tgt gcg gat aac ctg att agc ggc aat gcg      768
Val Lys Leu Phe Leu Cys Cys Ala Asp Asn Leu Ile Ser Gly Asn Ala
                245                 250                 255 ttc aag ctg ggc gat atc atc acc tat cgc aac ggt aaa aaa gtt gaa      816
Phe Lys Leu Gly Asp Ile Ile Thr Tyr Arg Asn Gly Lys Lys Val Glu
            260                 265                 270 gtg atg aac act gat gcc gaa ggg cgt ctg gtg ctt gcc gat ggt ctg      864
Val Met Asn Thr Asp Ala Glu Gly Arg Leu Val Leu Ala Asp Gly Leu
        275                 280                 285 att gat gcc agt gcg cag aaa ccg gaa atg atc att gat gcg gcg acc      912
Ile Asp Ala Ser Ala Gln Lys Pro Glu Met Ile Ile Asp Ala Ala Thr
    290                 295                 300 ctc acc ggg gcg gcg aaa act gcg ctg ggt aat gat tat cac gcg ctg      960
Leu Thr Gly Ala Ala Lys Thr Ala Leu Gly Asn Asp Tyr His Ala Leu
305                 310                 315                 320 ttc agt ttt gac gat gcg ctg gcc ggt cgc ttg ctg gcg agt gcc gcg     1008
Phe Ser Phe Asp Asp Ala Leu Ala Gly Arg Leu Leu Ala Ser Ala Ala
                325                 330                 335 cag gag aac gaa ccg ttc tgg cgt ctg ccg ctg gcg gag ttc cac cgc     1056
Gln Glu Asn Glu Pro Phe Trp Arg Leu Pro Leu Ala Glu Phe His Arg
            340                 345                 350 agc cag ctg ccg tct aac ttt gcc gaa ctg aac aat acc gga agc gcg     1104
Ser Gln Leu Pro Ser Asn Phe Ala Glu Leu Asn Asn Thr Gly Ser Ala
        355                 360                 365 gcg tat ccg gca ggc gcg agc acg gcg gcg ggc ttc ctg tcg cac ttt     1152
Ala Tyr Pro Ala Gly Ala Ser Thr Ala Ala Gly Phe Leu Ser His Phe
    370                 375                 380 gtt gag aac tat cag caa ggc tgg ctg cat atc gac tgc tcg gcg act     1200
Val Glu Asn Tyr Gln Gln Gly Trp Leu His Ile Asp Cys Ser Ala Thr
385                 390                 395                 400 tac cgt aaa gcg ccg gtt gaa cag tgg tct gcg ggc gct acg gga ctt     1248
Tyr Arg Lys Ala Pro Val Glu Gln Trp Ser Ala Gly Ala Thr Gly Leu
                405                 410                 415 ggt gtg cgc acg ata gct aat ctg tta acg gcg                         1281
Gly Val Arg Thr Ile Ala Asn Leu Leu Thr Ala
            420                 425

<210> SEQ ID NO 67
<211> LENGTH: 1455
<212> TYPE: DNA
<213> ORGANISM: Escherichia coli

<400> SEQUENCE: 67 gtg tct gaa ctg tct caa tta tct cca cag ccg ctg tgg gat att ttt       48
Val Ser Glu Leu Ser Gln Leu Ser Pro Gln Pro Leu Trp Asp Ile Phe
1               5                  10                  15 gcc aaa atc tgt tct att cct cac ccg tcc tat cat gaa gag caa ctc       96
Ala Lys Ile Cys Ser Ile Pro His Pro Ser Tyr His Glu Glu Gln Leu
            20                  25                  30 gct gaa tac att gtt ggt tgg gca aaa gag aaa ggt ttc cat gtc gaa      144
Ala Glu Tyr Ile Val Gly Trp Ala Lys Glu Lys Gly Phe His Val Glu
        35                  40                  45 cgc gat cag gta ggt aat atc ctg att cgt aaa cct gct acc gca ggt      192
Arg Asp Gln Val Gly Asn Ile Leu Ile Arg Lys Pro Ala Thr Ala Gly
    50                  55                  60 atg gaa aat cgt aaa ccg gtc gtc tta cag gcc cac ctc gat atg gtg      240
Met Glu Asn Arg Lys Pro Val Val Leu Gln Ala His Leu Asp Met Val
65                  70                  75                  80 ccg cag aaa aat aac gac acc gtg cat gac ttc acg aaa gat cct atc      288
```

-continued

```
                Pro Gln Lys Asn Asn Asp Thr Val His Asp Phe Thr Lys Asp Pro Ile
                                85                  90                  95 cag cct tat att gat ggc gaa tgg gtt aaa gcg cgc ggc acc acg ctg            336
Gln Pro Tyr Ile Asp Gly Glu Trp Val Lys Ala Arg Gly Thr Thr Leu
                100                 105                 110 ggt gcg gat aac ggc att ggt atg gcc tct gcg ctg gcg gtt ctg gct            384
Gly Ala Asp Asn Gly Ile Gly Met Ala Ser Ala Leu Ala Val Leu Ala
            115                 120                 125 gac gaa aac gtg gtt cac ggc ccg ctg gaa gtg ctg acc atg acc                432
Asp Glu Asn Val Val His Gly Pro Leu Glu Val Leu Thr Met Thr
        130                 135                 140 gaa gaa gcc ggt atg gac ggt gcg ttc ggc tta cag ggc aac tgg ttg            480
Glu Glu Ala Gly Met Asp Gly Ala Phe Gly Leu Gln Gly Asn Trp Leu
145                 150                 155                 160 cag gct gat att ctg att aac acc gac tcc gaa gaa gaa ggt gaa atc            528
Gln Ala Asp Ile Leu Ile Asn Thr Asp Ser Glu Glu Glu Gly Glu Ile
                165                 170                 175 tac atg ggt tgt gcg ggg ggt atc gac ttc acc tcc aac ctg cat tta            576
Tyr Met Gly Cys Ala Gly Gly Ile Asp Phe Thr Ser Asn Leu His Leu
            180                 185                 190 gat cgt gaa gcg gtt cca gct ggt ttt gaa acc ttc aag tta acc tta            624
Asp Arg Glu Ala Val Pro Ala Gly Phe Glu Thr Phe Lys Leu Thr Leu
        195                 200                 205 aaa ggt ctg aaa ggc ggt cac tcc ggc ggg gaa atc cac gtt ggg ctg            672
Lys Gly Leu Lys Gly Gly His Ser Gly Gly Glu Ile His Val Gly Leu
    210                 215                 220 ggt aat gcc aac aaa ctg ctg gtg cgc ttc ctg gcg ggt cat gcg gaa            720
Gly Asn Ala Asn Lys Leu Leu Val Arg Phe Leu Ala Gly His Ala Glu
225                 230                 235                 240 gaa ctg gat ctg cgc ctt atc gat ttc aac ggc ggc aca ctg cgt aac            768
Glu Leu Asp Leu Arg Leu Ile Asp Phe Asn Gly Gly Thr Leu Arg Asn
                245                 250                 255 gcc atc ccg cgt gaa gcc ttt gcg acc att gct gtc gca gct gat aaa            816
Ala Ile Pro Arg Glu Ala Phe Ala Thr Ile Ala Val Ala Ala Asp Lys
            260                 265                 270 gtc gac gtc ctg aaa tct ctg gtg aat acc tat cag gag atc ctg aaa            864
Val Asp Val Leu Lys Ser Leu Val Asn Thr Tyr Gln Glu Ile Leu Lys
        275                 280                 285 aac gag ctg gca gaa aaa gag aaa aat ctg gcc ttg ttg ctg gac tct            912
Asn Glu Leu Ala Glu Lys Glu Lys Asn Leu Ala Leu Leu Leu Asp Ser
    290                 295                 300 gta gcg aac gat aaa gct gcc ctg att gcg aaa tct cgc gat acc ttt            960
Val Ala Asn Asp Lys Ala Ala Leu Ile Ala Lys Ser Arg Asp Thr Phe
305                 310                 315                 320 att cgt ctg ctg aac gcc acc ccg aac ggt gtg att cgt aac tcc gat           1008
Ile Arg Leu Leu Asn Ala Thr Pro Asn Gly Val Ile Arg Asn Ser Asp
                325                 330                 335 gta gcc aaa ggt gtg gtt gaa acc tcc ctg aac gtc ggt gtg gtg acc           1056
Val Ala Lys Gly Val Val Glu Thr Ser Leu Asn Val Gly Val Val Thr
            340                 345                 350 atg act gac aat aac gta gaa att cac tgc ctg atc cgt tca ctg atc           1104
Met Thr Asp Asn Asn Val Glu Ile His Cys Leu Ile Arg Ser Leu Ile
        355                 360                 365 gac agc ggt aaa gac tac gtg gtg agc atg ctg gat tcg ctg ggt aaa           1152
Asp Ser Gly Lys Asp Tyr Val Val Ser Met Leu Asp Ser Leu Gly Lys
    370                 375                 380 ctg gct ggc gcg aaa acc gaa gcg aaa ggc gca tat cct ggc tgg cag           1200
Leu Ala Gly Ala Lys Thr Glu Ala Lys Gly Ala Tyr Pro Gly Trp Gln
385                 390                 395                 400 ccg gac gct aat tct ccg gtg atg cat ctg gta cgt gaa acc tat cag           1248
Pro Asp Ala Asn Ser Pro Val Met His Leu Val Arg Glu Thr Tyr Gln
```

```
Pro Asp Ala Asn Ser Pro Val Met His Leu Val Arg Glu Thr Tyr Gln
            405                 410                 415 cgc ctg ttc aac aag acg ccg aac atc cag att atc cac gcg ggc ctg      1296
Arg Leu Phe Asn Lys Thr Pro Asn Ile Gln Ile Ile His Ala Gly Leu
        420                 425                 430 gaa tgt ggt ctg ttc aaa aaa ccg tat ccg gaa atg gac atg gtt tct      1344
Glu Cys Gly Leu Phe Lys Lys Pro Tyr Pro Glu Met Asp Met Val Ser
            435                 440                 445 atc ggg cca act atc acc ggt cca cac tct ccg gat gag caa gtt cac      1392
Ile Gly Pro Thr Ile Thr Gly Pro His Ser Pro Asp Glu Gln Val His
        450                 455                 460 atc gaa agc gta ggt cat tac tgg aca ctg ctg act gaa ctg ctg aaa      1440
Ile Glu Ser Val Gly His Tyr Trp Thr Leu Leu Thr Glu Leu Leu Lys
465                 470                 475                 480 gaa att ccg gcg aag                                                   1455
Glu Ile Pro Ala Lys
            485

<210> SEQ ID NO 68
<211> LENGTH: 2610
<212> TYPE: DNA
<213> ORGANISM: Escherichia coli

<400> SEQUENCE: 68 atg act caa cag cca caa gcc aaa tac cgt cac gat tat cgt gcg ccg       48
Met Thr Gln Gln Pro Gln Ala Lys Tyr Arg His Asp Tyr Arg Ala Pro
  1               5                  10                  15 gat tac cag att act gat att gac ttg acc ttt gac ctc gac gcg caa       96
Asp Tyr Gln Ile Thr Asp Ile Asp Leu Thr Phe Asp Leu Asp Ala Gln
             20                  25                  30 aag acg gtc gtt acc gcg gtc agc cag gct gtc cgt cat ggt gca tca      144
Lys Thr Val Val Thr Ala Val Ser Gln Ala Val Arg His Gly Ala Ser
         35                  40                  45 gat gct ccc ctt cgt ctc aac ggc gaa gac ctc aaa ctg gtt tct gtt      192
Asp Ala Pro Leu Arg Leu Asn Gly Glu Asp Leu Lys Leu Val Ser Val
     50                  55                  60 cat att aat gat gag ccg tgg acc gcc tgg aaa gaa gaa gag ggc gca      240
His Ile Asn Asp Glu Pro Trp Thr Ala Trp Lys Glu Glu Glu Gly Ala
 65                  70                  75                  80 ctg gtt atc agt aat ttg ccg gag cgt ttt acg ctt aag atc att aat      288
Leu Val Ile Ser Asn Leu Pro Glu Arg Phe Thr Leu Lys Ile Ile Asn
                 85                  90                  95 gaa ata agc ccg gcg gcg aat acc gcg ctg gaa ggg ctt tat cag tca      336
Glu Ile Ser Pro Ala Ala Asn Thr Ala Leu Glu Gly Leu Tyr Gln Ser
            100                 105                 110 ggc gat gcg ctt tgc acc cag tgt gaa gcc gaa ggt ttc cgc cat att      384
Gly Asp Ala Leu Cys Thr Gln Cys Glu Ala Glu Gly Phe Arg His Ile
        115                 120                 125 acg tat tat ctc gac cgc ccg gac gtg ctg gcg cgt ttt acc acc aaa      432
Thr Tyr Tyr Leu Asp Arg Pro Asp Val Leu Ala Arg Phe Thr Thr Lys
    130                 135                 140 att att gcc gat aaa atc aaa tat ccc ttc ctg ctt tcc aat ggt aac      480
Ile Ile Ala Asp Lys Ile Lys Tyr Pro Phe Leu Leu Ser Asn Gly Asn
145                 150                 155                 160 cgc gtt gcg caa ggc gaa ctg gaa aac gga cgc cat tgg gta cag tgg      528
Arg Val Ala Gln Gly Glu Leu Glu Asn Gly Arg His Trp Val Gln Trp
                165                 170                 175 cag gac ccg ttc ccg aaa ccg tgc tac ctg ttt gcg ctg gtg gca ggc      576
Gln Asp Pro Phe Pro Lys Pro Cys Tyr Leu Phe Ala Leu Val Ala Gly
            180                 185                 190 gac ttt gat gta ctg cgc gat acc ttt acc acg cgt tct ggt cgc gaa      624
```

-continued

```
                Asp Phe Asp Val Leu Arg Asp Thr Phe Thr Thr Arg Ser Gly Arg Glu
                    195                 200                 205 gta gca ctg gag ctg tac gtc gat cgc ggc aac ctt gat cgc gcg ccg        672
Val Ala Leu Glu Leu Tyr Val Asp Arg Gly Asn Leu Asp Arg Ala Pro
210                 215                 220 tgg gcg atg acc tcg ctg aaa aac tcc atg aaa tgg gat gaa gaa cgc        720
Trp Ala Met Thr Ser Leu Lys Asn Ser Met Lys Trp Asp Glu Glu Arg
225                 230                 235                 240 ttt ggc ctg gag tat gac ctc gac atc tat atg atc gtc gcg gtg gat        768
Phe Gly Leu Glu Tyr Asp Leu Asp Ile Tyr Met Ile Val Ala Val Asp
                245                 250                 255 ttc ttc aat atg ggc gca atg gag aat aag ggg ctg aat atc ttt aac        816
Phe Phe Asn Met Gly Ala Met Glu Asn Lys Gly Leu Asn Ile Phe Asn
                260                 265                 270 tcc aaa tat gtg ctg gcc cgc acc gac acc gcc acc gac aaa gat tac        864
Ser Lys Tyr Val Leu Ala Arg Thr Asp Thr Ala Thr Asp Lys Asp Tyr
            275                 280                 285 ctc gat att gaa cgc gtt atc ggc cat gaa tat ttc cat aac tgg acc        912
Leu Asp Ile Glu Arg Val Ile Gly His Glu Tyr Phe His Asn Trp Thr
        290                 295                 300 ggt aac cga gtg acc tgt cgc gac tgg ttc cag ctc agc ctg aaa gaa        960
Gly Asn Arg Val Thr Cys Arg Asp Trp Phe Gln Leu Ser Leu Lys Glu
305                 310                 315                 320 ggt tta acc gtc ttc cgc gat cag gag ttc agc tct gac ctt ggt tcc       1008
Gly Leu Thr Val Phe Arg Asp Gln Glu Phe Ser Ser Asp Leu Gly Ser
                325                 330                 335 cgc gca gtt aac cgc atc aat aat gta cgc acc atg cgc gga ttg cag       1056
Arg Ala Val Asn Arg Ile Asn Asn Val Arg Thr Met Arg Gly Leu Gln
                340                 345                 350 ttt gca gaa gac gcc agc ccg atg gcg cac ccg atc cgc ccg gat atg       1104
Phe Ala Glu Asp Ala Ser Pro Met Ala His Pro Ile Arg Pro Asp Met
            355                 360                 365 gtc att gag atg aac aac ttc tac acc ctg acc gtt tac gag aag ggc       1152
Val Ile Glu Met Asn Asn Phe Tyr Thr Leu Thr Val Tyr Glu Lys Gly
        370                 375                 380 gcg gaa gtg att cgc atg atc cac acc ctg ctt ggc gaa gaa aac ttc       1200
Ala Glu Val Ile Arg Met Ile His Thr Leu Leu Gly Glu Glu Asn Phe
385                 390                 395                 400 cag aaa ggg atg cag ctt tat ttc gag cgt cat gat ggt agt gca gcg       1248
Gln Lys Gly Met Gln Leu Tyr Phe Glu Arg His Asp Gly Ser Ala Ala
                405                 410                 415 acc tgt gac gac ttt gtg cag gcg atg gaa gat gcg tcg aat gtc gat       1296
Thr Cys Asp Asp Phe Val Gln Ala Met Glu Asp Ala Ser Asn Val Asp
                420                 425                 430 ctc tcc cat ttc cgc cgt tgg tac agc cag tcc ggt aca ccg att gtg       1344
Leu Ser His Phe Arg Arg Trp Tyr Ser Gln Ser Gly Thr Pro Ile Val
            435                 440                 445 acc gtc aaa gac gac tac aat ccg gaa acc gag cag tac acc ctg acc       1392
Thr Val Lys Asp Asp Tyr Asn Pro Glu Thr Glu Gln Tyr Thr Leu Thr
450                 455                 460 atc agc cag cgc acg cca gcc acg ccg gat cag gca gaa aaa cag ccg       1440
Ile Ser Gln Arg Thr Pro Ala Thr Pro Asp Gln Ala Glu Lys Gln Pro
465                 470                 475                 480 ctg cat att ccg ttt gcc atc gaa ctg tat gat aac gaa ggc aaa gtg       1488
Leu His Ile Pro Phe Ala Ile Glu Leu Tyr Asp Asn Glu Gly Lys Val
                485                 490                 495 atc ccg ttg cag aaa ggc ggt cat ccg gtg aat tcc gtg ctg aac gtc       1536
Ile Pro Leu Gln Lys Gly Gly His Pro Val Asn Ser Val Leu Asn Val
            500                 505                 510 act cag gcg gaa cag acc ttt gtc ttt gat aat gtc tac ttc cag ccg       1584
```

-continued

```
                Thr Gln Ala Glu Gln Thr Phe Val Phe Asp Asn Val Tyr Phe Gln Pro
                    515                 520                 525 gtg cct gcg ctg ctg tgc gaa ttc tct gcg cca gtg aaa ctg gaa tat        1632
Val Pro Ala Leu Leu Cys Glu Phe Ser Ala Pro Val Lys Leu Glu Tyr
530                 535                 540 aag tgg agc gat cag caa ctg acc ttc ctg atg cgt cat gcg cgt aat        1680
Lys Trp Ser Asp Gln Gln Leu Thr Phe Leu Met Arg His Ala Arg Asn
545                 550                 555                 560 gat ttc tcc cgc tgg gat gcg gcg caa agt ttg ctg gca acc tac atc        1728
Asp Phe Ser Arg Trp Asp Ala Ala Gln Ser Leu Leu Ala Thr Tyr Ile
                565                 570                 575 aag ctg aac gtc gcg cgt cat cag caa ggt cag ccg ctg tct ctg ccg        1776
Lys Leu Asn Val Ala Arg His Gln Gln Gly Gln Pro Leu Ser Leu Pro
                580                 585                 590 gtg cat gtg gct gat gct ttc cgc gcg gta ctg ctt gat gag aag att        1824
Val His Val Ala Asp Ala Phe Arg Ala Val Leu Leu Asp Glu Lys Ile
                595                 600                 605 gat cca gcg ctg gcg gca gaa atc ctg acg ctg cct tct gtc aat gaa        1872
Asp Pro Ala Leu Ala Ala Glu Ile Leu Thr Leu Pro Ser Val Asn Glu
                610                 615                 620 atg gct gaa ttg ttc gat atc atc gac ccg att gct att gcc gaa gta        1920
Met Ala Glu Leu Phe Asp Ile Ile Asp Pro Ile Ala Ile Ala Glu Val
625                 630                 635                 640 cgc gaa gca ctc act cgt act ctg gcg act gaa ctg gcg gat gag cta        1968
Arg Glu Ala Leu Thr Arg Thr Leu Ala Thr Glu Leu Ala Asp Glu Leu
                645                 650                 655 ctg gct att tac aac gcg aat tac cag agc gag tac cgt gtt gag cat        2016
Leu Ala Ile Tyr Asn Ala Asn Tyr Gln Ser Glu Tyr Arg Val Glu His
                660                 665                 670 gaa gat att gca aaa cgc act ctg cgt aat gcc tgc ctg cgt ttc ctc        2064
Glu Asp Ile Ala Lys Arg Thr Leu Arg Asn Ala Cys Leu Arg Phe Leu
                675                 680                 685 gct ttt ggt gaa acg cat ctg gct gat gtg ctg gtg agc aag cag ttc        2112
Ala Phe Gly Glu Thr His Leu Ala Asp Val Leu Val Ser Lys Gln Phe
                690                 695                 700 cac gaa gca aac aat atg act gat gcg ctg gcg gcg ctt tct gcg gcg        2160
His Glu Ala Asn Asn Met Thr Asp Ala Leu Ala Ala Leu Ser Ala Ala
705                 710                 715                 720 gtt gcc gca cag ctg cct tgc cgt gac gcg ctg atg cag gag tac gac        2208
Val Ala Ala Gln Leu Pro Cys Arg Asp Ala Leu Met Gln Glu Tyr Asp
                725                 730                 735 gac aag tgg cat cag aac ggt ctg gtg atg gat aaa tgg ttt atc ctg        2256
Asp Lys Trp His Gln Asn Gly Leu Val Met Asp Lys Trp Phe Ile Leu
                740                 745                 750 caa gcc acc agc ccg gcg gcg aat gtg ctg gag acg gtg cgc ggc ctg        2304
Gln Ala Thr Ser Pro Ala Ala Asn Val Leu Glu Thr Val Arg Gly Leu
                755                 760                 765 ttg cag cat cgc tca ttt acc atg agc aac ccg aac cgt att cgt tcg        2352
Leu Gln His Arg Ser Phe Thr Met Ser Asn Pro Asn Arg Ile Arg Ser
770                 775                 780 ttg att ggc gcg ttt gcg ggc agc aat ccg gca gcg ttc cat gcc gaa        2400
Leu Ile Gly Ala Phe Ala Gly Ser Asn Pro Ala Ala Phe His Ala Glu
785                 790                 795                 800 gat ggc agc ggt tac ctg ttc ctg gtg gaa atg ctt acc gac ctc aac        2448
Asp Gly Ser Gly Tyr Leu Phe Leu Val Glu Met Leu Thr Asp Leu Asn
                805                 810                 815 agc cgt aac ccg cag gtg gct tca cgt ctg att gaa ccg ctg att cgc        2496
Ser Arg Asn Pro Gln Val Ala Ser Arg Leu Ile Glu Pro Leu Ile Arg
                820                 825                 830 ctg aaa cgt tac gat gcc aaa cgt cag gag aaa atg cgc gcg gcg ctg        2544
```

```
Leu Lys Arg Tyr Asp Ala Lys Arg Gln Glu Lys Met Arg Ala Ala Leu
        835                 840                 845 gaa cag ttg aaa ggg ctg gaa aat ctc tct ggc gat ctg tac gag aag      2592
Glu Gln Leu Lys Gly Leu Glu Asn Leu Ser Gly Asp Leu Tyr Glu Lys
        850                 855                 860 ata act aaa gca ctg gct                                              2610
Ile Thr Lys Ala Leu Ala
865                 870

<210> SEQ ID NO 69
<211> LENGTH: 1605
<212> TYPE: DNA
<213> ORGANISM: Escherichia coli

<400> SEQUENCE: 69 atg cgt att tcc ttg aaa aag tca ggg atg ctg aag ctt ggt ctc agc       48
Met Arg Ile Ser Leu Lys Lys Ser Gly Met Leu Lys Leu Gly Leu Ser
1               5                   10                  15 ctg gtg gct atg acc gtc gca gca agt gtt cag gct aaa act ctg gtt      96
Leu Val Ala Met Thr Val Ala Ala Ser Val Gln Ala Lys Thr Leu Val
            20                  25                  30 tat tgc tca gaa gga tct ccg gaa ggg ttt aac ccg cag ctg ttt acc     144
Tyr Cys Ser Glu Gly Ser Pro Glu Gly Phe Asn Pro Gln Leu Phe Thr
        35                  40                  45 tcc ggc acc acc tat gac gcc tct tcc gtc ccg ctt tat aac cgt ctg     192
Ser Gly Thr Thr Tyr Asp Ala Ser Ser Val Pro Leu Tyr Asn Arg Leu
    50                  55                  60 gtt gaa ttt aaa atc ggc acc acc gaa gtg atc ccg ggc ctc gct gaa     240
Val Glu Phe Lys Ile Gly Thr Thr Glu Val Ile Pro Gly Leu Ala Glu
65                  70                  75                  80 aag tgg gaa gtc agc gaa gac ggt aaa acc tat acc ttc cat ctg cgt     288
Lys Trp Glu Val Ser Glu Asp Gly Lys Thr Tyr Thr Phe His Leu Arg
                85                  90                  95 aaa ggt gtg aag tgg cac gac aat aaa gaa ttc aaa ccg acg cgt gaa     336
Lys Gly Val Lys Trp His Asp Asn Lys Glu Phe Lys Pro Thr Arg Glu
            100                 105                 110 ctg aac gcc gat gat gtg gtg ttc tcg ttc gat cgt cag aaa aac gcg     384
Leu Asn Ala Asp Asp Val Val Phe Ser Phe Asp Arg Gln Lys Asn Ala
        115                 120                 125 caa aac ccg tac cat aaa gtt tct ggc ggc agc tac gaa tac ttc gaa     432
Gln Asn Pro Tyr His Lys Val Ser Gly Gly Ser Tyr Glu Tyr Phe Glu
    130                 135                 140 ggc atg ggc ttg cca gag ctg atc agt gaa gtg aaa aag gtg gac gac     480
Gly Met Gly Leu Pro Glu Leu Ile Ser Glu Val Lys Lys Val Asp Asp
145                 150                 155                 160 aac acc gtt cag ttt gtg ctg act cgc ccg gaa gcg ccg ttc ctc gct     528
Asn Thr Val Gln Phe Val Leu Thr Arg Pro Glu Ala Pro Phe Leu Ala
                165                 170                 175 gac ctg gca atg gac ttc gcc tct att ctg tca aaa gaa tat gct gat     576
Asp Leu Ala Met Asp Phe Ala Ser Ile Leu Ser Lys Glu Tyr Ala Asp
            180                 185                 190 gcg atg atg aaa gcc ggt aca ccg gaa aaa ctg gac ctc aac cca atc     624
Ala Met Met Lys Ala Gly Thr Pro Glu Lys Leu Asp Leu Asn Pro Ile
        195                 200                 205 gga acc ggt ccg ttc cag tta cag cag tat caa aaa gat tcc cgt atc     672
Gly Thr Gly Pro Phe Gln Leu Gln Gln Tyr Gln Lys Asp Ser Arg Ile
    210                 215                 220 cgc tac aaa gcg ttt gat ggc tac tgg ggc acc aaa ccg cag atc gat     720
Arg Tyr Lys Ala Phe Asp Gly Tyr Trp Gly Thr Lys Pro Gln Ile Asp
225                 230                 235                 240 acg ctg gtt ttc tct att acc cct gac gct tcc gtg cgt tac gcg aaa     768
```

```
              Thr Leu Val Phe Ser Ile Thr Pro Asp Ala Ser Val Arg Tyr Ala Lys
                              245                 250                 255 ttg cag aag aat gaa tgc cag gtg atg ccg tac ccg aac ccg gca gat        816
Leu Gln Lys Asn Glu Cys Gln Val Met Pro Tyr Pro Asn Pro Ala Asp
            260                 265                 270 atc gct cgc atg aag cag gat aaa tcc atc aat ctg atg gaa atg ccg        864
Ile Ala Arg Met Lys Gln Asp Lys Ser Ile Asn Leu Met Glu Met Pro
        275                 280                 285 ggg ctg aac gtc ggt tat ctc tcg tat aac gtg cag aaa aaa cca ctc        912
Gly Leu Asn Val Gly Tyr Leu Ser Tyr Asn Val Gln Lys Lys Pro Leu
    290                 295                 300 gat gac gtg aaa gtt cgc cag gct ctg acc tac gcg gtg aac aaa gac        960
Asp Asp Val Lys Val Arg Gln Ala Leu Thr Tyr Ala Val Asn Lys Asp
305                 310                 315                 320 gcg atc atc aaa gcg gtt tat cag ggc gcg ggc gta tca gcg aaa aac       1008
Ala Ile Ile Lys Ala Val Tyr Gln Gly Ala Gly Val Ser Ala Lys Asn
                325                 330                 335 ctg atc ccg cca acc atg tgg ggc tat aac gac gac gtt cag gac tac       1056
Leu Ile Pro Pro Thr Met Trp Gly Tyr Asn Asp Asp Val Gln Asp Tyr
            340                 345                 350 acc tac gat cct gaa aaa gcg aaa gcc ttg ctg aaa gaa gcg ggt ctg       1104
Thr Tyr Asp Pro Glu Lys Ala Lys Ala Leu Leu Lys Glu Ala Gly Leu
        355                 360                 365 gaa aaa ggt ttc tcc atc gac ctg tgg gcg atg ccg gta caa cgt ccg       1152
Glu Lys Gly Phe Ser Ile Asp Leu Trp Ala Met Pro Val Gln Arg Pro
    370                 375                 380 tat aac ccg aac gct cgc cgc atg gcg gag atg att cag gca gac tgg       1200
Tyr Asn Pro Asn Ala Arg Arg Met Ala Glu Met Ile Gln Ala Asp Trp
385                 390                 395                 400 gcg aaa gtc ggc gtg cag gcc aaa att gtc acc tac gaa tgg ggt gag       1248
Ala Lys Val Gly Val Gln Ala Lys Ile Val Thr Tyr Glu Trp Gly Glu
                405                 410                 415 tac ctc aag cgt gcg aaa gat ggc gag cac cag acg gta atg atg ggc       1296
Tyr Leu Lys Arg Ala Lys Asp Gly Glu His Gln Thr Val Met Met Gly
            420                 425                 430 tgg act ggc gat aac ggg gat ccg gat aac ttc ttc gcc acc ctg ttc       1344
Trp Thr Gly Asp Asn Gly Asp Pro Asp Asn Phe Phe Ala Thr Leu Phe
        435                 440                 445 agc tgc gcc gcc tct gaa caa ggc tcc aac tac tca aaa tgg tgc tac       1392
Ser Cys Ala Ala Ser Glu Gln Gly Ser Asn Tyr Ser Lys Trp Cys Tyr
    450                 455                 460 aaa ccg ttt gaa gat ctg att caa ccg gcg cgt gct acc gac gac cac       1440
Lys Pro Phe Glu Asp Leu Ile Gln Pro Ala Arg Ala Thr Asp Asp His
465                 470                 475                 480 aat aaa cgc gtt gaa ctg tac aaa caa gcg cag gtg gtg atg cac gat       1488
Asn Lys Arg Val Glu Leu Tyr Lys Gln Ala Gln Val Val Met His Asp
                485                 490                 495 cag gct ccg gca ctg atc atc gct cac tcc acc gtg ttt gaa ccg gta       1536
Gln Ala Pro Ala Leu Ile Ile Ala His Ser Thr Val Phe Glu Pro Val
            500                 505                 510 cgt aaa gaa gtt aaa ggc tat gtg gtt gat cca tta ggc aaa cat cac       1584
Arg Lys Glu Val Lys Gly Tyr Val Val Asp Pro Leu Gly Lys His His
        515                 520                 525 ttc gaa aac gtc tct atc gaa                                           1605
Phe Glu Asn Val Ser Ile Glu
    530                 535

<210> SEQ ID NO 70
<211> LENGTH: 1017
<212> TYPE: DNA
<213> ORGANISM: Escherichia coli
```

<400> SEQUENCE: 70

```
atg ttg cag ttt att ctc cga cgt ttg gga ctc gtc atc ccc acg ttt      48
Met Leu Gln Phe Ile Leu Arg Arg Leu Gly Leu Val Ile Pro Thr Phe
1               5                   10                  15 atc ggt att acc ctt ctc aca ttt gcc ttt gtc cac atg atc ccg ggc      96
Ile Gly Ile Thr Leu Leu Thr Phe Ala Phe Val His Met Ile Pro Gly
            20                  25                  30 gat ccg gtg atg atc atg gcg ggc gaa cgt ggg atc tcc cca gag cgt     144
Asp Pro Val Met Ile Met Ala Gly Glu Arg Gly Ile Ser Pro Glu Arg
        35                  40                  45 cac gcg cag ctg ctg gct gaa ctc ggc tta gat aaa ccg atg tgg cag     192
His Ala Gln Leu Leu Ala Glu Leu Gly Leu Asp Lys Pro Met Trp Gln
    50                  55                  60 cag tat ctc cat tac att tgg ggc gtt atg cat ggc gat cta ggc att     240
Gln Tyr Leu His Tyr Ile Trp Gly Val Met His Gly Asp Leu Gly Ile
65                  70                  75                  80 tca atg aaa agc cgc atc ccg gtt tgg gaa gag ttc gtg ccg cgc ttc     288
Ser Met Lys Ser Arg Ile Pro Val Trp Glu Glu Phe Val Pro Arg Phe
                85                  90                  95 cag gcc acg ctg gaa ctt ggc gtc tgc gcg atg att ttt gct acg gca     336
Gln Ala Thr Leu Glu Leu Gly Val Cys Ala Met Ile Phe Ala Thr Ala
            100                 105                 110 gtc ggt att ccg gtc ggc gtg ctg gct gcg gtt aaa cgc ggt tcc att     384
Val Gly Ile Pro Val Gly Val Leu Ala Ala Val Lys Arg Gly Ser Ile
        115                 120                 125 ttc gat cac aca gcg gtt ggc ctg gcg ctg aca ggt tat tca atg cct     432
Phe Asp His Thr Ala Val Gly Leu Ala Leu Thr Gly Tyr Ser Met Pro
    130                 135                 140 atc ttc tgg tgg ggc atg atg ctg atc atg ctg gtt tcg gtg cac tgg     480
Ile Phe Trp Trp Gly Met Met Leu Ile Met Leu Val Ser Val His Trp
145                 150                 155                 160 aac ctg acg ccc gtc tcc ggt cgc gtg agc gat atg gtg ttc ctc gat     528
Asn Leu Thr Pro Val Ser Gly Arg Val Ser Asp Met Val Phe Leu Asp
                165                 170                 175 gac tcc aat ccg tta acc ggt ttt atg cta atc gac acc gcc atc tgg     576
Asp Ser Asn Pro Leu Thr Gly Phe Met Leu Ile Asp Thr Ala Ile Trp
            180                 185                 190 ggt gaa gac ggc aac ttt atc gat gcc gtc gcc cat atg atc ttg cct     624
Gly Glu Asp Gly Asn Phe Ile Asp Ala Val Ala His Met Ile Leu Pro
        195                 200                 205 gcc att gtg ctg ggt act att ccg ctg gcg gtc att gtg cgt atg aca     672
Ala Ile Val Leu Gly Thr Ile Pro Leu Ala Val Ile Val Arg Met Thr
    210                 215                 220 cgc tcc tcg atg ctg gaa gtg ctg ggc gag gat tac atc cgc acc gcg     720
Arg Ser Ser Met Leu Glu Val Leu Gly Glu Asp Tyr Ile Arg Thr Ala
225                 230                 235                 240 cgc gcc aaa ggg cta acc cgc atg cgg gtg att atc gtc cat gcg ctg     768
Arg Ala Lys Gly Leu Thr Arg Met Arg Val Ile Ile Val His Ala Leu
                245                 250                 255 cgt aac gcg atg ctg ccg gtg gtg acc gtt atc ggc ctg cag gtg gga     816
Arg Asn Ala Met Leu Pro Val Val Thr Val Ile Gly Leu Gln Val Gly
            260                 265                 270 aca ttg ctg gcg ggg gcg att ctg acc gaa acc atc ttc tcg tgg ccc     864
Thr Leu Leu Ala Gly Ala Ile Leu Thr Glu Thr Ile Phe Ser Trp Pro
        275                 280                 285 ggt ctg gga cgc tgg ttg att gac gca ctg caa cgc cgc gac tat ccg     912
Gly Leu Gly Arg Trp Leu Ile Asp Ala Leu Gln Arg Arg Asp Tyr Pro
    290                 295                 300 gta gtg cag ggc ggc gta ttg ctg gtg gcg acg atg att atc ctc gtc     960
```

```
Val Val Gln Gly Gly Val Leu Leu Val Ala Thr Met Ile Ile Leu Val
305                 310                 315                 320 aac ttg ctg gtc gat ctg ctg tac ggc gtg gtg aac ccg cgt att cgt      1008
Asn Leu Leu Val Asp Leu Leu Tyr Gly Val Val Asn Pro Arg Ile Arg
                    325                 330                 335 cat aag aag                                                          1017
His Lys Lys <210> SEQ ID NO 71
<211> LENGTH: 900
<212> TYPE: DNA
<213> ORGANISM: Escherichia coli

<400> SEQUENCE: 71 atg tca cag gtt act gaa aat aaa gtg att agc gca ccg gtg ccg atg        48
Met Ser Gln Val Thr Glu Asn Lys Val Ile Ser Ala Pro Val Pro Met
1               5                   10                  15 acc ccg tta cag gag ttc tgg cac tat ttt aaa cgc aac aaa ggc gcg        96
Thr Pro Leu Gln Glu Phe Trp His Tyr Phe Lys Arg Asn Lys Gly Ala
                20                  25                  30 gtc gtc ggg ctg gtt tac gtc gtc atc gtg ctg ttc atc gcg atc ttt       144
Val Val Gly Leu Val Tyr Val Val Ile Val Leu Phe Ile Ala Ile Phe
            35                  40                  45 gcc aac tgg att gca ccc tat aac ccg gcg gaa cag ttc cgc gat gca       192
Ala Asn Trp Ile Ala Pro Tyr Asn Pro Ala Glu Gln Phe Arg Asp Ala
        50                  55                  60 ctg ctc gcc ccg cca gcc tgg cag gaa ggc ggc agc atg gcg cac ttg       240
Leu Leu Ala Pro Pro Ala Trp Gln Glu Gly Gly Ser Met Ala His Leu
65                  70                  75                  80 ctg ggc acc gat gac gta ggc cgt gat gtg ctg tcg cgc ctg atg tac       288
Leu Gly Thr Asp Asp Val Gly Arg Asp Val Leu Ser Arg Leu Met Tyr
                85                  90                  95 ggt gcg cgc ctg tcg ctg ctg gtt ggc tgt ctg gta gtt gtg tta tcg       336
Gly Ala Arg Leu Ser Leu Leu Val Gly Cys Leu Val Val Val Leu Ser
            100                 105                 110 ctg att atg ggc gtt att ctc ggc ctg atc gcc ggt tac ttt ggc ggc       384
Leu Ile Met Gly Val Ile Leu Gly Leu Ile Ala Gly Tyr Phe Gly Gly
        115                 120                 125 ctg gtc gat aac atc att atg cgc gtg gtc gat atc atg ctg gcg ctg       432
Leu Val Asp Asn Ile Ile Met Arg Val Val Asp Ile Met Leu Ala Leu
130                 135                 140 cca agt ctg ctg ctg gcg ctg gtg ctg gtg gca att ttc ggc ccg tcg       480
Pro Ser Leu Leu Leu Ala Leu Val Leu Val Ala Ile Phe Gly Pro Ser
145                 150                 155                 160 att ggt aac gcc gcg ctg gca ctg acc ttc gtt gcc ttg ccg cac tat       528
Ile Gly Asn Ala Ala Leu Ala Leu Thr Phe Val Ala Leu Pro His Tyr
                165                 170                 175 gtg cgc tta acc cgc gcc gcc gtg ctg gtg gaa gtt aac cgc gat tac       576
Val Arg Leu Thr Arg Ala Ala Val Leu Val Glu Val Asn Arg Asp Tyr
            180                 185                 190 gtc acc gcg tct cgc gtg gcg ggt gcc ggg gcg atg cgt cag atg ttt       624
Val Thr Ala Ser Arg Val Ala Gly Ala Gly Ala Met Arg Gln Met Phe
        195                 200                 205 att aac atc ttc ccg aac tgc ctt gcg ccg ctg att gtt cag gcg tcg       672
Ile Asn Ile Phe Pro Asn Cys Leu Ala Pro Leu Ile Val Gln Ala Ser
210                 215                 220 ctc ggt ttc tct aac gcc att ctc gat atg gct gct ctt ggt ttc ctc       720
Leu Gly Phe Ser Asn Ala Ile Leu Asp Met Ala Ala Leu Gly Phe Leu
225                 230                 235                 240 ggc atg ggg gca cag ccg cca acg cct gag tgg ggc acc atg ctc tcc       768
Gly Met Gly Ala Gln Pro Pro Thr Pro Glu Trp Gly Thr Met Leu Ser
```

```
                          245                 250                 255
gac gtg ttg cag ttc gcg caa agc gcc tgg tgg gtc gtg acc ttc ccg      816
Asp Val Leu Gln Phe Ala Gln Ser Ala Trp Trp Val Val Thr Phe Pro
            260                 265                 270 ggt ctg gcg atc ctg ctg acg gtg ctg gca ttt aac ctg atg ggt gac      864
Gly Leu Ala Ile Leu Leu Thr Val Leu Ala Phe Asn Leu Met Gly Asp
        275                 280                 285 ggt ctg cgt gac gcg ctc gat ccc aaa ctg aag cag                      900
Gly Leu Arg Asp Ala Leu Asp Pro Lys Leu Lys Gln
    290                 295                 300

<210> SEQ ID NO 72
<211> LENGTH: 981
<212> TYPE: DNA
<213> ORGANISM: Escherichia coli

<400> SEQUENCE: 72 atg gcg tta tta aat gta gat aaa tta tcg gtg cat ttc ggc gac gaa       48
Met Ala Leu Leu Asn Val Asp Lys Leu Ser Val His Phe Gly Asp Glu
 1               5                  10                  15 agc gcg ccg ttc cgc gcc gta gac cgc atc agc tac agc gta aaa cag       96
Ser Ala Pro Phe Arg Ala Val Asp Arg Ile Ser Tyr Ser Val Lys Gln
                20                  25                  30 ggc gaa gtg gtc ggg att gtg ggt gag tcc ggc tcc ggt aag tcg gtc      144
Gly Glu Val Val Gly Ile Val Gly Glu Ser Gly Ser Gly Lys Ser Val
            35                  40                  45 agt tca ctg gcg att atg ggg ctg att gat tat ccg ggc cgc gta atg      192
Ser Ser Leu Ala Ile Met Gly Leu Ile Asp Tyr Pro Gly Arg Val Met
        50                  55                  60 gca gaa aaa ctg gag ttt aac ggc cag gat ttg cag cgt atc tca gaa      240
Ala Glu Lys Leu Glu Phe Asn Gly Gln Asp Leu Gln Arg Ile Ser Glu
65                  70                  75                  80 aaa gag cgc cgc aac ctg gtg ggt gcc gaa gtg gcg atg atc ttc cag      288
Lys Glu Arg Arg Asn Leu Val Gly Ala Glu Val Ala Met Ile Phe Gln
                85                  90                  95 gac ccg atg acc agc ctt aac ccg tgc tac acc gtg ggt ttc cag att      336
Asp Pro Met Thr Ser Leu Asn Pro Cys Tyr Thr Val Gly Phe Gln Ile
                100                 105                 110 atg gaa gcg att aag gtg cat cag ggc ggc aac aaa agt acc cgc cgt      384
Met Glu Ala Ile Lys Val His Gln Gly Gly Asn Lys Ser Thr Arg Arg
            115                 120                 125 cag cga gcg att gac ctg ctg aat cag gtc ggt att ccc gat ccg gca      432
Gln Arg Ala Ile Asp Leu Leu Asn Gln Val Gly Ile Pro Asp Pro Ala
        130                 135                 140 tcg cgt ctg gat gtt tac ccg cat cag ctt tcc ggc ggc atg agc cag      480
Ser Arg Leu Asp Val Tyr Pro His Gln Leu Ser Gly Gly Met Ser Gln
145                 150                 155                 160 cgc gtg atg atc gcc atg gcg att gcc tgt cgg cca aaa ctg ctg att      528
Arg Val Met Ile Ala Met Ala Ile Ala Cys Arg Pro Lys Leu Leu Ile
                165                 170                 175 gcc gat gaa ccg acc acc gcg ctg gac gtg acc att cag gcg caa atc      576
Ala Asp Glu Pro Thr Thr Ala Leu Asp Val Thr Ile Gln Ala Gln Ile
                180                 185                 190 atc gaa cta ctg ctg gag cta cag cag aaa gag aac atg gcg ctg gtg      624
Ile Glu Leu Leu Leu Glu Leu Gln Gln Lys Glu Asn Met Ala Leu Val
            195                 200                 205 tta att acc cat gac ctg gcg ctg gtg gcg gaa gcg gca cat aaa atc      672
Leu Ile Thr His Asp Leu Ala Leu Val Ala Glu Ala Ala His Lys Ile
        210                 215                 220 atc gtg atg tat gca ggc cag gtg gtg gaa acc ggt gat gcg cac gcc      720
Ile Val Met Tyr Ala Gly Gln Val Val Glu Thr Gly Asp Ala His Ala
```

```
225                 230                 235                 240 atc ttc cat gcg ccg cgt cac ccg tat act cag gca ttg ctg cgt gcg      768
Ile Phe His Ala Pro Arg His Pro Tyr Thr Gln Ala Leu Leu Arg Ala
            245                 250                 255 ctg cca gaa ttt gct cag gac aaa gaa cgt ctg gcg tcg ttg cca ggt      816
Leu Pro Glu Phe Ala Gln Asp Lys Glu Arg Leu Ala Ser Leu Pro Gly
            260                 265                 270 gtc gtt ccc ggc aag tac gac cgc ccg aac ggc tgc ctg ctt aac ccg      864
Val Val Pro Gly Lys Tyr Asp Arg Pro Asn Gly Cys Leu Leu Asn Pro
        275                 280                 285 cgc tgc ccc tat gcc act gac aga tgt cgc gct gaa gaa ccg gcg ctg      912
Arg Cys Pro Tyr Ala Thr Asp Arg Cys Arg Ala Glu Glu Pro Ala Leu
        290                 295                 300 aat atg ctc gct gac ggg cgt cag tcc aaa tgc cat tac cca ctt gat      960
Asn Met Leu Ala Asp Gly Arg Gln Ser Lys Cys His Tyr Pro Leu Asp
305                 310                 315                 320 gat gcc ggg agg ccg aca cta                                          981
Asp Ala Gly Arg Pro Thr Leu
            325

<210> SEQ ID NO 73
<211> LENGTH: 1002
<212> TYPE: DNA
<213> ORGANISM: Escherichia coli

<400> SEQUENCE: 73 atg agt acg caa gag gcc acc ctg caa caa ccg ctg ttg cag gct atc       48
Met Ser Thr Gln Glu Ala Thr Leu Gln Gln Pro Leu Leu Gln Ala Ile
1               5                   10                  15 gac ctg aaa aaa cat tat ccg gtg aag aaa ggc atg ttc gcg ccg gaa       96
Asp Leu Lys Lys His Tyr Pro Val Lys Lys Gly Met Phe Ala Pro Glu
            20                  25                  30 cgt ctg gtt aaa gcg ctg gat ggc gtt tcg ttt aac ctt gaa cgt ggc      144
Arg Leu Val Lys Ala Leu Asp Gly Val Ser Phe Asn Leu Glu Arg Gly
        35                  40                  45 aaa acg ctg gca gta gtg ggc gaa tct ggc tgc ggt aaa tcg acc ctc      192
Lys Thr Leu Ala Val Val Gly Glu Ser Gly Cys Gly Lys Ser Thr Leu
    50                  55                  60 ggt cgg ttg ctg acg atg att gaa atg ccc acc ggt ggc gag ctg tat      240
Gly Arg Leu Leu Thr Met Ile Glu Met Pro Thr Gly Gly Glu Leu Tyr
65                  70                  75                  80 tac cag ggg cag gat ctg ctt aag cac gat ccg cag gcg cag aag ctg      288
Tyr Gln Gly Gln Asp Leu Leu Lys His Asp Pro Gln Ala Gln Lys Leu
            85                  90                  95 cgt cgg cag aaa atc cag atc gtc ttc cag aac cct tac ggt tcg ctg      336
Arg Arg Gln Lys Ile Gln Ile Val Phe Gln Asn Pro Tyr Gly Ser Leu
        100                 105                 110 aat ccg cgt aaa aaa gtc ggg caa att ctt gaa gag ccg ctg ctg atc      384
Asn Pro Arg Lys Lys Val Gly Gln Ile Leu Glu Glu Pro Leu Leu Ile
    115                 120                 125 aac acc agc tta agc aaa gaa cag cgt cgg gaa aaa gcc ctg tcg atg      432
Asn Thr Ser Leu Ser Lys Glu Gln Arg Arg Glu Lys Ala Leu Ser Met
130                 135                 140 atg gcg aaa gtc ggc ctg aaa acc gag cac tat gac cgc tat ccg cat      480
Met Ala Lys Val Gly Leu Lys Thr Glu His Tyr Asp Arg Tyr Pro His
145                 150                 155                 160 atg ttc tcc ggc ggt cag cgt cag cgt atc gcc atc gcc cgt ggt ctg      528
Met Phe Ser Gly Gly Gln Arg Gln Arg Ile Ala Ile Ala Arg Gly Leu
            165                 170                 175 atg ctc gac ccg gat gtg gtg att gcc gat gaa ccg gtt tcc gcg ctg      576
Met Leu Asp Pro Asp Val Val Ile Ala Asp Glu Pro Val Ser Ala Leu
```

```
gat gtt tca gtg cgc gcg cag gtg ctg aat ctg atg atg gat ttg cag       624
Asp Val Ser Val Arg Ala Gln Val Leu Asn Leu Met Met Asp Leu Gln
        195                 200                 205 cag gag ttg ggg ctg tct tat gtc ttt atc tcc cac gac ctg tcg gtg       672
Gln Glu Leu Gly Leu Ser Tyr Val Phe Ile Ser His Asp Leu Ser Val
    210                 215                 220 gtg gag cac att gct gat gaa gtg atg gtg atg tac ctg ggc cgc tgc       720
Val Glu His Ile Ala Asp Glu Val Met Val Met Tyr Leu Gly Arg Cys
225                 230                 235                 240 gtg gag aag gga acg aaa gac caa atc ttc aat aac ccg cgc cat ccg       768
Val Glu Lys Gly Thr Lys Asp Gln Ile Phe Asn Asn Pro Arg His Pro
                245                 250                 255 tac act cag gcg cta ctt tcc gcg acg ccg cgc ctg aac ccg gac gat       816
Tyr Thr Gln Ala Leu Leu Ser Ala Thr Pro Arg Leu Asn Pro Asp Asp
            260                 265                 270 cgc cgc gag cgc atc aag ctc agc ggt gaa cta cca agc cca ctg aat       864
Arg Arg Glu Arg Ile Lys Leu Ser Gly Glu Leu Pro Ser Pro Leu Asn
        275                 280                 285 cca ccg ccg ggt tgc gcc ttc aac gcc cgc tgt cgt cgg cgc ttc ggc       912
Pro Pro Pro Gly Cys Ala Phe Asn Ala Arg Cys Arg Arg Arg Phe Gly
    290                 295                 300 ccc tgc acc cag ttg cag ccg cag cta aaa gac tac ggc ggt caa ctg       960
Pro Cys Thr Gln Leu Gln Pro Gln Leu Lys Asp Tyr Gly Gly Gln Leu
305                 310                 315                 320 gta gct tgt ttt gct gtt gat cag gat gaa aat ccg cag cgt              1002
Val Ala Cys Phe Ala Val Asp Gln Asp Glu Asn Pro Gln Arg
                325                 330

<210> SEQ ID NO 74
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
ctaaccctgt gacctgcaat actgttttgc gggtgagtgt aggctggagc tgcttc           56

<210> SEQ ID NO 75
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
gaaactgccg gaaggcgatt aaacgccatc cggcagcata tgaatatcct ccttag           56

<210> SEQ ID NO 76
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
ttacgcaaca ggaatagact gaacaccaga ctctatgtgt aggctggagc tgcttc           56

<210> SEQ ID NO 77
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
agaaaacagg ggtaaattcc ccgaatggcg gcgctacata tgaatatcct ccttag      56

<210> SEQ ID NO 78
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
atggagttta gtgtaaaaag cggtagcccg gagaaagtgt aggctggagc tgcttc      56

<210> SEQ ID NO 79
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 79
ttactcttcg ccgttaaacc cagcgcggtt taacagcata tgaatatcct ccttag      56

<210> SEQ ID NO 80
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
atgacagaag cgatgaagat taccctctct acccaagtgt aggctggagc tgcttc      56

<210> SEQ ID NO 81
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
ttacgccgtt aacagattag ctatcgtgcg cacacccata tgaatatcct ccttag      56

<210> SEQ ID NO 82
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
gcatccccac ctcataacgt tgacccgacc gggcaagtgt aggctggagc tgcttc      56

<210> SEQ ID NO 83
<211> LENGTH: 56
<212> TYPE: DNA
<213> ORGANISM: Artificial Sequence
```

<220> FEATURE:
<223> OTHER INFORMATION: Description of Artificial Sequence: Synthetic
      DNA

<400> SEQUENCE: 83
ctgtacggca ttttgctatg cttgtcgcca ctgttgcata tgaatatcct ccttag          56

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
gtgtctgaac tgtctcaatt a                                               21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 85
cggaatttct ttcagcagtt c                                               21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 86
atgactcaac agccacaagc c                                               21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
tgctttagtt atcttctcgt a                                               21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 88
agtgcctgca tcgtcgtggg c                                               21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic -continued

DNA

<400> SEQUENCE: 89
ggcgcctttt gctttaccag a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90
gacgcgcgct ggggagaaaa a                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 91
cgtagcgccc gcagaccact g                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 92
atgcgtattt ccttgaaaaa g                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 93
ttattcgata gagacgtttt c                                              21

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 94
tacactcgag attaaagagg agaaattaa                                      29

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA -continued

```
<400> SEQUENCE: 95
ttaggatcct catactggca gcacatactt                                        30

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 96
caagaattct catgtttgac agct                                              24

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 97
taactcgaga ttcccttttt acgtgaac                                          28

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 98
ttaaccatgg agagaaaaac agtattg                                           27

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 99
atatggatcc tactggcagc acatactttg                                        30

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 100
taccatgggt caggaaaagc tata                                              24

<210> SEQ ID NO 101
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 101
```

```
atggatcctt attcaggttg ttcgagtga                                              29

<210> SEQ ID NO 102
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 102
ggattcatat ggccgaagac cgcgcgatg                                              29

<210> SEQ ID NO 103
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 103
acgcgtcgac ccaaggctca tccctgacg                                              29

<210> SEQ ID NO 104
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 104
ggattcatat gcttgaacgc tgtattaccg atgtaaagc                                   39

<210> SEQ ID NO 105
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 105
acgcgtcgac cgatctcatc ttaatccaac ttcacc                                      36

<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 106
ggattcatat gaaaaaggcc aaggaaaatc ccgc                                        34

<210> SEQ ID NO 107
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 107
cccaagcttg cgagaaggcc tagccttcc                                              29
```

```
<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 108
catgccatgg gcttcctccc gatttccg                                         28

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 109
acgcgtcgac gcgggcaacc gtcacaagcg                                       30

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 110
ggattcatat gttcgaatct gccgaaatcg gc                                    32

<210> SEQ ID NO 111
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 111
cccaagcttc cttcggctat ttcttgtgct tggc                                  34

<210> SEQ ID NO 112
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 112
ggattcatat ggcactcgac gaagcaccg                                        29

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 113
cgcggatccg tcggaatcac ctgagaaaac c                                     31

<210> SEQ ID NO 114
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 114
ggattcatat gagtaactcg aaagacgagg tagaacg                              37

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 115
acgcgtcgac gagatgtcag tatttcgcag gaacg                                35

<210> SEQ ID NO 116
<211> LENGTH: 2064
<212> TYPE: DNA
<213> ORGANISM: Eschierichia coli W3110

<400> SEQUENCE: 116
```

| | | | | | | | | | | | | | | | | |
|---|---|---|---|---|---|---|---|---|---|---|---|---|---|---|---|---|
| atg | ggt | cag | gaa | aag | cta | tac | atc | gaa | aaa | gag | ctc | agt | tgg | tta | tcg | 48 |
| Met | Gly | Gln | Glu | Lys | Leu | Tyr | Ile | Glu | Lys | Glu | Leu | Ser | Trp | Leu | Ser | |
| 1 | | | | 5 | | | | | 10 | | | | | 15 | | |
| ttc | aat | gaa | cgc | gtg | ctt | cag | gaa | gcg | gcg | gac | aaa | tct | aac | ccg | ctg | 96 |
| Phe | Asn | Glu | Arg | Val | Leu | Gln | Glu | Ala | Ala | Asp | Lys | Ser | Asn | Pro | Leu | |
| | | | 20 | | | | | 25 | | | | | 30 | | | |
| att | gaa | agg | atg | cgt | ttc | ctg | ggg | atc | tat | tcc | aat | aac | ctt | gat | gag | 144 |
| Ile | Glu | Arg | Met | Arg | Phe | Leu | Gly | Ile | Tyr | Ser | Asn | Asn | Leu | Asp | Glu | |
| | 35 | | | | | 40 | | | | | 45 | | | | | |
| ttc | tat | aaa | gtc | cgc | ttc | gct | gaa | ctg | aag | cga | cgc | atc | att | att | agc | 192 |
| Phe | Tyr | Lys | Val | Arg | Phe | Ala | Glu | Leu | Lys | Arg | Arg | Ile | Ile | Ile | Ser | |
| 50 | | | | | 55 | | | | | 60 | | | | | | |
| gaa | gaa | caa | ggc | tcc | aac | tct | cat | tcc | cgc | cat | tta | ctg | ggc | aaa | att | 240 |
| Glu | Glu | Gln | Gly | Ser | Asn | Ser | His | Ser | Arg | His | Leu | Leu | Gly | Lys | Ile | |
| 65 | | | | | 70 | | | | | 75 | | | | | 80 | |
| cag | tcc | cgg | gtg | ctg | aaa | gcc | gat | cag | gaa | ttc | gac | ggc | ctc | tac | aac | 288 |
| Gln | Ser | Arg | Val | Leu | Lys | Ala | Asp | Gln | Glu | Phe | Asp | Gly | Leu | Tyr | Asn | |
| | | | | 85 | | | | | 90 | | | | | 95 | | |
| gag | cta | ttg | ctg | gag | atg | gcg | cgc | aac | cag | atc | ttc | ctg | att | aat | gaa | 336 |
| Glu | Leu | Leu | Leu | Glu | Met | Ala | Arg | Asn | Gln | Ile | Phe | Leu | Ile | Asn | Glu | |
| | | | 100 | | | | | 105 | | | | | 110 | | | |
| cgc | cag | ctc | tcc | gtc | aat | caa | caa | aac | tgg | ctg | cgt | cat | tat | ttt | aag | 384 |
| Arg | Gln | Leu | Ser | Val | Asn | Gln | Gln | Asn | Trp | Leu | Arg | His | Tyr | Phe | Lys | |
| | | 115 | | | | | 120 | | | | | 125 | | | | |
| cag | tat | ctg | cgt | cag | cac | att | acg | ccg | att | tta | atc | aat | cct | gac | act | 432 |
| Gln | Tyr | Leu | Arg | Gln | His | Ile | Thr | Pro | Ile | Leu | Ile | Asn | Pro | Asp | Thr | |
| | 130 | | | | | 135 | | | | | 140 | | | | | |
| gac | tta | gtg | cag | ttc | ctg | aaa | gat | gat | tac | acc | tat | ctg | gcg | gtg | gaa | 480 |
| Asp | Leu | Val | Gln | Phe | Leu | Lys | Asp | Asp | Tyr | Thr | Tyr | Leu | Ala | Val | Glu | |
| 145 | | | | | 150 | | | | | 155 | | | | | 160 | |
| att | atc | cgt | ggc | gat | acc | atc | cgt | tac | gcg | ctg | ctg | gag | atc | cca | tca | 528 |
| Ile | Ile | Arg | Gly | Asp | Thr | Ile | Arg | Tyr | Ala | Leu | Leu | Glu | Ile | Pro | Ser | |
| | | | | 165 | | | | | 170 | | | | | 175 | | |
| gat | aaa | gtg | ccg | cgc | ttt | gtg | aat | tta | ccg | cca | gaa | gcg | ccg | cgt | cga | 576 |
| Asp | Lys | Val | Pro | Arg | Phe | Val | Asn | Leu | Pro | Pro | Glu | Ala | Pro | Arg | Arg | |
| | | | 180 | | | | | 185 | | | | | 190 | | | |

```
cgc aag ccg atg att ctt ctg gat aac att ctg cgt tac tgc ctt gat      624
Arg Lys Pro Met Ile Leu Leu Asp Asn Ile Leu Arg Tyr Cys Leu Asp
        195                 200                 205 gat att ttc aaa ggc ttc ttt gat tat gac gcg ctg aat gcc tat tca      672
Asp Ile Phe Lys Gly Phe Phe Asp Tyr Asp Ala Leu Asn Ala Tyr Ser
    210                 215                 220 atg aag atg acc cgc gat gcc gaa tac gat tta gtg cat gag atg gaa      720
Met Lys Met Thr Arg Asp Ala Glu Tyr Asp Leu Val His Glu Met Glu
225                 230                 235                 240 gcc agc ctg atg gag ttg atg tct tcc agt ctc aag cag cgt tta act      768
Ala Ser Leu Met Glu Leu Met Ser Ser Ser Leu Lys Gln Arg Leu Thr
                245                 250                 255 gct gag ccg gtg cgt ttt gtt tat cag cgc gat atg ccc aat gcg ctg      816
Ala Glu Pro Val Arg Phe Val Tyr Gln Arg Asp Met Pro Asn Ala Leu
            260                 265                 270 gtt gaa gtg tta cgc gaa aaa ctg act att tcc cgc tac gac tcc atc      864
Val Glu Val Leu Arg Glu Lys Leu Thr Ile Ser Arg Tyr Asp Ser Ile
        275                 280                 285 gtc ccc ggc ggt cgt tat cat aat ttt aaa gac ttt att aat ttc ccc      912
Val Pro Gly Gly Arg Tyr His Asn Phe Lys Asp Phe Ile Asn Phe Pro
    290                 295                 300 aat gtc ggc aaa gcc aat ctg gtg aac aaa cca ctg ccg cgt tta cgc      960
Asn Val Gly Lys Ala Asn Leu Val Asn Lys Pro Leu Pro Arg Leu Arg
305                 310                 315                 320 cat att tgg ttt gat aaa gcc cag ttc cgc aat ggt ttt gat gcc att     1008
His Ile Trp Phe Asp Lys Ala Gln Phe Arg Asn Gly Phe Asp Ala Ile
                325                 330                 335 cgc gaa cgc gat gtg ttg ctc tat tat cct tat cac acc ttt gag cat     1056
Arg Glu Arg Asp Val Leu Leu Tyr Tyr Pro Tyr His Thr Phe Glu His
            340                 345                 350 gtg ctg gaa ctg ctg cgt cag gct tcg ttc gac ccg agc gta ctg gcg     1104
Val Leu Glu Leu Leu Arg Gln Ala Ser Phe Asp Pro Ser Val Leu Ala
        355                 360                 365 att aaa att aac att tac cgc gtg gcg aaa gat tca cgc atc atc gac     1152
Ile Lys Ile Asn Ile Tyr Arg Val Ala Lys Asp Ser Arg Ile Ile Asp
    370                 375                 380 tcg atg atc cac gcc gca cat aac ggt aag aaa gtc acc gtg gtg gtt     1200
Ser Met Ile His Ala Ala His Asn Gly Lys Lys Val Thr Val Val Val
385                 390                 395                 400 gag tta cag gcg cgt ttc gac gaa gaa gcc aac att cac tgg gcg aag     1248
Glu Leu Gln Ala Arg Phe Asp Glu Glu Ala Asn Ile His Trp Ala Lys
                405                 410                 415 cgc ctg acc gaa gca ggc gtg cac gtt atc ttc tct gcg ccg ggg ctg     1296
Arg Leu Thr Glu Ala Gly Val His Val Ile Phe Ser Ala Pro Gly Leu
            420                 425                 430 aaa att cac gcc aaa ctg ttc ctg att tca cgt aaa gaa aac ggt gaa     1344
Lys Ile His Ala Lys Leu Phe Leu Ile Ser Arg Lys Glu Asn Gly Glu
        435                 440                 445 gtg gtg cgt tat gca cac atc ggg acc ggg aac ttt aac gaa aaa acc     1392
Val Val Arg Tyr Ala His Ile Gly Thr Gly Asn Phe Asn Glu Lys Thr
    450                 455                 460 gcg cgt ctt tat act gac tat tcg ttg ctg acc gcc gat gcg cgc atc     1440
Ala Arg Leu Tyr Thr Asp Tyr Ser Leu Leu Thr Ala Asp Ala Arg Ile
465                 470                 475                 480 acc aac gaa gta cgg cgg gta ttt aac ttt att gaa aac cca tac cgt     1488
Thr Asn Glu Val Arg Arg Val Phe Asn Phe Ile Glu Asn Pro Tyr Arg
                485                 490                 495 ccg gtg aca ttt gat tat tta atg gta tcg ccg caa aac tcc cgc cgc     1536
Pro Val Thr Phe Asp Tyr Leu Met Val Ser Pro Gln Asn Ser Arg Arg
            500                 505                 510
```

```
cta ttg tat gaa atg gtg gac cgc gag atc gcc aac gcg cag caa ggg      1584
Leu Leu Tyr Glu Met Val Asp Arg Glu Ile Ala Asn Ala Gln Gln Gly
        515                 520                 525 ctg ccc agt ggt atc acc ctg aag cta aat aac ctt gtc gat aaa ggc      1632
Leu Pro Ser Gly Ile Thr Leu Lys Leu Asn Asn Leu Val Asp Lys Gly
530                 535                 540 ctg gtt gat cgt ctg tat gcg gcc tcc agc tcc ggc gta ccg gtt aat      1680
Leu Val Asp Arg Leu Tyr Ala Ala Ser Ser Ser Gly Val Pro Val Asn
545                 550                 555                 560 ctg ctg gtt cgc gga atg tgt tcg ctg atc ccc aat ctg gaa ggc att      1728
Leu Leu Val Arg Gly Met Cys Ser Leu Ile Pro Asn Leu Glu Gly Ile
                565                 570                 575 agc gac aac att cgt gcc atc agt att gtt gac cgt tac ctt gaa cat      1776
Ser Asp Asn Ile Arg Ala Ile Ser Ile Val Asp Arg Tyr Leu Glu His
            580                 585                 590 gac cgg gtt tat att ttt gaa aat ggc ggc gat aaa aag gtc tac ctt      1824
Asp Arg Val Tyr Ile Phe Glu Asn Gly Gly Asp Lys Lys Val Tyr Leu
        595                 600                 605 tct tcc gcc gac tgg atg acg cgc aat att gat tat cgt att gaa gtg      1872
Ser Ser Ala Asp Trp Met Thr Arg Asn Ile Asp Tyr Arg Ile Glu Val
610                 615                 620 gcg acg ccg ctg ctc gat ccg cgc ctg aag cag cgg gta ctg gac atc      1920
Ala Thr Pro Leu Leu Asp Pro Arg Leu Lys Gln Arg Val Leu Asp Ile
625                 630                 635                 640 atc gac ata ttg ttc agc gat acg gtc aaa gca cgt tat atc gat aaa      1968
Ile Asp Ile Leu Phe Ser Asp Thr Val Lys Ala Arg Tyr Ile Asp Lys
                645                 650                 655 gaa ctc agt aat cgc tac gtt ccc cgc ggc aat cgc cgc aaa gta cgg      2016
Glu Leu Ser Asn Arg Tyr Val Pro Arg Gly Asn Arg Arg Lys Val Arg
            660                 665                 670 gcg cag ttg gcg att tat gac tac atc aaa tca ctc gaa caa cct gaa      2064
Ala Gln Leu Ala Ile Tyr Asp Tyr Ile Lys Ser Leu Glu Gln Pro Glu
        675                 680                 685

<210> SEQ ID NO 117
<211> LENGTH: 1008
<212> TYPE: DNA
<213> ORGANISM: Rhodobacter sphaeroides ATCC17023

<400> SEQUENCE: 117 atg gcc gaa gac cgc gcg atg ccc gtg atg ccg cct gcc gca gac gcg       48
Met Ala Glu Asp Arg Ala Met Pro Val Met Pro Pro Ala Ala Asp Ala
1               5                   10                  15 gcc gag gcg gtg cct gcc gcc ccc acg gcc ctg ccg gaa gag ggg ccc       96
Ala Glu Ala Val Pro Ala Ala Pro Thr Ala Leu Pro Glu Glu Gly Pro
            20                  25                  30 gca ggg ccc gag gcc cct ctt cag acg ctg cac gga ccg cgc cat ttc      144
Ala Gly Pro Glu Ala Pro Leu Gln Thr Leu His Gly Pro Arg His Phe
        35                  40                  45 ccg gcc gtg gat gcg aat gcg ata cgg cag gcc ttc gag ggc ggg cat      192
Pro Ala Val Asp Ala Asn Ala Ile Arg Gln Ala Phe Glu Gly Gly His
    50                  55                  60 tat ccc tat ccg cgc cgg ttg ggc cgc gtg gtc tac gag gcc gag aaa      240
Tyr Pro Tyr Pro Arg Arg Leu Gly Arg Val Val Tyr Glu Ala Glu Lys
65                  70                  75                  80 gcc aga ttg cag gcc gaa ctg ctg aag gtg cag atc tgg gcg cag gag      288
Ala Arg Leu Gln Ala Glu Leu Leu Lys Val Gln Ile Trp Ala Gln Glu
                85                  90                  95 acc ggg cag aag ttc gtc atc ctg atg gaa ggg cgc gac gcc gcc ggc      336
Thr Gly Gln Lys Phe Val Ile Leu Met Glu Gly Arg Asp Ala Ala Gly
            100                 105                 110
```

```
aag ggt ggc acg atc aag cgc ttc atg gag cat ctc aat ccg cgc tat      384
Lys Gly Gly Thr Ile Lys Arg Phe Met Glu His Leu Asn Pro Arg Tyr
        115                 120                 125 gcc cgc gtc gtg gcc ctg acc aag ccc ggc gag cgc gag cgc ggc caa      432
Ala Arg Val Val Ala Leu Thr Lys Pro Gly Glu Arg Glu Arg Gly Gln
    130                 135                 140 tgg ttc ttt cag cgc tat atc gaa cat ctg ccg acc gcg ggc gag atc      480
Trp Phe Phe Gln Arg Tyr Ile Glu His Leu Pro Thr Ala Gly Glu Ile
145                 150                 155                 160 gtc ttt ttc gac cgc agc tgg tat aac cgc gcg ggc gtc gag cgg gtg      528
Val Phe Phe Asp Arg Ser Trp Tyr Asn Arg Ala Gly Val Glu Arg Val
                165                 170                 175 atg ggg ttc tgc acc ccc tcg gaa tat ctc gaa ttc atg cgc cag gcg      576
Met Gly Phe Cys Thr Pro Ser Glu Tyr Leu Glu Phe Met Arg Gln Ala
            180                 185                 190 ccc gag ctc gag cgg atg ctg gtc cgc tcg ggg atc cgg ctc tac aaa      624
Pro Glu Leu Glu Arg Met Leu Val Arg Ser Gly Ile Arg Leu Tyr Lys
        195                 200                 205 tac tgg ttc tcg gtg acg cgc gac gaa cag cgc gcc cgc ttc ctc gcc      672
Tyr Trp Phe Ser Val Thr Arg Asp Glu Gln Arg Ala Arg Phe Leu Ala
    210                 215                 220 cgc gag acc gat ccc ctg aaa cgc tgg aag ctc tcg ccc atc gac aag      720
Arg Glu Thr Asp Pro Leu Lys Arg Trp Lys Leu Ser Pro Ile Asp Lys
225                 230                 235                 240 gcg agc ctc gac aag tgg gac gat tat acc gag gcg aag gag gcg atg      768
Ala Ser Leu Asp Lys Trp Asp Asp Tyr Thr Glu Ala Lys Glu Ala Met
                245                 250                 255 ttc ttc tac acc gac acg gcc gat gcg ccc tgg acc atc gtc aag tcc      816
Phe Phe Tyr Thr Asp Thr Ala Asp Ala Pro Trp Thr Ile Val Lys Ser
            260                 265                 270 aac gac aag aag cgc gcg cgg ctg aac tgc atg cgg cac ttc ctg tcg      864
Asn Asp Lys Lys Arg Ala Arg Leu Asn Cys Met Arg His Phe Leu Ser
        275                 280                 285 agc ctc gac tat ccg ggc aag gac ccg gag gtg gtg ggc gtg ccc gat      912
Ser Leu Asp Tyr Pro Gly Lys Asp Pro Glu Val Val Gly Val Pro Asp
    290                 295                 300 ccg ctg atc gtg gga cgt gcg gcg cag gtg atc ggc acg gcg gcc gac      960
Pro Leu Ile Val Gly Arg Ala Ala Gln Val Ile Gly Thr Ala Ala Asp
305                 310                 315                 320 atc ctc gac agc gcc acg ccg ccc gcg ctg cgc aag ccg cgt cag gga     1008
Ile Leu Asp Ser Ala Thr Pro Pro Ala Leu Arg Lys Pro Arg Gln Gly
                325                 330                 335

<210> SEQ ID NO 118
<211> LENGTH: 1632
<212> TYPE: DNA
<213> ORGANISM: Chloroflexus aurantiacus ATCC29366

<400> SEQUENCE: 118 atg ctt gaa cgc tgt att acc gat gta aag ctc agc aag gaa gag tac       48
Met Leu Glu Arg Cys Ile Thr Asp Val Lys Leu Ser Lys Glu Glu Tyr
1               5                  10                  15 acg caa ctg gct ccg ggg ttg cag gcg cgg ctc ttt gat ctc gaa caa       96
Thr Gln Leu Ala Pro Gly Leu Gln Ala Arg Leu Phe Asp Leu Glu Gln
            20                  25                  30 atg ctg ctg gaa gcg cgc att ccg acc atc ttt gta ttt gaa ggc tgg      144
Met Leu Leu Glu Ala Arg Ile Pro Thr Ile Phe Val Phe Glu Gly Trp
        35                  40                  45 gcc ggc acc gcc aaa gcc cgc aca att gca acc ctg acc cgg cgc ctt      192
Ala Gly Thr Ala Lys Ala Arg Thr Ile Ala Thr Leu Thr Arg Arg Leu
    50                  55                  60
```

```
gat ccg cgt ggc ttt cgg gtg cat tcg att acc cca ccg cgt acc tat        240
Asp Pro Arg Gly Phe Arg Val His Ser Ile Thr Pro Pro Arg Thr Tyr
 65                  70                  75                  80 gag caa caa tat ccc tgg ttg tac cgt ttc tgg ctc aag ata ccc agc        288
Glu Gln Gln Tyr Pro Trp Leu Tyr Arg Phe Trp Leu Lys Ile Pro Ser
                 85                  90                  95 tac ggt cag atg agc ttc ttt gat cgc tcg tgg tac cgt gag ttg ctg        336
Tyr Gly Gln Met Ser Phe Phe Asp Arg Ser Trp Tyr Arg Glu Leu Leu
            100                 105                 110 gcg gcc tat act acc ggt ggc agc cgt gat gaa tgg cgc acg cat tgc        384
Ala Ala Tyr Thr Thr Gly Gly Ser Arg Asp Glu Trp Arg Thr His Cys
        115                 120                 125 gaa gat gcc gtc att ttc gag cgg caa ctg gcc gat gat ggt gcg ctc        432
Glu Asp Ala Val Ile Phe Glu Arg Gln Leu Ala Asp Asp Gly Ala Leu
    130                 135                 140 att ctc aag ttc tgg tta cat atc acg aaa aag cag cag gca cgg cgc        480
Ile Leu Lys Phe Trp Leu His Ile Thr Lys Lys Gln Gln Ala Arg Arg
145                 150                 155                 160 ttt gcg aaa tta ctg gcc gat ccg ctg aat gcc tgg cgg gtg acc gag        528
Phe Ala Lys Leu Leu Ala Asp Pro Leu Asn Ala Trp Arg Val Thr Glu
                165                 170                 175 gaa gat ctc tgg cag cac cgt cat tac aaa aag gtc tat ctg gcc gtc        576
Glu Asp Leu Trp Gln His Arg His Tyr Lys Lys Val Tyr Leu Ala Val
            180                 185                 190 gaa gag atg ctc tcg cgc acc gac acc gca ttt gca ccc tgg cac att        624
Glu Glu Met Leu Ser Arg Thr Asp Thr Ala Phe Ala Pro Trp His Ile
        195                 200                 205 att ccg gct gcc gac aag cgt tac gcc cgg ctc acc gtc ttg caa att        672
Ile Pro Ala Ala Asp Lys Arg Tyr Ala Arg Leu Thr Val Leu Gln Ile
    210                 215                 220 att gtc ggg gcg ctg gag agt cga ttg gga att acc gcc agt gat cgt        720
Ile Val Gly Ala Leu Glu Ser Arg Leu Gly Ile Thr Ala Ser Asp Arg
225                 230                 235                 240 gag gcc agt ctt gat gat agt ggt ctg gcg ttg cgg cgc tac tat ctc        768
Glu Ala Ser Leu Asp Asp Ser Gly Leu Ala Leu Arg Arg Tyr Tyr Leu
                245                 250                 255 gat ttg cgc acg ccg gtt gtc gct aca ccg cgt gca gca ccg gta gat        816
Asp Leu Arg Thr Pro Val Val Ala Thr Pro Arg Ala Ala Pro Val Asp
            260                 265                 270 gca ggc aat tcc tct acc atg act ctg caa cag gct gaa cca atc acg        864
Ala Gly Asn Ser Ser Thr Met Thr Leu Gln Gln Ala Glu Pro Ile Thr
        275                 280                 285 acc ccg gtg gtc gtg acg ccg gtc gcg cca ctg tta cgg gca gcc agc        912
Thr Pro Val Val Val Thr Pro Val Ala Pro Leu Leu Arg Ala Ala Ser
    290                 295                 300 ccc tta cag cgc gtt gat ttg agt ttg cgt ctt gat gat gat acc tac        960
Pro Leu Gln Arg Val Asp Leu Ser Leu Arg Leu Asp Asp Asp Thr Tyr
305                 310                 315                 320 cac cgg gaa ttg aaa cgg ttg cag gcc agg atg tat ctg ctc ggc ctg       1008
His Arg Glu Leu Lys Arg Leu Gln Ala Arg Met Tyr Leu Leu Gly Leu
                325                 330                 335 cag gtg tac cat cag aag cga ccg gtc gtg ttt gtg ttt gaa ggc tgg       1056
Gln Val Tyr His Gln Lys Arg Pro Val Val Phe Val Phe Glu Gly Trp
            340                 345                 350 gat gca gcg ggt aag ggg ggc gcc att cag cgc ctg acg gcg gag ctt       1104
Asp Ala Ala Gly Lys Gly Gly Ala Ile Gln Arg Leu Thr Ala Glu Leu
        355                 360                 365 gat ccg cgt gcc tat acc gtg cac gcg att gcc gcc ccc gcc ggc gat       1152
Asp Pro Arg Ala Tyr Thr Val His Ala Ile Ala Ala Pro Ala Gly Asp
    370                 375                 380
```

```
gat aaa gct cgc cac tac ctg tac cgc ttc tgg cgg cgg ttg ccg ccg        1200
Asp Lys Ala Arg His Tyr Leu Tyr Arg Phe Trp Arg Arg Leu Pro Pro
385                 390                 395                 400 cgt ggt cag ttt gcg atc ttc gac cgc tcg tgg tac ggt cgc gtg tta        1248
Arg Gly Gln Phe Ala Ile Phe Asp Arg Ser Trp Tyr Gly Arg Val Leu
            405                 410                 415 gtt gaa cgg gtg gaa ggg ttt gcc cgc ccc gac gaa tgg cgt cgt gcc        1296
Val Glu Arg Val Glu Gly Phe Ala Arg Pro Asp Glu Trp Arg Arg Ala
        420                 425                 430 tac gcc gag att aat cag ttt gaa cgc cag ttg gtt gat ttt ggc gcg        1344
Tyr Ala Glu Ile Asn Gln Phe Glu Arg Gln Leu Val Asp Phe Gly Ala
    435                 440                 445 att att gcc aaa ttc tgg ctg cac atc agc ccc gaa gag caa ttg cgc        1392
Ile Ile Ala Lys Phe Trp Leu His Ile Ser Pro Glu Glu Gln Leu Arg
450                 455                 460 cgt ttt gaa gaa cgg cag cat gtg ccg tac aaa gcc tgg aaa ttg acc        1440
Arg Phe Glu Glu Arg Gln His Val Pro Tyr Lys Ala Trp Lys Leu Thr
465                 470                 475                 480 gat gaa gac tgg cgc aat cgc gaa aag tgg ccg gca tat ctt gaa gca        1488
Asp Glu Asp Trp Arg Asn Arg Glu Lys Trp Pro Ala Tyr Leu Glu Ala
            485                 490                 495 gcc gat gag atg ctg ctt cgc acc agt acg ccc tat gcg ccg tgg acg        1536
Ala Asp Glu Met Leu Leu Arg Thr Ser Thr Pro Tyr Ala Pro Trp Thr
        500                 505                 510 att gtc gag gca gaa gat aaa aag tat gcc cgg att aag att ttg cgc        1584
Ile Val Glu Ala Glu Asp Lys Lys Tyr Ala Arg Ile Lys Ile Leu Arg
    515                 520                 525 act gcg gtt gag gtg ttg gaa gcg gaa ttg ggg ccg gtg aag ttg gat        1632
Thr Ala Val Glu Val Leu Glu Ala Glu Leu Gly Pro Val Lys Leu Asp
530                 535                 540

<210> SEQ ID NO 119
<211> LENGTH: 906
<212> TYPE: DNA
<213> ORGANISM: Mesorhixobium loti MAFF303099

<400> SEQUENCE: 119 atg aaa aag gcc aag gaa aat ccc gca acg cca acg tca ggt ccg ctg         48
Met Lys Lys Ala Lys Glu Asn Pro Ala Thr Pro Thr Ser Gly Pro Leu
1               5                   10                  15 aag atc agg atc ggg ggc aag gag cgg gag ttc gac atc gag aat ccc         96
Lys Ile Arg Ile Gly Gly Lys Glu Arg Glu Phe Asp Ile Glu Asn Pro
            20                  25                  30 gag ctc ccg gac tgg gtc gag gac aac aaa ctg acc gcg ggc ggc tac        144
Glu Leu Pro Asp Trp Val Glu Asp Asn Lys Leu Thr Ala Gly Gly Tyr
        35                  40                  45 ccc tac gac aag aag atg aac agc gat gag tat gac gag acg ctc gag        192
Pro Tyr Asp Lys Lys Met Asn Ser Asp Glu Tyr Asp Glu Thr Leu Glu
    50                  55                  60 aaa ttg cag atc gag ctg gtc aag gcg cag gca tgg ctg cag gcg acc        240
Lys Leu Gln Ile Glu Leu Val Lys Ala Gln Ala Trp Leu Gln Ala Thr
65                  70                  75                  80 ggc aaa cgg gtg atg gcg ttg ttc gag ggc cgc gac gcc gcc ggc aag        288
Gly Lys Arg Val Met Ala Leu Phe Glu Gly Arg Asp Ala Ala Gly Lys
            85                  90                  95 ggc gga acg atc ttc gtg gtg cgc cag tat ctc aat ccg cgc acg gcg        336
Gly Gly Thr Ile Phe Val Val Arg Gln Tyr Leu Asn Pro Arg Thr Ala
        100                 105                 110 cgc aac gtg gcg ctg acc aag ccg acc ccc act gaa ctg ggg caa tgg        384
Arg Asn Val Ala Leu Thr Lys Pro Thr Pro Thr Glu Leu Gly Gln Trp
    115                 120                 125
```

| | | | | | | | | | | | | | | | | |
|---|---|---|---|---|---|---|---|---|---|---|---|---|---|---|---|---|
| tac | tac | cag | cgt | tat | gtc | gac | cat | ttc | ccg | acg | gcg | ggc | gaa | ttc | gtc | 432 |
| Tyr | Tyr | Gln | Arg | Tyr | Val | Asp | His | Phe | Pro | Thr | Ala | Gly | Glu | Phe | Val | |
| 130 | | | | 135 | | | | | 140 | | | | | | | |

| | | | | | | | | | | | | | | | | |
|---|---|---|---|---|---|---|---|---|---|---|---|---|---|---|---|---|
| acc | ttc | gac | cgc | tcc | tgg | tac | aac | cgc | gcc | ggc | gtc | gag | ccg | gtg | atg | 480 |
| Thr | Phe | Asp | Arg | Ser | Trp | Tyr | Asn | Arg | Ala | Gly | Val | Glu | Pro | Val | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | ttc | tgc | acg | ccc | gaa | cag | cat | gag | aaa | ttt | ctc | gat | gag | acg | ccg | 528 |
| Gly | Phe | Cys | Thr | Pro | Glu | Gln | His | Glu | Lys | Phe | Leu | Asp | Glu | Thr | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| cat | ttc | gaa | cgg | atg | atc | gtc | aac | gac | gat | atc | cac | ttc | ttc | aaa | ttc | 576 |
| His | Phe | Glu | Arg | Met | Ile | Val | Asn | Asp | Asp | Ile | His | Phe | Phe | Lys | Phe | |
| | | | | 180 | | | | | 185 | | | | | 190 | | |

| | | | | | | | | | | | | | | | | |
|---|---|---|---|---|---|---|---|---|---|---|---|---|---|---|---|---|
| tgg | ctc | aac | atc | ggc | cgg | gaa | acg | cag | ctc | gag | cgc | ttt | cac | gat | cgc | 624 |
| Trp | Leu | Asn | Ile | Gly | Arg | Glu | Thr | Gln | Leu | Glu | Arg | Phe | His | Asp | Arg | |
| | | 195 | | | | | 200 | | | | | 205 | | | | |

| | | | | | | | | | | | | | | | | |
|---|---|---|---|---|---|---|---|---|---|---|---|---|---|---|---|---|
| cgc | tac | agc | ccg | ctg | aag | agc | tgg | aag | ttc | tcg | ccc | atc | gat | gtc | gcc | 672 |
| Arg | Tyr | Ser | Pro | Leu | Lys | Ser | Trp | Lys | Phe | Ser | Pro | Ile | Asp | Val | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| ggc | atc | acc | aaa | tgg | gac | gat | tac | acc | aag | gca | cgc | gac | agc | atg | ttc | 720 |
| Gly | Ile | Thr | Lys | Trp | Asp | Asp | Tyr | Thr | Lys | Ala | Arg | Asp | Ser | Met | Phe | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| aag | cgc | acc | cac | aag | gag | ttc | gcg | cca | tgg | atc | atc | gtg | cgg | gcc | aat | 768 |
| Lys | Arg | Thr | His | Lys | Glu | Phe | Ala | Pro | Trp | Ile | Ile | Val | Arg | Ala | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | aag | cgc | cgc | gcg | cgg | ctg | gcg | gtg | atg | cgg | cgt | atc | ctg | ttg | tcg | 816 |
| Asp | Lys | Arg | Arg | Ala | Arg | Leu | Ala | Val | Met | Arg | Arg | Ile | Leu | Leu | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| ctg | ccc | tat | gag | ggg | cgc | gat | ctc | gat | atc | gtc | ggc | aag | gaa | gac | aag | 864 |
| Leu | Pro | Tyr | Glu | Gly | Arg | Asp | Leu | Asp | Ile | Val | Gly | Lys | Glu | Asp | Lys | |
| | | | 275 | | | | | 280 | | | | | 285 | | | |

| | | | | | | | | | | | | | |
|---|---|---|---|---|---|---|---|---|---|---|---|---|---|
| aag | atc | atc | ggc | gaa | ggg | ccg | tca | ttc | ctc | ggc | aag | gaa | ggc | 906 |
| Lys | Ile | Ile | Gly | Glu | Gly | Pro | Ser | Phe | Leu | Gly | Lys | Glu | Gly | |
| | 290 | | | | | 295 | | | | | 300 | | | |

```
<210> SEQ ID NO 120
<211> LENGTH: 1020
<212> TYPE: DNA
<213> ORGANISM: Streptomyces coelicolor ATCC BAA-471

<400> SEQUENCE: 120
```

| | | | | | | | | | | | | | | | | |
|---|---|---|---|---|---|---|---|---|---|---|---|---|---|---|---|---|
| atg | ggc | ttc | ctc | ccg | att | tcc | gag | gtt | tcc | gga | gta | ccc | ggc | cgg | gag | 48 |
| Met | Gly | Phe | Leu | Pro | Ile | Ser | Glu | Val | Ser | Gly | Val | Pro | Gly | Arg | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cac | tct | tca | cac | gag | gcc | ccg | tgg | gag | tcc | acg | acg | acc | gac | acg | cct | 96 |
| His | Ser | Ser | His | Glu | Ala | Pro | Trp | Glu | Ser | Thr | Thr | Thr | Asp | Thr | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | cgg | ccg | tcg | gga | agc | cga | ccg | ggt | acc | ggt | acg | cga | tca | aca | cgc | 144 |
| Phe | Arg | Pro | Ser | Gly | Ser | Arg | Pro | Gly | Thr | Gly | Thr | Arg | Ser | Thr | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| ata | tgc | gcc | gct | cgt | gcc | cga | aca | gta | ccg | tgc | aga | cac | gga | acg | cat | 192 |
| Ile | Cys | Ala | Ala | Arg | Ala | Arg | Thr | Val | Pro | Cys | Arg | His | Gly | Thr | His | |
| | 50 | | | | | 55 | | | | | 60 | | | | | |

| | | | | | | | | | | | | | | | | |
|---|---|---|---|---|---|---|---|---|---|---|---|---|---|---|---|---|
| cgg | aac | tcg | gtg | gag | gca | gga | ggc | cgc | atg | gca | ggc | acg | gaa | ctc | cgc | 240 |
| Arg | Asn | Ser | Val | Glu | Ala | Gly | Gly | Arg | Met | Ala | Gly | Thr | Glu | Leu | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aaa | atc | tca | ggc | aag | gtg | tac | gag | aag | gag | ttg | cgg | cgc | ctg | cag | att | 288 |
| Lys | Ile | Ser | Gly | Lys | Val | Tyr | Glu | Lys | Glu | Leu | Arg | Arg | Leu | Gln | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | ttg | gtg | aac | ctt | cag | gaa | tgg | gtt | ctg | acc | gag | aag | aag | cgc | gtt | 336 |
| Glu | Leu | Val | Asn | Leu | Gln | Glu | Trp | Val | Leu | Thr | Glu | Lys | Lys | Arg | Val | |
| | | | 100 | | | | | 105 | | | | | 110 | | | |

| | | |
|---|---|---|
| gcc gtg gtg ttc gaa gga cgg gac gcg gcc gga aag ggc ggc acc atc<br>Ala Val Val Phe Glu Gly Arg Asp Ala Ala Gly Lys Gly Gly Thr Ile<br>              115                    120                    125 | 384 | |
| aag cgg ctc acg gaa cac ctc aac ccg cgg gtg acg cgg atc gtg gcg<br>Lys Arg Leu Thr Glu His Leu Asn Pro Arg Val Thr Arg Ile Val Ala<br>130                    135                    140 | 432 | |
| ctg ccc aga ccg acc gaa cga gaa cgg aca cag tgg tat ttc caa cgg<br>Leu Pro Arg Pro Thr Glu Arg Glu Arg Thr Gln Trp Tyr Phe Gln Arg<br>145                    150                    155                    160 | 480 | |
| tac gtg gag cag ctt ccg gcg ggc ggc gag atc gtt ctc ttc gat cgc<br>Tyr Val Glu Gln Leu Pro Ala Gly Gly Glu Ile Val Leu Phe Asp Arg<br>                    165                    170                    175 | 528 | |
| agc tgg tac aac cgg gcc ggg gtc gaa cac gtc atg ggg ttc tgc acc<br>Ser Trp Tyr Asn Arg Ala Gly Val Glu His Val Met Gly Phe Cys Thr<br>                  180                    185                    190 | 576 | |
| gac gac gaa tac cga cga ttc ctg cgt cat tgc cct gtc ttc gaa cga<br>Asp Asp Glu Tyr Arg Arg Phe Leu Arg His Cys Pro Val Phe Glu Arg<br>                  195                    200                    205 | 624 | |
| atg ctt gtc gag gac ggg ctc ctg ctc gcc aag tac tgg ttc tcg gtg<br>Met Leu Val Glu Asp Gly Leu Leu Leu Arg Lys Tyr Trp Phe Ser Val<br>210                    215                    220 | 672 | |
| agt gac gtg gag cag cag gag cgc ttt cga cgc cgc ctc cag gac ccg<br>Ser Asp Val Glu Gln Gln Glu Arg Phe Arg Arg Arg Leu Gln Asp Pro<br>225                    230                    235                    240 | 720 | |
| ctg aaa cgc tgg aaa ctc tcc acg atg gac ctg gag tcg atc act cgg<br>Leu Lys Arg Trp Lys Leu Ser Thr Met Asp Leu Glu Ser Ile Thr Arg<br>                  245                    250                    255 | 768 | |
| tgg gaa gcc tat tcc cgc gcc aag gac gag atg atg gcc gcc acg gac<br>Trp Glu Ala Tyr Ser Arg Ala Lys Asp Glu Met Met Ala Ala Thr Asp<br>                    260                    265                    270 | 816 | |
| acc ccc gag tcc ccg tgg tac gtg gtg gag agc gac gac aaa cgc cgg<br>Thr Pro Glu Ser Pro Trp Tyr Val Val Glu Ser Asp Asp Lys Arg Arg<br>                  275                    280                    285 | 864 | |
| gcg cgg ctc aac atg atc gcc cac ctc ttg gac tcc ctc ccc cat cac<br>Ala Arg Leu Asn Met Ile Ala His Leu Leu Asp Ser Leu Pro His His<br>                290                    295                    300 | 912 | |
| cgc gtg cca ccg cct tca ctc agg ttg ccg gaa cgc ccc ccg ccg acg<br>Arg Val Pro Pro Pro Ser Leu Arg Leu Pro Glu Arg Pro Pro Pro Thr<br>305                    310                    315                    320 | 960 | |
| ggt tac acg cgg tcg ccc cgg gac cgg cag acg tac gtc ccg gac cac<br>Gly Tyr Thr Arg Ser Pro Arg Asp Arg Gln Thr Tyr Val Pro Asp His<br>                    325                    330                    335 | 1008 | |
| gcg gct cgc ttg<br>Ala Ala Arg Leu<br>                  340 | 1020 | |

```
<210> SEQ ID NO 121
<211> LENGTH: 1491
<212> TYPE: DNA
<213> ORGANISM: Pseudomonas putida KT2440

<400> SEQUENCE: 121
```

| | | |
|---|---|---|
| atg ttc gaa tct gcc gaa atc ggc cac agc atc gac aag gag gct tac<br>Met Phe Glu Ser Ala Glu Ile Gly His Ser Ile Asp Lys Glu Ala Tyr<br>1                      5                        10                    15 | 48 | |
| gac gcc gag gta ccc gct tta cgc gag gcc ctg ctc gaa gcc cag tac<br>Asp Ala Glu Val Pro Ala Leu Arg Glu Ala Leu Leu Glu Ala Gln Tyr<br>                    20                    25                    30 | 96 | |
| gaa ctc aag cag cag gcg cgt ttt ccg gtg atc gtg ctg atc aac ggc<br>Glu Leu Lys Gln Gln Ala Arg Phe Pro Val Ile Val Leu Ile Asn Gly<br>                  35                    40                    45 | 144 | |

```
att gaa ggc gcc ggc aag ggt gag acg gta aaa ctg ctc aac gag tgg      192
Ile Glu Gly Ala Gly Lys Gly Glu Thr Val Lys Leu Leu Asn Glu Trp
    50              55                  60 atg gac ccg cgc atg atc gat gtg ctc acc ttc gac cag cag acc gac      240
Met Asp Pro Arg Met Ile Asp Val Leu Thr Phe Asp Gln Gln Thr Asp
65              70                  75                  80 gaa gag ctg gcc cgc ccg ccc gcc tgg cgc tat tgg cgg gcc ttg ccg      288
Glu Glu Leu Ala Arg Pro Pro Ala Trp Arg Tyr Trp Arg Ala Leu Pro
                85                  90                  95 ccc aag ggg cga atg ggc gtt ttc ttt ggc aac tgg tac agc cag atg      336
Pro Lys Gly Arg Met Gly Val Phe Phe Gly Asn Trp Tyr Ser Gln Met
            100                 105                 110 ctg cag ggg cgg gtg cac ggg gtg ttc aag gat gcc gtg ctc gat cag      384
Leu Gln Gly Arg Val His Gly Val Phe Lys Asp Ala Val Leu Asp Gln
        115                 120                 125 gcc att acc ggt gcc gaa cgc ctg gag gag atg ctg tgc gat gaa ggt      432
Ala Ile Thr Gly Ala Glu Arg Leu Glu Glu Met Leu Cys Asp Glu Gly
    130                 135                 140 gcg ctg atc atc aag ttc tgg ttc cac ctg tcc aag aag cag atg aag      480
Ala Leu Ile Ile Lys Phe Trp Phe His Leu Ser Lys Lys Gln Met Lys
145                 150                 155                 160 gca cgg ctg aaa tcg ctc aag gac gac ccg ctg cac agc tgg aag atc      528
Ala Arg Leu Lys Ser Leu Lys Asp Asp Pro Leu His Ser Trp Lys Ile
                165                 170                 175 agc ccg ctg gat tgg cag cag tcg caa acc tac gac cgt ttc gtg cgc      576
Ser Pro Leu Asp Trp Gln Gln Ser Gln Thr Tyr Asp Arg Phe Val Arg
            180                 185                 190 ttt ggc gag cgc gtg ctg cgc cgc acc agc cgt gac tat gcg cca tgg      624
Phe Gly Glu Arg Val Leu Arg Arg Thr Ser Arg Asp Tyr Ala Pro Trp
        195                 200                 205 cac atc atc gaa ggg gta gac ccg aat tac cgc agc ctg gcg gtg ggg      672
His Ile Ile Glu Gly Val Asp Pro Asn Tyr Arg Ser Leu Ala Val Gly
    210                 215                 220 cgc att ctg ctg gaa agc ctg caa gcc gcg ctg gcc cac aat ccc aag      720
Arg Ile Leu Leu Glu Ser Leu Gln Ala Ala Leu Ala His Asn Pro Lys
225                 230                 235                 240 ggc aag cac cag ggc aac gtg gct cca ttg ggc cgc agc atc gac gac      768
Gly Lys His Gln Gly Asn Val Ala Pro Leu Gly Arg Ser Ile Asp Asp
                245                 250                 255 cgc agc ctg ctt ggc gcc ctg gac atg acc ttg cgc ctg gac aag gcc      816
Arg Ser Leu Leu Gly Ala Leu Asp Met Thr Leu Arg Leu Asp Lys Ala
            260                 265                 270 gac tat cag gaa cag ttg atc acc gaa cag gcg cgt ctg gcc ggc ctg      864
Asp Tyr Gln Glu Gln Leu Ile Thr Glu Gln Ala Arg Leu Ala Gly Leu
        275                 280                 285 ctg cgt gac aag cgc atg cgc cgg cac gcc ctg gtg gcg gtg ttc gaa      912
Leu Arg Asp Lys Arg Met Arg Arg His Ala Leu Val Ala Val Phe Glu
    290                 295                 300 ggc aac gac gcc gcc ggc aag ggg ggc gcc atc cgc cgc gtg gcg gcg      960
Gly Asn Asp Ala Ala Gly Lys Gly Gly Ala Ile Arg Arg Val Ala Ala
305                 310                 315                 320 gcg ctg gac ccg cgt cag tac cgt atc gta ccg att gcc gcg ccg acc      1008
Ala Leu Asp Pro Arg Gln Tyr Arg Ile Val Pro Ile Ala Ala Pro Thr
                325                 330                 335 gaa gaa gag cgc gcc cag ccg tac ctg tgg cgg ttc tgg cgg cac atc      1056
Glu Glu Glu Arg Ala Gln Pro Tyr Leu Trp Arg Phe Trp Arg His Ile
            340                 345                 350 ccg gca cgc ggc aag ttc acc atc ttc gac cgt tcc tgg tat ggc cgg      1104
Pro Ala Arg Gly Lys Phe Thr Ile Phe Asp Arg Ser Trp Tyr Gly Arg
        355                 360                 365
```

```
gtg ctg gtg gag cgg gtg gaa ggc ttc tgc agc ccc gct gac tgg atg      1152
Val Leu Val Glu Arg Val Glu Gly Phe Cys Ser Pro Ala Asp Trp Met
    370             375                 380 cgt gcc tat agc gag atc aac gac ttt gaa gag cag ttg gtg gat gcc      1200
Arg Ala Tyr Ser Glu Ile Asn Asp Phe Glu Glu Gln Leu Val Asp Ala
385             390                 395                 400 ggc gtg gtg gtg gtc aag ttc tgg ctg gcg atc gac cag cag acc caa      1248
Gly Val Val Val Val Lys Phe Trp Leu Ala Ile Asp Gln Gln Thr Gln
                405                 410                 415 ctg gag cgc ttc gaa gag cgt gag cag att ccg ttc aaa cgc tac aag      1296
Leu Glu Arg Phe Glu Glu Arg Glu Gln Ile Pro Phe Lys Arg Tyr Lys
            420                 425                 430 atc acc gag gat gac tgg cgc aac cgc gac aag tgg gac gaa tac tcc      1344
Ile Thr Glu Asp Asp Trp Arg Asn Arg Asp Lys Trp Asp Glu Tyr Ser
        435                 440                 445 cag gcg gtg ggc gac atg gtc gac cgc acc agc agc gag att gcc cct      1392
Gln Ala Val Gly Asp Met Val Asp Arg Thr Ser Ser Glu Ile Ala Pro
    450                 455                 460 tgg acg ctg gtg gag gcc aat gac aag cgc tgg gcg cgg gtg aag gtg      1440
Trp Thr Leu Val Glu Ala Asn Asp Lys Arg Trp Ala Arg Val Lys Val
465             470                 475                 480 gtg cgc aca atc aac cag gcg ctt gag gcg gcg ttt gcc aag cac aag      1488
Val Arg Thr Ile Asn Gln Ala Leu Glu Ala Ala Phe Ala Lys His Lys
                485                 490                 495 aaa                                                                   1491
Lys

<210> SEQ ID NO 122
<211> LENGTH: 900
<212> TYPE: DNA
<213> ORGANISM: Sinorhizobium meliloti ATCC51124

<400> SEQUENCE: 122 atg gca ctc gac gaa gca ccg gcc gaa gca agg ccg ggg agc cgg gcg        48
Met Ala Leu Asp Glu Ala Pro Ala Glu Ala Arg Pro Gly Ser Arg Ala
  1               5                  10                  15 gtc gaa ctg gag atc gac ggc aga agc cgc atc ttc gac atc gac gat        96
Val Glu Leu Glu Ile Asp Gly Arg Ser Arg Ile Phe Asp Ile Asp Asp
                 20                  25                  30 ccg gac ctg ccg aaa tgg atc gac gag gag gcc ttc cgc tcc gac gat       144
Pro Asp Leu Pro Lys Trp Ile Asp Glu Glu Ala Phe Arg Ser Asp Asp
             35                  40                  45 tac ccc tac aag aaa aaa ctc gat cgg gag gaa tac gaa gaa acg ctg       192
Tyr Pro Tyr Lys Lys Lys Leu Asp Arg Glu Glu Tyr Glu Glu Thr Leu
         50                  55                  60 acg aag ctg cag atc gaa ctg gtc aag gtc cag ttc tgg atg cag gcg       240
Thr Lys Leu Gln Ile Glu Leu Val Lys Val Gln Phe Trp Met Gln Ala
 65                  70                  75                  80 acc ggc aag cgc gtg atg gcg gtc ttc gag gga cgc gac gct gcc ggc       288
Thr Gly Lys Arg Val Met Ala Val Phe Glu Gly Arg Asp Ala Ala Gly
                 85                  90                  95 aag ggt ggt gcg atc cac gcg acg acg gcc aat atg aac ccc cgc tcc       336
Lys Gly Gly Ala Ile His Ala Thr Thr Ala Asn Met Asn Pro Arg Ser
            100                 105                 110 gcg cgc gtc gtc gca ctg acg aaa ccg acg gag acc gaa cgg ggc cag       384
Ala Arg Val Val Ala Leu Thr Lys Pro Thr Glu Thr Glu Arg Gly Gln
        115                 120                 125 tgg tac ttc cag cgc tat gtc gca acc ttc ccg acc gcc ggc gag ttc       432
Trp Tyr Phe Gln Arg Tyr Val Ala Thr Phe Pro Thr Ala Gly Glu Phe
    130                 135                 140 gtc ctt ttc gac cgc tcc tgg tac aac cgc gcc ggt gtc gaa ccg gtc       480
Val Leu Phe Asp Arg Ser Trp Tyr Asn Arg Ala Gly Val Glu Pro Val
```

```
Val Leu Phe Asp Arg Ser Trp Tyr Asn Arg Ala Gly Val Glu Pro Val
145                 150                 155                 160 atg ggc ttt tgc acc ccc gac cag tac gag caa ttc ctt aaa gag gcg      528
Met Gly Phe Cys Thr Pro Asp Gln Tyr Glu Gln Phe Leu Lys Glu Ala
                165                 170                 175 ccc cgc ttc gag gag atg atc gcg aac gag ggc atc cat ctc ttc aag      576
Pro Arg Phe Glu Glu Met Ile Ala Asn Glu Gly Ile His Leu Phe Lys
            180                 185                 190 ttt tgg atc aat atc ggc cgg gaa atg caa ctg aag cgc ttc cat gac      624
Phe Trp Ile Asn Ile Gly Arg Glu Met Gln Leu Lys Arg Phe His Asp
        195                 200                 205 cgg cgc cac gat ccg ttg aag atc tgg aag ctt tcg ccg atg gac atc      672
Arg Arg His Asp Pro Leu Lys Ile Trp Lys Leu Ser Pro Met Asp Ile
    210                 215                 220 gcg gcg ctg agc aag tgg gac gac tac acc gga aaa cgc gac cgt atg      720
Ala Ala Leu Ser Lys Trp Asp Asp Tyr Thr Gly Lys Arg Asp Arg Met
225                 230                 235                 240 ctg aag gaa acg cac acg gag cac ggg cca tgg gcg gtc atc cgc ggc      768
Leu Lys Glu Thr His Thr Glu His Gly Pro Trp Ala Val Ile Arg Gly
                245                 250                 255 aac gac aag cgc cgc tcg cgg atc aac gtg atc cgc cac atg ctg acg      816
Asn Asp Lys Arg Arg Ser Arg Ile Asn Val Ile Arg His Met Leu Thr
            260                 265                 270 aag ctc gac tat gac ggc aag gac gag gcg gcg atc gga gag gtc gac      864
Lys Leu Asp Tyr Asp Gly Lys Asp Glu Ala Ala Ile Gly Glu Val Asp
        275                 280                 285 gaa aag atc ctc ggc tcc ggc ccc ggt ttt ctc agg                      900
Glu Lys Ile Leu Gly Ser Gly Pro Gly Phe Leu Arg
    290                 295                 300

<210> SEQ ID NO 123
<211> LENGTH: 918
<212> TYPE: DNA
<213> ORGANISM: Sinorhizobium meliloti ATCC51124

<400> SEQUENCE: 123 atg agt aac tcg aaa gac gag gta gaa cgc atc gat tgg ctc gaa gcg       48
Met Ser Asn Ser Lys Asp Glu Val Glu Arg Ile Asp Trp Leu Glu Ala
1               5                   10                  15 gag ctt gct gac aca atc gac gag gat tac gag ctt gag ctt tca gaa       96
Glu Leu Ala Asp Thr Ile Asp Glu Asp Tyr Glu Leu Glu Leu Ser Glu
                20                  25                  30 ccg acc tta tcc gag aaa atc cgc gag att tac cgt aaa gcg cat cct      144
Pro Thr Leu Ser Glu Lys Ile Arg Glu Ile Tyr Arg Lys Ala His Pro
            35                  40                  45 ccg gcg ctt ccc cgc atg gat tat ttc cgc gcg ctc ctg gcc ttg cag      192
Pro Ala Leu Pro Arg Met Asp Tyr Phe Arg Ala Leu Leu Ala Leu Gln
    50                  55                  60 gcg gag cta atc aag ctg cag gac tgg gtc gtc tac cac aag cag aag      240
Ala Glu Leu Ile Lys Leu Gln Asp Trp Val Val Tyr His Lys Gln Lys
65                  70                  75                  80 gtc gtt gtg atc ttc gag gga cgc gac gcg gct gga aag ggc ggc gtc      288
Val Val Val Ile Phe Glu Gly Arg Asp Ala Ala Gly Lys Gly Gly Val
                85                  90                  95 atc aag cgc atc acc cag cga ctc aat ccg cgc atc gtt aga acg gtg      336
Ile Lys Arg Ile Thr Gln Arg Leu Asn Pro Arg Ile Val Arg Thr Val
            100                 105                 110 gcg ctg ccg gcg ccg tcc gat cgc gaa aag acc caa tgg tat ttc cag      384
Ala Leu Pro Ala Pro Ser Asp Arg Glu Lys Thr Gln Trp Tyr Phe Gln
    115                 120                 125 cgt tac gta cca cat ctg ccg gcg ggc ggc gaa atc gtc ctc ttc gac      432
```

```
cgc tcc tgg tac aat cgc tgc ggc gtc gaa cgc gtc atg ggc ttt gcg    480
Arg Ser Trp Tyr Asn Arg Cys Gly Val Glu Arg Val Met Gly Phe Ala
145                 150                 155                 160 acc gag gag gag gtc gag cag ttc ttc gac gac gtg ccg gaa ttc gaa    528
Thr Glu Glu Glu Val Glu Gln Phe Phe Asp Asp Val Pro Glu Phe Glu
                165                 170                 175 cgc atg ctg gtg cgc tcc ggc gtt cgg ctg gtt aag tac tgg ttc tcg    576
Arg Met Leu Val Arg Ser Gly Val Arg Leu Val Lys Tyr Trp Phe Ser
            180                 185                 190 atc acc gac gag gaa cag cag ctg cgc ttt ctg acg cgc atc cac gac    624
Ile Thr Asp Glu Glu Gln Gln Leu Arg Phe Leu Thr Arg Ile His Asp
        195                 200                 205 ccg ttg aaa cag tgg aag ctc tcg ccg atg gac ctg caa tcg cgc gtc    672
Pro Leu Lys Gln Trp Lys Leu Ser Pro Met Asp Leu Gln Ser Arg Val
    210                 215                 220 cgt tgg gaa gcg tac acc aag gcc aag gaa gag acc ttc gcc cgt acc    720
Arg Trp Glu Ala Tyr Thr Lys Ala Lys Glu Glu Thr Phe Ala Arg Thr
225                 230                 235                 240 aac att cgc gaa gcg cca tgg cat atc gtc gag gcc aac gac aag aag    768
Asn Ile Arg Glu Ala Pro Trp His Ile Val Glu Ala Asn Asp Lys Lys
                245                 250                 255 cgg gcc cgg ctc aac tgc atc gac cat ctc ttg aag caa atc ccc tat    816
Arg Ala Arg Leu Asn Cys Ile Asp His Leu Leu Lys Gln Ile Pro Tyr
            260                 265                 270 gag gat gtg ccg cac gag gat atc acc ttg ccg gag cgc att ttc aat    864
Glu Asp Val Pro His Glu Asp Ile Thr Leu Pro Glu Arg Ile Phe Asn
        275                 280                 285 ccc aac tac gag cgg aag gtc ctg cct ccg gag ctt tac gtt cct gcg    912
Pro Asn Tyr Glu Arg Lys Val Leu Pro Pro Glu Leu Tyr Val Pro Ala
    290                 295                 300 aaa tac                                                             918
Lys Tyr
305

<210> SEQ ID NO 124
<211> LENGTH: 688
<212> TYPE: PRT
<213> ORGANISM: Eschierichia coli W3110

<400> SEQUENCE: 124

Met Gly Gln Glu Lys Leu Tyr Ile Glu Lys Glu Leu Ser Trp Leu Ser
1               5                   10                  15

Phe Asn Glu Arg Val Leu Gln Glu Ala Ala Asp Lys Ser Asn Pro Leu
            20                  25                  30

Ile Glu Arg Met Arg Phe Leu Gly Ile Tyr Ser Asn Asn Leu Asp Glu
        35                  40                  45

Phe Tyr Lys Val Arg Phe Ala Glu Leu Lys Arg Ile Ile Ile Ser
    50                  55                  60

Glu Glu Gln Gly Ser Asn Ser His Ser Arg His Leu Leu Gly Lys Ile
65              70                  75                  80

Gln Ser Arg Val Leu Lys Ala Asp Gln Glu Phe Asp Gly Leu Tyr Asn
                85                  90                  95

Glu Leu Leu Leu Glu Met Ala Arg Asn Gln Ile Phe Leu Ile Asn Glu
            100                 105                 110

Arg Gln Leu Ser Val Asn Gln Asn Trp Leu Arg His Tyr Phe Lys
        115                 120                 125

Gln Tyr Leu Arg Gln His Ile Thr Pro Ile Leu Ile Asn Pro Asp Thr
```

-continued

```
            130                 135                 140
Asp Leu Val Gln Phe Leu Lys Asp Asp Tyr Thr Tyr Leu Ala Val Glu
145                 150                 155                 160
Ile Ile Arg Gly Asp Thr Ile Arg Tyr Ala Leu Leu Glu Ile Pro Ser
                165                 170                 175
Asp Lys Val Pro Arg Phe Val Asn Leu Pro Pro Glu Ala Pro Arg Arg
            180                 185                 190
Arg Lys Pro Met Ile Leu Leu Asp Asn Ile Leu Arg Tyr Cys Leu Asp
        195                 200                 205
Asp Ile Phe Lys Gly Phe Phe Asp Tyr Asp Ala Leu Asn Ala Tyr Ser
    210                 215                 220
Met Lys Met Thr Arg Asp Ala Glu Tyr Asp Leu Val His Glu Met Glu
225                 230                 235                 240
Ala Ser Leu Met Glu Leu Met Ser Ser Leu Lys Gln Arg Leu Thr
                245                 250                 255
Ala Glu Pro Val Arg Phe Val Tyr Gln Arg Asp Met Pro Asn Ala Leu
            260                 265                 270
Val Glu Val Leu Arg Glu Lys Leu Thr Ile Ser Arg Tyr Asp Ser Ile
        275                 280                 285
Val Pro Gly Gly Arg Tyr His Asn Phe Lys Asp Phe Ile Asn Phe Pro
    290                 295                 300
Asn Val Gly Lys Ala Asn Leu Val Asn Lys Pro Leu Pro Arg Leu Arg
305                 310                 315                 320
His Ile Trp Phe Asp Lys Ala Gln Phe Arg Asn Gly Phe Asp Ala Ile
                325                 330                 335
Arg Glu Arg Asp Val Leu Leu Tyr Tyr Pro Tyr His Thr Phe Glu His
            340                 345                 350
Val Leu Glu Leu Leu Arg Gln Ala Ser Phe Asp Pro Ser Val Leu Ala
        355                 360                 365
Ile Lys Ile Asn Ile Tyr Arg Val Ala Lys Asp Ser Arg Ile Ile Asp
    370                 375                 380
Ser Met Ile His Ala Ala His Asn Gly Lys Lys Val Thr Val Val
385                 390                 395                 400
Glu Leu Gln Ala Arg Phe Asp Glu Glu Ala Asn Ile His Trp Ala Lys
                405                 410                 415
Arg Leu Thr Glu Ala Gly Val His Val Ile Phe Ser Ala Pro Gly Leu
            420                 425                 430
Lys Ile His Ala Lys Leu Phe Leu Ile Ser Arg Lys Glu Asn Gly Glu
        435                 440                 445
Val Val Arg Tyr Ala His Ile Gly Thr Gly Asn Phe Asn Glu Lys Thr
    450                 455                 460
Ala Arg Leu Tyr Thr Asp Tyr Ser Leu Leu Thr Ala Asp Ala Arg Ile
465                 470                 475                 480
Thr Asn Glu Val Arg Arg Val Phe Asn Phe Ile Glu Asn Pro Tyr Arg
                485                 490                 495
Pro Val Thr Phe Asp Tyr Leu Met Val Ser Pro Gln Asn Ser Arg Arg
            500                 505                 510
Leu Leu Tyr Glu Met Val Asp Arg Glu Ile Ala Asn Ala Gln Gln Gly
        515                 520                 525
Leu Pro Ser Gly Ile Thr Leu Lys Leu Asn Asn Leu Val Asp Lys Gly
    530                 535                 540
Leu Val Asp Arg Leu Tyr Ala Ala Ser Ser Gly Val Pro Val Asn
545                 550                 555                 560
```

```
Leu Leu Val Arg Gly Met Cys Ser Leu Ile Pro Asn Leu Glu Gly Ile
            565                 570                 575

Ser Asp Asn Ile Arg Ala Ile Ser Ile Val Asp Arg Tyr Leu Glu His
        580                 585                 590

Asp Arg Val Tyr Ile Phe Glu Asn Gly Gly Asp Lys Lys Val Tyr Leu
    595                 600                 605

Ser Ser Ala Asp Trp Met Thr Arg Asn Ile Asp Tyr Arg Ile Glu Val
610                 615                 620

Ala Thr Pro Leu Leu Asp Pro Arg Leu Lys Gln Arg Val Leu Asp Ile
625                 630                 635                 640

Ile Asp Ile Leu Phe Ser Asp Thr Val Lys Ala Arg Tyr Ile Asp Lys
                645                 650                 655

Glu Leu Ser Asn Arg Tyr Val Pro Arg Gly Asn Arg Lys Val Arg
            660                 665                 670

Ala Gln Leu Ala Ile Tyr Asp Tyr Ile Lys Ser Leu Glu Gln Pro Glu
        675                 680                 685

<210> SEQ ID NO 125
<211> LENGTH: 336
<212> TYPE: PRT
<213> ORGANISM: Rhodobacter sphaeroides ATCC17023

<400> SEQUENCE: 125

Met Ala Glu Asp Arg Ala Met Pro Val Met Pro Pro Ala Ala Asp Ala
1               5                   10                  15

Ala Glu Ala Val Pro Ala Ala Pro Thr Ala Leu Pro Glu Glu Gly Pro
            20                  25                  30

Ala Gly Pro Glu Ala Pro Leu Gln Thr Leu His Gly Pro Arg His Phe
        35                  40                  45

Pro Ala Val Asp Ala Asn Ala Ile Arg Gln Ala Phe Glu Gly Gly His
    50                  55                  60

Tyr Pro Tyr Pro Arg Arg Leu Gly Arg Val Val Tyr Glu Ala Glu Lys
65                  70                  75                  80

Ala Arg Leu Gln Ala Glu Leu Leu Lys Val Gln Ile Trp Ala Gln Glu
                85                  90                  95

Thr Gly Gln Lys Phe Val Ile Leu Met Glu Gly Arg Asp Ala Ala Gly
            100                 105                 110

Lys Gly Gly Thr Ile Lys Arg Phe Met Glu His Leu Asn Pro Arg Tyr
        115                 120                 125

Ala Arg Val Val Ala Leu Thr Lys Pro Gly Glu Arg Glu Arg Gly Gln
    130                 135                 140

Trp Phe Phe Gln Arg Tyr Ile Glu His Leu Pro Thr Ala Gly Glu Ile
145                 150                 155                 160

Val Phe Phe Asp Arg Ser Trp Tyr Asn Arg Ala Gly Val Glu Arg Val
                165                 170                 175

Met Gly Phe Cys Thr Pro Ser Glu Tyr Leu Glu Phe Met Arg Gln Ala
            180                 185                 190

Pro Glu Leu Glu Arg Met Leu Val Arg Ser Gly Ile Arg Leu Tyr Lys
        195                 200                 205

Tyr Trp Phe Ser Val Thr Arg Asp Glu Gln Arg Ala Arg Phe Leu Ala
    210                 215                 220

Arg Glu Thr Asp Pro Leu Lys Arg Trp Lys Leu Ser Pro Ile Asp Lys
225                 230                 235                 240

Ala Ser Leu Asp Lys Trp Asp Asp Tyr Thr Glu Ala Lys Glu Ala Met
                245                 250                 255
```

```
Phe Phe Tyr Thr Asp Thr Ala Asp Ala Pro Trp Thr Ile Val Lys Ser
            260                 265                 270

Asn Asp Lys Lys Arg Ala Arg Leu Asn Cys Met Arg His Phe Leu Ser
        275                 280                 285

Ser Leu Asp Tyr Pro Gly Lys Asp Pro Glu Val Val Gly Val Pro Asp
    290                 295                 300

Pro Leu Ile Val Gly Arg Ala Ala Gln Val Ile Gly Thr Ala Ala Asp
305                 310                 315                 320

Ile Leu Asp Ser Ala Thr Pro Pro Ala Leu Arg Lys Pro Arg Gln Gly
                325                 330                 335

<210> SEQ ID NO 126
<211> LENGTH: 544
<212> TYPE: PRT
<213> ORGANISM: Chloroflexus aurantiacus ATCC29366

<400> SEQUENCE: 126

Met Leu Glu Arg Cys Ile Thr Asp Val Lys Leu Ser Lys Glu Glu Tyr
  1               5                  10                  15

Thr Gln Leu Ala Pro Gly Leu Gln Ala Arg Leu Phe Asp Leu Glu Gln
             20                  25                  30

Met Leu Leu Glu Ala Arg Ile Pro Thr Ile Phe Val Phe Glu Gly Trp
         35                  40                  45

Ala Gly Thr Ala Lys Ala Arg Thr Ile Ala Thr Leu Thr Arg Arg Leu
     50                  55                  60

Asp Pro Arg Gly Phe Arg Val His Ser Ile Thr Pro Pro Arg Thr Tyr
 65                  70                  75                  80

Glu Gln Gln Tyr Pro Trp Leu Tyr Arg Phe Trp Leu Lys Ile Pro Ser
                 85                  90                  95

Tyr Gly Gln Met Ser Phe Phe Asp Arg Ser Trp Tyr Arg Glu Leu Leu
            100                 105                 110

Ala Ala Tyr Thr Thr Gly Gly Ser Arg Asp Glu Trp Arg Thr His Cys
        115                 120                 125

Glu Asp Ala Val Ile Phe Glu Arg Gln Leu Ala Asp Asp Gly Ala Leu
    130                 135                 140

Ile Leu Lys Phe Trp Leu His Ile Thr Lys Lys Gln Gln Ala Arg Arg
145                 150                 155                 160

Phe Ala Lys Leu Leu Ala Asp Pro Leu Asn Ala Trp Arg Val Thr Glu
                165                 170                 175

Glu Asp Leu Trp Gln His Arg His Tyr Lys Lys Val Tyr Leu Ala Val
            180                 185                 190

Glu Glu Met Leu Ser Arg Thr Asp Thr Ala Phe Ala Pro Trp His Ile
        195                 200                 205

Ile Pro Ala Ala Asp Lys Arg Tyr Ala Arg Leu Thr Val Leu Gln Ile
    210                 215                 220

Ile Val Gly Ala Leu Glu Ser Arg Leu Gly Ile Thr Ala Ser Asp Arg
225                 230                 235                 240

Glu Ala Ser Leu Asp Asp Ser Gly Leu Ala Leu Arg Arg Tyr Tyr Leu
                245                 250                 255

Asp Leu Arg Thr Pro Val Val Ala Thr Pro Arg Ala Ala Pro Val Asp
            260                 265                 270

Ala Gly Asn Ser Ser Thr Met Thr Leu Gln Gln Ala Glu Pro Ile Thr
        275                 280                 285

Thr Pro Val Val Val Thr Pro Val Ala Pro Leu Leu Arg Ala Ala Ser
    290                 295                 300
```

Pro Leu Gln Arg Val Asp Leu Ser Leu Arg Leu Asp Asp Thr Tyr
305                 310                 315                 320

His Arg Glu Leu Lys Arg Leu Gln Ala Arg Met Tyr Leu Leu Gly Leu
            325                 330                 335

Gln Val Tyr His Gln Lys Arg Pro Val Val Phe Val Phe Glu Gly Trp
        340                 345                 350

Asp Ala Ala Gly Lys Gly Gly Ala Ile Gln Arg Leu Thr Ala Glu Leu
    355                 360                 365

Asp Pro Arg Ala Tyr Thr Val His Ala Ile Ala Pro Ala Gly Asp
370                 375                 380

Asp Lys Ala Arg His Tyr Leu Tyr Arg Phe Trp Arg Arg Leu Pro Pro
385                 390                 395                 400

Arg Gly Gln Phe Ala Ile Phe Asp Arg Ser Trp Tyr Gly Arg Val Leu
            405                 410                 415

Val Glu Arg Val Glu Gly Phe Ala Arg Pro Asp Glu Trp Arg Arg Ala
        420                 425                 430

Tyr Ala Glu Ile Asn Gln Phe Glu Arg Gln Leu Val Asp Phe Gly Ala
    435                 440                 445

Ile Ile Ala Lys Phe Trp Leu His Ile Ser Pro Glu Glu Gln Leu Arg
450                 455                 460

Arg Phe Glu Glu Arg Gln His Val Pro Tyr Lys Ala Trp Lys Leu Thr
465                 470                 475                 480

Asp Glu Asp Trp Arg Asn Arg Glu Lys Trp Pro Ala Tyr Leu Glu Ala
            485                 490                 495

Ala Asp Glu Met Leu Leu Arg Thr Ser Thr Pro Tyr Ala Pro Trp Thr
        500                 505                 510

Ile Val Glu Ala Glu Asp Lys Lys Tyr Ala Arg Ile Lys Ile Leu Arg
    515                 520                 525

Thr Ala Val Glu Val Leu Glu Ala Glu Leu Gly Pro Val Lys Leu Asp
530                 535                 540

<210> SEQ ID NO 127
<211> LENGTH: 302
<212> TYPE: PRT
<213> ORGANISM: Mesorhixobium loti MAFF303099

<400> SEQUENCE: 127

Met Lys Lys Ala Lys Glu Asn Pro Ala Thr Pro Ser Gly Pro Leu
1               5                   10                  15

Lys Ile Arg Ile Gly Gly Lys Glu Arg Glu Phe Asp Ile Glu Asn Pro
            20                  25                  30

Glu Leu Pro Asp Trp Val Glu Asp Asn Lys Leu Thr Ala Gly Gly Tyr
        35                  40                  45

Pro Tyr Asp Lys Lys Met Asn Ser Asp Glu Tyr Asp Glu Thr Leu Glu
    50                  55                  60

Lys Leu Gln Ile Glu Leu Val Lys Ala Gln Ala Trp Leu Gln Ala Thr
65                  70                  75                  80

Gly Lys Arg Val Met Ala Leu Phe Glu Gly Arg Asp Ala Ala Gly Lys
            85                  90                  95

Gly Gly Thr Ile Phe Val Val Arg Gln Tyr Leu Asn Pro Arg Thr Ala
        100                 105                 110

Arg Asn Val Ala Leu Thr Lys Pro Thr Pro Thr Glu Leu Gly Gln Trp
    115                 120                 125

Tyr Tyr Gln Arg Tyr Val Asp His Phe Pro Thr Ala Gly Glu Phe Val
    130                 135                 140

```
Thr Phe Asp Arg Ser Trp Tyr Asn Arg Ala Gly Val Glu Pro Val Met
145                 150                 155                 160

Gly Phe Cys Thr Pro Glu Gln His Glu Lys Phe Leu Asp Glu Thr Pro
                165                 170                 175

His Phe Glu Arg Met Ile Val Asn Asp Asp Ile His Phe Phe Lys Phe
            180                 185                 190

Trp Leu Asn Ile Gly Arg Glu Thr Gln Leu Glu Arg Phe His Asp Arg
        195                 200                 205

Arg Tyr Ser Pro Leu Lys Ser Trp Lys Phe Ser Pro Ile Asp Val Ala
    210                 215                 220

Gly Ile Thr Lys Trp Asp Asp Tyr Thr Lys Ala Arg Asp Ser Met Phe
225                 230                 235                 240

Lys Arg Thr His Lys Glu Phe Ala Pro Trp Ile Val Arg Ala Asn
                245                 250                 255

Asp Lys Arg Arg Ala Arg Leu Ala Val Met Arg Arg Ile Leu Leu Ser
                260                 265                 270

Leu Pro Tyr Glu Gly Arg Asp Leu Asp Ile Val Gly Lys Glu Asp Lys
                275                 280                 285

Lys Ile Ile Gly Glu Gly Pro Ser Phe Leu Gly Lys Glu Gly
    290                 295                 300

<210> SEQ ID NO 128
<211> LENGTH: 340
<212> TYPE: PRT
<213> ORGANISM: Streptomyces coelicolor ATCC BAA-471

<400> SEQUENCE: 128

Met Gly Phe Leu Pro Ile Ser Glu Val Ser Gly Val Pro Gly Arg Glu
1               5                   10                  15

His Ser Ser His Glu Ala Pro Trp Glu Ser Thr Thr Thr Asp Thr Pro
            20                  25                  30

Phe Arg Pro Ser Gly Ser Arg Pro Gly Thr Gly Thr Arg Ser Thr Arg
        35                  40                  45

Ile Cys Ala Ala Arg Ala Arg Thr Val Pro Cys Arg His Gly Thr His
    50                  55                  60

Arg Asn Ser Val Glu Ala Gly Arg Met Ala Gly Thr Glu Leu Arg
65              70                  75                  80

Lys Ile Ser Gly Lys Val Tyr Glu Lys Leu Arg Arg Leu Gln Ile
                85                  90                  95

Glu Leu Val Asn Leu Gln Glu Trp Val Leu Thr Glu Lys Lys Arg Val
            100                 105                 110

Ala Val Val Phe Glu Gly Arg Asp Ala Ala Gly Lys Gly Gly Thr Ile
        115                 120                 125

Lys Arg Leu Thr Glu His Leu Asn Pro Arg Val Thr Arg Ile Val Ala
    130                 135                 140

Leu Pro Arg Pro Thr Glu Arg Glu Arg Thr Gln Trp Tyr Phe Gln Arg
145                 150                 155                 160

Tyr Val Glu Gln Leu Pro Ala Gly Gly Glu Ile Val Leu Phe Asp Arg
                165                 170                 175

Ser Trp Tyr Asn Arg Ala Gly Val Glu His Val Met Gly Phe Cys Thr
            180                 185                 190

Asp Asp Glu Tyr Arg Arg Phe Leu Arg His Cys Pro Val Phe Glu Arg
        195                 200                 205

Met Leu Val Glu Asp Gly Leu Leu Leu Arg Lys Tyr Trp Phe Ser Val
    210                 215                 220
```

```
Ser Asp Val Glu Gln Gln Glu Arg Phe Arg Arg Leu Gln Asp Pro
225                 230                 235                 240

Leu Lys Arg Trp Lys Leu Ser Thr Met Asp Leu Glu Ser Ile Thr Arg
        245                 250                 255

Trp Glu Ala Tyr Ser Arg Ala Lys Asp Glu Met Met Ala Ala Thr Asp
            260                 265                 270

Thr Pro Glu Ser Pro Trp Tyr Val Val Glu Ser Asp Lys Arg Arg
        275                 280                 285

Ala Arg Leu Asn Met Ile Ala His Leu Leu Asp Ser Leu Pro His His
    290                 295                 300

Arg Val Pro Pro Pro Ser Leu Arg Leu Pro Glu Arg Pro Pro Thr
305                 310                 315                 320

Gly Tyr Thr Arg Ser Pro Arg Asp Arg Gln Thr Tyr Val Pro Asp His
            325                 330                 335

Ala Ala Arg Leu
            340

<210> SEQ ID NO 129
<211> LENGTH: 497
<212> TYPE: PRT
<213> ORGANISM: Pseudomonas putida KT2440

<400> SEQUENCE: 129

Met Phe Glu Ser Ala Glu Ile Gly His Ser Ile Asp Lys Glu Ala Tyr
1               5                   10                  15

Asp Ala Glu Val Pro Ala Leu Arg Glu Ala Leu Leu Glu Ala Gln Tyr
            20                  25                  30

Glu Leu Lys Gln Gln Ala Arg Phe Pro Val Ile Val Leu Ile Asn Gly
        35                  40                  45

Ile Glu Gly Ala Gly Lys Gly Glu Thr Val Lys Leu Leu Asn Glu Trp
    50                  55                  60

Met Asp Pro Arg Met Ile Asp Val Leu Thr Phe Asp Gln Gln Thr Asp
65                  70                  75                  80

Glu Glu Leu Ala Arg Pro Pro Ala Trp Arg Tyr Trp Arg Ala Leu Pro
                85                  90                  95

Pro Lys Gly Arg Met Gly Val Phe Phe Gly Asn Trp Tyr Ser Gln Met
            100                 105                 110

Leu Gln Gly Arg Val His Gly Val Phe Lys Asp Ala Val Leu Asp Gln
        115                 120                 125

Ala Ile Thr Gly Ala Glu Arg Leu Glu Glu Met Leu Cys Asp Glu Gly
    130                 135                 140

Ala Leu Ile Ile Lys Phe Trp Phe His Leu Ser Lys Lys Gln Met Lys
145                 150                 155                 160

Ala Arg Leu Lys Ser Leu Lys Asp Asp Pro Leu His Ser Trp Lys Ile
                165                 170                 175

Ser Pro Leu Asp Trp Gln Gln Ser Gln Thr Tyr Asp Arg Phe Val Arg
            180                 185                 190

Phe Gly Glu Arg Val Leu Arg Arg Thr Ser Arg Asp Tyr Ala Pro Trp
        195                 200                 205

His Ile Ile Glu Gly Val Asp Pro Asn Tyr Arg Ser Leu Ala Val Gly
    210                 215                 220

Arg Ile Leu Leu Glu Ser Leu Gln Ala Ala Leu Ala His Asn Pro Lys
225                 230                 235                 240

Gly Lys His Gln Gly Asn Val Ala Pro Leu Gly Arg Ser Ile Asp Asp
                245                 250                 255
```

```
Arg Ser Leu Leu Gly Ala Leu Asp Met Thr Leu Arg Leu Asp Lys Ala
            260                 265                 270
Asp Tyr Gln Glu Gln Leu Ile Thr Glu Gln Ala Arg Leu Ala Gly Leu
        275                 280                 285
Leu Arg Asp Lys Arg Met Arg Arg His Ala Leu Val Ala Val Phe Glu
    290                 295                 300
Gly Asn Asp Ala Ala Gly Lys Gly Gly Ala Ile Arg Arg Val Ala Ala
305                 310                 315                 320
Ala Leu Asp Pro Arg Gln Tyr Arg Ile Val Pro Ile Ala Ala Pro Thr
                325                 330                 335
Glu Glu Glu Arg Ala Gln Pro Tyr Leu Trp Arg Phe Trp Arg His Ile
            340                 345                 350
Pro Ala Arg Gly Lys Phe Thr Ile Phe Asp Arg Ser Trp Tyr Gly Arg
        355                 360                 365
Val Leu Val Glu Arg Val Glu Gly Phe Cys Ser Pro Ala Asp Trp Met
    370                 375                 380
Arg Ala Tyr Ser Glu Ile Asn Asp Phe Glu Glu Gln Leu Val Asp Ala
385                 390                 395                 400
Gly Val Val Val Val Lys Phe Trp Leu Ala Ile Asp Gln Gln Thr Gln
                405                 410                 415
Leu Glu Arg Phe Glu Glu Arg Glu Gln Ile Pro Phe Lys Arg Tyr Lys
            420                 425                 430
Ile Thr Glu Asp Asp Trp Arg Asn Arg Asp Lys Trp Asp Glu Tyr Ser
        435                 440                 445
Gln Ala Val Gly Asp Met Val Asp Arg Thr Ser Ser Glu Ile Ala Pro
    450                 455                 460
Trp Thr Leu Val Glu Ala Asn Asp Lys Arg Trp Ala Arg Val Lys Val
465                 470                 475                 480
Val Arg Thr Ile Asn Gln Ala Leu Glu Ala Ala Phe Ala Lys His Lys
                485                 490                 495
Lys

<210> SEQ ID NO 130
<211> LENGTH: 300
<212> TYPE: PRT
<213> ORGANISM: Sinorhizobium meliloti ATCC51124

<400> SEQUENCE: 130

Met Ala Leu Asp Glu Ala Pro Ala Glu Ala Arg Pro Gly Ser Arg Ala
  1               5                  10                  15
Val Glu Leu Glu Ile Asp Gly Arg Ser Arg Ile Phe Asp Ile Asp Asp
                20                  25                  30
Pro Asp Leu Pro Lys Trp Ile Asp Glu Ala Phe Arg Ser Asp Asp
            35                  40                  45
Tyr Pro Tyr Lys Lys Lys Leu Asp Arg Glu Glu Tyr Glu Glu Thr Leu
        50                  55                  60
Thr Lys Leu Gln Ile Glu Leu Val Lys Val Gln Phe Trp Met Gln Ala
 65                  70                  75                  80
Thr Gly Lys Arg Val Met Ala Val Phe Glu Gly Arg Asp Ala Ala Gly
                 85                  90                  95
Lys Gly Gly Ala Ile His Ala Thr Thr Ala Asn Met Asn Pro Arg Ser
                100                 105                 110
Ala Arg Val Val Ala Leu Thr Lys Pro Thr Gly Thr Glu Arg Gly Gln
            115                 120                 125
Trp Tyr Phe Gln Arg Tyr Val Ala Thr Phe Pro Thr Ala Gly Glu Phe
```

```
                130                 135                 140
Val Leu Phe Asp Arg Ser Trp Tyr Asn Arg Ala Gly Val Glu Pro Val
145                 150                 155                 160

Met Gly Phe Cys Thr Pro Asp Gln Tyr Glu Gln Phe Leu Lys Glu Ala
                165                 170                 175

Pro Arg Phe Glu Glu Met Ile Ala Asn Glu Gly Ile His Leu Phe Lys
                180                 185                 190

Phe Trp Ile Asn Ile Gly Arg Glu Met Gln Leu Lys Arg Phe His Asp
                195                 200                 205

Arg Arg His Asp Pro Leu Lys Ile Trp Lys Leu Ser Pro Met Asp Ile
                210                 215                 220

Ala Ala Leu Ser Lys Trp Asp Asp Tyr Thr Gly Lys Arg Asp Arg Met
225                 230                 235                 240

Leu Lys Glu Thr His Thr Glu His Gly Pro Trp Ala Val Ile Arg Gly
                245                 250                 255

Asn Asp Lys Arg Arg Ser Arg Ile Asn Val Ile Arg His Met Leu Thr
                260                 265                 270

Lys Leu Asp Tyr Asp Gly Lys Asp Glu Ala Ala Ile Gly Glu Val Asp
                275                 280                 285

Glu Lys Ile Leu Gly Ser Gly Pro Gly Phe Leu Arg
                290                 295                 300

<210> SEQ ID NO 131
<211> LENGTH: 306
<212> TYPE: PRT
<213> ORGANISM: Sinorhizobium meliloti ATCC51124

<400> SEQUENCE: 131

Met Ser Asn Ser Lys Asp Glu Val Glu Arg Ile Asp Trp Leu Glu Ala
1               5                   10                  15

Glu Leu Ala Asp Thr Ile Asp Glu Asp Tyr Glu Leu Glu Leu Ser Glu
                20                  25                  30

Pro Thr Leu Ser Glu Lys Ile Arg Glu Ile Tyr Arg Lys Ala His Pro
                35                  40                  45

Pro Ala Leu Pro Arg Met Asp Tyr Phe Arg Ala Leu Leu Ala Leu Gln
                50                  55                  60

Ala Glu Leu Ile Lys Leu Gln Asp Trp Val Val Tyr His Lys Gln Lys
65              70                  75                  80

Val Val Val Ile Phe Glu Gly Arg Asp Ala Ala Gly Lys Gly Gly Val
                85                  90                  95

Ile Lys Arg Ile Thr Gln Arg Leu Asn Pro Arg Ile Val Arg Thr Val
                100                 105                 110

Ala Leu Pro Ala Pro Ser Asp Arg Glu Lys Thr Gln Trp Tyr Phe Gln
                115                 120                 125

Arg Tyr Val Pro His Leu Pro Ala Gly Gly Glu Ile Val Leu Phe Asp
                130                 135                 140

Arg Ser Trp Tyr Asn Arg Cys Gly Val Glu Arg Val Met Gly Phe Ala
145                 150                 155                 160

Thr Glu Glu Glu Val Glu Gln Phe Phe Asp Asp Val Pro Glu Phe Glu
                165                 170                 175

Arg Met Leu Val Arg Ser Gly Val Arg Leu Val Lys Tyr Trp Phe Ser
                180                 185                 190

Ile Thr Asp Glu Glu Gln Gln Leu Arg Phe Leu Thr Arg Ile His Asp
                195                 200                 205

Pro Leu Lys Gln Trp Lys Leu Ser Pro Met Asp Leu Gln Ser Arg Val
```

|   |   |   |   |   |   |   |   |   |   |   |   |   |   |   |
|---|---|---|---|---|---|---|---|---|---|---|---|---|---|---|
|   |   |   | 210 |   |   |   |   | 215 |   |   |   |   | 220 |   |
| Arg | Trp | Glu | Ala | Tyr | Thr | Lys | Ala | Lys | Glu | Glu | Thr | Phe | Ala | Arg | Thr |
| 225 |   |   |   |   | 230 |   |   |   |   | 235 |   |   |   |   | 240 |
| Asn | Ile | Arg | Glu | Ala | Pro | Trp | His | Ile | Val | Glu | Ala | Asn | Asp | Lys | Lys |
|   |   |   |   | 245 |   |   |   |   | 250 |   |   |   |   | 255 |   |
| Arg | Ala | Arg | Leu | Asn | Cys | Ile | Asp | His | Leu | Leu | Lys | Gln | Ile | Pro | Tyr |
|   |   |   |   | 260 |   |   |   |   | 265 |   |   |   |   | 270 |   |
| Glu | Asp | Val | Pro | His | Glu | Asp | Ile | Thr | Leu | Pro | Glu | Arg | Ile | Phe | Asn |
|   |   |   | 275 |   |   |   |   | 280 |   |   |   |   | 285 |   |   |
| Pro | Asn | Tyr | Glu | Arg | Lys | Val | Leu | Pro | Pro | Glu | Leu | Tyr | Val | Pro | Ala |
|   |   | 290 |   |   |   |   | 295 |   |   |   |   | 300 |   |   |   |
| Lys | Tyr |   |   |   |   |   |   |   |   |   |   |   |   |   |   |
| 305 |   |   |   |   |   |   |   |   |   |   |   |   |   |   |   |

PROCESS FOR PRODUCING DIPEPTIDES OR DIPEPTIDE DERIVATIVES

The present application claims benefit of JP 2004-189007, filed 25 Jun. 2004, the entire contents of which is incorporated herein by reference.

BACKGROUND OF THE INVENTION

The present invention relates to a process for efficiently producing dipeptides or dipeptide derivatives from amino acids or amino acid derivatives.

Chemical synthesis methods (liquid phase method and solid phase method), enzymatic synthesis methods and biological synthesis methods utilizing recombinant DNA techniques are known as the methods for large-scale peptide synthesis. Currently, the enzymatic synthesis methods and biological synthesis methods are employed for the synthesis of long-chain peptides longer than 50 residues, and the chemical synthesis methods and enzymatic synthesis methods are mainly employed for the synthesis of dipeptides.

In the synthesis of dipeptides by the chemical synthesis methods, operations such as introduction and removal of protective groups for functional groups are necessary, and racemates are also formed. The chemical synthesis methods are thus considered to be disadvantageous in respect of cost and efficiency. They are unfavorable also from the viewpoint of environmental hygiene because of the use of large amounts of organic solvents and the like.

As to the synthesis of dipeptides by the enzymatic methods, the following methods are known: a method utilizing reverse reaction of protease (J. Biol. Chem., 119, 707-720 (1937)); methods utilizing thermostable aminoacyl t-RNA synthetase (Japanese Published Unexamined Patent Application No. 146539/83, Japanese Published Unexamined Patent Application No. 209991/83, Japanese Published Unexamined Patent Application No. 209992/83 and Japanese Published Unexamined Patent Application No. 106298/84); and methods utilizing non-ribosomal peptide synthetase (hereinafter referred to as NRPS) (Chem. Biol., 7, 373-384 (2000), FEBS Lett., 498, 42-45 (2001), U.S. Pat. No. 5,795,738 and U.S. Pat. No. 5,652,116).

However, the method utilizing reverse reaction of protease requires introduction and removal of protective groups for functional groups of amino acids used as substrates, which causes difficulties in raising the efficiency of peptide-forming reaction and in preventing peptidolytic reaction. The methods utilizing thermostable aminoacyl t-RNA synthetase have the defects that the expression of the enzyme and the prevention of side reactions forming by-products other than the desired products are difficult. The methods utilizing NRPS are inefficient because NRPS requires adenosine-5'-triphosphate (ATP) for reaction and it is necessary to add a large amount of ATP to the reaction system.

A group of peptide synthetases such as γ-glutamylcysteine synthetase, glutathione synthetase, D-alanyl-D-alanine (D-Ala-D-Ala) ligase and poly-γ-glutamate synthetase are also known as proteins having dipeptide-synthesizing activity. However, most of these enzymes utilize D-amino acids as substrates or catalyze peptide bond formation at the γ-carboxyl group. Because of such properties, they can not be used for the synthesis of dipeptides by peptide bond formation at the α-carboxyl group of L-amino acid.

The only known example of an enzyme capable of dipeptide synthesis by the activity to form a peptide bond at the α-carboxyl group of L-amino acid is bacilysin (dipeptide antibiotic derived from a microorganism belonging to the genus Bacillus) synthetase. Bacilysin synthetase is known to have the activity to synthesize bacilysin [L-alanyl-L-anticapsin (L-Ala-L-anticapsin)] and L-alanyl-L-alanine (L-Ala-L-Ala), but there is no information about its activity to synthesize other dipeptides (J. Ind. Microbiol., 2, 201-208 (1987) and Enzyme. Microbial. Technol., 29, 400-406 (2001)).

As for the bacilysin biosynthetase genes in Bacillus subtilis 168 whose entire genome information has been clarified (Nature, 390, 249-256 (1997)), it is known that the productivity of bacilysin is increased by amplification of bacilysin operons containing ORFs ywfA-F (WO00/03009 pamphlet). However, it is not known whether an ORF encoding a protein having the activity to ligate two or more amino acids by peptide bond is contained in these ORFs, and if contained, which ORF encodes the protein.

It is reported that a protein bearing no similarity to NRPS (albC gene product) is responsible for the synthesis of the cyclo(L-phenylalanyl-L-leucine) structure in Streptomyces noursei ATCC 11455 known as a strain producing the antibiotic albonoursin and that albonoursin was detected when cyclo dipeptide oxidase was made to act on the culture liquor of Escherichia coli and Streptomyces lividans into which the albC gene was introduced (Chemistry & Biol., 9, 1355-1364 (2002)). However, there is no report that the albC gene product forms a straight-chain dipeptide.

As to the method of supplying ATP, which is an energy source in various enzyme reactions, regeneration of ATP from ADP utilizing the glycolytic pathway and regeneration of ATP from ADP utilizing polyphosphate kinase and polyphosphoric acid (Agric. Biol. Chem., 52, 1471-1477 (1988), Biotech. Appl. Biochem., 10, 107-117 (1988) and Biotech. Appl. Biochem., 15, 125-133 (1992)) are known. The system of regenerating ATP from ADP utilizing the glycolytic pathway is present in all the microorganisms having the glycolytic pathway. Polyphosphate kinase capable of regenerating ATP from ADP utilizing polyphosphoric acid is known to be widely present in bacteria (Agric. Biol. Chem., 52(6), 1471-1477 (1988), Biotech. Appl. Biochem., 10, 107-117 (1988), Biotech. Appl. Biochem., 15, 125-133 (1992) and J. Biol. Chem., 267, 22556-22561 (1992)), yeast (J. Biol. Chem., 234, 2595-2604 (1959) and Arch. Biochem. Biophys., 83, 259-267 (1959)), plants (Biochem. J., 124, 407-417 (1971)) and animals (Biochem. J., 75, 417-428 (1960)).

However, it is not known that dipeptides can be efficiently produced by combining dipeptide-forming reaction requiring ATP and ATP-regenerating reaction utilizing polyphosphate kinase and polyphosphoric acid.

An object of the present invention is to provide a process for efficiently producing dipeptides or dipeptide derivatives.

SUMMARY OF THE INVENTION

The present invention relates to the following (1) to (34).

(1) A process for producing a dipeptide or a dipeptide derivative (hereinafter referred to as dipeptide or dipeptide derivative PI), which comprises:

allowing (i) a phosphate donor, (ii) a substance selected from the group consisting of adenosine-5'-monophosphate (hereinafter abbreviated as AMP), adenosine-5'-diphosphate (hereinafter abbreviated as ADP) and adenosine-5'-triphosphate (hereinafter abbreviated as ATP), (iii) a protein having polyphosphate kinase activity, or a culture of cells having the ability to produce the protein or a treated matter of the culture, (iv) a protein having the activity to ATP-dependently form dipeptide or dipeptide derivative PI from one or more kinds of amino acids or amino acid derivatives, or a culture of cells having the ability to produce the protein or a treated matter of the culture and (v) one or more kinds of amino acids or amino acid derivatives to be present in an aqueous medium;

allowing dipeptide or dipeptide derivative PI to form and accumulate in the aqueous medium; and recovering dipeptide or dipeptide derivative PI from the aqueous medium.

(2) A process for producing a dipeptide or a dipeptide derivative (hereinafter referred to as dipeptide or dipeptide derivative PII), which comprises:

allowing (i) a phosphate donor, (ii) a substance selected from the group consisting of AMP, ADP and ATP, (iii) a protein having polyphosphate kinase activity, or a culture of cells having the ability to produce the protein or a treated matter of the culture, (iv) a protein having the activity to ATP-dependently form dipeptide or dipeptide derivative PI from one or more kinds of amino acids or amino acid derivatives, or a culture of cells having the ability to produce the protein or a treated matter of the culture and (v) one or more kinds of amino acids or amino acid derivatives to be present in an aqueous medium;

allowing dipeptide or dipeptide derivative PI to form and accumulate in the aqueous medium;

subjecting dipeptide or dipeptide derivative PI, as such or after recovery, to modification to form dipeptide or dipeptide derivative PII; and recovering dipeptide or dipeptide derivative PII.

(3) The process according to the above (1) or (2), wherein the protein having the activity to ATP-dependently form dipeptide or dipeptide derivative PI from one or more kinds of amino acids or amino acid derivatives is a protein selected from the group consisting of the following [1] to [8]:

[1] a protein having the amino acid sequence shown in any of SEQ ID NOS: 1 to 13;

[2] a protein consisting of an amino acid sequence wherein one or more amino acid residues are deleted, substituted or added in the amino acid sequence shown in any of SEQ ID NOS: 1 to 13 and having the activity to ATP-dependently form dipeptide or dipeptide derivative PI from one or more kinds of amino acids or amino acid derivatives;

[3] a protein consisting of an amino acid sequence which has 65% or more homology to the amino acid sequence shown in any of SEQ ID NOS: 1 to 13 and having the activity to ATP-dependently form dipeptide or dipeptide derivative PI from one or more kinds of amino acids or amino acid derivatives;

[4] a protein having an amino acid sequence which has 80% or more homology to the amino acid sequence shown in SEQ ID NO: 27 and having the activity to ATP-dependently form dipeptide or dipeptide derivative PI from one or more kinds of amino acids or amino acid derivatives;

[5] a protein having the amino acid sequence shown in SEQ ID NO: 47 or 48;

[6] a protein consisting of an amino acid sequence wherein one or more amino acid residues are deleted, substituted or added in the amino acid sequence shown in SEQ ID NO: 47 or 48 and having the activity to ATP-dependently form dipeptide or dipeptide derivative PI from one or more kinds of amino acids or amino acid derivatives;

[7] a protein consisting of an amino acid sequence which has 65% or more homology to the amino acid sequence shown in SEQ ID NO: 47 or 48 and having the activity to ATP-dependently form dipeptide or dipeptide derivative PI from one or more kinds of amino acids or amino acid derivatives; and

[8] a protein having non-ribosomal peptide synthetase (hereinafter referred to as NRPS) activity.

(4) The process according to any of the above (1) to (3), wherein the cells having the ability to produce the protein having the activity to ATP-dependently form dipeptide or dipeptide derivative PI from one or more kinds of amino acids or amino acid derivatives are cells carrying DNA selected from the group consisting of the following [1] to [6]:

[1] DNA having the nucleotide sequence shown in any of SEQ ID NOS: 14 to 26 and 46;

[2] DNA which hybridizes with DNA having a nucleotide sequence complementary to the nucleotide sequence shown in any of SEQ ID NOS: 14 to 26 and 46 under stringent conditions and which encodes a protein having the activity to ATP-dependently form dipeptide or dipeptide derivative PI from one or more kinds of amino acids or amino acid derivatives;

[3] DNA which hybridizes with DNA having a nucleotide sequence complementary to the nucleotide sequence in SEQ ID NO: 28 and encoding a protein having the activity to ATP-dependently form dipeptide or dipeptide derivative PI from one or more kinds of amino acids or amino acid derivatives;

[4] DNA having the nucleotide sequence shown in SEQ ID NO: 49 or 50;

[5] DNA which hybridizes with DNA having a nucleotide sequence complementary to the nucleotide sequence shown in SEQ ID NO: 49 or 50 under stringent conditions and which encodes a protein having the activity to ATP-dependently form dipeptide or dipeptide derivative PI from one or more kinds of amino acids or amino acid derivatives; and

[6] DNA encoding a protein having NRPS activity.

(5) The process according to any of the above (1) to (4), wherein the protein having polyphosphate kinase activity is a protein selected from the group consisting of the following [1] to [3]:

[1] a protein having the amino acid sequence shown in any of SEQ ID NOS: 124 to 131;

[2] a protein consisting of an amino acid sequence wherein one or more amino acid residues are deleted, substituted or added in the amino acid sequence shown in any of SEQ ID NOS: 124 to 131 and having polyphosphate kinase activity; and

[3] a protein consisting of an amino acid sequence which has 65% or more homology to the amino acid sequence shown in any of SEQ ID NOS: 124 to 131 and having polyphosphate kinase activity.

(6) The process according to any of the above (1) to (5), wherein the cells having the ability to produce the protein having polyphosphate kinase activity are cells carrying DNA according to the following [1] or [2]:

[1] DNA having the nucleotide sequence shown in any of SEQ ID NOS: 116 to 123;

[2] DNA which hybridizes with DNA having a nucleotide sequence complementary to the nucleotide sequence shown in any of SEQ ID NOS: 116 to 123 under stringent conditions and which encodes a protein having polyphosphate kinase activity.

(7) The process according to any of the above (1) to (6), wherein the amino acids or amino acid derivatives are amino acids or amino acid derivatives represented by formula (I):

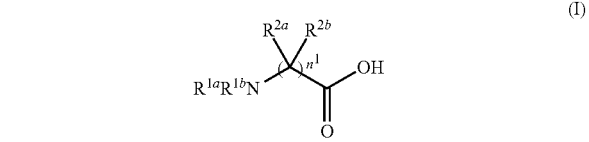

(wherein $n^1$ represents an integer of 1 to 3;

$R^{1a}$ and $R^{1b}$, which may be the same or different, each represent a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or either $R^{1a}$ or $R^{1b}$ may form a substituted or unsubstituted heterocyclic group together with the adjacent nitrogen atom, the carbon atom adjacent to the nitrogen atom and either $R^{2a}$ or $R^{2b}$ on the carbon atom; and $R^{2a}$ and $R^{2b}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{2a}$ or $R^{2b}$ on the carbon atom adjacent to $R^{1a}R^{1b}N$ may form a substituted or unsubstituted heterocyclic group together with the adjacent carbon atom, the nitrogen atom adjacent to the carbon atom and either $R^{1a}$ or $R^{1b}$, and when $n^1$ is 2 or 3, two or three $R^{2a}$s and two or three $R^{2b}$s may be the same or different, respectively), or formula (II):

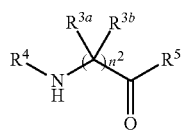

(II)

[wherein $n^2$ has the same significance as the above $n^1$;

$R^{3a}$ and $R^{3b}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{3a}$ or $R^{3b}$ on the carbon atom adjacent to $R^4HN$ may form a substituted or unsubstituted heterocyclic group together with the adjacent carbon atom, the nitrogen atom adjacent to the carbon atom and $R^4$, and when $n^2$ is 2 or 3, two or three $R^{3a}$s and two or three $R^{3b}$s may be the same or different, respectively;

$R^4$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or $R^4$ may form a substituted or unsubstituted heterocyclic group together with the adjacent nitrogen atom, the carbon atom adjacent to the nitrogen atom and either $R^{3a}$ or $R^{3b}$ on the carbon atom; and $R^5$ represents amino, hydroxy, substituted or unsubstituted lower alkoxy, mono(substituted or unsubstituted lower alkyl)amino, di(substituted or unsubstituted lower alkyl)amino, or an alicyclic heterocyclic group], provided that when all the amino acids or amino acid derivatives are amino acids or amino acid derivatives represented by formula (I), at least one of $R^{1a}$ and $R^{1b}$ is a hydrogen atom, and when all the amino acids or amino acid derivatives are amino acids or amino acid derivatives represented by formula (II), $R^5$ is hydroxy.

(8) The process according to any of the above (1) to (6), wherein the amino acids or amino acid derivatives are amino acids or amino acid derivatives represented by formula (III):

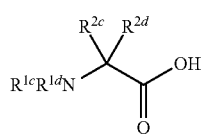

(III)

(wherein $R^{1c}$ and $R^{1d}$, which may be the same or different, each represent a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl; and $R^{2c}$ and $R^{2d}$, which may be the same or different, each represent a hydrogen atom or substituted or unsubstituted lower alkyl), or formula (IV):

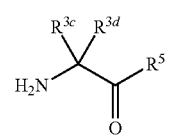

(IV)

(wherein $R^{3c}$ and $R^{3d}$, which may be the same or different, each represent a hydrogen atom, substituted or unsubstituted lower alkyl, substituted or unsubstituted aralkyl, or substituted or unsubstituted aryl; and $R^5$ has the same significance as defined above), provided that when all the amino acids or amino acid derivatives are amino acids or amino acid derivatives represented by formula (III), at least one of $R^{1c}$ and $R^{1d}$ is a hydrogen atom, and when all the amino acids or amino acid derivatives are amino acids or amino acid derivatives represented by formula (IV), $R^5$ is hydroxy.

(9) The process according to any of the above (1) to (6), wherein the amino acids or amino acid derivatives are amino acids or amino acid derivatives represented by formula (V):

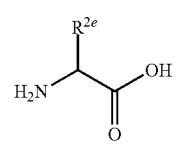

(V)

(wherein $R^{2e}$ represents substituted or unsubstituted methyl), or formula (VI):

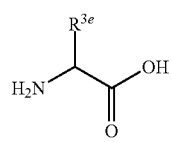

(VI)

(wherein $R^{3e}$ represents substituted or unsubstituted lower alkyl, substituted or unsubstituted aralkyl, or substituted or unsubstituted aryl).

(10) The process according to any of the above (1) to (6), wherein the amino acids or amino acid derivatives are amino acids selected from the group consisting of L-amino acids, glycine and β-alanine, or derivatives thereof.

(11) The process according to the above (10), wherein the L-amino acid is an L-amino acid selected from the group consisting of L-alanine, L-glutamine, L-glutamic acid, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-azaserine, L-theanine, L-4-hydroxyproline, L-3-hydroxyproline, L-ornithine, L-citrulline and L-6-diazo-5-oxo-norleucine.

(12) The process according to any of the above (1) to (7), wherein dipeptide or dipeptide derivative PI is a dipeptide or a dipeptide derivative represented by formula (VIIa):

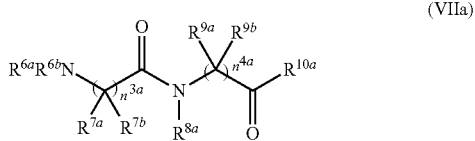

(VIIa)

[wherein $n^{3a}$ and $n^{4a}$ each have the same significance as the above $n^1$;

$R^{6a}$ and $R^{6b}$, which may be the same or different, each represent a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or either $R^{6a}$ or $R^{6b}$ may form a substituted or unsubstituted heterocyclic group together with the adjacent nitrogen atom, the carbon atom adjacent to the nitrogen atom and either $R^{7a}$ or $R^{7b}$ on the carbon atom;

$R^{7a}$ and $R^{7b}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{7a}$ or $R^{7b}$ on the carbon atom adjacent to $R^{6a}R^{6b}N$ may form a substituted or unsubstituted heterocyclic group together with the adjacent carbon atom, the nitrogen atom adjacent to the carbon atom and either $R^{6a}$ or $R^{6b}$, and when $n^{3a}$ is 2 or 3, two or three $R^{7a}$s and two or three $R^{7b}$s may be the same or different, respectively;

$R^{8a}$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or $R^{8a}$ may form a substituted or unsubstituted heterocyclic group together with the adjacent nitrogen atom, the carbon atom adjacent to the nitrogen atom and bound to $R^{9a}$ and $R^{9b}$, and either $R^{9a}$ or $R^{9b}$ on the carbon atom;

$R^{9a}$ and $R^{9b}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{9a}$ or $R^{9b}$ on the carbon atom adjacent to —$R^{8a}$N— may form a substituted or unsubstituted heterocyclic group together with the adjacent carbon atom, the nitrogen atom adjacent to the carbon atom and $R^{8a}$, and when $n^{4a}$ is 2 or 3, two or three $R^{9a}$s and two or three $R^{9b}$s may be the same or different, respectively; and $R^{10a}$ represents amino, hydroxy, substituted or unsubstituted lower alkoxy, mono(substituted or unsubstituted lower alkyl)amino, di(substituted or unsubstituted lower alkyl) amino, or an alicyclic heterocyclic group].

(13) The process according to any of the above (1) to (7), wherein dipeptide or dipeptide derivative PII is a dipeptide or a dipeptide derivative represented by formula (VIIb):

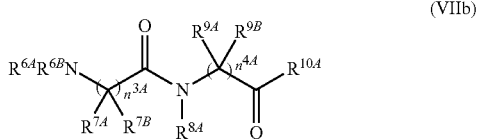

(VIIb)

(wherein $n^{3A}$ and $n^{4A}$ each have the same significance as the above $n^1$;

$R^{6A}$ and $R^{6B}$, which may be the same or different, each represent a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or either $R^{6A}$ or $R^{6B}$ may form a substituted or unsubstituted heterocyclic group together with the adjacent nitrogen atom, the carbon atom adjacent to the nitrogen atom and either $R^{7A}$ or $R^{7B}$ on the carbon atom;

$R^{7A}$ and $R^{7B}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{7A}$ or $R^{7B}$ on the carbon atom adjacent to $R^{6A}R^{6B}N$ may form a substituted or unsubstituted heterocyclic group together with the adjacent carbon atom, the nitrogen atom adjacent to the carbon atom and either $R^{6A}$ or $R^{6B}$, and when $n^{3A}$ is 2 or 3, two or three $R^{7A}$s and two or three $R^{7B}$s may be the same or different, respectively;

$R^{8A}$ represents a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl, or $R^{8A}$ may form a substituted or unsubstituted heterocyclic group together with the adjacent nitrogen atom, the carbon atom adjacent to the nitrogen atom and bound to $R^{9A}$ and $R^{9B}$, and either $R^{9A}$ or $R^{9B}$ on the carbon atom;

$R^{9A}$ and $R^{9B}$, which may be the same or different, each represent a hydrogen atom, substituted or unsubstituted lower alkyl, substituted or unsubstituted aralkyl, substituted or unsubstituted aryl, or substituted or unsubstituted heterocyclic alkyl, or either $R^{9A}$ or $R^{9B}$ on the carbon atom adjacent to —$R^{8A}$N— may form a substituted or unsubstituted heterocyclic group together with the adjacent carbon atom, the nitrogen atom adjacent to the carbon atom and $R^{8A}$, and when $n^{4A}$ is 2 or 3, two or three $R^{9A}$s and two or three $R^{9B}$s may be the same or different, respectively; and $R^{10A}$ has the same significance as the above $R^{10a}$).

(14) The process according to any of the above (1) to (8), wherein dipeptide or dipeptide derivative PI is a dipeptide or a dipeptide derivative represented by formula (VIIIa):

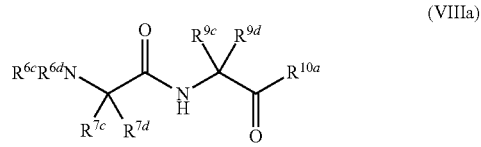

(VIIIa)

(wherein $R^{6c}$ and $R^{6d}$, which may be the same or different, each represent a hydrogen atom, substituted or unsubstituted lower alkyl, substituted or unsubstituted lower alkenyl, substituted or unsubstituted lower alkynyl, substituted or unsubstituted aralkyl, substituted or unsubstituted lower alkanoyl, substituted or unsubstituted lower alkoxycarbonyl, substituted or unsubstituted aryl, or substituted or unsubstituted aroyl;

$R^{7c}$ and $R^{7d}$, which may be the same or different, each represent a hydrogen atom or substituted or unsubstituted lower alkyl;

$R^{9c}$ and $R^{9d}$, which may be the same or different, each represent a hydrogen atom, substituted or unsubstituted lower alkyl, substituted or unsubstituted aralkyl, or substituted or unsubstituted aryl; and $R^{10a}$ has the same significance as defined above).

(15) The process according to any of the above (1) to (8), wherein dipeptide or dipeptide derivative PII is a dipeptide or a dipeptide derivative represented by formula (VIIIb):

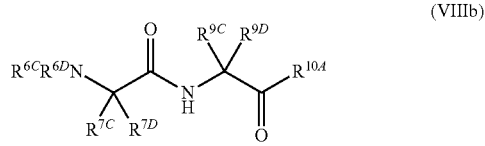
(VIIIb)

(wherein $R^{6C}$, $R^{6D}$, $R^{7C}$, $R^{7D}$, $R^{9C}$ and $R^{9D}$ have the same significances as the above $R^{6c}$, $R^{6d}$, $R^{7c}$, $R^{7d}$, $R^{9c}$ and $R^{9d}$, respectively; and $R^{10A}$ has the same significance as defined above).

(16) The process according to any of the above (1) to (9), wherein dipeptide or dipeptide derivative PI is a dipeptide or a dipeptide derivative represented by formula (IXa):

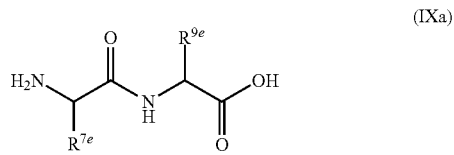
(IXa)

(wherein $R^{7e}$ represents substituted or unsubstituted methyl; and $R^{9e}$ represents substituted or unsubstituted lower alkyl, substituted or unsubstituted aralkyl, or substituted or unsubstituted aryl).

(17) The process according to any of the above (1) to (9), wherein dipeptide or dipeptide derivative PII is a dipeptide or a dipeptide derivative represented by formula (IXb):

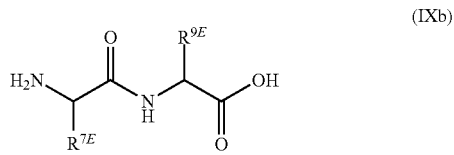
(IXb)

(wherein $R^{7E}$ and $R^{9E}$ have the same significances as the above $R^{7e}$ and $R^{9e}$, respectively).

(18) The process according to any of the above (1) to (10), wherein dipeptide or dipeptide derivative PI or dipeptide or dipeptide derivative PII is a dipeptide or a dipeptide derivative in which the same or different amino acids or amino acid derivatives selected from the group consisting of L-amino acids, glycine, β-alanine and their derivatives are linked with each other by peptide bond.

(19) The process according to the above (18), wherein the L-amino acid is an L-amino acid selected from the group consisting of L-alanine, L-glutamine, L-glutamic acid, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-azaserine, L-theanine, L-4-hydroxyproline, L-3-hydroxyproline, L-ornithine, L-citrulline and L-6-diazo-5-oxo-norleucine.

(20) The process according to any of the above (1) to (19), wherein the cells are cells of a microorganism.

(21) The process according to the above (20), wherein the microorganism is a procaryote.

(22) The process according to the above (21), wherein the procaryote is a microorganism in which the activities of one or more kinds of peptidases and one or more kinds of proteins having peptide-permeating/transporting activity (hereinafter referred to also as peptide-permeating/transporting proteins) are reduced or lost.

(23) The process according to the above (21), wherein the procaryote is a microorganism in which the activities of three or more kinds of peptidases are reduced or lost.

(24) The process according to the above (22) or (23), wherein the peptidase is a protein having the amino acid sequence shown in any of SEQ ID NOS: 55 to 58, or a protein having an amino acid sequence which has 80% or more homology to the amino acid sequence shown in any of SEQ ID NOS: 55 to 58 and having peptidase activity.

(25) The process according to the above (22) or (24), wherein the peptide-permeating/transporting protein is a protein having the amino acid sequence shown in any of SEQ ID NOS: 59 to 63, or a protein having an amino acid sequence which has 80% or more homology to the amino acid sequence shown in any of SEQ ID NOS: 59 to 63 and having peptide-permeating/transporting activity.

(26) The process according to any of the above (21) to (25), wherein the procaryote is a microorganism belonging to the genus *Escherichia*, *Bacillus* or *Corynebacterium*.

(27) The process according to the above (26), wherein the microorganism belonging to the genus *Escherichia*, *Bacillus* or *Corynebacterium* is *Escherichia coli*, *Corynebacterium glutamicum*, *Corynebacterium ammoniagenes*, *Corynebacterium lactofermentum*, *Corynebacterium flavum*, *Corynebacterium efficiens*, *Bacillus subtilis* or *Bacillus megaterium*.

(28) The process according to any of the above (1) to (27), wherein the treated matter of the culture is a treated matter which is selected from the group consisting of heat-treated culture, concentrated culture, dried culture, cells obtained by centrifuging the culture, products obtained by subjecting the cells to heat treatment, drying, freeze-drying, treatment with a surfactant, ultrasonication, mechanical friction, treatment with a solvent, enzymatic treatment, protein fractionation and immobilization, and an enzyme preparation obtained by extracting the cells, and which has the activity to ATP-dependently form dipeptide or dipeptide derivative PI from one or more kinds of amino acids or amino acid derivatives, or polyphosphate kinase activity.

(29) The process according to the above (28), wherein the heated-treated culture or cells are those in which the dipeptide-hydrolyzing enzyme activity of the culture or cells is reduced or lost.

(30) A protein having the amino acid sequence shown in any of SEQ ID NOS: 9 to 13.

(31) A DNA having the nucleotide sequence shown in any of SEQ ID NOS: 22 to 26.

(32) A recombinant DNA which is obtained by ligating the DNA according to the above (31) to a vector DNA.

(33) A cell carrying the recombinant DNA according to the above (32).

(34) A process for producing the protein according to the above (30), which comprises culturing the cells according to the above (33) in a medium, allowing the protein to form and accumulate in the culture, and recovering the protein from the culture.

In accordance with the present invention, dipeptides or dipeptide derivatives can be efficiently produced from one or more kinds of amino acids or amino acid derivatives.

Figure 1:
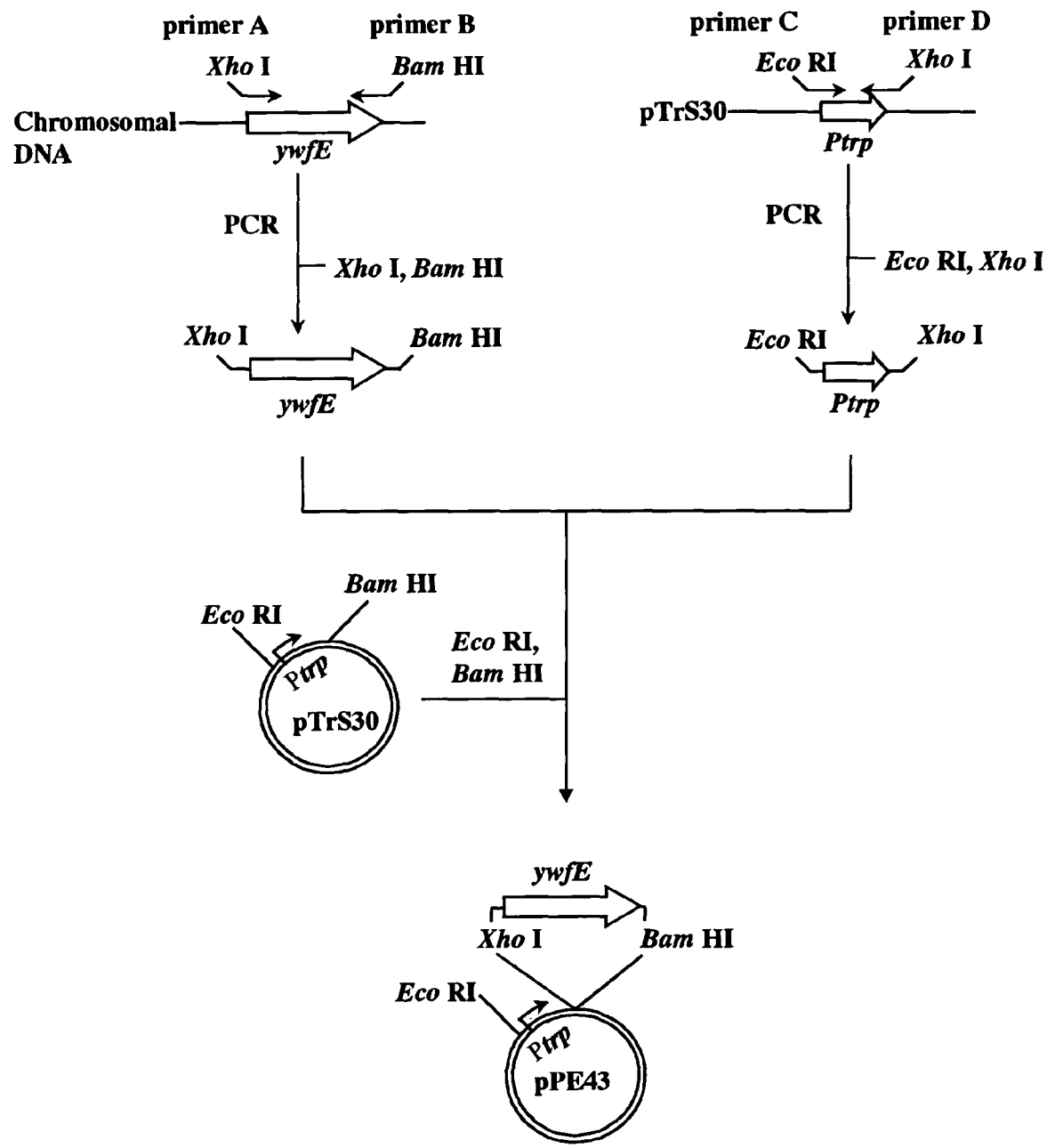
FIG. 1 shows the steps for constructing plasmid pPE43.

EXPLANATION OF SYMBOLS ywfE: ywfE gene derived from *Bacillus subtilis* 168
Ptrp: Tryptophan promoter gene
PT5: T5 promoter
Amp$^r$: Ampicillin resistance gene
lacI$^q$: Lactose repressor gene
albC: albC gene or albC-analogous gene

DETAILED DESCRIPTION OF THE INVENTION

1. Proteins Having the Activity to ATP-dependently Form Dipeptide or Dipeptide Derivative PI from One or More Kinds of Amino Acids or Amino Acid Derivatives Used in the Present Invention The proteins having the activity to ATP-dependently form dipeptide or dipeptide derivative PI from one or more kinds of amino acids or amino acid derivatives (hereinafter referred to also as proteins having the dipeptide-forming activity) used in the present invention may be of any origin and may be prepared by any methods, so far as they have this activity. Examples of such proteins include proteins of the following [1] to [8]:

[1] a protein having the amino acid sequence shown in any of SEQ ID NOS: 1 to 13;

[2] a protein consisting of an amino acid sequence wherein one or more amino acid residues are deleted, substituted or added in the amino acid sequence shown in any of SEQ ID NOS: 1 to 13 and having the activity to ATP-dependently form dipeptide or dipeptide derivative PI from one or more kinds of amino acids or amino acid derivatives;

[3] a protein consisting of an amino acid sequence which has 65% or more homology to the amino acid sequence shown in any of SEQ ID NOS: 1 to 13 and having the activity to ATP-dependently form dipeptide or dipeptide derivative PI from one or more kinds of amino acids or amino acid derivatives;

[4] a protein having an amino acid sequence which has 80% or more homology to the amino acid sequence shown in SEQ ID NO: 27 and having the activity to ATP-dependently form dipeptide or dipeptide derivative PI from one or more kinds of amino acids or amino acid derivatives;

[5] a protein having the amino acid sequence shown in SEQ ID NO: 47 or 48;

[6] a protein consisting of an amino acid sequence wherein one or more amino acid residues are deleted, substituted or added in the amino acid sequence shown in SEQ ID NO: 47 or 48 and having the activity to ATP-dependently form dipeptide or dipeptide derivative PI from one or more kinds of amino acids or amino acid derivatives;

[7] a protein consisting of an amino acid sequence which has 65% or more homology to the amino acid sequence shown in SEQ ID NO: 47 or 48 and having the activity to ATP-dependently form dipeptide or dipeptide derivative PI from one or more kinds of amino acids or amino acid derivatives; and

[8] a protein having NRPS activity.

Examples of the proteins having NRPS activity include a protein having the amino acid sequence shown in SEQ ID NO: 53, a protein consisting of an amino acid sequence wherein one or more amino acid residues are deleted, substituted or added in the amino acid sequence shown in SEQ ID NO: 53 and having NRPS activity, and a protein having an amino acid sequence which has 65% or more homology to the amino acid sequence shown in SEQ ID NO: 53 and having NRPS activity.

The above protein consisting of an amino acid sequence wherein one or more amino acid residues are deleted, substituted or added and having the activity to ATP-dependently form dipeptide or dipeptide derivative PI from one or more kinds of amino acids or amino acid derivatives can be obtained, for example, by introducing a site-directed mutation into DNA encoding a protein consisting of the amino acid sequence shown in any of SEQ ID NOS: 1 to 13, 47, 48 and 53, by site-directed mutagenesis described in Molecular Cloning, A Laboratory Manual, Third Edition, Cold Spring Harbor Laboratory Press (2001) (hereinafter referred to as Molecular Cloning, Third Edition); Current Protocols in Molecular Biology, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

The expression "one or more amino acid residues are deleted, substituted or added in the amino acid sequence shown in any of SEQ ID NOS: 1 to 13, 47, 48 and 53" means that the amino acid sequence may contain deletion, substitution or addition of a single or plural amino acid residues at an arbitrary position therein.

Amino acid residues that may be substituted are, for example, those which are not conserved in all of the amino acid sequences shown in SEQ ID NOS: 1 to 13, 47 and 48 when the sequences are compared using known alignment software. An example of known alignment software is alignment analysis software contained in gene analysis software Genetyx (Software Development Co., Ltd.). As analysis parameters for the analysis software, default values can be used.

Deletion or addition of amino acid residues may be contained, for example, in the N-terminal region or the C-terminal region of the amino acid sequence shown in any of SEQ ID NOS: 1 to 13, 47, 48 and 53.

Deletion, substitution and addition may be simultaneously contained in one sequence, and amino acids to be substituted or added may be either natural or not. Examples of the natural amino acids are L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine In order that the protein consisting of an amino acid sequence wherein one or more amino acid residues are deleted, substituted or added in the amino acid sequence shown in any of SEQ ID NOS: 1 to 13, 47, 48 and 53 may have the dipeptide-forming activity, it is desirable that the homology of its amino acid sequence to the amino acid sequence shown in any of SEQ ID NOS: 1 to 13, 47, 48 and 53, preferably SEQ ID NO: 1, 47 or 53, is 65% or more, preferably 75% or more, more preferably 85% or more, further preferably 90% or more, particularly preferably 95% or more, and most preferably 98% or more.

The homology among amino acid sequences and nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known (http://www.ncbi.nlm.nih.gov.).

A protein consisting of an amino acid sequence which has 65% or more, preferably 75% or more, more preferably 85% or more, further preferably 90% or more, particularly preferably 95% or more, most preferably 98% or more homology to the amino acid sequence shown in any of SEQ ID NOS: 1 to 13, 47, 48 and 53, preferably SEQ ID NO: 1, 47 or 53, and having the dipeptide-forming activity is also included in the proteins used in the present invention. The homology-among amino acid sequences can be determined by using BLAST or FASTA as described above.

The amino acid sequence shown in SEQ ID NO: 27 is a region conserved among the proteins having the amino acid sequences shown in SEQ ID NOS: 1 to 7 and is also a region corresponding to the consensus sequence of proteins having Ala-Ala ligase activity derived from various microorganisms.

A protein having an amino acid sequence which has 80% or more, preferably 90% or more, further preferably 95% or more homology to the amino acid sequence shown in SEQ ID NO: 27 and having the dipeptide-forming activity is also included in the proteins used in the present invention.

In order that the protein having an amino acid sequence which has 80% or more, preferably 90% or more, further preferably 95% or more homology to the amino acid sequence shown in SEQ ID NO: 27 may have the dipeptide-forming activity, it is desirable that the homology of its amino acid sequence to the amino acid sequence shown in any of SEQ ID NOS: 1 to 8 is at least 80% or more, usually 90% or more, and particularly 95% or more.

The homology among amino acid sequences can be determined by using BLAST or FASTA as described above.

It is possible to confirm that the protein used in the present invention is a protein having the dipeptide-forming activity, for example, in the following manner. That is, a transformant expressing the protein used in the present invention is prepared by recombinant DNA techniques, the protein used in the present invention is produced using the transformant, and then the protein, one or more kinds of amino acids or amino acid derivatives and ATP are allowed to be present in an aqueous medium, followed by HPLC analysis or the like to know whether dipeptide or dipeptide derivative PI is formed and accumulated in the aqueous medium.

2. Proteins Having Polyphosphate Kinase Activity Used in the Present Invention

The proteins having polyphosphate kinase activity used in the present invention may be of any origin and may be prepared by any methods, so far as they have this activity. Examples of such proteins include proteins of the following [1] to [3]:

[1] a protein having the amino acid sequence shown in any of SEQ ID NOS: 124 to 131;

[2] a protein consisting of an amino acid sequence wherein one or more amino acid residues are deleted, substituted or added in the amino acid sequence shown in any of SEQ ID NOS: 124 to 131 and having polyphosphate kinase activity; and

[3] a protein consisting of an amino acid sequence which has 65% or more homology to the amino acid sequence shown in any of SEQ ID NOS: 124 to 131 and having polyphosphate kinase activity.

The above amino acid sequence wherein one or more amino acid residues are deleted, substituted or added in the amino acid sequence shown in any of SEQ ID NOS: 124 to 131 and the above amino acid sequence which has 65% or more homology to the amino acid sequence shown in any of SEQ ID NOS: 124 to 131 are amino acid sequences having the same definitions as in the above 1 except that the proteins having the sequences have polyphosphate kinase activity.

It is possible to confirm that the protein used in the present invention is a protein having polyphosphate kinase activity, for example, in the following manner. That is, a transformant expressing the protein used in the present invention is prepared by recombinant DNA techniques, the protein used in the present invention is produced using the transformant, and then the protein, ADP and polyphosphoric acid are allowed to be present in an aqueous medium, followed by HPLC analysis or the like to know whether ATP is formed and accumulated in the aqueous medium.

3. DNAs Encoding the Proteins Having the Activity to Form Dipeptide or Dipeptide Derivative PI from One or More Kinds of Amino Acids or Amino Acid Derivatives Used in the Present Invention Examples of the DNAs encoding the proteins having the activity to form dipeptide or dipeptide derivative PI from one or more kinds of amino acids or amino acid derivatives used in the present invention (hereinafter referred to as DNAs encoding the proteins having the dipeptide-forming activity) include DNAs of the following [1] to [6]:

[1] DNA having the nucleotide sequence shown in any of SEQ ID NOS: 14 to 26 and 46;

[2] DNA which hybridizes with DNA having a nucleotide sequence complementary to the nucleotide sequence shown in any of SEQ ID NOS: 14 to 26 and 46 under stringent conditions and which encodes a protein having the activity to ATP-dependently form dipeptide or dipeptide derivative PI from one or more kinds of amino acids or amino acid derivatives;

[3] DNA which hybridizes with DNA having a nucleotide sequence complementary to the nucleotide sequence in SEQ ID NO: 28 and encoding a protein having the activity to ATP-dependently form dipeptide or dipeptide derivative PI from one or more kinds of amino acids or amino acid derivatives;

[4] DNA having the nucleotide sequence shown in SEQ ID NO: 49 or 50;

[5] DNA which hybridizes with DNA having a nucleotide sequence complementary to the nucleotide sequence shown in SEQ ID NO: 49 or 50 under stringent conditions and which encodes a protein having the activity to ATP-dependently form dipeptide or dipeptide derivative PI from one or more kinds of amino acids or amino acid derivatives; and

[6] DNA encoding a protein-having NRPS activity.

Examples of the DNAs encoding the proteins having NRPS activity include DNA having the nucleotide sequence shown in SEQ ID NO: 54, and DNA which hybridizes with DNA having a nucleotide sequence complementary to the nucleotide sequence shown in SEQ ID NO: 54 under stringent conditions and which encodes a protein having NRPS activity.

The above DNA capable of hybridization under stringent conditions refers to DNA which is obtained by colony hybridization, plaque hybridization, Southern blot hybridization, or the like using a part or the whole of the DNA having a nucleotide sequence complementary to the nucleotide sequence shown in any of SEQ ID NOS: 14 to 26, 28, 46, 49, 50 and 54 as a probe. A specific example of such DNA is DNA which can be identified by performing hybridization at 65° C. in the presence of 0.7 to 1.0 mol/l, preferably 0.9 mol/l sodium chloride using a filter with colony- or plaque-derived DNA immobilized thereon, and then washing the filter at 65° C. with a 0.1 to 2-fold conc., preferably 0.1-fold conc. SSC solution (1-fold conc. SSC solution: 150 mmol/l sodium chloride and 15 mmol/l sodium citrate). Hybridization can be carried out according to the methods described in Molecular Cloning, Third Edition; Current Protocols in Molecular Biology; DNA Cloning 1: Core Techniques, A Practical Approach, Second Edition, Oxford University (1995), etc. Specifically, the hybridizable DNA includes DNA having at least 75% or more homology, preferably 85% or more homology, further preferably 90% or more homology, particularly preferably 95% or more homology to the nucleotide sequence shown in any of SEQ ID NOS: 14 to 26, 28, 46, 49, 50 and 54 as calculated by use of BLAST or FASTA described above based on the above parameters.

It is possible to confirm that the DNA which hybridizes with DNA having the nucleotide sequence shown in any of SEQ ID NOS: 14 to 26, 28, 46, 49, 50 and 54 under stringent conditions is DNA encoding a protein having the dipeptide-forming activity, for example, by producing a protein encoded by the DNA by recombinant DNA techniques and measuring the activity of the protein as described above.

4. DNAs Encoding the Proteins Having Polyphosphate Kinase Activity Used in the Present Invention Examples of the DNAs encoding the proteins having polyphosphate kinase activity used in the present invention include DNAs of the following [1] and [2]:

[1] DNA having the nucleotide sequence shown in any of SEQ ID NOS: 116 to 123; and

[2] DNA which hybridizes with DNA having a nucleotide sequence complementary to the nucleotide sequence shown in any of SEQ ID NOS: 116 to 123 under stringent conditions and which encodes a protein having polyphosphate kinase activity.

The DNA which hybridizes with DNA having a nucleotide sequence complementary to the nucleotide sequence shown in any of SEQ ID NOS: 116 to 123 under stringent conditions and which encodes a protein having polyphosphate kinase activity is DNA having the same definition as in the above 3 except that the protein encoded by the DNA has polyphosphate kinase activity.

It is possible to confirm that the DNA which hybridizes with DNA having the nucleotide sequence shown in any of SEQ ID NOS: 116 to 123 under stringent conditions is DNA encoding a protein having polyphosphate kinase activity, for example, by producing a protein encoded by the DNA by recombinant DNA techniques and measuring the activity of the protein as described above.

5. Proteins of the Present Invention

The proteins of the present invention include proteins having the amino acid sequences shown in SEQ ID NOS: 9 to 13.

6. DNAs of the Present Invention

The DNAs of the present invention include DNAs having the nucleotide sequences shown in SEQ ID NOS: 22 to 26.

7. Preparation of DNA Encoding the Protein Having the Activity to ATP-dependently Form Dipeptide or Dipeptide Derivative PI from One or More Kinds of Amino Acids or Amino Acid Derivatives and DNA Encoding the Protein Having Polyphosphate Kinase Activity The DNA encoding the protein having the dipeptide-forming activity can be obtained by Southern hybridization of a chromosomal DNA library from a microorganism belonging to the genus *Bacillus* or *Streptomyces* using a probe designed based on the nucleotide sequence shown in any of SEQ ID NOS: 14 to 26, 46, 49, 50 and 54, or by PCR [PCR Protocols, Academic Press (1990)] using primer DNAs designed based on the nucleotide sequence shown in any of SEQ ID NOS: 14 to 26, 46, 49, 50 and 54 and, as a template, the chromosomal DNA of a microorganism belonging to the genus *Bacillus* or *Streptomyces*. The DNA encoding the protein having polyphosphate kinase activity can be obtained by Southern hybridization of a chromosomal DNA library from a microorganism belonging to the genus *Escherichia, Rhodobacter, Chloroflexus, Mesorhizobium, Streptomyces, Pseudomonas* or *Sinorhizobium* using a probe designed based on the nucleotide sequence shown in any of SEQ ID NOS: 116 to 123, or by PCR using primer DNAs designed based on the nucleotide sequence shown in any of SEQ ID NOS: 116 to 123 and, as a template, the chromosomal DNA of a microorganism belonging to the genus *Escherichia, Rhodobacter, Chloroflexus, Mesorhizobium, Streptomyces, Pseudomonas* or *Sinorhizobium*.

The DNA used in the present invention can also be obtained by conducting a search through various gene sequence databases for a sequence having 75% or more homology, preferably 85% or more homology, more preferably 90% or more homology, further preferably 95% or more homology, particularly preferably 98% or more homology to the nucleotide sequence of DNA encoding the amino acid sequence shown in any of SEQ ID NOS: 14 to 26, 46, 49, 50 and 54, or in any of SEQ ID NOS: 116 to 123, and obtaining the desired DNA, based on the nucleotide sequence obtained by the search, from a chromosomal DNA or cDNA library of an organism having the nucleotide sequence according to the above-described method.

The obtained DNA, as such or after cleavage with appropriate restriction enzymes, is inserted into a vector by a conventional method, and the obtained recombinant DNA is introduced into a host cell. Then, the nucleotide sequence of the DNA can be determined by a conventional sequencing method such as the dideoxy method [Proc. Natl. Acad. Sci., USA, 74, 5463 (1977)] or by using a nucleotide sequencer such as 373A DNA Sequencer (Perkin-Elmer Corp.).

In cases where the obtained DNA is found to be a partial DNA by the analysis of nucleotide sequence, the full length DNA can be obtained by Southern hybridization of a chromosomal DNA library using the partial DNA as a probe.

It is also possible to prepare the desired DNA by chemical synthesis using a DNA synthesizer (e.g., Model 8905, PerSeptive Biosystems) based on the determined nucleotide sequence of the DNA.

Examples of the DNAs that can be obtained by the above-described method are DNAs having the nucleotide sequences shown in SEQ ID NOS: 14 to 26, 46, 49, 50 and 54, which are DNAs encoding the proteins having the dipeptide-forming activity, and DNAs having the nucleotide sequences shown in SEQ ID NOS: 116 to 123, which are DNAs encoding the proteins having polyphosphate kinase activity.

Examples of the vectors for inserting the DNA used in the production process of the present invention include pBluescriptII KS(+) (Stratagene), pDIRECT [Nucleic Acids Res., 18, 6069 (1990)], pCR-Script Amp SK(+) (Stratagene), pT7 Blue (Novagen, Inc.), pCR II (Invitrogen Corp.) and pCR-TRAP (Genhunter Corp.).

As the host cell, microorganisms belonging to the genus *Escherichia*, etc. can be used. Examples of the microorganisms belonging to the genus *Escherichia* include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522 and *Escherichia coli* ME8415.

Introduction of the recombinant DNA can be carried out by any of the methods for introducing DNA into the above host cells, for example, the method using calcium ion (Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

Examples of the microorganisms carrying the DNAs used in the production process of the present invention obtained by the above method are *Escherichia coli* NM522/pPE43, which is a microorganism carrying a recombinant DNA comprising DNA having the nucleotide sequence shown in SEQ ID NO: 14, and *Escherichia coli* BL21-Gold(DE3)/pPK-Ec1, which is a microorganism carrying a recombinant DNA comprising DNA having the nucleotide sequence shown in SEQ ID NO: 122.

8. Preparation of Cells Used in the Present Invention (1) The cells used in the present invention include cells having the ability to produce the protein having the dipeptide-forming activity, cells having the ability to produce the protein having polyphosphate kinase activity, and cells having the ability to produce both the protein having the dipeptide-forming activity and the protein having polyphosphate kinase activity.

Examples of the cells having the ability to produce the protein having the dipeptide-forming activity include bacteria belonging to the genus *Bacillus* or *Streptomyces* which carry the DNA of the above 3 on the chromosomal DNA, preferably, bacteria belonging to the genus *Bacillus* which have bacilysin-synthesizing activity and bacteria belonging to the genus *Streptomyces* which have the ability to produce albonoursin, more preferably, bacteria belonging to a species selected from the group consisting of *Bacillus subtilis*, *Bacillus amyloliquefaciens*, *Bacillus coagulans*, *Bacillus licheniformis*, *Bacillus megaterium*, *Bacillus pumilus*, *Streptomyces albulus* and *Streptomyces noursei*, further preferably, bacteria selected from the group consisting of the strains *Bacillus subtilis* ATCC 15245, *Bacillus subtilis* ATCC 6633, *Bacillus subtilis* IAM 1213, *Bacillus subtilis* IAM 1107, *Bacillus subtilis* IAM 1214, *Bacillus subtilis* ATCC 9466, *Bacillus subtilis* IAM 1033, *Bacillus subtilis* ATCC 21555, *Bacillus amyloliquefaciens* IFO 3022, *Bacillus pumilus* NRRL B-12025, *Streptomyces noursei* IFO 15452 and *Streptomyces albulus* IFO 14147, and transformants that can be prepared by introducing DNA obtained by the method of the above 3 into host cells using the methods described in Molecular Cloning, Third Edition, Current Protocols in Molecular Biology, etc., for example, according to the method described below.

Examples of the cells having the ability to produce the protein having polyphosphate kinase activity include bacteria belonging to the genus *Escherichia, Rhodobacter, Chloroflexus, Mesorhizobium, Streptomyces, Pseudomonas* or *Sinorhizobium* which carry the DNA of the above 4 on the chromosomal DNA, more preferably, bacteria selected from the group consisting of the strains *Escherichia coli* W3110, *Rhodobacter sphaeroides* ATCC 17023, *Chloroflexus aurantiacus* ATCC 29366, *Streptomyces coelicolor* ATCC BAA-471, *Pseudomonas putida* KT 2440 and *Sinorhizobium meliloti* ATCC 51124, and transformants that can be prepared by introducing DNA obtained by the method of the above 4 into host cells using the methods described in Molecular Cloning, Third Edition, Current Protocols in Molecular Biology, etc., for example, according to the method described below.

The above transformants can be prepared, for example, by the following method.

On the basis of the DNA of the above 3 or 4, a DNA fragment of an appropriate length comprising a region encoding the protein used in the present invention is prepared according to need. Cells with enhanced productivity of the protein can be obtained by replacing a nucleotide in the nucleotide sequence of the region encoding the protein so as to make a codon most suitable for the expression in a host cell.

The DNA fragment is inserted downstream of a promoter in an appropriate expression vector to prepare a recombinant DNA.

A transformant producing the protein of the present invention can be obtained by introducing the recombinant DNA into a host cell suited for the expression vector.

As the host cell, any cells that are capable of expressing the desired gene can be used. Suitable cells include cells of microorganisms such as procaryotes and yeast, animal cells, insect cells, plant cells, etc., preferably microorganisms, more preferably procaryotes, further preferably bacteria.

The expression vectors that can be employed are those capable of autonomous replication or integration into the chromosome in the above host cells and comprising a promoter at a position appropriate for the transcription of the DNA of the present invention or the DNA used in the production process of the present invention.

When a procaryote such as a bacterium is used as the host cell, it is preferred that the recombinant DNA comprising the DNA used in the present invention is a recombinant DNA which is capable of autonomous replication in the procaryote and which comprises a promoter, a ribosome binding sequence, the DNA of the present invention or the DNA used in the production process of the present invention, and a transcription termination sequence. The recombinant DNA may further comprise a gene regulating the promoter.

Examples of suitable expression vectors are pBTrp2, pBTac1 and pBTac2 (products of Boehringer Mannheim GmbH), pHelix1 (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306

(1985)], pBluescript II SK(+), pBluescript II KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343), pUC19 [Gene, 33, 103 (1985)], pSTV28 (Takara Shuzo Co., Ltd.), pUC118 (Takara Shuzo Co., Ltd.), pPA1 (Japanese Published Unexamined Patent Application No. 233798/88), pWH1520 (MoBiTec), pCS299P (WO00/63388), pVLT31 [Gene, 123, 17 (1993)] and pIJ702 (Genetic Manipulation of *Streptomyces*: a Laboratory Manual: John Innes Foundation).

As the promoter, any promoters capable of functioning in host cells such as *Escherichia coli* can be used. For example, promoters derived from *Escherichia coli* or phage, such as trp promoter ($P_{trp}$), lac promoter ($P_{lac}$), $P_L$ promoter, $P_R$ promoter and $P_{SE}$ promoter, SPO1 promoter, SPO2 promoter and penP promoter can be used. Artificially designed and modified promoters such as a promoter in which two $P_{trp}$s are combined in tandem, tac promoter, lacT7 promoter and letI promoter, etc. can also be used.

Also useful are xylA promoter for the expression in microorganisms belonging to the genus *Bacillus* [Appl. Microbiol. Biotechnol., 35, 594-599 (1991)], P54-6 promoter for the expression in microorganisms belonging to the genus *Corynebacterium* [Appl. Microbiol. Biotechnol., 53, 674-679 (2000)], tac promoter for the expression in microorganisms belonging to the genus *Pseudomonas* [Gene, 123, 17-24 (1993)] and xylA promoter for the expression in microorganisms belonging to the genus *Streptomyces* (Genetic Manipulation of *Streptomyces*: a Laboratory Manual: John Innes Foundation).

It is preferred to use a plasmid in which the distance between the Shine-Dalgarno sequence (ribosome binding sequence) and the initiation codon is adjusted to an appropriate length (e.g., 6 to 18 nucleotides).

In the recombinant DNA wherein the DNA used in the present invention is ligated to an expression vector, the transcription termination sequence is not essential, but it is preferred to place the transcription termination sequence immediately downstream of the structural gene.

Examples of such recombinant DNAs are pPE43 and pPK-Ec1.

Examples of suitable procaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. Specific examples are *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Bacillus subtilis* ATCC 33712, *Bacillus megaterium, Bacillus* sp. FERM BP-6030, *Bacillus amyloliquefaciens, Bacillus coagulans, Bacillus licheniformis, Bacillus pumilus, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 14297, *Corynebacterium efficiens, Corynebacterium acetoacidophilum* ATCC 13870, *Microbacterium ammoniaphilum* ATCC 15354, *Serratia ficaria, Serratia fonticola, Serratia liquefaciens, Serratia marcescens, Pseudomonas* sp. D-0110, *Agrobacterium radiobacter, Agrobacterium rhizogenes, Agrobacterium rubi, Anabaena cylindrica, Anabaena doliolum, Anabaena flosaquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium* sp. ATCC 29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus* and *Zymomonas mobilis*. Preferred procaryotes include bacteria belonging to the genera *Escherichia, Serratia, Bacillus, Brevibacterium, Corynebacterium, Pseudomonas* and *Streptomyces*, for example, the above-mentioned species belonging to the genera *Escherichia, Serratia, Bacillus, Brevibacterium, Corynebacterium, Pseudomonas* and *Streptomyces*. More preferred bacteria include *Escherichia coli, Corynebacterium glutamicum, Corynebacterium ammoniagenes, Corynebacterium lactofermentum, Corynebacterium flavum, Corynebacterium efficiens, Bacillus subtilis, Bacillus megaterium, Serratia marcescens, Pseudomonas putida, Pseudomonas aeruginosa, Streptomyces coelicolor* and *Streptomyces lividans*, among which *Escherichia coli* is particularly preferred.

Introduction of the recombinant DNA can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a yeast strain is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast strains can be used. Suitable promoters include PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are yeast strains belonging to the genera *Saccharomyces, Schizosaccharomyces, Kluyveromyces, Trichosporon, Schwanniomyces, Pichia* and *Candida*, specifically, *Saccharomyces cerevisiae, Schizosaccharomyces pombe, Kluyveromyces lactis, Trichosporon pullulans, Schwanniomyces alluvius, Pichia pastoris* and *Candida utilis*.

Introduction of the recombinant DNA can be carried out by any of the methods for introducing DNA into yeast, for example, electroporation [Methods Enzymol., 194, 182 (1990)], the spheroplast method [Proc. Natl. Acad. Sci. USA, 81, 4889 (1984)] and the lithium acetate method [J. Bacteriol., 153, 163 (1983)].

When an animal cell is used as the host cell, pcDNAI, pcDM8 (commercially available from Funakoshi Co., Ltd.), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (Invitrogen Corp.), pREP4 (Invitrogen Corp.), pAGE103 [J. Biochem., 101, 1307 (1987)], pAGE210, pAMo, pAMoA, etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SRα promoter, etc. The enhancer of IE gene of human CMV may be used in combination with the promoter.

Examples of suitable host cells are mouse myeloma cells, rat myeloma cells, mouse hybridomas, human-derived Namalwa cells and Namalwa KJM-1 cells, human embryonic kidney cells, human leukemia cells, African green monkey kidney cells, Chinese hamster-derived CHO cells, and HBT5637 (Japanese Published Unexamined Patent Application No. 299/88).

The mouse myeloma cells include SP2/0 and NSO; the rat myeloma cells include YB2/0; the human embryonic kidney-cells include HEK293 (ATCC CRL-1573); the human leukemia cells include BALL-1; and the African green monkey kidney cells include COS-1 and COS-7.

Introduction of the recombinant DNA can be carried out by any of the methods for introducing DNA into animal cells, for example, electroporation [Cytotechnology, 3, 133 (1990)], the calcium phosphate method (Japanese Published Unexamined Patent Application No. 227075/90), lipofection [Proc. Natl. Acad. Sci. USA, 84, 7413 (1987)], and the method described in Virology, 52, 456 (1973).

When an insect cell is used as the host cell, the protein can be produced by using the methods described in Baculovirus Expression Vectors, A Laboratory Manual, W.H. Freeman and Company, New York (1992); Current Protocols in Molecular Biology; Molecular Biology, A Laboratory Manual; Bio/Technology, 6, 47 (1988), etc.

That is, the recombinant gene transfer vector and a baculovirus are cotransfected into insect cells to obtain a recombinant virus in the culture supernatant of the insect cells, and then insect cells are infected with the recombinant virus, whereby the protein can be produced.

The gene transfer vectors useful in this method include pVL1392, pVL1393 and pBlueBacIII (products of Invitrogen Corp.).

An example of the baculovirus is *Autographa californica* nuclear polyhedrosis virus, which is a virus infecting insects belonging to the family Barathra.

Examples of the insect cells are ovarian cells of *Spodoptera frugiperda*, ovarian cells of *Trichoplusia ni*, and cultured cells derived from silkworm ovary.

The ovarian cells of *Spodoptera frugiperda* include Sf9 and Sf21 (Baculovirus Expression Vectors, A Laboratory Manual); the ovarian cells of *Trichoplusia ni* include High 5 and BTI-TN-5B1-4 (Invitrogen Corp.); and the cultured cells derived from silkworm ovary include *Bombyx mori* N4.

Cotransfection of the above recombinant gene transfer vector and the above baculovirus into insect cells for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

When a plant cell is used as the host cell, Ti plasmid, tobacco mosaic virus vector, etc. can be used as the expression vector.

As the promoter, any promoters capable of functioning in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

When the DNA is expressed in yeast, an animal cell, an insect cell or a plant cell, a cell producing a glycosylated protein can be obtained.

(2) The microorganisms used in the production process of the present invention include microorganisms prepared by the method of the above (1) in which the activities of one or more kinds of peptidases and one or more kinds of proteins having peptide-permeating/transporting activity (hereinafter referred to as peptide-permeating/transporting proteins) are reduced or lost, and those in which the activities of three or more kinds of peptidases are reduced or lost.

Such microorganisms can be obtained, for example, by any of the following methods: (a) methods of imparting, by the method of the above (1), the ability to produce the protein having the dipeptide-forming activity or the ability to produce the protein having polyphosphate kinase activity to microorganisms in which the functions of one or more kinds of peptidases and one or more kinds of proteins having peptide-permeating/transporting activity are reduced or lost, or microorganisms in which the functions of three or more kinds of peptidases are reduced or lost; and (b) methods of reducing or causing loss of the functions of a) one or more kinds of peptidases and one or more kinds of peptide-permeating/transporting proteins or b) three or more kinds of peptidases of microorganisms having the ability to produce the protein having the dipeptide-forming activity or the ability to produce the protein having polyphosphate kinase activity which can be prepared by the method of the above (1).

The microorganisms in which the activities of one or more kinds of peptidases and one or more kinds of peptide-permeating/transporting proteins are reduced or lost include microorganisms in which the activities of one or more arbitrary kinds of peptidases and one or more arbitrary kinds of peptide-permeating/transporting proteins are reduced or lost provided that the microorganisms can normally grow, specifically, microorganisms in which the activities of preferably one to nine kinds, more preferably one to seven kinds, further preferably one to four kinds of peptidases and preferably one to five kinds, more preferably one to three kinds, further preferably one or two kinds, particularly preferably one kind of peptide-permeating/transporting protein are reduced or lost.

Examples of such microorganisms are microorganisms in which the activities of one or more kinds of peptidases and one or more kinds of peptide-permeating/transporting proteins are reduced or lost because the nucleotide sequences of one or more kinds of genes encoding peptidases (hereinafter referred to as peptidase genes) and one or more kinds of genes encoding peptide-permeating/transporting proteins (hereinafter referred to as peptide-permeating/transporting protein genes) among the peptidase genes and peptide-permeating/transporting protein genes existing on the genomic DNA of the microorganisms are entirely or partially deleted or said nucleotide sequences contain nucleotide substitutions or additions.

The expression "the activity of peptidase is reduced" means that the peptidolytic activity is reduced, or reduced to normally 80% or less, preferably 50% or less, more preferably 30% or less, further preferably 20% or less, particularly preferably 10% or less, most preferably 5% or less compared with peptidase having none of the above deletions, substitutions and additions of nucleotides.

The peptidolytic activity of a microorganism can be measured by allowing a peptide as a substrate and microorganism cells to be present in an aqueous medium, thereby performing peptidolytic reaction, and then determining the amount of the remaining peptide by a known method, e.g., HPLC analysis.

The above peptidases may be any proteins having peptidolytic activity. Preferred are proteins having high dipeptide-hydrolyzing activity. More preferred are dipeptidases.

Examples of peptidases include: those existing in *Escherichia coli* such as PepA having the amino acid sequence shown in SEQ ID NO: 55, PepB having the amino acid sequence shown in SEQ ID NO: 56, PepD having the amino acid sequence shown in SEQ ID NO: 57, PepN having the amino acid sequence shown in SEQ ID NO: 58, PepP [GenBank accession No. (hereinafter abbreviated as Genbank) AAC75946], PepQ (GenBank AAC76850), PepE (GenBank AAC76991), PepT (GenBank AAC74211), Dcp (GenBank AAC74611) and IadA (GenBank AAC77284); those existing in *Bacillus subtilis* such as AmpS (GenBank AF012285), PepT (GenBank X99339), YbaC (GenBank Z99104), YcdD (GenBank Z99105), YjbG (GenBank Z99110), YkvY (GenBank Z99111), YqjE (GenBank Z99116) and YwaD (GenBank Z99123); and those existing in *Corynebacterium glutamicum* such as proteins having the amino acid sequences represented by BAB97732, BAB97858, BAB98080, BAB98880, BAB98892, BAB99013, BAB99598 and BAB99819 (registration Nos. of DNA Data Bank of Japan). Examples of dipeptidases include PepA, PepB, PepD and PepN having the amino acid sequences shown in SEQ ID NOS: 55 to 58, PepQ, PepE and IadA. Proteins having amino acid sequences which have 80% or more, preferably 90% or more, more preferably 95% or more homology to the amino acid sequence shown in any of SEQ ID NOS: 55 to 58 and having peptidase activity are also included in the proteins having high dipeptide-hydrolyzing activity. The homology among amino acid sequences and nucleotide sequences can be determined by using BLAST, FASTA or the like described above.

The expression "the activity of a peptide-permeating/transporting protein is reduced" means that the peptide-uptaking activity is reduced, or reduced to normally 80% or less, preferably 50% or less, more preferably 30% or less, further preferably 20% or less, particularly preferably 10% or less, most preferably 5% or less compared with a peptide-permeating/transporting protein having none of the above deletions, substitutions and additions of nucleotides.

The peptide-uptaking activity of a microorganism can be measured by allowing a peptide as a substrate and microorganism cells to be present in an aqueous medium, thereby performing peptide-uptaking reaction, and then determining the amount of the remaining peptide by a known method, e.g., HPLC analysis.

The above peptide-permeating/transporting proteins may be any proteins involved in peptide incorporation of microorganisms, for example, proteins encoded by genes forming an operon on chromosomal DNA which form a complex on cell membrane to express dipeptide-uptaking activity and those which have peptide-uptaking activity as individual proteins. Preferred are proteins having high peptide-uptaking activity.

Examples of the peptide-permeating/transporting proteins include: those existing in *Escherichia coli* such as DppA having the amino acid sequence shown in SEQ ID NO: 59, DppB having the amino acid sequence shown in SEQ ID NO: 60, DppC having the amino acid sequence shown in SEQ ID NO: 61, DppD having the amino acid sequence shown in SEQ ID NO: 62, DppF having the amino acid sequence shown in SEQ ID NO: 63, OppA (GenBank AAC76569), OppB (GenBank AAC76568), OppC (GenBank AAC76567), OppD (GenBank AAC76566), OppF (GenBank AAC76565), YddO (GenBank AAC74556), YddP (GenBank AAC74557), YddQ (GenBank AAC74558), YddR (GenBank AAC74559), YddS (GenBank AAC74560), YbiK (GenBank AAC73915), MppA (GenBank AAC74411), SapA (GenBank AAC74376), SapB (GenBank AAC74375), SapC (GenBank AAC74374), SapD (GenBank AAC74373) and SapF (GenBank AAC74372); those existing in *Bacillus subtilis* such as DppA (GenBank CAA40002), DppB (GenBank CAA40003), DppC (GenBank CAA40004), DppD (GenBank CAA40005), DppE (GenBank CAA40006), OppA (GenBank CAA39787), OppB (GenBank CAA39788), OppC (GenBank CAA39789), OppD (GenBank CAA39790), OppF (GenBank CAA39791), AppA (GenBank CAA62358), AppB (GenBank CAA62359), AppC (GenBank CAA62360), AppD (GenBank CAA62356), AppF (GenBank CAA62357), YclF (GenBank CAB12175) and YkfD (GenBank CAB13157); and those existing in *Corynebacterium glutamicum* such as proteins having the amino acid sequences represented by BAB99048, BAB99383, BAB99384, BAB99385, BAB99713, BAB99714, BAB99715, BAB99830, BAB99831 and BAB99832 (registration Nos. of DNA Data Bank of Japan). Examples of the proteins having high peptide-permeating/transporting activity include DppA, DppB, DppC, DppD and DppF having the amino acid sequences shown in SEQ ID NOS: 59 to 63, and proteins having amino acid sequences which have 80% or more, preferably 90% or more, more preferably 95% or more homology to the amino acid sequence shown in any of SEQ ID NOS: 59 to 63.

The homology among amino acid sequences can be determined by using programs such as BLAST and FASTA described above.

The microorganisms in which the activities of three or more kinds of peptidases are reduced or lost include microorganisms in which the activities of three or more arbitrary kinds of peptidases are reduced or lost provided that the microorganisms can normally grow, specifically, microorganisms in which the activities of preferably three to nine kinds, more preferably three to six kinds, further preferably three or four kinds of peptidases are reduced or lost.

Examples of peptidases include the above-described peptidases and dipeptidases existing in *Escherichia coli*, *Bacillus subtilis* and *Corynebacterium glutamicum*. Proteins consisting of amino acid sequences which have 80% or more, preferably 90% or more, more preferably 95% or more homology to the amino acid sequence shown in any of SEQ ID NOS: 55 to 58 and having peptidase activity are also included in the proteins having high dipeptide-hydrolyzing activity.

The homology among amino acid sequences can be determined by using programs such as BLAST and FASTA described above.

The microorganisms in which the activities of peptidases and peptide-permeating/transporting proteins are reduced or lost may be obtained by any method capable of preparing such microorganisms. For example, they can be obtained by introducing a deletion, substitution or addition of a nucleotide into peptidase genes and peptide-permeating/transporting protein genes on chromosomal DNAs of microorganisms as described below.

The methods for introducing a deletion, substitution or addition of a nucleotide into a gene on the chromosomal DNA of a microorganism include methods utilizing homologous recombination. An example of the methods utilizing general homologous recombination is a method using a plasmid for homologous recombination prepared by ligating a mutant gene having an introduced nucleotide deletion, substitution or addition to a plasmid DNA incapable of autonomous replication in a host cell into which the nucleotide deletion or the like is to be introduced and carrying a drug resistance gene.

The plasmid for homologous recombination is introduced into a host cell by an ordinary method, followed by selection of a transformant in which the plasmid for homologous recombination has been integrated into the chromosomal DNA by homologous recombination using the drug resistance as a marker. The obtained transformant is cultured using a medium which does not contain the drug for several hours to one day, and then spread on an agar medium containing the drug and on an agar medium without the drug. By selecting a strain which does not grow on the former medium but can grow on the latter medium, the strain in which second homologous recombination occurred on the chromosomal DNA can be obtained. Introduction of a nucleotide deletion, substitution or addition into a desired gene on the chromosomal DNA can be confirmed by determining the nucleotide sequence of a region of the chromosomal DNA containing the gene into which the deletion or the like has been introduced.

By use of the above method, a nucleotide deletion, substitution or addition can be introduced into desired genes on chromosomal DNAs of microorganisms such as those belonging to the genera *Escherichia*, *Bacillus* and *Corynebacterium*.

Further, a nucleotide deletion, substitution or addition can be efficiently introduced into plural genes by utilizing homologous recombination according to a method using a straight-chain DNA.

Specifically, a straight-chain DNA containing a gene into which a nucleotide deletion, substitution or addition is to be introduced is incorporated into a cell to cause homologous recombination between chromosomal DNA and the introduced straight-chain DNA. This method is applicable to any microorganisms capable of efficiently incorporating a straight-chain DNA. Preferred microorganisms are those belonging to the genera *Escherichia* and *Bacillus*. *Escherichia coli* is more preferred, and *Escherichia coli* expressing a group of recombinant proteins derived from λ phage (Red recombination system) is further preferred.

An example of *Escherichia coli* expressing λ Red recombination system is *Escherichia coli* JM101 carrying pKD46, which is a plasmid DNA comprising a λ Red recombination system gene (available from *Escherichia coli* Genetic Stock Center, Yale University, U.S.A.).

Examples of the DNAs useful for homologous recombination are as follows:

(a) straight-chain DNA in which DNAs present on the outside of a region of chromosomal DNA to be subjected to introduction of a nucleotide deletion, substitution or addition are present at both termini of a drug resistance gene;

(b) straight-chain DNA in which DNAs present on the outside of a region of chromosomal DNA to be subjected to introduction of a nucleotide deletion, substitution or addition are directly ligated to each other;

(c) straight-chain DNA in which. DNAs present on the outside of a region of chromosomal DNA to be subjected to introduction of a nucleotide deletion, substitution or addition are present at both termini of a drug resistance gene and a gene that can be used for negative selection; and (d) straight-chain DNA of the above (a) in which a nucleotide sequence recognized by yeast-derived Flp recombinase [Proc. Natl. Acad. Sci. USA., 82, 5875 (1985)] is additionally present between the drug resistance gene and the DNAs present on the outside of a region of chromosomal DNA.

As the drug resistance gene, any drug resistance genes that impart resistance to a drug to which the host microorganism shows sensitivity can be used. When *Escherichia coli* is used as the host microorganism, examples of the drug resistance genes are kanamycin resistance gene, chloramphenicol resistance gene, gentamicin resistance gene, spectinomycin resistance gene, tetracycline resistance gene and ampicillin resistance gene.

The "gene that can be used for negative selection" refers to a gene that is fatal to a host microorganism under certain culture conditions when the gene is expressed in the host microorganism. Examples of the genes are sacB gene derived from a microorganism belonging to the genus *Bacillus* [Appl. Environ. Microbiol., 59, 1361-1366 (1993)] and rpsL gene derived from a microorganism belonging to the genus *Escherichia* (Genomics, 72, 99-104 (2001)].

The DNAs having homology to the DNAs present on the outside of a region of chromosomal DNA to be subjected to introduction of a substitution or deletion in the above straight-chain DNAs are located in the same direction as that on the chromosomal DNA, and their length is preferably about 10 bp to 100 kbp, more preferably about 20 bp to 50 bp, and further preferably about 30 bp to 40 bp.

The nucleotide sequence recognized by yeast-derived Flp recombinase is not specifically limited so long as it is a nucleotide sequence recognized by the said protein and catalyzing homologous recombination. Preferred examples are DNA having the nucleotide sequence shown in SEQ ID NO: 64, and DNA having a nucleotide sequence wherein one to several nucleotides are deleted, substituted or added in the said DNA and having a nucleotide sequence recognized by yeast-derived Flp recombinase and catalyzing homologous recombination.

The above "DNA having homology" refers to DNA having such a degree of homology that allows occurrence of homologous recombination between the subject region of chromosomal DNA and the above straight-chain DNA, specifically, DNA having 80% or more homology, preferably 90% or more homology, more preferably 95% or more homology, further preferably 100% homology.

The homology among nucleotide sequences can be determined by using programs such as BLAST and FASTA described above.

The above straight-chain DNA fragments can be prepared by PCR. The desired straight-chain DNA can also be obtained by constructing DNA containing the above straight-chain DNA on plasmid and then carrying out treatment with restriction enzymes.

Examples of the methods for introducing a nucleotide deletion, substitution or addition into the chromosomal DNA of a microorganism include the following Methods 1 to 4.

Method 1:

A method which comprises introducing the straight-chain DNA of the above (a) or (d) into a host microorganism and selecting a transformant carrying the straight-chain DNA inserted on its chromosomal DNA by homologous recombination using the drug resistance as a marker.

Method 2:

A method which comprises introducing the straight-chain DNA of the above (b) into the transformant obtained according to the above Method 1 and eliminating the drug resistance gene inserted on its chromosomal DNA by Method 1 to substitute or delete a region of the chromosomal DNA of the microorganism.

Method 3:

A method which comprises:

[1] introducing the straight-chain DNA of the above (c) into a host microorganism and selecting a transformant carrying the straight-chain DNA inserted on its chromosomal DNA by homologous recombination using the drug resistance as a marker;

[2] synthesizing DNA by ligating DNAs having homology to the DNAs present on the outside of a region of chromosomal DNA to be subjected to introduction of a substitution or deletion in the same direction as that on the chromosomal DNA, and introducing the synthesized DNA into the transformant obtained in the above [1]; and

[3] culturing the transformant subjected to the operation of the above [2] under conditions such that the gene that can be used for negative selection is expressed, and selecting a strain capable of growing by the culturing as a strain in which the drug resistance gene and the gene that can be used for negative selection are eliminated from the chromosomal DNA.

Method 4:

A method which comprises:

[1] introducing the straight-chain DNA of the above (d) into a host microorganism and selecting a transformant carrying the straight-chain DNA inserted on its chromosomal DNA by homologous recombination using the drug resistance as a marker; and

[2] introducing a Flp recombinase gene expression plasmid into the transformant obtained in the above [1], and after expression of the gene, obtaining a strain sensitive to the drug used in the above [1].

In the above methods, introduction of the straight-chain DNA into a host microorganism can be carried-out by any of the methods for introducing DNA into the microorganism, for example, the method using calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

By using a straight-chain DNA in which an arbitrary gene to be inserted to chromosomal DNA is incorporated in the center part of the straight-chain DNA used in Method 2 or Method 3 [2], it is possible to eliminate the drug resistance gene and at the same time to insert an arbitrary gene to the chromosomal DNA.

The above Methods 2 to 4 are methods that leave no foreign genes such as a drug resistance gene and a gene usable for negative selection on the chromosomal DNA of the transformant to be finally obtained. Therefore, it is possible to readily produce a microorganism having nucleotide deletions, substitutions or additions in two or more different regions of the chromosomal DNA by repeating the operations of Methods 1 and 2, Method 3 [1] to [3], and Method 4 [1] and [2] using the same drug resistance gene and the same gene usable for negative selection.

9. Preparation of the Protein of the Present Invention and the Protein Used in the Present Invention The protein of the present invention and the protein used in the present invention (hereinafter referred to as protein used in the present invention) can be produced by culturing the transformant obtained by the method of the above 8 in a medium, allowing the protein used in the present invention to form and accumulate in the culture, and recovering the protein from the culture.

The host of the above transformant for producing the protein used in the present invention may be any microorganism such as procaryote or yeast, animal cell, insect cell, plant cell or the like, but is preferably a microorganism, more preferably a procaryote, further preferably a bacterium, particularly preferably a bacterium belonging to the genus *Escherichia*, and most preferably *Escherichia coli*.

Culturing of the above transformant in a medium can be carried out by conventional methods for culturing the host cell.

For the culturing of the transformant microorganism obtained by using a procaryote such as *Escherichia coli* or a eucaryote such as yeast as the host cell, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

For the culturing of the transformant obtained by using an animal cell as the host cell, generally employed media such as RPMI1640 medium [J. Am. Med. Assoc., 199, 519 (1967)], Eagle's MEM [Science, 122, 501 (1952)], DMEM [Virology, 8, 396 (1959)] and 199 medium [Proc. Soc. Biol. Med., 73, 1 (1950)], media prepared by adding fetal calf serum or the like to these media, etc. can be used as the medium.

Culturing is usually carried out at pH 6 to 8 at 25 to 40° C. for 1 to 7 days in the presence of 5% $CO_2$.

If necessary, antibiotics such as kanamycin, penicillin and streptomycin may be added to the medium during the culturing.

For the culturing of the transformant obtained by using an insect cell as the host cell, generally employed media such as TNM-FH medium (PharMingen, Inc.), Sf-900 II SFM medium (Life Technologies, Inc.), ExCell 400 and ExCell 405 (JRH Biosciences, Inc.) and Grace's Insect Medium [Nature, 195, 788 (1962)] can be used as the medium.

Culturing is usually carried out at pH 6 to 7 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out at pH 5 to 9 at 20 to 40° C. for 3 to 60 days.

If necessary, antibiotics such as kanamycin and hygromycin may be added to the medium during the culturing.

The protein used in the present invention may be produced by intracellular production by host cells, extracellular secretion by host cells or production on outer membranes by host cells. A desirable production method can be adopted by changing the kind of the host cells used or the structure of the protein to be produced.

When the protein used in the present invention is produced in host cells or on outer membranes of host cells, it is possible to force the protein to be secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, extracellular secretion of the protein used in the present invention by host cells can be caused by expressing it in the form of a protein in which a signal peptide is added upstream of a protein containing the active site of the protein used in the present invention by the use of recombinant DNA techniques.

It is also possible to increase the protein production by utilizing a gene amplification system using a dihydrofolate reductase gene or the like according to the method described in Japanese Published Unexamined Patent Application No. 227075/90.

Further, the protein used in the present invention can be produced using an animal having an introduced gene (non-human transgenic animal) or a plant having an introduced gene (transgenic plant) constructed by redifferentiation of animal or plant cells carrying the introduced gene.

When the transformant producing the protein used in the present invention is an animal or plant, the protein can be produced by raising or culturing the animal or plant in a usual manner, allowing the protein to form and accumulate therein, and recovering the protein from the animal or plant.

Production of the protein used in the present invention using an animal can be carried out, for example, by producing the protein in an animal constructed by introducing the gene according to known methods [Am. J. Clin. Nutr., 63, 639S (1996); Am. J. Clin. Nutr., 63, 627S (1996); Bio/Technology, 9, 830 (1991)].

In the case of an animal, the protein used in the present invention can be produced, for example, by raising a non-human transgenic animal carrying the introduced DNA used in the present invention, allowing the protein to form and accumulate in the animal, and recovering the protein from the animal. The places where the protein is formed and accumulated include milk (Japanese Published Unexamined Patent Application No. 309192/88), egg, etc. of the animal. As the promoter in this process, any promoters capable of functioning in an animal can be used. Preferred promoters include mammary gland cell-specific promoters such as α casein promoter, β casein promoter, β lactoglobulin promoter and whey acidic protein promoter.

Production of the protein used in the present invention using a plant can be carried out, for example, by culturing a transgenic plant carrying the introduced DNA encoding the protein used in the present invention according to known methods [Soshiki Baiyo (Tissue Culture), 20, (1994); Soshiki Baiyo, 21, (1995); Trends Biotechnol., 15, 45 (1997)], allowing the protein to form and accumulate in the plant, and recovering the protein from the plant.

The protein used in the present invention produced by using the transformant producing the protein can be isolated and purified by conventional methods for isolating and purifying enzymes.

For example, when the protein used in the present invention is produced in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract.

A purified protein preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the protein is produced as an inclusion body in cells, the cells are similarly recovered and disrupted, followed by centrifugation to obtain a precipitate fraction. After the protein is recovered from the precipitate fraction by an ordinary method, the inclusion body of the protein is solubilized with a protein-denaturing agent.

The solubilized protein solution is diluted with or dialyzed against a solution containing no protein-denaturing agent or a solution containing the protein-denaturing agent at such a low concentration that denaturation of protein is not caused, whereby the protein is renatured to have normal higher-order structure. Then, a purified protein preparation can be obtained by the same isolation and purification steps as described above.

When the protein used in the present invention or its derivative such as a glycosylated form is extracellularly secreted, the protein or its derivative such as a glycosylated form can be recovered in the culture supernatant.

That is, the culture is treated by the same means as above, e.g., centrifugation, to obtain a soluble fraction. A purified protein preparation can be obtained from the soluble fraction by using the same isolation and purification methods as described above.

Examples of the proteins obtained in the above manner are proteins respectively consisting of the amino acid sequences shown in SEQ ID NOS: 1 to 13, 47, 48, 53 and 124 to 131.

It is also possible to produce the protein used in the present invention as a fusion protein with another protein and to purify it by affinity chromatography using a substance having affinity for the fused protein.

Examples of the proteins to be fused include β-galactosidase, protein A, immunoglobulin G-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescent protein, FLAG peptide and arbitrary antibody epitopes [Akio Yamakawa, Experimental Medicine, 13, 469-474 (1995)].

Examples of the substances having affinity for the above proteins to be fused include antibodies recognizing β-galactosidase, protein A, immunoglobulin G-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescent protein, FLAG peptide and arbitrary antibody epitopes, such as immunoglobulin G.

Specifically, when the protein used in the present invention is produced as a fusion protein with protein A, the fusion protein can be purified according to the method of Lowe, et al. [Proc. Natl. Acad. Sci. USA, 86, 8227 (1989); Genes Develop., 4, 1288 (1990)] and the methods described in Japanese Published Unexamined Patent Application No. 336963/93 and WO94/23021. When the protein used in the present invention is produced as a fusion protein with a Flag peptide, the fusion protein can be purified according to the methods described in Proc. Natl. Acad. Sci. USA, 86, 8227 (1989); Genes Develop., 4, 1288 (1990), etc. The protein can also be purified by affinity chromatography using an antibody against said protein.

The protein used in the present invention can also be produced by chemical synthetic methods such as the Fmoc method (the fluorenylmethyloxycarbonyl method) and the tBoc method (the t-butyloxycarbonyl method) based on the amino acid information on the protein obtained above. Further, the protein can be chemically synthesized by using peptide synthesizers from Advanced ChemTech, Perkin-Elmer, Pharmacia, Protein Technology Instrument, Synthecell-Vega, PerSeptive, Shimadzu Corporation, etc.

10. Process for Producing Dipeptides or Dipeptide Derivatives of the Present Invention The production processes of the present invention include:

(1) a process for producing dipeptide or dipeptide derivative PI, which comprises:

allowing (i) a phosphate donor, (ii) a substance selected from the group consisting of AMP, ADP and ATP, (iii) a protein having polyphosphate kinase activity, or a culture of cells having the ability to produce the protein or a treated matter of the culture, (iv) a protein having the activity to ATP-dependently form dipeptide or dipeptide derivative PI from one or more kinds of amino acids or amino acid derivatives, or a culture of cells having the ability to produce the protein or a treated matter of the culture and (v) one or more kinds, preferably one or two kinds of amino acids or amino acid derivatives to be present in an aqueous medium;

allowing dipeptide or dipeptide derivative PI to form and accumulate in the aqueous medium; and recovering dipeptide or dipeptide derivative PI from the aqueous medium; and (2) a process for producing dipeptide or dipeptide derivative PII, which comprises:

allowing (i) a phosphate donor, (ii) a substance selected from the group consisting of AMP, ADP and ATP, (iii) a protein having polyphosphate kinase activity, or a culture of cells having the ability to produce the protein or a treated matter of the culture, (iv) a protein having the activity to ATP-dependently form dipeptide or dipeptide derivative PI from one or more kinds of amino acids or amino acid derivatives, or a culture of cells having the ability to produce the protein or a treated matter of the culture and (v) one or more kinds, preferably one or two kinds of amino acids or amino acid derivatives to be present in an aqueous medium;

allowing dipeptide or dipeptide derivative PI to form and accumulate in the aqueous medium;

subjecting dipeptide or dipeptide derivative PI, as such or after recovery, to modification to form dipeptide or dipeptide derivative PII; and recovering dipeptide or dipeptide derivative PII.

Modification of dipeptide or dipeptide derivative PI to form dipeptide or dipeptide derivative PII can be carried out by known organic synthesis techniques.

The above amino acids or amino acid derivatives include amino acids or amino acid derivatives represented by formula (I):

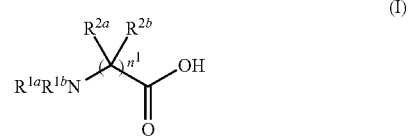

(wherein $n^1$, $R^{1a}$, $R^{1b}$, $R^{2a}$ and $R^{2b}$ have the same significances as defined above) or formula (II):

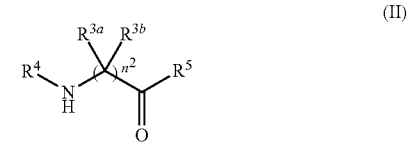

(wherein $n^2$, $R^{3a}$, $R^{3b}$, $R^4$ and $R^5$ have the same significances as defined above) [provided that when all the amino acids or amino acid derivatives used are amino acids or amino acid derivatives represented by formula (I), at least one of $R^{1a}$ and $R^{1b}$ is a hydrogen atom, and when all the amino acids or amino acid derivatives used are amino acids or amino acid derivatives represented by formula (II), $R^5$ is hydroxy]. Preferred amino acids or amino acid derivatives are those represented by formula (III):

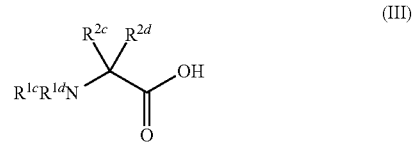

(wherein $R^{1c}$, $R^{1d}$, $R^{2c}$ and $R^{2d}$ have the same significances as defined above) or formula (IV):

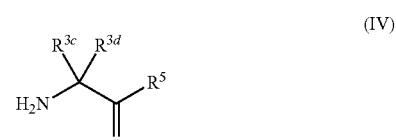

(wherein $R^{3c}$, $R^{3d}$ and $R^5$ have the same significances as defined above) [provided that when all the amino acids or amino acid derivatives used are amino acids or amino acid derivatives represented by formula (III), at least one of $R^{1c}$ and $R^{1d}$ is a hydrogen atom, and when all the amino acids or amino acid derivatives used are amino acids or amino acid derivatives represented by formula (IV), $R^5$ is hydroxy]. More preferred amino acids or amino acid derivatives are those represented by formula (V):

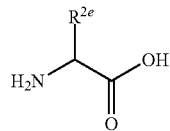

(wherein $R^{2e}$ has the same significance as defined above) or formula (VI):

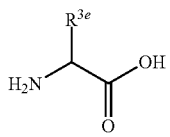

(wherein $R^{3e}$ has the same significance as defined above).

Examples of dipeptide or dipeptide derivative PI produced by the above process include dipeptides or dipeptide derivatives represented by formula (VIIa):

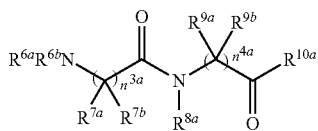

(wherein $n^{3a}$, $n^{4a}$, $R^{6a}$, $R^{6b}$, $R^{7a}$, $R^{7b}$, $R^{8a}$, $R^{9a}$, $R^{9b}$ and $R^{10a}$ have the same significances as defined above), preferably, dipeptides or dipeptide derivatives represented by formula (VIIIa):

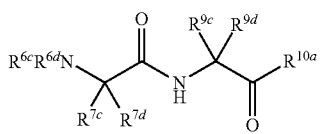

(wherein $R^{6c}$, $R^{6d}$, $R^{7c}$, $R^{7d}$, $R^{9c}$, $R^{9d}$ and $R^{10a}$ have the same significances as defined above), more preferably, dipeptides or dipeptide derivatives represented by formula (IXa):

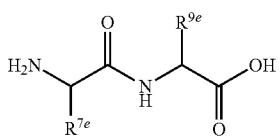

(wherein $R^{7e}$ and $R^{9e}$ have the same significances as defined above).

Examples of dipeptide or dipeptide derivative PII produced by the above process include dipeptides or dipeptide derivatives represented by formula (VIIb):

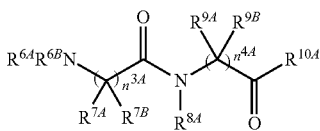

(wherein $n^{3A}$, $n^{4A}$, $R^{6A}$, $R^{6B}$, $R^{7A}$, $R^{7B}$, $R^{8A}$, $R^{9A}$, $R^{9B}$ and $R^{10A}$ have the same significances as defined above), preferably, dipeptides or dipeptide derivatives represented by formula (VIIIb):

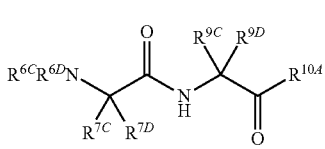

(wherein $R^{6C}$, $R^{6D}$, $R^{7C}$, $R^{7D}$, $R^{9C}$, $R^{9D}$ and $R^{10A}$ have the same significances as defined above), more preferably, dipeptides or dipeptide derivatives represented by formula (IXb):

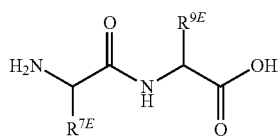

(wherein $R^{7E}$ and $R^{9E}$ have the same significances as defined above). The above dipeptides or dipeptide derivatives do not include compounds in which the same or different amino acids selected from the group consisting of L-alanine, L-glutamine, L-glutamic acid, L-valine, L-leucine, L-isoleucine, L-proline, L-phenylalanine, L-tryptophan, L-methionine, L-serine, L-threonine, L-cysteine, L-asparagine, L-tyrosine, L-lysine, L-arginine, L-histidine, L-aspartic acid, L-α-aminobutyric acid, L-azaserine, L-theanine, L-4-hydroxyproline, L-3-hydroxyproline, L-ornithine, L-citrulline, L-6-diazo-5-oxo-norleucine, glycine and β-alanine are linked with each other by peptide bond.

In the definitions of the groups in formulae (I) to (VI), (VIIa), (VIIb), (VIIIa), (VIIIb), (IXa) and (IXb), the lower alkyl moiety of the lower alkyl, the lower alkoxy, the lower alkanoyl, the lower alkoxycarbonyl, the mono(lower alkyl)amino and the di(lower alkyl)amino includes alkyl groups with 1 to 10 carbon atoms having a straight-chain structure, a branched-chain structure, a cyclic structure or a combination thereof. Examples of the straight-chain or branched-chain alkyl groups are methyl, ethyl, n-propyl, isopropyl, n-butyl, isobutyl, sec-butyl, tert-butyl, n-pentyl, neopentyl, n-hexyl, n-heptyl, n-octyl, n-nonyl and n-decyl. Examples of the cyclic alkyl groups are cyclopropyl, cyclobutyl, cyclopentyl, cyclohexyl, cycloheptyl, cyclooctyl, cyclodecyl, noradamantyl, adamantyl, bicyclo[2.2.1]heptyl, bicyclo[2.2.2]octyl, bicyclo[3.3.0]octyl and bicyclo[3.3.1]nonyl. Examples of the alkyl groups having a combination of a straight-chain or branched-chain structure and a cyclic structure are cyclopropylmethyl, cyclopentylmethyl and cyclooctylethyl. Two lower alkyl moieties of the di(lower alkyl)amino may be the same or different.

The lower alkenyl includes straight-chain or branched-chain alkenyl groups having 2 to 10 carbon atoms, such as vinyl, allyl, 1-propenyl, 1-butenyl, 3-butenyl, 2-pentenyl, 4-pentenyl, 2-hexenyl, 5-hexenyl, 2-decenyl and 9-decenyl.

The lower alkynyl includes straight-chain or branched-chain alkynyl groups having 2 to 10 carbon atoms, such as ethynyl, 2-propynyl, 3-butynyl, 4-pentynyl, 5-hexynyl and 9-decynyl.

The aryl moiety of the aryl, the aralkyl and the aroyl includes monocyclic aryl groups and condensed-ring aryl groups in which two or more rings are condensed, specifically, aryl groups having 6 to 14 ring-constituting carbon atoms, such as phenyl, naphthyl, indenyl and anthranyl.

The alicyclic heterocyclic group includes monocyclic ones and condensed-ring ones in which two or more rings are condensed. Though the kind and number of heteroatoms contained in the alicyclic heterocyclic group are not specifically limited, the alicyclic heterocyclic group may contain, for example, one or more heteroatoms selected from the group consisting of nitrogen atom, sulfur atom and oxygen atom. Specific examples of the alicyclic heterocyclic groups are pyrrolidinyl, 2,5-dioxopyrrolidinyl, thiazolidinyl, oxazolidinyl, piperidyl, 1,2-dihydropyridyl, piperazinyl, homopiperazinyl, morpholinyl, thiomorpholinyl, pyrazolinyl, oxazolinyl, dioxolanyl, tetrahydropyranyl, tetrahydrothiopyranyl, tetrahydrofuryl, tetrahydroquinolyl, tetrahydroisoquinolyl, tetrahydroquinoxalinyl, octahydroquinolyl, dihydroindolyl and 1,3-dioxoisoindolinyl.

The heterocyclic group moiety of the heterocyclic alkyl includes, for example, aromatic heterocyclic groups and alicyclic heterocyclic groups. The aromatic heterocyclic groups include monocyclic ones and condensed-ring ones in which two or more rings are condensed. Though the kind and number of heteroatoms contained in the aromatic heterocyclic group are not specifically limited, the aromatic heterocyclic group may contain, for example, one or more heteroatoms selected from the group consisting of nitrogen atom, sulfur atom and oxygen atom. Specific examples of the aromatic heterocyclic groups are those having 5 to 14 ring-constituting atoms, such as furyl, thienyl, pyrrolyl, imidazolyl, pyrazolyl, triazolyl, tetrazolyl, oxazolyl, oxadiazolyl, thiazolyl, pyridyl, pyrazinyl, pyrimidinyl, pyridazinyl, triazinyl, indolyl, indazolyl, benzimidazolyl, benzoxazolyl, benzothiazolyl, quinolyl, isoquinolyl, phthalazinyl, naphthyridinyl, quinoxalinyl, quinazolinyl, cinnolinyl, purinyl and coumarinyl. The alicyclic heterocyclic group has the same significance as defined above.

The alkylene moiety of the aralkyl and the heterocyclic alkyl has the same significance as the straight-chain or branched-chain alkyl among the above-described lower alkyl groups except one hydrogen atom is removed therefrom.

The heterocyclic group formed together with the adjacent nitrogen atom and the carbon atom adjacent to the nitrogen atom and the heterocyclic group formed together with the adjacent carbon atom and the nitrogen atom adjacent to the carbon atom include 5- or 6-membered monocyclic alicyclic heterocyclic groups containing at least one nitrogen atom (the monocyclic alicyclic heterocyclic groups may also contain another nitrogen atom, oxygen atom or sulfur atom), and bicyclic or tricyclic condensed-ring heterocyclic groups containing at least one nitrogen atom in which 3- to 8-membered rings are condensed (the condensed-ring heterocyclic groups may also contain another nitrogen atom, oxygen atom or sulfur atom), specifically, pyrrolidinyl, piperidyl, piperazinyl, morpholinyl, thiomorpholinyl, homopiperidinyl, homopiperazinyl, tetrahydropyridyl, tetrahydroquinolyl and tetrahydroisoquinolyl.

The substituted lower alkyl, the substituted lower alkenyl, the substituted lower alkynyl, the substituted lower alkoxy, the substituted lower alkanoyl, the substituted lower alkoxycarbonyl, the substituted aralkyl, the substituted aryl, the substituted aroyl, the substituted heterocyclic alkyl, the mono (substituted lower alkyl)amino, the lower alkyl(substituted lower alkyl)amino, the di(substituted lower alkyl)amino, the substituted heterocyclic group formed together with the adjacent nitrogen atom and the carbon atom adjacent to the nitrogen atom, and the substituted heterocyclic group formed together with the adjacent carbon atom and the nitrogen atom adjacent to the carbon atom each have one to a substitutable number, preferably 1 to 3 substituents which are the same or different. Examples of the substituents include halogen, amino, nitro, hydroxy, mercapto, guanidino, ureido, cyano, formyl, carboxyl, aminocarbonyl, diazoacetyl, lower alkyl, lower alkoxy, lower alkanoyl, lower alkoxycarbonyl, mono or di(lower alkyl)aminocarbonyl, lower alkylthio, aryl, aralkyl, aroyl and heterocyclic carbonyl. The lower alkyl moiety of the lower alkyl, the lower alkoxy, the lower alkanoyl and the lower alkoxycarbonyl, the aryl moiety of the aryl, the aralkyl and the aroyl, and the alkylene moiety of the aralkyl have the same significances as defined above, respectively. The lower alkyl moiety of the mono or di(lower alkyl)aminocarbonyl and the lower alkylthio has the same significance as the above lower alkyl, and the heterocyclic group moiety of the heterocyclic carbonyl has the same significance as the heterocyclic group moiety of the above heterocyclic alkyl. The halogen includes fluorine, chlorine, bromine and iodine atoms. Two lower alkyl moieties of the di(lower alkyl)aminocarbonyl may be the same or different.

Preferred amino acids or amid acid derivatives also include those selected from the group consisting of L-amino acids, glycine (Gly), β-alanine (βAla) and their derivatives. Examples of L-amino acids are L-alanine (L-Ala), L-glutamine (L-Gln), L-glutamic acid (L-Glu), L-valine (L-Val), L-leucine (L-Leu), L-isoleucine (L-Ile), L-proline (L-Pro), L-phenylalanine (L-Phe), L-tryptophan (L-Trp), L-methionine (L-Met), L-serine (L-Ser), L-threonine (L-Thr), L-cysteine (L-Cys), L-asparagine (L-Asn), L-tyrosine (L-Tyr), L-lysine (L-Lys), L-arginine (L-Arg), L-histidine (L-His), L-aspartic acid (L-Asp), L-α-aminobutyric acid (L-α-AB), L-azaserine, L-theanine, L-4-hydroxyproline (L-4-HYP), L-3-hydroxyproline (L-3-HYP), L-ornithine (L-Orn), L-citrulline (L-Cit) and L-6-diazo-5-oxo-norleucine.

Combinations of amino acids or amino acid derivatives used in the above production processes include the following: a combination of one kind of amino acid selected from the group consisting of L-Ala, Gly, L-Met, L-Ser, L-Thr and β-Ala, or its derivative, and one kind of amino acid selected from the group consisting of L-Ala, L-Gln, L-Glu, Gly, L-Val, L-Leu, L-Ile, L-Pro, L-Phe, L-Trp, L-Met, L-Ser, L-Thr, L-Cys, L-Asn, L-Tyr, L-Lys, L-Arg, L-His, L-Asp, L-α-AB, β-Ala, L-azaserine, L-theanine, L-4-HYP, L-3-HYP, L-Orn, L-Cit and L-6-diazo-5-oxo-norleucine, or its derivative; a combination of L-Gln or its derivative and L-Phe or its derivative; and a combination of L-α-AB or its derivative, and one kind of amino acid selected from the group consisting of L-Gln, L-Arg and L-α-AB, or its derivative. Further preferred combinations are: a combination of L-Ala or its derivative, and one kind of amino acid selected from the group consisting of L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit and L-theanine, or its derivative; a combination of Gly or its derivative, and one kind of amino acid selected from the group consisting of L-Gln, Gly, L-Phe, L-Trp, L-Met, L-Ser, L-Thr, L-Cys, L-Tyr, L-Lys, L-Arg, L-α-AB and L-Cit, or its derivative; a combination of L-Met or its derivative, and one kind of amino acid selected from the group consisting of L-Phe, L-Met, L-Ser, L-Thr, L-Cys, L-Tyr, L-Lys and L-His, or its derivative; a combination of L-Ser or its derivative, and one kind of amino acid selected from the group consisting of L-Gln, L-Phe, L-Ser, L-Thr, L-Tyr, L-His and L-α-AB, or its derivative; a combination of L-Thr or its derivative, and one kind of amino acid selected from the group consisting of L-Gln, L-Phe, L-Leu, L-Thr and L-α-AB, or its derivative; a combination of L-Gln or its derivative and L-Phe or its derivative; a combination of β-Ala or its derivative, and one kind of amino acid selected from the group consisting of L-Phe, L-Met, L-His and L-Cit, or its derivative; and a combination of L-α-AB or its derivative, and one kind of amino acid selected from the group consisting of L-Gln, L-Arg and L-α-AB, or its derivative.

When the protein itself is used as the enzyme source in the above production processes, the amount of the protein in the aqueous medium is 0.01 to 100 mg, preferably 0.1 to 10 mg per mg of amino acid or amino acid derivative used as a substrate. When the culture of cells having the ability to produce the protein having the dipeptide-forming activity or cells having the ability to produce the protein having polyphosphate kinase activity, or a treated matter of the culture is used as the enzyme source, the amount of the enzyme source to be added varies according to its specific activity, etc., but is, for example, 5 to 1000 mg (wet cell weight), preferably 10 to 400 mg per mg of amino acid or amino acid derivative used as a substrate.

The treated matters of the culture include treated matters which are selected from the group consisting of heat-treated culture, concentrated culture, dried culture, cells obtained by centrifuging the culture, products obtained by subjecting the cells to heat treatment, drying, freeze-drying, treatment with a surfactant, ultrasonication, mechanical friction, treatment with a solvent, enzymatic treatment, protein fractionation and immobilization, and an enzyme preparation obtained by extracting the cells, and which have the activity to ATP-dependently form dipeptide or dipeptide derivative PI from one or more kinds of amino acids or amino acid derivatives, or polyphosphate kinase activity. Preferred are heat-treated culture or cells. The heat treatment may be carried out under any conditions without specific restrictions, provided that the heat-treated culture or cells have the activity to form dipeptide or dipeptide derivative PI and polyphosphate kinase activity required for the reaction and that the dipeptide- or dipeptide derivative-hydrolyzing activity can be reduced or lost. For example, the heat treatment can be carried out at 40 to 90° C. for 5 to 120 minutes, preferably at 45 to 70° C. for 10 to 60 minutes.

When the above heat-treated culture or cells are used as the enzyme source, it is preferred to employ a protein having the dipeptide-forming activity and a protein having polyphosphate kinase activity which are thermostable. Cells having the ability to produce the protein having the dipeptide-forming activity and the protein having polyphosphate kinase activity which are thermostable can be obtained by introducing a mutation, for example, into DNA having the nucleotide sequence shown in SEQ ID NO: 14 or 117 by using techniques such as error-prone PCR [Technique, 1, 11-15 (1989)], preparing transformants producing a protein encoded by the above DNA by the method of the above 3 to produce the protein, and selecting a transformant producing the protein retaining the dipeptide-forming activity or polyphosphate kinase activity after the heat treatment under the above conditions. An example of such cells is a cell carrying DNA having the nucleotide sequence shown in any of SEQ ID NOS: 22 to 26 obtained by introducing a mutation into DNA having the nucleotide sequence shown in SEQ ID NO: 14 by error-prone PCR.

In the above production processes, the amino acids or amino acid derivatives used as substrates are added to the aqueous-medium at the start or in the course of reaction to give a concentration of 0.1 to 500 g/l, preferably 0.2 to 200 g/l.

The substance selected from the group consisting of AMP, ADP and ATP used in the above production processes may be used at any concentration that allows start of coupling of ATP-consuming reaction (reaction to form dipeptide or dipeptide derivative PI) and ATP-regenerating reaction (ATP-forming reaction by polyphosphate kinase). The concentration of the substance is usually 0.1 mmol/l to 100 mol/l, preferably 1 mmol/l to 10 mol/l, more preferably 2 mmol/l to 5 mol/l.

When the culture of cells or a treated matter of the culture is used as the enzyme source in the above production processes, precursors of AMP, ADP or ATP which are converted into AMP, ADP or ATP by the metabolic ability of cells, or substances which serve as sources of AMP, ADP or ATP, for example, sugars such as glucose, alcohols such as ethanol, and organic acids such as acetic acid, can be used instead of AMP, ADP or ATP.

As the phosphate donor in the above production processes, any phosphate donors that are substrates for polyphosphate kinase can be used. Preferably, polyphosphoric acids are used. Any polyphosphoric acids that are substrates for polyphosphate kinase can be used, and suitable ones are those having the polymerization degree of 8 to 1000, preferably 10 to 75. Polyphosphoric acid is added to the aqueous medium to give a concentration of 0.5 to 200 g/l, preferably 5 to 100 g/l.

The aqueous medium used in the above production processes may comprise any components and may have any composition so far as the dipeptide- or dipeptide derivative-forming reaction is not inhibited. Suitable aqueous media include water and buffers such as phosphate buffer, carbonate buffer, acetate buffer, borate buffer, citrate buffer and Tris buffer. The aqueous medium may comprise alcohols such as methanol and ethanol, esters such as ethyl acetate, ketones such as acetone, and amides such as acetamide. When the culture of cells or a treated matter of the culture is used as the enzyme source, the culture liquor of the cells can also be used as the aqueous medium.

Further, when the culture of, cells or a treated matter of the culture is used as the enzyme source in the above production processes, a surfactant or an organic solvent may be added to the aqueous medium according to need. Suitable surfactants include nonionic surfactants such as polyoxyethylene octadecylamine (e.g., Nymeen S-215, NOF Corporation), cationic surfactants such as cetyltrimethylammonium bromide and alkyldimethylbenzylammonium chloride (e.g., Cation F2-40E, NOF Corporation), anionic surfactants such as lauroyl sarcosinate, and tertiary amines such as alkyldimethylamine (e.g., Tertiary Amine FB, NOF Corporation). Suitable organic solvents include xylene, toluene, aliphatic alcohols, acetone and ethyl acetate. Any surfactants and organic solvents may be used alone or in combination provided that the cells used in the production processes of the present invention have the activity to form dipeptide or dipeptide derivative PI from amino acids or amino acid derivatives. The kind and concentration of the surfactant and organic solvent can be arbitrarily selected so long as the cells used in the present invention have the above activity. For example, the surfactant is usually used at a concentration of 0.1 to 50 g/l, and the organic solvent is usually used at a concentration of 0.1 to 50 ml/l.

If necessary, chelating agents such as EDTA, EGTA and phytic acid, protease inhibitors such as PMSF (phenylmethylsulfonyl fluoride) and -4-amidinophenyl benzoate, peptidase inhibitors such as actinonin and diprotin A, and metal ions such as cadmium and chromium may be added to the aqueous medium in order to inhibit hydrolysis of the formed dipeptide or dipeptide derivative. They can be used at the following concentrations: chelating agent, 0.01 to 100 mmol/l; protease or peptidase inhibitor, 0.01 to 10 mmol/l; metal ion, 0.1 to 100 mg/l.

The dipeptide- or dipeptide derivative-forming reaction is carried out in the aqueous medium at pH 5 to 11, preferably pH 6 to 10, at 20 to 50° C., preferably 25 to 45° C., for 2 to 150 hours, preferably 6 to 120 hours.

In the above production processes, recovery of the dipeptide or dipeptide derivative formed and accumulated in the aqueous medium can be carried out by ordinary methods using active carbon, ion-exchange resins, etc. or by means such as extraction with an organic solvent, crystallization, thin layer chromatography and high performance liquid chromatography.

The methods for preparing the DNA, protein and cells used in the present invention are illustrated in the following experimental examples, but the preparation methods are not limited to the following experimental examples.

EXPERIMENTAL EXAMPLE 1

Search for a Protein Having the Dipeptide-Synthesizing Activity Utilizing a Database By using, as a query, the amino acid sequence of D-Ala-D-Ala ligase gene derived from *Bacillus subtilis* 168 [Nature, 390, 249-256 (1997)], a search for a gene encoding a protein having homology which is present in the genomic DNA sequences of *Bacillus subtilis* 168 was carried out using the homology search function of Subtilist (http://genolist.pasteur.fr/SubtiList/) which is a database of the genomic DNA of *Bacillus subtilis* 168.

From the sequences obtained as a result of the search, genes encoding the amino acid sequences shown in SEQ ID NOS: 43, 44 and 45 which are D-Ala-D-Ala ligase motifs [Biochemistry, 30, 1673 (1991)] and encoding proteins whose function had already been clarified were excluded. Of the remaining sequences, the sequence showing the highest homology (29.1%) to the D-Ala-D-Ala ligase motif was selected as a gene of unknown function ywfE.

The nucleotide sequence of ywfE is shown in SEQ ID NO: 14, and the amino acid sequence of the protein encoded by the nucleotide sequence is shown in SEQ ID NO: 1.

EXPERIMENTAL EXAMPLE 2

Construction of a Strain Expressing ywfE Gene

On the basis of the information on the nucleotide sequence obtained in Experimental Example 1, a ywfE gene fragment of *Bacillus subtilis* was obtained in the following manner.

That is, *Bacillus subtilis* 168 (ATCC 23857) was inoculated into LB medium [10 g/l Bacto-tryptone (Difco), 5 g/l yeast extract (Difco) and 5 g/l sodium chloride] and subjected to static culture overnight at 30° C. After the culturing, the chromosomal DNA of the microorganism was isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 29 to 32 (hereinafter referred to as primer A, primer B, primer C and primer D, respectively) were synthesized. Primer A has a sequence wherein a nucleotide sequence containing the XhoI recognition sequence is added to the 5' end of a region of the *Bacillus subtilis* chromosomal DNA containing the initiation codon of ywfE. Primer B has a sequence wherein a nucleotide sequence containing the BamHI recognition sequence is added to the 5' end of a nucleotide sequence complementary to a sequence containing the termination codon of ywfE. Primer C has a sequence wherein a nucleotide sequence containing the EcoRI recognition sequence is added to the 5' end of the nucleotide sequence of trp promoter region of expression vector pTrS30 containing trp promoter [prepared from *Escherichia coli* JM109/pTrS30 (FERM BP-5407)]. Primer D has a sequence wherein a nucleotide sequence containing the XhoI recognition sequence is added to the 5' end of a sequence complementary to the sequence of trp promoter region of expression vector pTrS30 containing trp promoter.

A ywfE gene fragment was amplified by PCR using the above primer A and primer B, and as a template, the chromosomal DNA of *Bacillus subtilis*. A trp promoter region fragment was amplified by PCR using primer C and primer D, and as a template, pTrS30. PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA or 10 ng of pTrS30 as a template, 0.5 µmol/l each of the primers, 2.5 units of Pfu DNA polymerase (Stratagene), 4 µl of buffer for Pfu DNA polymerase (10×) (Stratagene) and 200 µmol/l each of dNTPs (dATP, dGTP, dCTP and dTTP).

One-tenth of each of the resulting reaction mixtures was subjected to agarose gel electrophoresis to confirm that a ca. 1.4 kb DNA fragment corresponding to the ywfE gene fragment and a ca. 0.3 kb DNA fragment corresponding to the trp promoter region fragment were respectively amplified in the PCR using primer A and primer B and the PCR using primer C and primer D. Then, the remaining reaction mixture was mixed with an equal amount of phenol/chloroform (1 vol/1 vol) saturated with TE (10 mmol/l Tris-HCl (pH 8.0), 1 mmol/l EDTA]. The resulting solution was centrifuged, and the obtained upper layer was mixed with a two-fold volume of cold ethanol and allowed to stand at −80° C. for 30 minutes. The resulting solution was centrifuged to precipitate DNA, and the obtained DNA was dissolved in 20 µl of TE.

The thus obtained solutions (5 µl each) were respectively subjected to reaction to cleave the DNA amplified using primer A and primer B with restriction enzymes XhoI and BamHI and to reaction to cleave the DNA amplified using primer C and primer D with restriction enzymes EcoRI and XhoI. DNA fragments were separated by agarose gel electrophoresis, and a 1.4 kb fragment containing ywfE and a 0.3 kb fragment containing trp promoter region were respectively recovered using GENECLEAN II Kit (BIO 101).

pTrs30 [a trp promoter-containing expression vector prepared from *Escherichia coli* JM109/pTrS30 (FERM BP-5407), 0.2 µg] was cleaved with restriction enzymes EcoRI and BamHI. DNA fragments were separated by agarose gel electrophoresis and a 4.5 kb DNA fragment was recovered in the same manner as above.

The 1.4 kb fragment containing ywfE, the 0.3 kb fragment containing trp promoter region and the 4.5 kb DNA fragment obtained above were subjected to ligation reaction using a ligation kit (Takara Bio Inc.) at 16° C. for 16 hours.

*Escherichia coli* NM522 (Stratagene) was transformed using the reaction mixture according to the method using calcium ion [Proc. Natl. Acad. Sci. USA, 69, 2110 (1972)], spread on LB agar medium containing 50 μg/ml ampicillin, and cultured overnight at 30° C.

A plasmid was extracted from a colony of the transformant that grew on the medium according to a known method and the structure of the plasmid was analyzed using restriction enzymes, whereby it was confirmed that expression vector pPE43 containing ywfE ligated downstream of the trp promoter was obtained (FIG. 1).

EXPERIMENTAL EXAMPLE 3

Production of a Dipeptide

*Escherichia coli* NM522 carrying pPE43 (*Escherichia coli* NM522/pPE43) obtained in Experimental Example 2 was inoculated into 8 ml of LB medium containing 50 μg/ml ampicillin in a test tube, and cultured at 28° C. for 17 hours. The resulting culture was centrifuged to obtain wet cells.

A reaction mixture (0.1 ml) comprising 60 mg/ml (final concentration) wet cells, 120 mmol/l potassium phosphate buffer (pH 7.4), 60 mmol/l magnesium chloride, 60 mmol/l ATP, 30 mmol/l L-Ala, 30 mmol/l L-Gln and 0.4% Nymeen S-215 was prepared, and reaction was carried out at 37° C. for 3 minutes.

After the completion of reaction, the reaction product was derivatized by the dinitrophenol method and then analyzed by HPLC. The HPLC analysis was carried out using, as a separation column, Lichrosorb-RP-18 column (Kanto Kagaku) and, as an eluent, 1% (v/v) phosphoric acid and 25% (v/v) acetonitrile at a flow rate of 0.7 ml/min. As a result, it was confirmed that 120 mg/l L-alanyl-L-glutamine (L-Ala-L-Gln) was formed and accumulated in the reaction mixture.

Formation of L-Ala-L-Gln was not observed when the reaction was carried out using cells of *Escherichia coli* NM522/pTrS31, which is a control strain carrying only a vector.

EXPERIMENTAL EXAMPLE 4

Purification of C-Terminal His-Tagged Recombinant Dipeptide Synthetase

By using the above DNA synthesizer, DNAs having the nucleotide sequences-shown in SEQ ID NOS: 33 and 34 (hereinafter referred to as primer E and primer F, respectively) were synthesized. Primer E has a nucleotide sequence containing a region wherein the initiation codon of ywfE (atg) is substituted by the NcoI recognition sequence (ccatgg). Primer F has a nucleotide sequence containing a region wherein the termination codon of ywfE is substituted by the BamHI recognition sequence (ggatcc).

PCR was carried out using the chromosomal DNA of *Bacillus subtilis* 168 (ATCC 23857) as a template and the above primer E and primer F as a set of primers. That is, PCR was carried out by 30 cycles, one cycle consisting of reaction at 94° C. for one minute, reaction at 55° C. for 2 minutes and reaction at 72° C. for 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of dNTPs.

One-tenth of the resulting reaction mixture was subjected to agarose gel electrophoresis to confirm that a ca. 1.4 kb fragment corresponding to the ywfE fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 μl of TE.

The thus obtained solution (5 μl) was subjected to reaction to cleave the amplified DNA with restriction enzymes NcoI and BamHI. DNA fragments were separated by agarose gel electrophoresis, and a 1.4 kb DNA fragment containing ywfE was recovered using GENECLEAN II Kit.

C-Terminal His-tagged recombinant expression vector pQE60 (Qiagen, Inc.) (0.2 g) was cleaved with restriction enzymes NcoI and BamHI. DNA fragments were separated by agarose gel electrophoresis, and a 3.4 kb DNA fragment was recovered in the same manner as above.

The 1.4 kb DNA fragment containing ywfE and the 3.4 kb DNA fragment obtained above were subjected to ligation reaction using a ligation kit at 16° C. for 16 hours.

*Escherichia coli* NM522 was transformed using the ligation reaction mixture according to the method using calcium ion, spread on LB agar medium containing 50 μg/ml ampicillin, and cultured overnight at 30° C.

Figure 2:
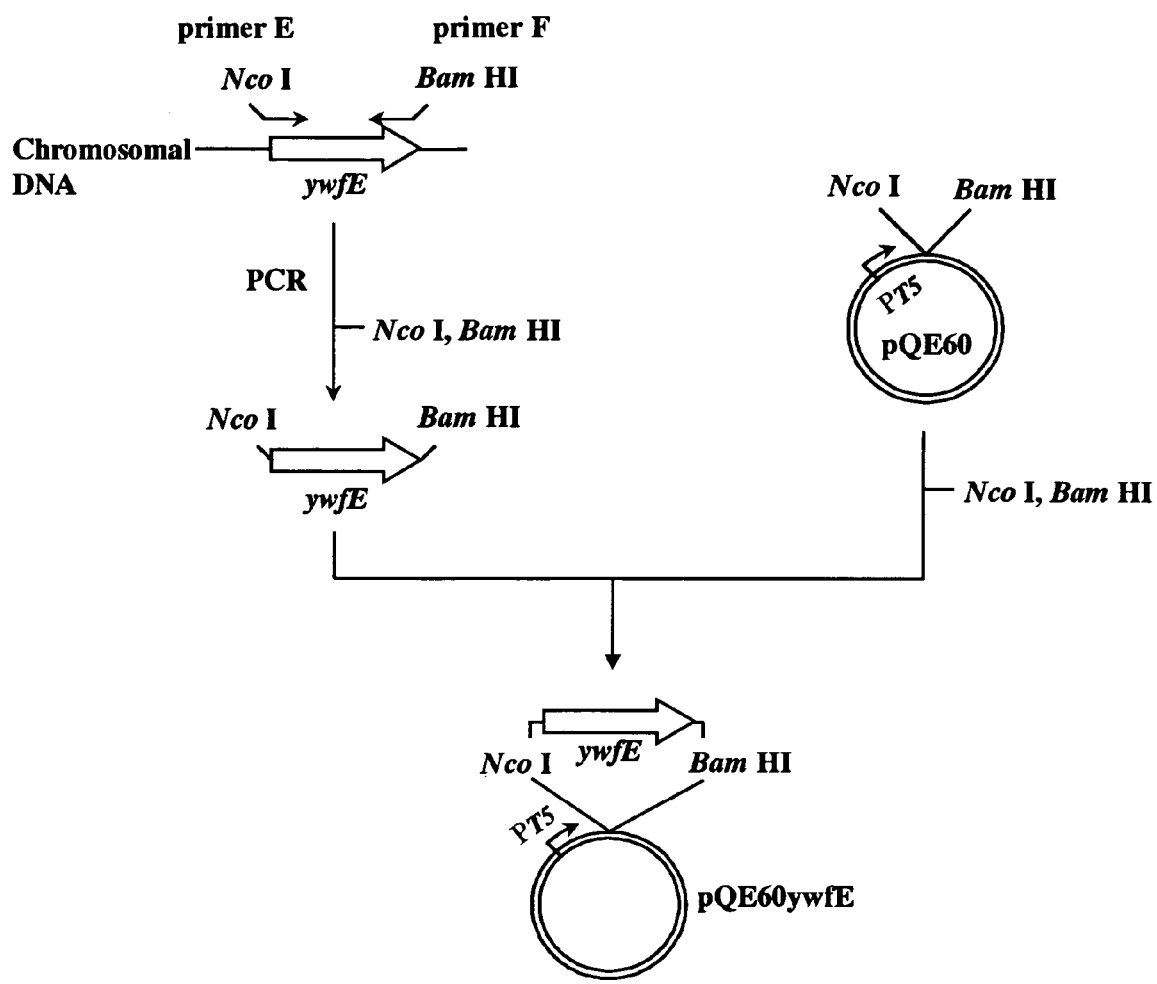
FIG. 2 shows the steps for constructing plasmid pQE60ywfE.

A plasmid was extracted from a colony of the transformant that grew on the medium according to a known method and the structure of the plasmid was analyzed using restriction enzymes, whereby it was confirmed that pQE60ywfE, which is a C-terminal His-tagged ywfE expression vector, was obtained (FIG. 2).

*Escherichia coli* NM522 carrying pQE60ywfE (*Escherichia coli* NM522/pQE60ywfE) was inoculated into 8 ml of LB medium containing 50 μg/ml ampicillin in a test tube, and cultured at 28° C. for 17 hours. The resulting culture was inoculated into 50 ml of LB medium containing 50 μg/ml ampicillin in a 250-ml Erlenmeyer flask, and cultured at 30° C. for 3 hours. Then, isopropyl-β-D-thiogalactopyranoside (IPTG) was added to give a final concentration of 1 mmol/l, followed by further culturing at 30° C. for 4 hours. The resulting culture was centrifuged to obtain wet cells, and a His-tagged recombinant enzyme was purified from the wet cells using HisTrap (His-tagged protein purification kit, Amersham Pharmacia Biotech) according to the instructions attached thereto.

EXPERIMENTAL EXAMPLE 5

Production of Dipeptides Using the His-Tagged Recombinant Enzyme (1)

(i) A reaction mixture (0.1 ml) comprising 0.04 mg of the purified His-tagged recombinant enzyme obtained in Experimental Example 4, 100 mmol/l Tris-HCl (pH 8.0), 60 mmol/l magnesium chloride, 60 mmol/l ATP, 30 mmol/l L-Ala and 30 mmol/l L-Gln was prepared, and reaction was carried out at 37° C. for 16 hours.

After the completion of reaction, the reaction product was analyzed in the same manner as in Experimental Example 3 above, whereby it was confirmed that 3.7 g/l L-Ala-L-Gln and 0.3 g/l L-alanyl-L-alanine (L-Ala-L-Ala) were formed and accumulated in the reaction mixture.

(ii) Reactions were carried out under the same conditions as in the above (i) using reaction mixtures having the same composition as that of the reaction mixture of the above (i) except that 0.01 mg of the enzyme was used and L-Phe, L-Met, L-Leu and L-Val, respectively, were used in place of L-Gln.

After the completion of reactions, the reaction products were analyzed in the same manner as in Experimental Example 3 above, whereby it was confirmed that the following dipeptides were formed and accumulated in the respective reaction mixtures: 7.0 g/l L-alanyl-L-phenylalanine (L-Ala-L-Phe) alone; 7.0 g/l L-alanyl-L-methionine (L-Ala-L-Met) and 0.03 g/l L-Ala-L-Ala; 5.0 g/l L-alanyl-L-leucine (L-Ala-L-Leu) and 0.2 g/l L-Ala-L-Ala; and 1.6 g/l L-alanyl-L-valine (L-Ala-L-Val) and 0.3 g/l L-Ala-L-Ala.

(iii) Reactions were carried out under the same conditions as in the above (i) using reaction mixtures having the same composition as that of the reaction mixture of the above (i) except that 0.01 mg of the enzyme was used, Gly was used in place of L-Ala, and L-Phe and L-Met, respectively, were used in place of L-Gln.

After the completion of reactions, the reaction products were analyzed in the same manner as in Experimental Example 3 above, whereby it was confirmed that 5.2 g/l glycyl-L-phenylalanine (Gly-L-Phe) and 1.1 g/l glycyl-L-methionine (Gly-L-Met) were formed and accumulated in the respective reaction mixtures.

When ATP was excluded from the compositions of the above reaction mixtures, no dipeptide was formed.

The above results revealed that the ywfE gene product has the activity to produce, in the presence of ATP, the following dipeptides: L-Ala-L-Gln plus L-Ala-L-Ala, L-Ala-L-Phe, L-Ala-L-Met plus L-Ala-L-Ala, L-Ala-L-Leu plus L-Ala-L-Ala, or L-Ala-L-Val plus L-Ala-L-Ala from L-Ala plus L-Gln, L-Phe, L-Met, L-Leu or L-Val; and Gly-L-Phe or Gly-L-Met from Gly plus L-Phe or L-Met.

EXPERIMENTAL EXAMPLE 6

Production of Dipeptides Using the His-Tagged Recombinant Enzyme (2)

A reaction mixture (0.1 ml) comprising 0.04 mg of the purified His-tagged recombinant enzyme obtained in Experimental Example 4, 100 mmol/l Tris-HCl (pH 8.0), 60 mmol/l magnesium chloride and 60 mmol/l ATP was prepared. To this mixture were respectively added combinations of various L-amino acids, Gly and β-Ala selected from the amino acids shown in the first row of Table 1 and in the leftmost column of Table 1 to give a concentration of 30 mmol/l each, and the resulting mixtures were subjected to reaction at 37° C. for 16 hours. After the completion of reactions, the reaction products were analyzed by HPLC, whereby it was confirmed that the dipeptides shown in Table 1 were formed.

TABLE 1

|       | Ala    | Gln              | Glu    | Gly              | Val              | Leu              | Ile              | Pro    |
|-------|--------|------------------|--------|------------------|------------------|------------------|------------------|--------|
| Ala   | AlaAla | AlaGln AlaAla    | AlaAla | AlaGly AlaAla    | AlaVal AlaAla    | AlaLeu AlaAla    | AlaIle AlaAla    | AlaAla |
| Gln   |        | X                | X      | GlyGln GlyGly    | X                | X                | X                | X      |
| Glu   |        |                  |        | GlyGly           |                  |                  |                  |        |
| Gly   |        |                  |        | GlyGly           |                  |                  |                  | GlyGly |
| Val   |        |                  |        |                  |                  |                  |                  |        |
| Leu   |        |                  |        |                  |                  |                  |                  |        |
| Ile   |        |                  |        |                  |                  |                  |                  |        |
| Pro   |        |                  |        |                  |                  |                  |                  |        |
| Phe   |        |                  |        |                  |                  |                  |                  |        |
| Trp   |        |                  |        |                  |                  |                  |                  |        |
| Met   |        |                  |        |                  |                  |                  |                  |        |
| Ser   |        |                  |        |                  |                  |                  |                  |        |
| Thr   |        |                  |        |                  |                  |                  |                  |        |
| Cys   |        |                  |        |                  |                  |                  |                  |        |
| Asn   |        |                  |        |                  |                  |                  |                  |        |
| Tyr   |        |                  |        |                  |                  |                  |                  |        |
| Lys   |        |                  |        |                  |                  |                  |                  |        |
| Arg   |        |                  |        |                  |                  |                  |                  |        |
| His   |        |                  |        |                  |                  |                  |                  |        |
| Asp   |        |                  |        |                  |                  |                  |                  |        |
| α AB  |        |                  |        |                  |                  |                  |                  |        |
| β-Ala |        |                  |        |                  |                  |                  |                  |        |
| Cit   |        |                  |        |                  |                  |                  |                  |        |

TABLE 1-continued

|     | Phe              | Trp              | Met                        | Ser                                  | Thr                                  | Cys        | Asn              | Tyr                |
|-----|------------------|------------------|----------------------------|--------------------------------------|--------------------------------------|------------|------------------|--------------------|
| Ala | AlaPhe<br>AlaAla | AlaTrp<br>AlaAla | AlaMet<br>AlaAla           | AlaSer<br>AlaAla                     | AlaThr<br>AlaAla                     | AlaAla<br>○ | AlaAsn<br>AlaAla | AlaTyr<br>AlaAla   |
| Gln |                  | ○                | X                          | MetMet                               | SerGln<br>SerSer                     | ThrGln<br>ThrThr | ○        | X                  | X                  |
| Glu |                  |                  |                            |                                      |                                      |            |                  |                    |
| Gly | GlyPhe<br>○      | GlyGly           | GlyMet<br>GlyGly           | GlySer<br>GlyGly<br>SerGly<br>SerSer | GlyThr<br>GlyGly<br>ThrGly<br>ThrThr | GlyGly<br>○ | GlyGly           | GlyTyr<br>GlyGly   |
| Val |                  |                  | X                          |                                      |                                      |            |                  |                    |
| Leu |                  |                  | MetMet                     |                                      | ThrLeu                               |            |                  |                    |
| Ile |                  |                  | MetMet                     |                                      |                                      |            |                  |                    |
| Pro |                  |                  | MetMet                     | SerSer                               | ThrThr                               |            |                  |                    |
| Phe |                  |                  | MetPhe<br>MetMet           | SerPhe                               | ThrPhe<br>ThrThr                     |            |                  |                    |
| Trp |                  |                  |                            |                                      |                                      |            |                  |                    |
| Met |                  |                  | MetMet                     | SerMet                               | ThrMet<br>ThrThr                     | MetMet<br>○ |                  | MetTyr<br>MetMet   |
| Ser |                  |                  |                            | SerSer                               | SerThr<br>SerSer<br>ThrSer<br>ThrThr |            |                  | SerTyr<br>SerSer   |
| Thr |                  |                  |                            |                                      | ThrThr                               |            |                  |                    |
| Cys |                  |                  |                            |                                      |                                      |            |                  |                    |
| Asn |                  |                  |                            |                                      |                                      |            |                  |                    |
| Tyr |                  |                  |                            |                                      |                                      |            |                  |                    |
| Lys |                  |                  |                            |                                      |                                      |            |                  |                    |
| Arg |                  |                  |                            |                                      |                                      |            |                  |                    |
| His |                  |                  |                            |                                      |                                      |            |                  |                    |
| Asp |                  |                  |                            |                                      |                                      |            |                  |                    |
| α-AB |                 |                  |                            |                                      |                                      |            |                  |                    |
| β-Ala |                |                  |                            |                                      |                                      |            |                  |                    |
| Cit |                  |                  |                            |                                      |                                      |            |                  |                    |

|       | Lys              | Arg              | His              | Asp              | α-AB             | β-Ala  | Cit         | Aza-serine  | Thea-nine   |
|-------|------------------|------------------|------------------|------------------|------------------|--------|-------------|-------------|-------------|
| Ala   | AlaAla<br>○      | AlaArg<br>AlaAla | AlaHis<br>AlaAla | AlaAla<br>○      | AlaAla           |        | AlaAla<br>○ | AlaAla<br>○ | AlaAla<br>○ |
| Gln   | X                | X                | X                | X                | ○                |        |             |             |             |
| Glu   |                  |                  |                  |                  |                  |        |             |             |             |
| Gly   | GlyGly<br>○      | GlyArg<br>GlyGly | GlyGly           | GlyGly           | GlyGly<br>○      |        | ○           |             |             |
| Val   |                  |                  |                  |                  |                  |        |             |             |             |
| Leu   |                  |                  |                  |                  |                  |        |             |             |             |
| Ile   |                  |                  |                  |                  |                  |        |             |             |             |
| Pro   |                  |                  |                  |                  |                  |        |             |             |             |
| Phe   |                  |                  | X                |                  | ○                |        |             |             |             |

TABLE 1-continued

| | | | | |
|---|---|---|---|---|
| Trp | | | | |
| Met | MetMet | MetHet | | ○ |
| Ser | | SerHis | SerSer ○ | |
| Thr | | | ThrThr ○ | |
| Cys | | | | |
| Asn | | | | |
| Tyr | | | | |
| Lys | | | | |
| Arg | | | ○ | |
| His | | | | β-AlaHis |
| Asp | | | | |
| α-AB | | | ○ | |
| β-Ala | | | | |
| Cit | | | ○ | |

The dipeptides formed by the reaction using, as substrates, two (or one) kinds of L-amino acids, Gly and β-Ala shown in the first row and the leftmost column of Table 1 are shown in the respective cells of the table. In the table, ○ means that a dipeptide was formed though its sequence was unidentified; X means that formation of a dipeptide was not confirmed; and a blank means that reaction was not carried out.

EXPERIMENTAL EXAMPLE 7

Production of a Dipeptide Using the Strain Expressing the His-Tagged Recombinant Enzyme

*Escherichia coli* NM522/pQE60ywfE obtained in Experimental Example 4 was inoculated into 8 ml of LB medium containing 50 µg/ml ampicillin in a test tube, and cultured at 28° C. for 17 hours. The resulting culture was inoculated into 50 ml of LB medium containing 50 µg/ml ampicillin in a 250-ml Erlenmeyer flask, and cultured at 30° C. for 3 hours. Then, IPTG was added to give a final concentration of 1 mmol/l, followed by further culturing at 30° C. for 4 hours. The resulting culture was centrifuged to obtain wet cells.

A reaction mixture (20 ml, pH 7.2) comprising 200 g/l wet cells, 50 g/l glucose, 5 g/l phytic acid (diluted to neutrality with 33% conc. sodium hydroxide solution), 15 g/l potassium dihydrogenphosphate, 5 g/l magnesium sulfate heptahydrate, 4 g/l Nymeen S-215, 10 ml/l xylene, 200 mmol/l L-Ala and 200 mmol/l L-Gln was put in a 50-ml beaker, and reaction was carried out at 32° C. at 900 rpm for 2 hours. During the reaction, the pH of the reaction mixture was maintained at 7.2 by using 2 mol/l potassium hydroxide.

The reaction product was analyzed by the same method as in Experimental Example 3, whereby it was confirmed that 25 mg/l L-Ala-L-Gln was accumulated.

EXPERIMENTAL EXAMPLE 8

Cloning of Genes Corresponding to the ywfE Gene from Various Microorganisms of the Genus *Bacillus* and Analysis Thereof On the basis of the nucleotide sequence shown in SEQ ID NO: 14, genes corresponding to the ywfE gene which exist in *Bacillus subtilis* ATCC 15245, ATCC 6633, IAM 1213; IAM 1107, IAM 1214, ATCC 9466, IAM 1033 and ATCC 21555, *Bacillus amyloliquefaciens* IFO 3022 and *Bacillus pumilus* NRRL B-12025 were obtained in the following manner.

That is, *Bacillus subtilis* ATCC 15245, ATCC 6633, IAM 1213, IAM 1107, IAM 1214, ATCC 9466, IAM 1033 and ATCC 21555, *Bacillus amyloliquefaciens* IFO 3022 and *Bacillus pumilus* NRRL B-12025 were respectively inoculated into LB medium and subjected to static culture overnight at 30° C. After the culturing, the chromosomal DNAs of the respective microorganisms were isolated and purified according to the method using saturated phenol described in Current Protocols in Molecular Biology.

By using a DNA synthesizer (Model 8905, PerSeptive Biosystems, Inc.), DNAs having the nucleotide sequences shown in SEQ ID NOS: 35 and 36 (hereinafter referred to as primer G and primer H, respectively) were synthesized. Primer G has a sequence containing a region upstream of the initiation codon of ywfE on the chromosomal DNA of *Bacillus subtilis* 168, and primer H has a sequence complementary to a sequence containing a region downstream of the termination codon of ywfE.

PCR was carried out using each of the chromosomal DNAs of *Bacillus subtilis* ATCC 15245, ATCC 6633, IAM 1213, IAM 1107, IAM 1214, ATCC 9466, IAM 1033 and ATCC 21555 and *Bacillus amyloliquefaciens* IFO 3022 as a template and the above primer G and primer H as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

One-tenth of each of the resulting reaction mixtures was subjected to agarose gel electrophoresis to confirm that a ca. 1.6 kb fragment corresponding to the ywfE fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

Each of the thus obtained 1.4 kb DNA fragments derived from the chromosomal DNAs of the respective strains and pCR-blunt (Invitrogen Corp.) were subjected to ligation reaction using a ligation kit at 16° C. for 16 hours.

*Escherichia coli* NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following plasmids containing a gene corresponding to the ywfE gene were obtained: pYWFE1 (derived from ATCC 15245, DNA having the nucleotide sequence shown in SEQ ID NO: 46), pYWFE2 (derived from ATCC 6633, DNA having the nucleotide sequence shown in SEQ ID NO: 15), pYWFE3 (derived from IAM 1213, DNA having the nucleotide sequence shown in SEQ ID NO: 16), pYWFE4 (derived from IAM 1107, DNA having the nucleotide sequence shown in SEQ ID NO: 17), pYWFE5 (derived from IAM 1214, DNA having the nucleotide sequence shown in SEQ ID NO: 18), pYWFE6 (derived from ATCC 9466, DNA having the nucleotide sequence shown in SEQ ID NO: 14), pYWFE7 (derived from IAM 1033, DNA having the nucleotide sequence shown in SEQ ID NO: 46), pYWFE8 (derived from ATCC 21555, DNA having the nucleotide sequence shown in SEQ ID NO: 19) and pYWFE9 (derived from IFO 3022, DNA having the nucleotide sequence shown in SEQ ID NO: 20).

On the other hand, a gene corresponding to ywfE derived from *Bacillus pumilus* NRRL B-12025 (DNA having the nucleotide sequence shown in SEQ ID NO: 21) was obtained in the following manner.

PCR was carried out using the chromosomal DNA of the NRRL B-12025 strain prepared above as a template and DNAs respectively consisting of the nucleotide sequences shown in SEQ ID NOS: 37 and 38 as a set of primers. That is, PCR was carried out by 30 cycles, one cycle consisting of reaction at 98° C. for 5 seconds, reaction at 55° C. for 30 seconds and reaction at 72° C. for one minute, using 50 µl of a reaction mixture comprising 0.1 µg of the chromosomal DNA, 0.5 µmol/l each of the primers, 2.5 units of Z-taq polymerase (Takara Bio Inc.), 5 µl of buffer for Z-taq polymerase (10×) (Takara Bio Inc.) and 200 µmol/l each of dNTPs.

One-tenth of the resulting reaction mixture was subjected to agarose gel electrophoresis to confirm that a ca. 0.8 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes.

The resulting solution was centrifuged, and the obtained DNA precipitate was dissolved in 20 µl of TE.

The thus obtained 0.8 kb fragment derived from the chromosomal DNA and pGEM T-easy (Promega Corp.) were subjected to ligation reaction using a ligation kit at 16° C. for 16 hours.

*Escherichia coli* DH5α was transformed using the reaction mixture according to the method using calcium ion, spread on LB agar medium containing 50 µg/ml ampicillin, and cultured overnight at 30° C.

A plasmid was extracted from the transformant obtained above and the nucleotide sequence of the ca. 0.8 kb DNA insert was determined, whereby a sequence from nucleotides 358 to 1160 in the nucleotide sequence shown in SEQ ID NO: 21 was confirmed.

The above plasmid was cleaved with EcoRI and then subjected to agarose gel electrophoresis to separate a DNA fragment. The DNA fragment was purified using GENECLEAN II Kit, and about 0.5 µg of the purified DNA fragment was DIG-labeled using DIG-High Prime DNA Labeling & Detection Starter Kit I (Roche Diagnostics Corp.) according to the instructions attached thereto.

Southern analysis of the chromosomal DNA of the NRRL B-12025 strain was carried out using the DIG-labeled DNA obtained above.

The chromosomal DNA of the NRRL B-12025 strain was completely digested with BamHI, EcoRI, HindIII, KpnI, PstI, SacI, SalI and SphI, respectively, and subjected to agarose gel electrophoresis to separate DNA fragments, followed by transfer to nylon membrane plus charge (Roche Diagnostics Corp.) according to an ordinary method.

After the DNA fragments were fixed on the nylon membrane by UV irradiation, Southern hybridization was carried out using the above probe DNA and the nylon membrane.

The hybridization was carried out by contacting the nylon membrane with the probe DNA at 65° C. for 16 hours, washing the nylon membrane twice with a solution consisting of 0.1% SDS and 2×SSC at room temperature for 5 minutes, and further washing the membrane twice with a solution consisting of 0.1% SDS and 0.5×SSC at 65° C. for 15 minutes. The other operations and conditions and detection of the hybridized DNA were carried out according to the instructions attached to the above-mentioned DIG-High Prime DNA Labeling & Detection Starter Kit I.

As a result, color development was observed at around 3.5 kbp of the fragments completely digested with HindIII and PstI.

Subsequently, the chromosomal DNA of the NRRL B-12025 strain was completely digested with HindIII and PstI, respectively, and subjected to agarose gel electrophoresis to separate DNA fragments. From the respective restriction enzyme-digested DNAs, 3-4 kbp fragments were purified using GENECLEAN II Kit, followed by autocyclization using a ligation kit.

On the basis of the nucleotide sequence of the 0.8 kb DNA fragment determined above, the nucleotide sequences shown in SEQ ID NOS: 39 and 40 were designed and synthesized, and they were used in PCR using the cyclized DNA obtained above as a template. PCR was carried out by 30 cycles, one cycle consisting of reaction at 98° C. for 5 seconds, reaction at 55° C. for 30 seconds and reaction at 72° C. for 3 minutes and 30 seconds, using 50 µl of a reaction mixture comprising 10 ng of the cyclized DNA, 0.5 µmol/l each of the primers, 2.5 units of pyrobest polymerase (Takara Bio Inc.), 5 µl of buffer for pyrobest polymerase (10×) (Takara Bio Inc.) and 200 µmol/l each of dNTPs.

One-tenth of the resulting reaction mixture was subjected to agarose gel electrophoresis to confirm that a ca. 3.0 kb fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

The thus obtained DNA fragment and Zero Blunt PCR Cloning Kit (Invitrogen Corp.) were subjected to ligation reaction using a ligation kit.

Escherichia coli NM522 was transformed using the reaction mixture according to the method using calcium ion, spread on LB agar medium containing 50 µg/ml ampicillin, and cultured overnight at 30° C.

A plasmid was extracted from a colony of the transformant that grew on the medium according to a known method and the structure of the plasmid was analyzed using restriction enzymes. As a result, it was confirmed that plasmid pYWFE10 (derived from NRRL B-12025, DNA having the nucleotide sequence shown in SEQ ID NO: 21) containing a gene corresponding to the ywfE gene was obtained.

The nucleotide sequences of the genes corresponding to the ywfE gene which are respectively contained in the plasmids pYWFE1 to pYWFE10 obtained above were determined using 373A DNA Sequencer.

The amino acid sequences of the proteins encoded by the genes respectively contained in pYWFE1, pYWFE6 and pYWFE7 were identical with the amino acid sequence of the protein encoded by the ywfE gene, whereas those of the proteins encoded by the genes respectively contained in pYWFE2, pYWFE3, pYWFE4, pYWFE5, pYWFE8, pYWFE9 and pYWFE10 were different from the amino acid sequence of the protein encoded by the ywfE gene.

The amino acid sequences of the proteins encoded by the genes corresponding to the ywfE gene which are contained in pYWFE2, pYWFE3, pYWFE4, pYWFE5, pYWFE8, pYWFE9 and pYWFE10, and pYWFE1 and pYWFE7 are shown in SEQ ID NOS: 2 to 8 and 1, respectively, and the nucleotide sequences of these genes are shown in SEQ ID NOS: 14 to 21 and 46, respectively.

EXPERIMENTAL EXAMPLE 9

Purification of C-Terminal His-Tagged Recombinant Dipeptide Synthetase

PCR was carried out using each of the chromosomal DNAs of Bacillus subtilis ATCC 15245, ATCC 6633, IAM 1213, IAM 1107, IAM 1214, ATCC 9466, IAM 1033 and ATCC 21555 and Bacillus amyloliquefaciens IFO 3022 as a template and primer A and primer B described in Experimental Example 2 as a set of primers. That is, PCR was carried out by 30 cycles, one cycle consisting of reaction at 94° C. for one minute, reaction at 55° C. for 2 minutes and reaction at 72° C. for 3 minutes, using 40 µl of a reaction mixture comprising 0.1 µg of the chromosomal DNA, 0.5 µmol/l each of the primers, 2.5 units of Pfu DNA polymerase, 4 µl of buffer for Pfu DNA polymerase (10×) and 200 µmol/l each of dNTPs.

When the chromosomal DNA of Bacillus pumilus NRRL B-12025 was used as a template, PCR was carried out using DNAs respectively having the nucleotide sequences shown in SEQ ID NOS: 41 and 42 as a set of primers under the same conditions as above.

One-tenth of each of the resulting reaction mixtures was subjected to agarose gel electrophoresis to confirm that a ca. 1.4 kb DNA fragment corresponding to the ywfE fragment was amplified. Then, the remaining reaction mixture was mixed with an equal amount of phenol/chloroform saturated with TE. The resulting mixture was centrifuged, and the obtained upper layer was mixed with a two-fold volume of cold ethanol and allowed to stand at −80° C. for 30 minutes. The resulting solution was centrifuged, and the obtained DNA precipitate was dissolved in 20 µl of TE.

Each of the thus obtained solutions (5 µl) was subjected to reaction to cleave the amplified DNA with restriction enzymes NcoI and BamHI. DNA fragments were separated by agarose gel electrophoresis, and a 1.4 kb DNA fragment containing a gene corresponding to the ywfE gene was recovered using GENECLEAN II Kit.

Subsequently, 0.2 µg of the C-terminal His-tagged recombinant expression vector pQE60 was cleaved with restriction enzymes NcoI and BamHI. DNA fragments were separated by agarose gel electrophoresis, and a 3.4 kb DNA fragment was recovered in the same manner as above.

Each of the 1.4 kb DNA fragments containing a gene corresponding to the ywfE gene of Bacillus subtilis 168 and the 3.4 kb DNA fragment obtained above were subjected to ligation reaction using a ligation kit at 16° C. Fog 16 hours. Escherichia coli NM522 was transformed using each ligation reaction mixture according to the method using calcium ion, spread on LB agar medium containing 50 µg/ml ampicillin, and cultured overnight at 30° C.

A plasmid was extracted from a colony of each transformant that grew on the medium according to a known method and the structure of each plasmid was analyzed using restriction enzymes. As a result, it was confirmed that the following C-terminal His-tagged gene expression vectors were obtained: pQE60ywfE1 (a vector containing the gene derived from ATCC 15245), pQE60ywfE2 (a vector containing the gene derived from ATCC 6633), pQE60ywfE3 (a vector containing the gene derived from IAM 1213), pQE60ywfE4 (a vector containing the gene derived from IAM 1107), pQE60ywfE5 (a vector containing the gene derived from IAM 1214), pQE60ywfE6 (a vector containing the gene derived from ATCC 9466), pQE60ywfE7 (a vector containing the gene derived from IAM 1033), pQE60ywfE8 (a vector containing the gene derived from ATCC 21555), pQE60ywfE9 (a vector containing the gene derived from IFO 3022) and pQE60ywfE10 (a vector containing the gene derived from NRRL B-12025).

Escherichia coli NM522/pQE60ywfE1 to NM522/pQE60ywfE10 strains obtained above were respectively inoculated into 8 ml of LB medium containing 50 µg/ml ampicillin in a test tube, and cultured at 28° C. Fog 17 hours. Each of the resulting cultures was inoculated into 50 ml of LB medium containing 50 µg/ml ampicillin in a 250-ml Erlenmeyer flask, and cultured at 30° C. Fog 3 hours. Then, IPTG was added to give a final concentration of 1 mmol/l, followed by further culturing at 30° C. Fog 4 hours. The resulting culture was centrifuged to obtain wet cells, and His-tagged recombinant enzymes were purified from the respective wet cells using HisTrap according to the instructions attached thereto.

EXPERIMENTAL EXAMPLE 10

Production of Dipeptides Using Purified Enzymes

Reaction mixtures (0.1 ml each) comprising 0.04 mg of the respective recombinant enzymes obtained in Experimental Example 9, 100 mmol/l Tris-HCl (pH-8.0), 60 mmol/l magnesium chloride, 60 mmol/l ATP, 30 mmol/l L-Ala and 30 mmol/l L-Gln were prepared, and reactions were carried out at 37° C. Fog 16 hours.

After the completion of reactions, the reaction mixtures were analyzed by the method described in Experimental Example 3, whereby it was confirmed that 3.0 to 3.5 g/l L-Ala-L-Gln and 0.25 to 0.3 g/l L-Ala-L-Ala were formed and accumulated.

When ATP was excluded from the compositions of the above reaction mixtures, L-Ala-L-Gln or L-Ala-L-Ala was not formed at all.

The above results revealed that all of the products of the genes obtained in Experimental Example 8 have the activity to produce L-Ala-L-Gln and L-Ala-L-Ala from L-Ala and L-Gln in the presence of ATP.

EXPERIMENTAL EXAMPLE 11

Acquisition of the albC Gene and Its Analogous Gene

The albC gene and its analogous gene were obtained from *Streptomyces noursei* and *Streptomyces albulus* based on the nucleotide sequence of the albC gene of *Streptomyces noursei* [Chemistry & Biol., 9, 1355 (2002)] in the following manner.

*Streptomyces noursei* IFO15452 and *Streptomyces albulus* IFO14147 were inoculated into KM73 medium [2 g/l yeast extract (Difco) and 10 g/l soluble starch (Wako Pure Chemical Industries, Ltd.)] containing 1% glycine and KP medium [15 g/l glucose, 10 g/l glycerol, 10 g/l polypeptone (Nihon Pharmaceutical Co., Ltd.), 10 g/l meat extract (Kyokuto Pharmaceutical Industrial Co., Ltd.) and 4 g/l calcium carbonate)], respectively, and subjected to shaking culture overnight at 28° C. *Streptomyces noursei* IFO15452 and *Streptomyces albulus* IFO14147 were distributed by National Institute of Technology and Evaluation (NITE) Biological Resource Center (BRC) (2-5-8, Kazusakamatari, Kisarazu-shi, Chiba 292-0818 Japan).

After the culturing, the chromosomal DNAs of the respective microorganisms were isolated and purified according to the method described in Genetic Manipulation of *Streptomyces*: a Laboratory Manual: John Innes Foundation.

On the basis of the nucleotide sequence of the albC gene, DNAs having the nucleotide sequences shown in SEQ ID NOS: 51 and 52 (hereinafter referred to as primer J and primer K, respectively) were synthesized by using a DNA synthesizer (Model 8905, PerSeptive Biosystems, Inc.). Primer J has a sequence wherein a sequence containing the NcoI recognition sequence is added to the 5' end of a region containing the initiation codon of the albC gene on the chromosomal DNA of *Streptomyces noursei*. Primer K has a sequence wherein a sequence containing the BglII recognition sequence is added to the 5' end of a sequence complementary to a sequence containing the termination codon of the albC gene.

PCR was carried out using each of the chromosomal DNAs of *Streptomyces noursei* and *Streptomyces albulus* as a template and the above primer J and primer K as a set of primers. That is, PCR was carried out by 30 cycles, one cycle consisting of reaction at 94° C. Fog one minute, reaction at 55° C. Fog 30 seconds and reaction at 72° C. Fog one minute, using 50 μl of a reaction mixture comprising 0.1 μg of the chromosomal DNA as a template, 0.5 μmol/l each of the primers, 2.5 units of Ex Taq DNA polymerase (Takara Bio Inc.), 5 μl of buffer for Ex Taq DNA polymerase (10×) (Takara Bio Inc.), 200 μmol/l each of dNTPs and 5 μl of dimethyl sulfoxide.

One-tenth of each of the resulting reaction mixtures was subjected to agarose gel electrophoresis to confirm that a ca. 0.7 kb DNA fragment was amplified. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. Fog 30 minutes. The resulting solution was centrifuged to precipitate DNA, and the obtained DNA was dissolved in 20 μl of TE.

Each of the thus obtained solutions (5 μl) was subjected to reaction to cleave the amplified DNA with restriction enzymes NcoI and BglII. DNA fragments were separated by agarose gel electrophoresis, and a 700 bp DNA fragment was recovered using GENECLEAN II Kit.

Subsequently, 0.2 μg of the expression vector pQE60 containing phage T5 promoter was cleaved with restriction enzymes NcoI and BglII. DNA fragments were separated by agarose gel electrophoresis, and a 3.4 kb DNA fragment was recovered in the same manner as above.

Each of the actinomycetes-derived 0.7 kb DNA fragments and the pQE60-derived 3.4 kb DNA fragment obtained above were subjected to ligation reaction using a ligation kit at 16° C. Fog 16 hours.

*Escherichia coli* NM522 was transformed using each ligation reaction mixture according to the method using calcium ion, spread on LB agar medium containing 50 μg/ml ampicillin, and cultured overnight at 30° C.

Figure 3:
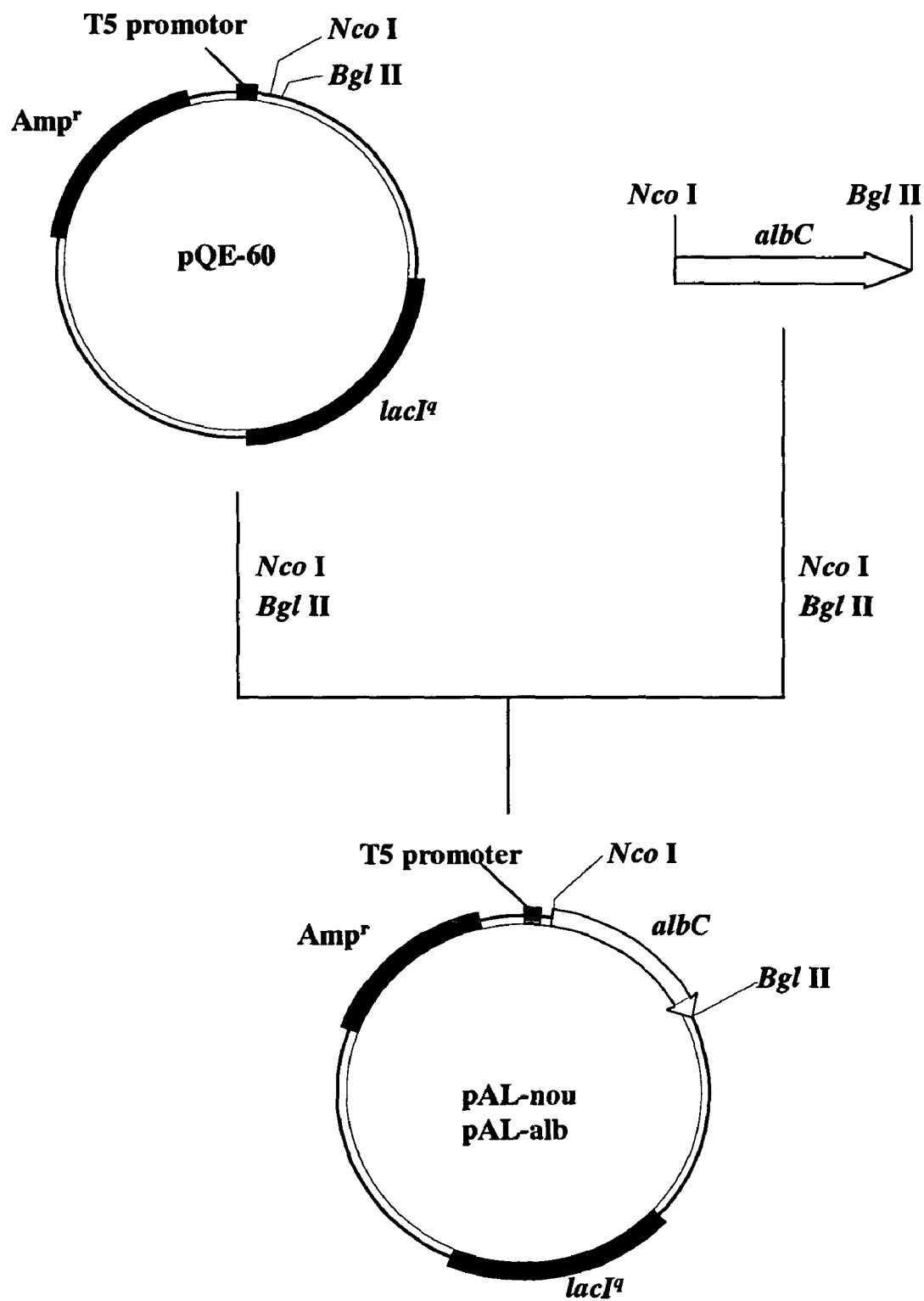
FIG. 3 shows the steps for constructing pAL-nou and, pAL-alb, which are plasmid vectors for the expression of proteins having the activity to synthesize a straight-chain dipeptide.

A plasmid was extracted from a colony of each transformant that grew on the medium according to a known method, and the structure of each plasmid was analyzed using restriction enzymes. As a result, it was confirmed that expression vector pAL-nou containing the DNA derived from *Streptomyces noursei* in a downstream position of the phage T5 promoter and expression vector pAL-alb containing the DNA derived from *Streptomyces albulus* were obtained (FIG. 3).

The nucleotide sequence of each actinomycete-derived DNA inserted into the resective plasmid was determined by using a nucleotide sequencer (373A DNA Sequencer), whereby it was confirmed that pAL-alb contained DNA encoding a protein having the amino acid sequence shown in SEQ ID NO: 47, i.e. DNA having the nucleotide sequence shown in SEQ ID NO: 49, and pAL-nou contained DNA encoding a protein having the amino acid sequence shown in SEQ ID NO: 48, i.e. DNA having the nucleotide sequence shown in SEQ ID NO: 50.

EXPERIMENTAL EXAMPLE 12

Production of Straight-Chain Dipeptides by the Use of Cells as an Enzyme Source

*Escherichia coli* NM522 carrying pAL-nou or pAL-alb obtained in Experimental Example 11 (*Escherichia coli* NM522/pAL-nou or NM522/pAL-alb) and *Escherichia coli* NM522 without a plasmid were respectively inoculated into 10 ml of LB medium containing 50 μg/ml ampicillin in a test tube (no addition of ampicillin in the case of a strain carrying no plasmid, hereinafter the same shall apply), and cultured at 30° C. Fog 17 hours. Each of the resulting cultures (0.5 ml) was inoculated into 50 ml of LB medium in a 250-ml Erlenmeyer flask and subjected to shaking culture at 30° C. Fog one hour. Then, IPTG was added to give a final concentration of 1 mmol/l, followed by further culturing for 4 hours. The resulting culture was centrifuged to obtain wet cells.

A reaction mixture (3.0 ml) comprising 100 mg/ml (final concentration) wet cells, 60 mmol/l potassium phosphate buffer (pH 7.2), 10 mmol/l magnesium chloride, 10 mmol/l ATP, 1 g/l L-Leu and 1 g/l L-Phe was prepared, and reaction was carried out at 30° C. One hour after the start of the reaction, the reaction mixture was sampled and acetonitrile was added thereto to a concentration of 20% (v/v). Then, the obtained reaction product was analyzed by HPLC. The HPLC analysis was carried out by using ODS-HA column (YMC Co., Ltd.) as a separation column and 30% (v/v) acetonitrile as an eluent at a flow rate of 0.6 ml/min, and by measuring ultraviolet absorption at 215 nm.

As a result, it was confirmed that 36.7 mg/l cyclo(L-leucyl-L-phenylalanine) [cyclo(L-Leu-L-Phe)] was accumulated in the reaction mixture of *Escherichia coli* NM522/pAL-nou. However, no cyclo(L-Leu-L-Phe) was detected in the reaction mixture of *Escherichia coli* NM522. The same reaction mixtures were analyzed by HPLC under the following conditions to measure straight-chain dipeptides L-leucyl-L-phenylalanine (L-Leu-L-Phe) and L-phenylalanyl-L-leucine (L-Phe-L-Leu).

Both the straight-chain dipeptides were derivatized by the F-moc method and then analyzed by HPLC. The HPLC analysis was carried out by using ODS-HG5 (Nomura Kagaku Co., Ltd.) as a separation column and solution A (6 ml/l acetic acid and 20% (v/v) acetonitrile, pH adjusted to 4.8 with triethylamine) and solution B (6 ml/l acetic acid and 70% (v/v) acetonitrile, pH adjusted to 4.8 with triethylamine) as eluents at a flow rate of 0.6 ml/min, and by detecting the dipeptides at an excitation wavelength of 254 nm and a fluorescence wavelength of 630 nm. The ratio of solution A to solution B was 8:2 during the first 5 minutes of elution and thereafter changed with a linear gradient so that the ratio became 1:1 at 20 minutes after the start of elution.

As a result, it was confirmed that 21.9 mg/l L-Leu-L-Phe and 12.0 mg/l L-Phe-L-Leu were accumulated in the reaction mixture of *Escherichia coli* NM522/pAL-nou and no straight-chain dipeptide was detected in the reaction mixture of *Escherichia coli* NM522 used as a control strain.

The above result revealed that the cyclodipeptide-synthesizing enzyme obtained in Experimental Example 11 has the ability to synthesize straight-chain dipeptides.

EXPERIMENTAL EXAMPLE 13

Production of Straight-Chain Dipeptides Using the Purified Enzyme (1)

*Escherichia coli* NM522/pAL-nou was cultured in the same manner as in Experimental Example 12. After the completion of the culturing, centrifugation was carried out to obtain wet cells. The obtained wet cells were washed with a 60 mmol/l potassium phosphate buffer (pH 7.2) and suspended in a 20 mmol/l potassium phosphate buffer containing 10 mmol/l imidazole. The resulting suspension was subjected to ultrasonication at 4° C. to obtain a disrupted cell suspension. The obtained suspension (10 ml: containing 0.863 mg of protein) was passed through a His-tag purification column (Amersham Biosciences K.K.) and then 15 ml of a 20 mmol/l potassium phosphate buffer containing 10 mmol/l imidazole was passed through the column for washing to purify a His-tagged albC protein in the column. Then, 2 ml of a reaction mixture having the same composition as that in Example 2 [composition: 60 mmol/l potassium phosphate buffer (pH 7.2), 10 mmol/l magnesium chloride, 10 mmol/l ATP, 1 g/l L-Leu, 1 g/l L-Phe] was put into the column containing the His-tagged albC protein, followed by incubation at 30° C., during which the substrates were held in the column. After 24 hours, the reaction mixture in the column was eluted with 3 ml of a reaction mixture having the same composition, and the cyclodipeptide and straight-chain dipeptides in the reaction mixture were determined in the same manner as in Experimental Example 12.

As a result, it was confirmed that 6.8 mg/l cyclo(L-Leu-L-Phe), 28.7 mg/l L-Leu-L-Phe and 18.5 mg/l L-Phe-L-Leu were formed. No cyclopeptide or straight-chain peptide was detected in the reaction mixture without ATP incubated in the same manner.

EXPERIMENTAL EXAMPLE 14

Production of Straight-Chain Dipeptides Using the Purified Enzyme (2)

Enzymatic reaction was carried out in the same manner as in Experimental Example 13 except that the amino acids as substrates were replaced by another amino acid and the obtained product was analyzed. As the reaction mixture, a mixture having the same composition as that of Experimental Example 13 except that the amino acids as the substrates were replaced by 1 g/l L-Ala, L-Leu or L-Phe was used.

As a result, it was revealed that 9.41 mg/l L-Ala-L-Ala, 7.85 mg/l L-Leu-L-Leu and 5.20 mg/l L-Phe-L-Phe were respectively formed in 24 hours after the start of the reaction.

EXPERIMENTAL EXAMPLE 15

Construction of *Escherichia coli* for Enhanced Expression of the ywfE Gene

By using a DNA synthesizer (Model 8905, PerSeptive Biosystems, Inc.), DNAs having the sequences shown in SEQ ID NOS: 94 to 97 (hereinafter referred to as primer L, primer M, primer N and primer O, respectively) were synthesized. The sequence of SEQ ID NO: 94 is a sequence wherein a sequence containing the XhoI recognition sequence is added to the 5' end of a region containing the Shine-Dalgarno sequence (ribosome binding sequence) of the ywfE gene on the plasmid pQE60ywfE. The sequence of SEQ ID NO: 95 is a sequence wherein a sequence containing the BamHI recognition sequence is added to the 5' end of a sequence complementary to a sequence containing the termination codon of the ywfE gene. The sequence of SEQ ID NO: 96 is a sequence wherein a sequence containing the EcoRI recognition sequence is added to the 5' end of the sequence of trp promoter region of expression vector pTrS30 containing trp promoter. The sequence of SEQ ID NO: 97 is a sequence wherein a sequence containing the XhoI recognition sequence is added to the 5' end of a sequence complementary to the sequence of trp promoter region of expression vector pTrS30 containing trp promoter.

A ywfE gene fragment and a trp promoter region fragment were amplified by PCR using the above primers L and M and primers N and O as a set of primers, respectively, and the plasmid pQE60ywfE as a template. PCR was carried out by 30 cycles, one cycle consisting of reaction at 94° C. Fog one minute, reaction at 55° C. Fog 2 minutes and reaction at 72° C. Fog 3 minutes, using 40 µl of a reaction mixture comprising 10 ng of pQE60ywfE, 0.5 µmol/l each of the primers, 2.5 units of Pfu DNA polymerase, 4 µl of buffer for Pfu DNA polymerase (10×) and 200 µmol/l each of dNTPs.

One-tenth of each of the resulting reaction mixtures was subjected to agarose gel electrophoresis to confirm that a ca. 1.4 kb fragment corresponding to the ywfE gene fragment and a ca. 0.3 kb fragment corresponding to the trp promoter region fragment were respectively amplified in the PCR using primer L and primer M and the PCR using primer N and primer O. Then, the remaining reaction mixture was mixed with an equal amount of phenol/chloroform saturated with TE. The resulting solution was centrifuged, and the obtained upper layer was mixed with a two-fold volume of cold ethanol and allowed to stand at −80° C. Fog 30 minutes. The resulting solution was centrifuged, and the obtained DNA was dissolved in 20 µl of TE.

The thus obtained DNA solutions (5 µl each) were respectively subjected to reaction to cleave the DNA amplified using primer L and primer M with restriction enzymes XhoI and BamHI and to reaction to cleave the DNA amplified using primer N and primer O with restriction enzymes EcoRI and XhoI. DNA fragments were separated by agarose gel electrophoresis, and a 1.4 kb fragment containing the ywfE gene and a 0.3 kb fragment containing trp promoter region were respectively recovered using GENECLEAN II Kit.

pTrs30 (a trp promoter-containing expression vector, 0.2 µg) was cleaved with restriction enzymes EcoRI and BamHI. DNA fragments were separated by agarose gel electrophoresis and a 4.5 kb DNA fragment was recovered in the same manner as above.

The 1.4 kb fragment containing the ywfE gene, the 0.3 kb fragment containing trp promoter region and the 4.5 kb DNA fragment obtained above were subjected to ligation reaction using a ligation kit at 16° C. Fog 16 hours.

*Escherichia coli* NM522 was transformed using the reaction mixture according to the method using calcium ion, spread on LB agar medium containing 50 µg/ml ampicillin, and cultured overnight at 30° C.

Figure 4:
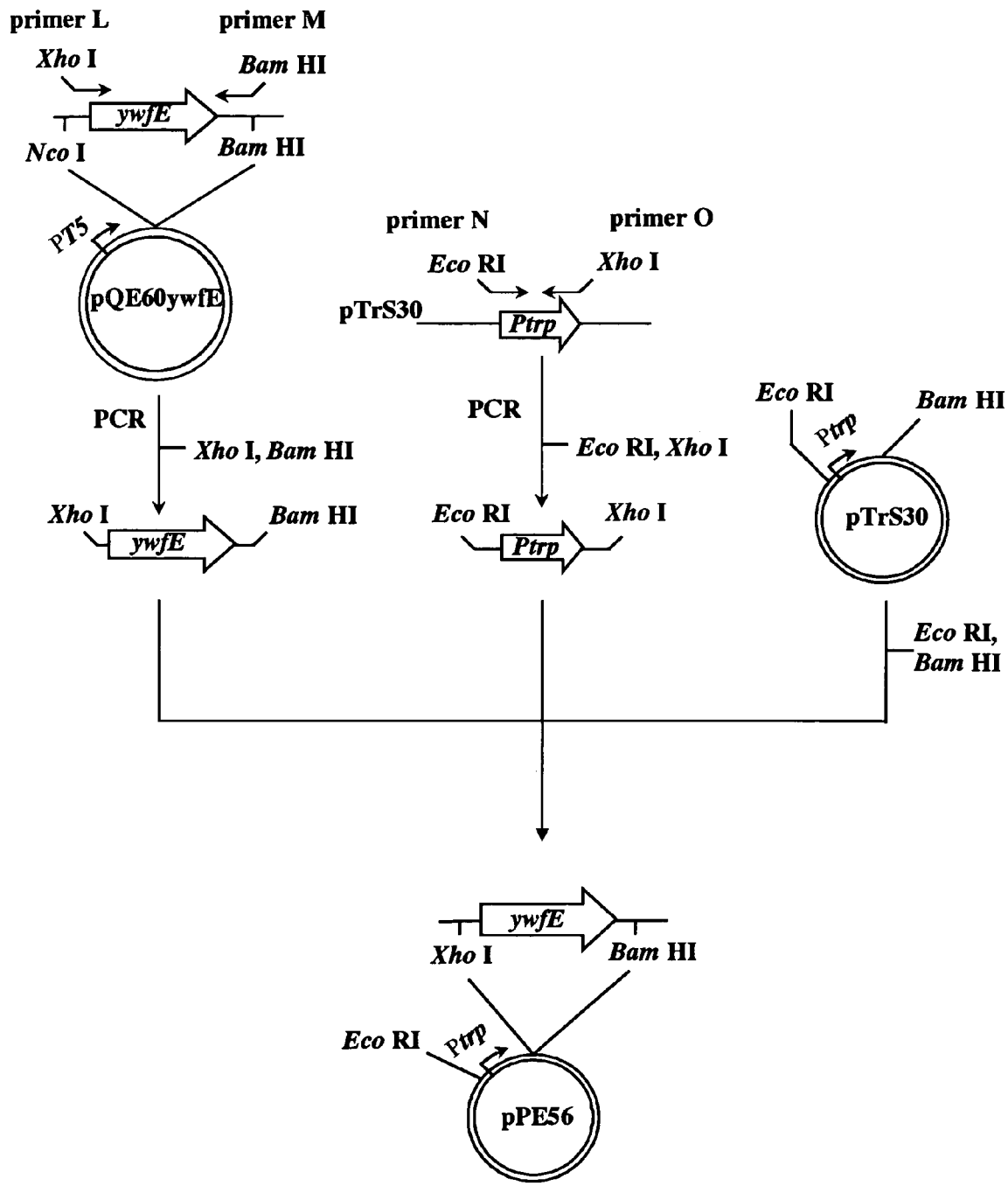
FIG. 4 shows the steps for constructing ywfE gene expression-enhanced vector pPE56.

A plasmid was extracted from a colony of the transformant that grew on the medium according to a known method, whereby expression vector pPE56 containing the ywfE gene in a downstream position of the trp promoter was obtained. The structure of the vector was confirmed by digestion with restriction enzymes (FIG. 4).

EXPERIMENTAL EXAMPLE 16

Preparation of Strains Having Deletions of the pepD, pepN, pepB and pepA Genes and the dpp Operon Strains in which specific genes on *Escherichia coli* chromosomal DNA are deleted were prepared according to the method utilizing the homologous recombination system of lambda phage [Proc. Natl. Acad. Sci. USA, 97, 6641-6645 (2000)].

Plasmids pKD46, pKD3 and pCP20 used below were prepared by extraction, according to a known method, from *Escherichia coli* strains carrying them which were obtained from *Escherichia coli* Genetic Stock Center, Yale University, U.S.A.

(1) Cloning of DNA Fragments for Gene Deletion

For the purpose of deleting the following genes existing on the chromosomal DNA of *Escherichia coli* K12, DNAs having nucleotide sequences homologous to 36-bp nucleotide sequences that lie upstream and downstream of the respective genes to be deleted on the chromosomal DNA of *Escherichia coli* K12 and the nucleotide sequence shown in SEQ ID NO: 64 which is recognized by yeast-derived Flp recombinase were synthesized using a DNA synthesizer (Model 8905, PerSeptive Biosystems, Inc.). The genes to be deleted are the pepD gene having the nucleotide sequence shown in SEQ ID NO: 65, the pepN gene having the nucleotide sequence shown in SEQ ID NO: 66, the pepB gene having the nucleotide sequence shown in SEQ ID NO: 67, the pepA gene having the nucleotide sequence shown in SEQ ID NO: 68, the dppA gene having the nucleotide sequence shown in SEQ ID NO: 69, the dppB gene having the nucleotide sequence shown in SEQ ID NO: 70, the dppC gene having the nucleotide sequence shown in SEQ ID NO: 71, the dppD gene having the nucleotide sequence shown in SEQ ID NO: 72 and the dppF gene having the nucleotide sequence shown in SEQ ID NO: 73. In the case of the dppA, dppB, dppC, dppD and dppF genes, which form an operon, DNAs having nucleotide sequences homologous to the nucleotide sequences that lie upstream and downstream of the operon were synthesized.

That is, DNAs consisting of the following nucleotide sequences were synthesized as respective sets of primers for amplification of DNA fragments for gene deletion: SEQ ID NOS: 74 and 75 for pepD gene deletion; SEQ ID NOS: 76 and 77 for pepN gene deletion; SEQ ID NOS: 78 and 79 for pepA gene deletion; SEQ ID NOS: 80 and 81 for pepB gene deletion; and SEQ ID NOS: 82 and 83 for dpp operon deletion.

Subsequently, PCR was carried out using each set of the above synthetic DNAs as a set of primers and pKD3 DNA as a template. That is, PCR was carried out by 30 cycles, one cycle consisting of reaction at 94° C. Fog one minute, reaction at 55° C. Fog 2 minutes and reaction at 72° C. Fog 3 minutes, using 40 µl of a reaction mixture comprising 10 ng of the plasmid DNA, 0.5 µmol/l each of the primers, 2.5 units of Pfu DNA polymerase, 4 µl of buffer for Pfu DNA polymerase (10×) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal amount of phenol/chloroform saturated with TE.

The resulting mixture was centrifuged, and the obtained upper layer was mixed with a two-fold volume of cold ethanol and allowed to stand at −80° C. Fog 30 minutes, followed by centrifugation. By this procedure, chloramphenicol resistance gene-containing DNA fragments for deletion of the pepD, pepN, pepB and pepA genes and the dpp operon were obtained.

(2) Preparation of *Escherichia coli* JM101 Having pepD Gene Deletion

*Escherichia coli* JM101 was transformed with pKD46, spread on LB agar medium containing 100 mg/l ampicillin, and cultured at 30° C. to select *Escherichia coli* JM101 carrying pKD46 (hereinafter referred to as *Escherichia coli* JM101/pKD46).

The plasmid pKD46 carries λ Red recombinase gene the expression of which can be induced by L-arabinose. Accordingly, when *Escherichia coli* carrying pKD46 grown in the presence of L-arabinose is transformed using a straight-chain DNA, homologous recombination occurs with high frequency. Further, as pKD46 has a thermosensitive replication origin, curing of the plasmid can be readily caused by culturing the strain at 42° C.

The chloramphenicol resistance gene-containing DNA fragment for pepD gene deletion obtained above was introduced into *Escherichia coli* JM101/pKD46 obtained by culturing in the presence of 10 mmol/l L-arabinose and 50 µg/ml ampicillin by electroporation. The resulting cells were spread on LB agar medium (10 g/l Bacto-tryptone, 5 g/l Bacto-yeast extract, 5 g/l sodium chloride and 15 g/l agar) containing 25 mg/l chloramphenicol and cultured at 30° C. to select a transformant in which the chloramphenicol resistance gene-containing DNA fragment for pepD gene deletion was integrated into the chromosomal DNA of *Escherichia coli* JM101 by homologous recombination.

The selected chloramphenicol-resistant strain was inoculated onto LB agar medium containing 25 mg/l chloramphenicol and cultured at 42° C. Fog 14 hours, followed by single colony isolation. Replicas of the obtained colonies were made on LB agar medium containing 25 mg/l chloramphenicol and LB agar medium containing 100 mg/l ampicillin, followed by culturing at 37° C. By selecting a colony showing chloramphenicol resistance and ampicillin sensitivity, a pKD46-cured strain was obtained.

The pKD46-cured strain thus obtained was transformed using pCP20, followed by selection on LB agar medium containing 100 mg/l ampicillin to obtain a pKD46-cured strain carrying pCP20.

The plasmid pCP20 carries yeast-derived Flp recombinase gene the expression of which can be induced at a temperature of 42° C.

The chloramphenicol resistance gene-containing DNA fragments for deletion of the pepD, pepN, pepB and pepA genes and the dpp operon prepared above contain nucleotide sequences recognized by Flp recombinase at both termini of the chloramphenicol resistance gene. Therefore, the resistance gene can be readily deleted by homologous recombination catalyzed by Flp recombinase.

Further, as pCP20 has a thermosensitive replication origin, expression of Flp recombinase and curing of pCP20 can be simultaneously induced by culturing the pCP20-carrying strain at 42° C.

The pCP20-carrying pKD46-cured strain obtained above was inoculated onto drug-free LB agar medium and cultured at 42° C. Fog 14 hours, followed by single colony isolation. Replicas of the obtained colonies were made on drug-free LB agar medium, LB agar medium containing 25 mg/l chloramphenicol and LB agar medium containing 100 mg/l ampicillin, followed by culturing at 30° C. Then, colonies showing chloramphenicol sensitivity and ampicillin sensitivity were selected.

Chromosomal DNAs were prepared from the respective strains selected above according to an ordinary method [Seibutsukogaku Jikkensho (Experiments in Biotechnology), edited by The Society for Biotechnology, Japan, p. 97-98, Baifukan (1992)]. PCR was carried out using, as a set of primers, DNAs having the nucleotide sequences shown in SEQ ID NOS: 84 and 85 which were designed based on an inner nucleotide sequence of the pepD gene to be deleted, and using each of the chromosomal DNAs as a template. That is, PCR was carried out by 30 cycles, one cycle consisting of reaction at 94° C. Fog one minute, reaction at 55° C. Fog 2 minutes and reaction at 72° C. Fog 3 minutes, using 40 μl of a reaction mixture comprising 0.1 μg of the chromosomal DNA, 0.5 μmol/l each of the primers, 2.5 units of Pfu DNA polymerase, 4 μl of buffer for Pfu DNA polymerase (10×) and 200 μmol/l each of deoxyNTPs.

A strain with which no amplified DNA fragment was detected in the above PCR was identified as a strain having pepD gene deletion and was designated as *Escherichia coli* JPD1.

(3) Preparation of a Strain in Which the pepD and pepN Genes on the Chromosomal DNA of *Escherichia coli* JM101 are Deleted

*Escherichia coli* JPD1 obtained in the above (2) was transformed with pKD46, spread on LB agar medium containing 100 mg/l ampicillin, and cultured at 30° C. to select *Escherichia coli* JPD1 carrying pKD46 (hereinafter referred to as *Escherichia coli* JPD1/pKD46). The chloramphenicol resistance gene-containing DNA fragment for pepN gene deletion was introduced into *Escherichia coli* JPD1/pKD46 by electroporation to obtain a transformant in which the chloramphenicol resistance gene-containing DNA fragment for pepN gene deletion was integrated into the chromosomal DNA of *Escherichia coli* JPD1/pKD46 by homologous recombination.

Subsequently, the same procedure as in the above (2) was carried out to obtain a strain in which the chloramphenicol resistance gene was deleted from the chromosomal DNA, which was designated as *Escherichia coli* JPDN2.

(4) Preparation of Strains in Which the pepN, pepA or pepB Gene or the dpp Operon on the Chromosomal DNA of *Escherichia coli* JM101 is Deleted and Strains Having Multiple Gene Deletion The strains having pepN, pepA or pepB gene or dpp operon deletion were prepared according to the same procedure as in the above (2) using the respective chloramphenicol resistance gene-containing DNA fragments for gene or operon deletion prepared in the above (1).

Acquisition of the strains having gene deletions by the above method was confirmed by carrying out PCR in the same manner as in the above (2) using, as sets of primers, DNAs having the nucleotide sequences shown in SEQ ID NOS: 86 to 93 which were designed and syntheseized based on inner nucleotide sequences of the respective genes to be deleted. That is, DNAs having the following nucleotide sequences were used as respective sets of primers for the confirmation of gene deletion: SEQ ID NOS: 86 and 87 for pepN deletion; SEQ ID NOS: 88 and 89 for pepA deletion; SEQ ID NOS: 90 and 91 for pepB deletion; and SEQ ID NOS: 92 and 93 for dpp operon deletion.

The thus obtained dpp operon-deleted strain, pepN gene-deleted strain, pepA gene-deleted strain and pepB gene-deleted strain were designated as *Escherichia coli* JDPP1, *Escherichia coli* JPN1, *Escherichia coli* JPA1 and *Escherichia coli* JPB7, respectively.

Further, strains having multiple gene deletions, i.e., deletions of two or more genes or operon selected from the group consisting of the pepD, pepN, pepA and pepB genes and the dpp operon were prepared according to the method of the above (3). Acquisition of the strains having multiple gene deletions was confirmed by PCR similar to that in the above (2). The thus obtained double gene-deleted strain having pepD gene and dpp operon deletions was designated as *Escherichia coli* JPDP49, triple gene-deleted strain having pepB, pepD and pepN gene deletions as *Escherichia coli* JPDNB43, triple gene-deleted strain having pepD and pepN gene and dpp operon deletions as *Escherichia coli* JPNDDP36, quadruple gene-deleted strain having pepA, pepD and pepN gene and dpp operon deletions as *Escherichia coli* JPNDAP5, and quadruple gene-deleted strain having pepB, pepD and pepN gene and dpp operon deletions as *Escherichia coli* JPNDBP7. The genes deleted in the gene-deleted strains are shown in Table 2.

TABLE 2

| Strain | Deleted gene |
| --- | --- |
| JM101 | none |
| JDPP1 | dpp operon |
| JPN1 | pepN |
| JPA1 | pepA |
| JPB7 | pepB |
| JPD1 | pepD |
| JPDN2 | pepD, pepN |
| JPDNB43 | pepB, pepD, pepN |
| JPDP49 | pepD, dpp operon |
| JPNDDP36 | pepD, pepN, dpp operon |
| JPNDAP5 | pepA, pepD, pepN, dpp operon |
| JPNDBP7 | pepB, pepD, pepN, dpp operon |

EXPERIMENTAL EXAMPLE 17

Evaluation of Productivity of L-Ala-L-Gln and L-Ala-L-Ala by *Escherichia coli* Strains in Which Peptidase and Dipeptide-Permeating/Transporting Protein Activities are Lost The strains having deletions of genes encoding various peptidases and dipeptide-permeating/transporting protein which were obtained in EXPERIMENTAL EXAMPLE 16 were transformed using the plasmid pPE56 constructed in Experimental Example 15 to obtain ampicillin-resistant transformants.

Each of the obtained transformants was inoculated into 8 ml of LB medium containing 50 µg/ml ampicillin in a test tube and cultured at 28° C. Fog 17 hours. The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l L-Ala, 2.5 g/l L-Gln, 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide solution; L-Gln was added after sterilization by filtration of a 10-fold conc. solution; glucose, vitamin $B_1$, magnesium sulfate heptahydrate and ferrous sulfate heptahydrate were added after separate steam sterilization] containing 100 µg/ml ampicillin in a test tube in an amount of 1% and subjected to reaction at 30° C. Fog 24 hours. The resulting aqueous medium was centrifuged to obtain a supernatant.

The product in the supernatant was derivatized by the F-moc method and then analyzed by HPLC. The HPLC analysis was carried out using ODS-HG5 (Nomura Kagaku Co., Ltd.) as a separation column and solution A (6 ml/l acetic acid and 20% (v/v) acetonitrile, pH adjusted to 4.8 with triethylamine) and solution B (6 ml/l acetic acid and 70% (v/v) acetonitrile, pH adjusted to 4.8 with triethylamine) as eluents. The ratio of solution A to solution B was 8:2 during the first 5 minutes of elution and thereafter changed with a linear gradient so that the ratio became 1:1 at 20 minutes after the start of elution. The results of analysis are shown in Table 3.

TABLE 3

| Strain | Deleted gene | Ala-Gln (g/l) | Ala-Ala (g/l) |
|---|---|---|---|
| JM101 | none | 0 | 0 |
| JDPP1 | dpp operon | 0.02 | 0.01 |
| JPN1 | pepN | 0.01 | 0.01 |
| JPA1 | pepA | 0.01 | 0.01 |
| JPB7 | pepB | 0.01 | 0.01 |
| JPD1 | pepD | 0.01 | 0.01 |
| JPDN2 | pepD, pepN | 0.02 | 0.03 |
| JPNDB43 | pepB, pepD, pepN | 0.05 | 0.12 |
| JPDP49 | pepD, dpp operon | 0.11 | 0.08 |
| JPNDDP36 | pepD, pepN, dpp operon | 0.16 | 0.21 |
| JPNDAP5 | pepA, pepD, pepN, dpp operon | 0.28 | 0.26 |
| JPNDBP7 | pepB, pepD, pepN, dpp operon | 0.43 | 0.22 |

As can be seen from Table 3, small amounts of dipeptides were formed and accumulated by use of the microorganisms having deletions of two or less kinds of peptidase genes or one operon encoding a peptide-permeating/transporting protein, whereas the amounts of dipeptides formed and accumulated were greatly increased by use of the microorganisms having deletions of one or more kinds of peptidase genes and one operon encoding a peptide-permeating/transporting protein or microorganisms having deletions of three or more kinds of peptidase genes.

EXPERIMENTAL EXAMPLE 18

Evaluation of Productivity of L-Alanyl-L-valine (hereinafter referred to as L-Ala-L-Val) by *Escherichia coli* Strains in Which Peptidase and Peptide-permeating/transporting Protein Activities are Lost Similarly to Experimental Example 17, the *Escherichia coli* strains having deletions of genes encoding various peptidases and peptide-permeating/transporting protein were transformed using pPE56. Each of the obtained transformants was inoculated into 8 ml of LB medium containing 50 µg/ml ampicillin in a test tube and cultured at 28° C. Fog 17 hours. The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l L-Ala, 2.5 g/l L-Val, 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide solution; glucose, vitamin $B_1$, magnesium sulfate heptahydrate and ferrous sulfate heptahydrate were added after separate steam sterilization] containing 100 µg/ml ampicillin in a test tube in an amount of 1% and subjected to reaction at 30° C. for 24 hours. The resulting aqueous medium was centrifuged to obtain a supernatant.

The product in the culture supernatant was analyzed by the method described in Experimental Example 17. The results are shown in Table 4.

TABLE 4

| Strain | Deleted gene | Ala-Val (g/l) |
|---|---|---|
| JM101 | none | 0 |
| JDPP1 | dpp operon | 0 |
| JPN1 | pepN | 0 |
| JPA1 | pepA | 0 |
| JPB7 | pepB | 0 |
| JPD1 | pepD | 0 |
| JPDN2 | pepD, pepN | 0 |
| JPNDB43 | pepB, pepD, pepN | 0.04 |
| JPDP49 | pepD, dpp operon | 0.11 |
| JPNDDP36 | pepD, pepN, dpp operon | 0.22 |
| JPNDBP7 | pepB, pepD, pepN, dpp operon | 0.20 |

As can be seen from Table 4, the dipeptide was not produced by use of the microorganisms having deletions of two or less kinds of peptidase genes or one operon encoding a peptide-permeating/transporting protein, whereas the dipeptide was produced by use of the microorganisms having deletions of three or more kinds of peptidase genes or microorganisms having deletions of one or more kinds of peptidase genes and one operon encoding a peptide-permeating/transporting protein.

EXPERIMENTAL EXAMPLE 19

Evaluation of Productivity of Glycyl-L-glutamine (hereinafter referred to as Gly-L-Gln) by *Escherichia coli* Strains in Which Peptidase and Dipeptide-permeating/transporting Protein Activities are Lost Similarly to Experimental Example 17, the strains having deletions of various peptidase genes and an operon encoding a dipeptide-permeating/transporting protein were transformed using pPE56. Each of the obtained transformants was inoculated into 8 ml of LB medium containing 50 μg/ml ampicillin in a test tube and cultured at 28° C. Fog 17 hours.

The resulting culture was added to 8 ml of an aqueous medium [16 g/l dipotassium hydrogenphosphate, 14 g/l potassium dihydrogenphosphate, 5 g/l ammonium sulfate, 1 g/l citric acid (anhydrous), 0.5 g/l Casamino acid (Difco), 1 g/l L-Pro, 2.5 g/l Gly, 2.5 g/l L-Gln, 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide solution; L-Gln was added after sterilization by filtration of a 10-fold conc. solution; glucose, vitamin $B_1$, magnesium sulfate heptahydrate and ferrous sulfate heptahydrate were added after separate steam sterilization] containing 100 μg/ml ampicillin in a test tube in an amount of 1% and subjected to reaction at 30° C. Fog 24 hours. The resulting aqueous medium was centrifuged to obtain a supernatant.

The product in the culture supernatant was analyzed by the method described in Experimental Example 17. The results are shown in Table 5.

TABLE 5

| Strain | Deleted gene | Gly-Gln (g/l) |
| --- | --- | --- |
| JM101 | none | 0 |
| JDPP1 | dpp operon | 0 |
| JPDN2 | pepD, pepN | 0 |
| JPNDB43 | pepB, pepD, pepN | 0.01 |
| JPNDDP36 | pepD, pepN, dpp operon | 0.02 |
| JPNDBP7 | pepB, pepD, pepN, dpp operon | 0.03 |

As can be seen from Table 5, the dipeptide was not produced by use of the microorganisms having deletions of two or less kinds of peptidase genes or one operon encoding a peptide-permeating/transporting protein, whereas the dipeptide was produced by use of the microorganisms having deletions of three or more kinds of peptidase genes or microorganisms having deletions of two or more kinds of peptidase genes and one operon encoding a peptide-permeating/transporting protein.

EXPERIMENTAL EXAMPLE 20

Enzymatic Process for Production of Dipeptides or Dipeptide Derivatives Using Amino Acids or Amino Acid Derivatives as Substrates A reaction mixture (0.1 ml) comprising 40 mg/l purified His-tagged recombinant enzyme obtained in Experimental Example 4, 100 mmol/l Tris-HCl (pH 9.0), 30 mmol/l magnesium chloride, 10 mmol/l ATP and 10 mmol/l each of amino acid and amino acid derivative shown in Table 6 was prepared, and reaction was carried out at 37° C. Fog 2 hours.

After the completion of reaction, a termination buffer (4 mol/l urea, 100 mmol/l EDTA disodium salt) (100 times amount of the reaction mixture) was added to the reaction mixture to terminate the reaction, and the amount of ADP formed when ATP was consumed by enzymatic reaction was determined by HPLC, whereby it was confirmed that the reaction proceeded. The HPLC analysis was carried out by using Develosil C30-UG-5 (150×4.6 mm, Nomura Kagaku Co., Ltd.) as a column and a solution comprising 200 mmol/l acetic acid and 200 mmol/l triethylamine (pH 6.6) as a mobile phase at a flow rate of 1.0 ml/min at room temperature, and by measuring ultraviolet absorption at 254 nm. The results are shown in Table 6.

TABLE 6-1

| Amino acid added | Amount of ADP formed (mmol/l) |
| --- | --- |
| none | 0.05 |
| Ala | 0.13 |
| Ala + cyc(5)Ala | 5.67 |
| Ala + cyc(3)Ala | 3.64 |
| Ala + cyc(6)Ala | 3.78 |

TABLE 6-2

| Amino acid added | Amount of ADP formed (mmol/l) |
| --- | --- |
| none | 0.05 |
| Ala | 0.13 |
| Phe | 0.02 |
| Ala + Phe | 5.84 |
| Cl-Ala + Phe | 2.75 |
| CN-Ala + Phe | 1.11 |
| Ala + Cl-Phe | 4.78 |
| Ala + F-Phe | 4.44 |
| Ala + p-Ni-Phe | 4.42 |
| Ala + NH2-Phe | 1.89 |
| Ala + Kynurenin | 2.11 |

TABLE 6-3

| Amino acid added | Amount of ADP formed (mmol/l) |
| --- | --- |
| none | 0.05 |
| Ala | 0.13 |
| Glu | 0.13 |
| Ala + Glu(OMe) | 2.60 |
| Ala + Glu(OEt) | 3.93 |
| Ala + Glu(OtBu) | 6.43 |
| Ala + Glu(OBzl) | 6.01 |

TABLE 6-4

| Amino acid added | Amount of ADP formed (mmol/l) |
| --- | --- |
| none | 0.05 |
| Ala | 0.13 |
| Asp | 0.16 |
| Ala + Asp(OMe) | 0.54 |
| Ala + Asp(OtBu) | 4.42 |
| Ala + Asp(OBzl) | 3.23 |

TABLE 6-5

| Amino acid added | Amount of ADP formed (mmol/l) |
| --- | --- |
| none | 0.05 |
| Ala | 0.13 |
| Lys | 0.17 |
| Ala + Lys(Ac) | 0.75 |
| Ala + Lys(Boc) | 3.64 |

Tables 6-1 to 6-5 respectively show the results of experiments using the following substrates: 6-1, L-Ala and L-Ala derivatives; 6-2, L-Ala and L-Phe derivatives; 6-3, L-Ala and L-Glu derivatives; 6-4, L-Ala and L-Asp derivatives; and 6-5, L-Ala and L-Lys derivatives. The abbreviations for the amino acids and amino acid derivatives used as the substrates are as follows.
Ala: L-alanine
Phe: L-phenylalanine
Glu: L-glutamic acid
Asp: L-aspartic acid
Lys: L-lysine
Cl-Ala: β-chloro-L-alanine
CN-Ala: β-cyano-L-alanine
cyc(5)Ala: β-cyclopentyl-DL-alanine
cyc(3)Ala: β-cyclopropylalanine
cyc(6)Ala: β-cyclohexylalanine
Cl-Phe: 4-chlorophenylalanine
F-Phe: 4-fluorophenylalanine
Ni-Phe: p-nitrophenylalanine
$NH_2$-Phe: p-aminophenylalanine
Phe-$NH_2$: phenylalanine amide
Kynurenin: L-kynurenin
Glu(OMe): glutamic acid-γ-methyl ester
Glu(OEt): glutamic acid-γ-ethyl ester
Glu(OtBu): glutamic acid-γ-t-butyl ester
Glu(OBzl): glutamic acid-γ-benzyl ester
Asp(OMe): aspartic acid-β-methyl ester
Asp(OtBu): aspartic acid-β-t-butyl ester
Asp(OBzl): aspartic acid-β-benzyl ester
Lys(Ac): acetyllysine
Lys(Boc): Boc-lysine As shown in Table 6, the amounts of ADP formed in the control experiment using no substrate and the experiments respectively using L-Ala, L-Phe, L-Glu, L-Asp and L-Lys as the sole substrate were 0.02 to 0.16 mmol/l. On the other hand, as much as 0.54 to 6.43 mmol/l ADP was formed by using the combinations of amino acids and amino acid derivatives shown in Table 6.

The structural analysis of compounds that existed in the reaction mixtures obtained under reaction conditions similar to those as mentioned above was carried out by proton NMR analysis. The concentration of an amino acid or an amino acid derivative used as the substrate was 20 mmol/L in reaction mixtures 1, 4, 10 and 11, and 10 mmol/L in the remaining reaction mixtures, respectively.

The proton NMR analysis was carried out by using DMX500 manufactured by Bruker Co. under the conditions described below.
Temperature; 303K
Standard compound; 1 mmol/L 3-(Trimethylsilyl)-Propionic acid-D4 sodium salt (TSP)
Medium; light water (in the case of measuring reaction mixtures 4, 10 and 11) or heavy water (in the case of measuring the other reaction mixtures)

The structure of each of the compounds in the reaction mixtures was identified based on the Chemical shift of the proton of the a position. As the area of TSP was assumed to be an internal standard, the concentration of each of the compounds was calculated based on the area of the signal of the proton of the a position (Table 7). However, because the concentration of L-Ala-L-Ala was low, and because the signal of the proton of the a position overlapped with other signals, the concentration of L-Ala-L-Ala was calculated based on the area of the signal of the proton of the B position. The Chemical shift of the proton of the a position of each of the compounds are shown in parentheses (the unit is ppm).

The reaction mixture using Cl-Ala and Phe as substrates (Reaction mixture 1)
Cl-Ala(4.20), Phe(4.02), Cl-Ala-Phe(3.93, 4.50), Aziridine-2-carboxylic acid [Azc](2.73), Azc-Phe(2.59, 4.47)

The reaction mixture using CN-Ala and Phe as substrates (Reaction mixture 2)
CN-Ala(3.87), Phe(4.00), CN-Ala-Phe(3.71, 4.48)

The reaction mixture using Ala and Cl-Phe as substrates (Reaction mixture 3)
Ala(3.79), Cl-Phe(3.97), Ala-Cl-Phe(3.90, 4.43)

The reaction mixture using Ala and $NH_2$-Phe as substrates (Reaction mixture 4)
Ala(3.78), $NH_2$-Phe(3.93), Ala-$NH_2$-Phe(3.95, 4.39), Ala-Ala(β; 1.55, 1.36)

The reaction mixture using Ala and Kinurenine as substrates (Reaction mixture 5)
Ala(3.79), Kinurenine(4.16), Ala-Kinurenine(3.96, 4.64)

The reaction mixture using Ala and Phe-$NH_2$ as substrates (Reaction mixture 6)
Ala(3.79), Phe-$NH_2$ (4.02), Ala-Phe-$NH_2$ (3.90, 4.60)

The reaction mixture using Ala and Glu(OMe) as substrates (Reaction mixture 7)
Ala(3.79), Glu(OMe)(3.76), Ala-Glu(OMe)(4.05, 4.18), Ala-Ala(B; 1.55, 1.36)

The reaction mixture using Ala and Glu(OtBu) as substrates (Reaction mixture 8)
Ala(3.79), Glu(OtBu)(3.76), Ala-Glu(OtBu)(4.04, 4.18)

The reaction mixture using Ala and Asp(OtBu) as substrates (Reaction mixture 9)
Ala(3.81), Asp(OtBu)(3.98), Ala-Asp(OtBu)(4.04, 4.46)

The reaction mixture using Ala and Lys(Boc) as substrates (Reaction mixture 10)
Ala(3.78), Lys(Boc)(3.73), Ala-Lys(Boc)(4.02, 4.14)

The reaction mixture using Ala and cyc(3)Ala as substrates (Reaction mixture 11)
Ala(3.78), cyc(3)Ala (3.82), Ala-cyc(3)Ala(4.08, 4.24)

The reaction mixture using Ala and cyc(6)Ala as substrates (Reaction mixture 12)
Ala(3.79), cyc(6)Ala (3.76), Ala-cyc(6)Ala(4.02, 4.22)

TABLE 7

| Reaction mixture No | dipeptide | conc. (mmol/L) |
|---|---|---|
| 1 | Cl-Ala-Phe | 3.5 |
|  | Azc-Phe | 5.3 |
| 2 | Cl-Ala | 8.4 |
|  | (Cl-Ala)X2 | overlap |
| 3 | Ala-Cl-Phe | 4.3 |
| 4 | Ala-$NH_2$-Phe | 10.6 |
|  | Ala-Ala | 0.3 |
| 5 | Ala-Kinurenine | 4.0 |
| 6 | Ala-Phe-$NH_2$ | 9.7 |
| 7 | Ala-Glu(OMe) | 6.5 |
|  | Ala-Ala | 0.5 |
| 8 | Ala-Glu(OtBu) | 9.7 |
| 9 | Ala-Asp(OtBu) | 10.6 |
| 10 | Ala-Lys(Boc) | 6.6 |
| 11 | Ala-Cyc(3)Ala | 10.5 |
| 12 | Ala-Cyc(6)Ala | 6.6 |

The term "overlap" in the table means that an accurately fixed quantity could not be determined because the signals were overlapped.

It was thus revealed that a dipeptide derivative in which an amino acid and an amino acid derivative are directly linked by peptide bond can be produced using the amino-acid and amino acid derivative as substrates according to the process of the present invention.

EXPERIMENTAL EXAMPLE 21

Production of
N-[2-(Acetylamino)propionyl]phenylalanine

L-Ala-L-Phe obtained in Experimental Example 6 (100 mg, 0.423 mmol) is suspended in methylene chloride (10 ml), and pyridine (10 ml) and acetic anhydride (1 ml, 11 mmol) are added to the suspension at room temperature. After stirring at room temperature for 24 hours, water is added and the resulting mixture is extracted three times with chloroform. The organic layer is washed with a saturated aqueous solution of sodium chloride and dried over anhydrous magnesium sulfate, and then the solvent is distilled away under reduced pressure to obtain N-[2-(acetylamino)propionyl]phenylalanine.

EXPERIMENTAL EXAMPLE 22

Production of 1-{(2-[N-((Acetylamino)acetyl)amino]-3-phenylpropionyl}piperidine

N-[2-(Acetylamino)propionyl]phenylalanine obtained in Experimental Example 21 (10 mg, 0.036 mmol) is suspended in N,N-dimethylformamide (5 ml), and 1-(3-dimethylaminopropyl)-3-ethylcarbodiimide hydrochloride (14 mg, 0.073 mmol), 1-hydroxybenzotriazole (15 mg, 0.11 mmol) and piperidine (40 µl, 0.40 mmol) are added to the suspension at room temperature, followed by stirring at 50° C. Fog 24 hours. To the reaction mixture is added water, and the resulting mixture is extracted three times with chloroform. The organic layer is washed with 10% hydrochloric acid and a saturated aqueous solution of sodium chloride, and dried over anhydrous magnesium sulfate. After the solvent is distilled away under reduced pressure, the residue is purified by silica gel column chromatography to obtain 1-{2-[N-(2-(acetylamino)propionyl)amino]-3-phenylpropionyl}piperidine.

Certain embodiments of the present invention are illustrated in the following examples. These examples are not to be construed as limiting the scope of the invention.

In the following examples, dipeptides and amino acids were analyzed by HPLC after being derivatized by the dinitrophenol method. The HPLC analyses were carried out by using Lichrosorb-RP-18 column (Kanto Kagaku) as a separation column and 1% (v/v) phosphoric acid and 25% (v/v) acetonitrile as an eluent at a flow rate of 0.7 ml/min.
Analysis and Determination of ATP, ADP and AMP:

ATP, ADP and AMP were analyzed by HPLC after 400-fold dilution of the reaction mixture with a termination solution [4 mol/l urea, 100 mmol/l EDTA.2Na (pH 8.0)]. The HPLC analyses were carried out by using Develosil C30-UG-5 (150×4.6 mm, Nomura Kagaku Co., Ltd.) as a separation column and 200 mmol/l acetic acid and 200 mmol/l triethylamine (pH 6.6) as an eluent at a flow rate of 1.0 ml/min, and by measuring absorption at 254 nm.

EXAMPLE 1

Acquisition of Genes Encoding Thermostable ywfE Proteins

Error-prone PCR [Technique, 1, 11-15 (1989)] was carried out using, as a set of primers, DNA having the nucleotide sequence shown in SEQ ID NO: 98 which lies upstream of the 5' end of the DNA encoding the ywfE protein on the plasmid pQE60ywfE comprising the ywfE gene obtained in Experimental Example 4 and DNA having the nucleotide sequence shown in SEQ ID NO: 99 which lies downstream of the 3' end of said DNA, and as a template DNA, the plasmid pQE60ywfE. That is, PCR was carried out by 30 cycles, one cycle consisting of reaction at 94° C. Fog 30 seconds, reaction at 57° C. Fog 30 seconds and reaction at 72° C. Fog 1 minute and 30 seconds, followed by incubation at 72° C. Fog 3 minutes, using 50 µl of a reaction mixture comprising 0.1 µg of the template DNA, 0.5 µmol/l each of the primers, 2.5 units of Taq DNA polymerase (Takara Bio Inc.), 5 µl of buffer for Taq DNA polymerase (10×), 200 µmol/l each of deoxyNTPs and 0.075 mmol/l manganese chloride. The amplified fragments were cleaved with restriction enzymes NcoI and BamHI and then recovered in the same manner as in Experimental Example 1. The recovered fragments were ligated to the vector plasmid pQE60 cleaved with restriction enzymes NcoI and BamHI to construct expression plasmids. *Escherichia coli* DH5α/pREP4 [strain obtained by transformation of *Escherichia coli* DH5α using pREP4 (Qiagen, Inc.)] was transformed using the obtained plasmids and pQE60ywfE to obtain transformants. The resulting transformants were designated as *Escherichia coli* DH5α/pBTS1 to pBTS5 and *Escherichia coli* DH5α/pQE60ywfE, respectively. A plasmid was extracted from each of *Escherichia coli* DH5α/pBTS1 to pBTS5 according to a known method and its nucleotide sequence was determined. The nucleotide sequences of the DNAs contained in pBTS1, pBTS2, pBTS3, pBTS4 and pBTS5 are shown in SEQ ID NOS: 22, 23, 24, 25 and 26, respectively. The amino acid sequences encoded by the DNAs contained in pBTS1, pBTS2, pBTS3, pBTS4 and pBTS5 are shown in SEQ ID NOS: 9, 10, 11, 12 and 13, respectively.

The proteins produced by *Escherichia coli* DH5α/pBTS1 to pBTS5 and *Escherichia coli* DH5α/pQE60ywfE (abbreviated as pBTS1 to pBTS5 and pQE60ywfE in Table 8 below) were respectively purified according to the method described in Experimental Example 4. Each protein was subjected to heat treatment at 55° C. Fog 15 minutes and then to dipeptide-forming reaction.

The dipeptide-forming reaction was carried out by preparing a reaction mixture (0.1 ml) comprising 50 mg/l protein purified above, 100 mmol/l Tris-HCl (pH 8.0), 30 mmol/l magnesium chloride and 60 mmol/l ATP, adding 30 mmol/l each of L-Ala and L-Gln thereto, and subjecting the mixture to reaction at 37° C. Fog one hour. The amount of L-Ala-L-Gln formed by using the heat-treated protein was measured as the residual activity (%) based on the amount of L-Ala-L-Gln formed by using the protein produced by *Escherichia coli* DH5α/pQE60ywfE without heat treatment. The results are shown in Table 8.

TABLE 8

| Strain | Residual activity (%) |
|---|---|
| pQE60ywfE | 0 |
| pBTS1 | 45 |
| pBTS2 | 40 |
| pBTS3 | 58 |
| pBTS4 | 37 |
| pBTS5 | 37 |

The results shown in Table 8 revealed that mutant dipeptide synthetases having enhanced thermostability compared with the wild-type ywfE protein (dipeptide synthetase) consisting of the amino acid sequence shown in SEQ ID NO: 1 were obtained.

EXAMPLE 2

Construction of Cells Producing Polyphosphate Kinase (1) Preparation of Chromosomal DNAs of Various Bacteria The following bacteria were respectively cultured at 30° C. Fog 24 hours using the following media:

*Escherichia coli* W3110, *Rhodobacter sphaeroides* ATCC 17023, *Pseudomonas putida* KT2440 (ATCC 47054) and *Sinorhizobium meliloti* ATCC 51124: LB medium;

*Chloroflexus aurantiacus* ATCC 29366: ATCC medium 920 [0.1 g/l nitrilotriacetic acid, 0.06 g/l calcium sulfate dihydrate, 0.1 g/l magnesium sulfate heptahydrate, 0.008 g/l sodium chloride, 0.103 g/l potassium nitrate, 0.689 g/l sodium nitrate, 0.111 g/l disodium hydrogenphosphate, 0.2 g/l ammonium chloride, 0.5 g/l yeast extract, 0.5 g/l glycylglycine, 0.5 g/l sodium sulfate, 1 ml/l trace metal solution (solution containing 0.5 ml/l conc. sulfuric acid, 2.28 g/l manganese sulfate heptahydrate, 0.5 g/l zinc sulfate heptahydrate, 0.5 g/l boric acid, 0.025 g/l copper sulfate dihydrate, 0.025 g/l sodium molybdate dihydrate ($NA_2MoO_4.2H_2O$) and 0.045 g/l cobalt chloride hexahydrate) and 1 ml/l solution of ferric chloride (solution containing 0.2905 g/l $FeCl_3$), pH 8.2 to 8.4];

*Mesorhizobium loti* MAFF 303099 (distributed by Kazusa DNA Research Institute): a medium comprising 1 g/l yeast extract, 5 g/l mannitol, 0.7 g/l dipotassium hydrogenphosphate, 0.1 g/l potassium dihydrogenphosphate and 1 g/l magnesium sulfate heptahydrate (pH 7.0 to 7.2); and

*Streptomyces coelicolor* ATCC BAA-471: a medium comprising 5 g/l tryptone peptone (Difco) and 3 g/l yeast extract (Difco) (pH 7.0 to 7.2). Each of the resulting cultures was centrifuged to obtain cells.

The chromosomal DNAs were isolated and purified from the cells of the respective bacteria according to the method described in Current Protocols in Molecular Biology.

(2) Amplification of Genes Encoding Polyphosphate Kinase Derived from Various Bacteria The genes encoding polyphosphate kinase (hereinafter abbreviated as ppk genes) of the bacteria of the above (1) were obtained by PCR using the respective chromosomal DNAs as a template and the following DNAs as a set of primers: *Escherichia coli* W3110, DNAs having the nucleotide sequences shown in SEQ ID NOS: 100 and 101; *Rhodobacter sphaeroides* ATCC 17023, DNAs having the nucleotide sequences shown in SEQ ID NOS: 102 and 103; *Chloroflexus aurantiacus* ATCC 29366, DNAs having the nucleotide sequences shown in SEQ ID NOS: 104 and 105; *Mesorhizobium loti* MAFF 303099, DNAs having the nucleotide sequences shown in SEQ ID NOS: 106 and 107; *Streptomyces coelicolor* ATCC BAA-471, DNAs having the nucleotide sequences shown in SEQ ID NOS: 108 and 109; *Pseudomonas putida* KT2440, DNAs having the nucleotide sequences shown in SEQ ID NOS: 110 and 111; and *Sinorhizobium meliloti* ATCC 51124, DNAs having the nucleotide sequences shown in SEQ ID NOS: 112 and 113 or DNAs having the nucleotide sequences shown in SEQ ID NOS: 114 and 115.

PCR was carried out by 30 cycles, one cycle consisting of reaction at 98° C. Fog 5 seconds, reaction at 59° C. Fog 40 seconds and reaction at 72° C. Fog 2 minutes, followed by incubation at 72° C. Fog 2 minutes, using 50 µl of a reaction mixture comprising 0.1 µg of the chromosomal DNA, 0.5 µmol/l each of the primers, 2.5 units of Pyrobest DNA polymerase (Takara Bio Inc.), 5 µl of buffer for Pyrobest DNA polymerase (10×) and 200 µmol/l each of deoxyNTPs.

Each of the resulting reaction mixtures was mixed with an equal amount of phenol/chloroform saturated with TE.

The resulting mixture was centrifuged, and the obtained upper layer was mixed with a two-fold volume of cold ethanol and allowed to stand at −80° C. Fog 30 minutes. The resulting solution was centrifuged, and the obtained DNA was dissolved in TE.

(3) Cloning of DNAs Encoding Polyphosphate Kinase

The DNA fragment amplified in the above (2) by using the chromosomal DNA of *Escherichia coli* W3110 as a template was digested with NcoI and BamHI, and subjected to agarose gel electrophoresis to separate a ca. 1.4 kb DNA fragment. The DNA fragment was recovered using GENECLEAN Kit and then dissolved in TE. The obtained DNA fragment and pET-28a(+) vector (Novagen) digested with NcoI and BamHI were subjected to ligation reaction using a ligation kit at 16° C. Fog one hour to obtain a recombinant DNA.

*Escherichia coli* TOP10 (Invitrogen) was transformed using the recombinant DNA, spread on LB agar medium containing 50 µg/ml kanamycin, and cultured overnight at 30° C.

A plasmid was extracted from a colony of the transformant that grew on the medium according to the method described in Molecular Biology, Third Edition, and the structure of the plasmid was analyzed using restriction enzymes. As a result, it was confirmed that plasmid pPK-Ec1 expressing the ppk gene derived from *Escherichia coli* having the nucleotide sequence shown in SEQ ID NO: 116 was obtained.

The DNA fragments amplified by using, as templates, the chromosomal DNAs of *Rhodobacter sphaeroides* ATCC 17023, *Chloroflexus aurantiacus* ATCC 29366, *Mesorhizobium loti* MAFF 303099, *Streptomyces coelicolor* ATCC BAA-471, *Pseudomonas putida* KT2440 and *Sinorhizobium meliloti* ATCC 51124 were respectively ligated to pCR-Blunt vector (Invitrogen) according to the protocols of Invitrogen.

*Escherichia coli* TOP10 was transformed using each of the obtained recombinant DNAs, spread on LB agar medium containing 50 µg/ml kanamycin, and cultured overnight at 30° C.

A plasmid was extracted from a colony of each transformant that grew on the medium according to the method described in Molecular Biology, Third Edition. The plasmids thus obtained were respectively digested with the following restriction enzymes: plasmid carrying the DNA derived from *Rhodobacter sphaeroides* ATCC 17023 and plasmid carrying the DNA derived from *Chloroflexus aurantiacus* ATCC 29366, NdeI and SalI; plasmid carrying the DNA derived from *Mesorhizobium loti* MAFF 303099 and plasmid carrying the DNA derived from *Pseudomonas putida* KT2440, NdeI and HindIII; plasmid carrying the DNA derived from *Streptomyces coelicolor* ATCC BAA-471, NcoI and SalI; plasmid carrying the DNA derived from *Sinorhizobium meliloti* ATCC 51124 which was amplified by using the primer DNAs consisting of the nucleotide sequences shown in SEQ ID NOS: 112 and 113, NdeI and SalI; and plasmid carrying the DNA derived from *Sinorhizobium meliloti* ATCC 51124 which was amplified by using the primer DNAs consisting of the nucleotide sequences shown in SEQ ID NOS: 114 and 115, NdeI and BamHI. The digested DNA fragments were separated by agarose gel electrophoresis, recovered using GENECLEAN Kit, and then dissolved in TE.

The obtained DNA fragments were ligated to pET-27b(+) vector (Novagen) digested with the above respective restriction enzymes by reaction using a ligation kit at 16° C. Fog one hour.

*Escherichia coli* TOP10 was transformed using each of the obtained recombinant DNAs, spread on LB agar medium containing 50 μg/ml kanamycin, and cultured overnight at 30° C.

A plasmid was extracted from a colony of each transformant that grew on the medium according to the method described in Molecular Biology, Third Edition, and the structure of each plasmid was analyzed using restriction enzymes. As a result, it was confirmed that the desired ppk gene expression plasmids were obtained. The plasmid expressing the ppk gene derived from *Rhodobacter sphaeroides* ATCC 17023 having the nucleotide sequence shown in SEQ ID NO: 117 was designated as pPK-Rs-21, the plasmid expressing the ppk gene derived from *Chloroflexus aurantiacus* ATCC 29366 having the nucleotide sequence shown in SEQ ID NO: 118 as pPK-Ca-2, the plasmid expressing the ppk gene derived from *Mesorhizobium loti* MAFF 303099 having the nucleotide sequence shown in SEQ ID NO: 119 as pPK-M12-1, the plasmid expressing the ppk gene derived from *Streptomyces coelicolor* ATCC BAA-471 having the nucleotide sequence shown in SEQ ID NO: 120 as pPK-Sc2, the plasmid expressing the ppk gene derived from *Pseudomonas putida* KT2440 having the nucleotide sequence shown in SEQ ID NO: 121 as pPK-Pp2-2, the plasmid expressing the ppk gene derived from *Sinorhizobium meliloti* ATCC 51124 having the nucleotide sequence shown in SEQ ID NO: 122 as pPK-Sm2-1, and the plasmid expressing the ppk gene derived from *Sinorhizobium meliloti* ATCC 51124 having the nucleotide sequence shown in SEQ ID NO: 123 as pPK-Sm2-2. The amino acid sequences of polyphosphate kinases encoded by the DNAs consisting of the nucleotide sequences shown in SEQ ID NOS: 116 to 123 are shown in SEQ ID NOS: 124 to 131, respectively.

(4) Construction of Polyphosphate Kinase-Producing Strains

*Escherichia coli* BL21-Gold(DE3) (Stratagene) was transformed using each of the expression plasmids obtained in the above (3), spread on LB agar medium containing 50 μg/ml kanamycin, and cultured overnight at 30° C.

A plasmid was extracted from a colony of each transformant that grew on the medium according to a known method. It was confirmed that *Escherichia coli* BL21-Gold(DE3) strains carrying the expression plasmids obtained in the above (3) were obtained, and the strains were designated as *Escherichia coli* BL21-Gold(DE3)/pPK-Ec1, *Escherichia coli* BL21-Gold(DE3)/pPK-Rs-21, *Escherichia coli* BL21-Gold(DE3)/pPK-Ca-2, *Escherichia coli* BL21-Gold(DE3)/pPK-M12-1, *Escherichia coli* BL21-Gold(DE3)/pPK-Sc2, *Escherichia coli* BL21-Gold(DE3)/pPK-Pp2-2, *Escherichia coli* BL21-Gold(DE3)/pPK-Sm2-1 and *Escherichia coli* BL21-Gold(DE3)/pPK-Sm2-2, respectively.

EXAMPLE 3

Production of Polyphosphate Kinase

The polyphosphate kinase-producing *Escherichia coli* transformants obtained in Example 2 were respectively cultured at 30° C. using LB medium. When OD (660 nm) reached 3.0 to 5.0, IPTG was added to the culture to give a final concentration of 2 mmol/l, and culturing was continued until OD (660 nm) reached 8.0. Each of the resulting cultures was centrifuged and the obtained cells were suspended in a reaction mixture [5 mmol/l polyphosphoric acid (Sigma, P8510), 5 mmol/l AMP, 1 mmol/l ADP, 20 mmol/l magnesium chloride, 100, mmol/l ammonium sulfate and 60 mmol/l HEPES-KOH, pH 7.2] to give a concentration of 50 g/l. The resulting suspension was subjected to reaction at 37° C. Fog one hour.

After the completion of the reaction, the supernatant of each reaction mixture was analyzed by HPLC as described above, whereby polyphosphoric acid-dependent ATP formation was observed in all of the reaction mixtures. It was thus confirmed that all of the transformants obtained in Example 2 produce polyphosphate kinase.

EXAMPLE 4

Production of Dipeptides by the Use of Cells as an Enzyme Source (1)

*Escherichia coli* DH5α/pQE60ywfE obtained in Example 1, which expresses the protein having the dipeptide-forming activity and having the sequence shown in SEQ ID NO: 1, was inoculated into 8 ml of LB medium containing 50 μg/ml ampicillin in a test tube, and cultured at 28° C. Fog 17 hours. The resulting culture was inoculated into 50 ml of LB medium containing 50 μg/ml ampicillin in a 250-ml Erlenmeyer flask, and cultured at 30° C. Fog 3 hours. Then, IPTG was added to give a final concentration of 1 mmol/l, followed by further culturing at 30° C. Fog 4 hours. The resulting culture was centrifuged to obtain wet cells.

*Escherichia coli* BL21-Gold(DE3)/pPK-Ec1 obtained in Example 2, which produces polyphosphate kinase derived from *Escherichia coli* W3110, was inoculated into 8 ml of LB medium containing 50 μg/ml kanamycin in a test tube, and cultured at 28° C. Fog 17 hours. The resulting culture was inoculated into 50 ml of LB medium containing 50 μg/ml kanamycin in a 250-ml Erlenmeyer flask, and cultured at 30° C. Fog 3 hours. Then, IPTG was added to give a final concentration of 1 mmol/l, followed by further culturing at 30° C. Fog 4 hours. The resulting culture was centrifuged to obtain wet cells.

The wet cells of *Escherichia coli* DH5α/pQE60ywfE and the wet cells of *Escherichia coli* BL21-Gold(DE3)/pPK-Ec1 were added to a reaction mixture [100 mmol/l phosphate buffer (pH 8.0), 50 g/l polyphosphoric acid, 100 mmol/l magnesium sulfate, 5 mmol/l ATP and 50 mmol/l each of substrate amino acids] to give concentrations of 30 g/l and 20 g/l, respectively. The resulting mixture was subjected to reaction at 37° C. Fog one hour. The results are shown in Table 9.

TABLE 9

| | Substrate amino acid | | | |
|---|---|---|---|---|
| | L-Ala L-Met | L-Ala L-Leu | L-Ala L-Val | L-Ala L-Ile |
| | Dipeptide formed | | | |
| | L-Ala-L-Met | L-Ala-L-Leu | L-Ala-L-Val | L-Ala-L-Ile |
| Amount of dipeptide formed (g/l) | 0.5 | 0.7 | 0.4 | 0.4 |

The results shown in Table 9 revealed that dipeptides can be efficiently produced by coupling of ATP-consuming reaction (ADP-forming reaction) by dipeptide synthetase and ATP-regenerating reaction (reaction using ADP as a substrate) by polyphosphate kinase even in the presence of ATP in the amount as small as 5 mmol/l.

EXAMPLE 5

Production of Dipeptides by the Use of Cells as an Enzyme Source (2)

*Escherichia coli* BL21-Gold(DE3)/pPK-Rs2-1 obtained in Example 2, which produces polyphosphate kinase derived from *Rhodobacter sphaeroides* ATCC 17023, was inoculated into 8 ml of LB medium containing 50 µg/ml kanamycin in a test tube, and cultured at 28° C. Fog 17 hours. The resulting culture was inoculated into 50 ml of LB medium containing 50 µg/ml kanamycin in a 250-ml Erlenmeyer flask, and cultured at 30° C. Fog 3 hours. Then, IPTG was added to give a final concentration of 1 mmol/l, followed by further culturing at 30° C. Fog 4 hours. The resulting culture was centrifuged to obtain wet cells.

The wet cells of *Escherichia coli* DH5α/pQE60ywfE prepared in Example 4 and the wet cells of *Escherichia coli* BL21-Gold(DE3)/pPK-Rs2-1 were added to the reaction mixture described in Example 4 to give concentrations of 30 g/l and 20 g/l, respectively. The resulting mixture was subjected to reaction at 37° C. Fog one hour. The results are shown in Table 10.

TABLE 10

| | Substrate amino acid | | | | |
|---|---|---|---|---|---|
| | L-Ala L-Met | L-Ala L-Leu | L-Ala L-Val | L-Ala L-Ile | Gly L-Met |
| | Dipeptide formed | | | | |
| | L-Ala-L-Met | L-Ala-L-Leu | L-Ala-L-Val | L-Ala-L-Ile | Gly-L-Met |
| Amount of dipeptide formed (g/l) | 3.0 | 3.2 | 1.1 | 1.2 | 0.2 |

The results shown in Table 10 revealed that dipeptides can be further efficiently produced by using polyphosphate kinase derived from *Rhodobacter sphaeroides*.

EXAMPLE 6

Production of Dipeptides by the Use of Cells as an Enzyme Source (3)

Wet cells of *Escherichia coli* BL21-Gold(DE3)/pPK-Ec1 were prepared in the same manner as in Example 4. The wet cells were added to a 100 mmol/l phosphate buffer (pH 8.0) containing 50 g/l polyphosphoric acid and 100 mmol/l magnesium sulfate to give a concentration of 20 g/l, followed by heat treatment at 45° C. Fog one hour. After the resulting solution was cooled to 37° C., the wet cells of *Escherichia coli* DH5α/pQE60ywfE prepared in Example 4, ATP and substrate amino acids were added thereto to give final concentrations of 30 g/l, 5 mmol/l and 200 mmol/l each, respectively. The resulting mixture was subjected to reaction at 37° C. Fog 2 hours. As a control experiment, dipeptide-forming reaction was carried out in the same manner as above using the wet cells of *Escherichia coli* BL21-Gold(DE3)/pPK-Ec1 without the heat treatment. The results are shown in Table 11.

TABLE 11

| | | Substrate amino acid | | | |
|---|---|---|---|---|---|
| | | L-Ala L-Met | L-Ala L-Leu | L-Ala L-Val | L-Ala L-Ile |
| | | Dipeptide formed | | | |
| | | L-Ala-L-Met | L-Ala-L-Leu | L-Ala-L-Val | L-Ala-L-Ile |
| Amount of dipeptide formed (g/l) | No heat treatment | 0.5 | 0.4 | 0.3 | 0.5 |
| | Heat treatment | 1.5 | 1.3 | 0.7 | 0.8 |

The results shown in Table 11 revealed that the dipeptide production is remarkably improved by using the heat-treated cells compared with that by using the non-heat-treated cells.

EXAMPLE 7

Production of Dipeptides by the Use of Cells as an Enzyme Source (4)

The wet cells of *Escherichia coli* DH5α/pQE60ywfE prepared in Example 4 and the wet cells of *Escherichia coli* BL21-Gold(DE3)/pPK-Rs2-1 prepared in Example 5 were added to a 100 mmol/l phosphate buffer (pH 8.0) containing 50 g/l polyphosphoric acid and 100 mmol/l magnesium sulfate to give concentrations of 30 g/l and 20 g/l, respectively, followed by heat treatment at 45° C. Fog one hour. After the resulting solution was cooled to 37° C., ATP and substrate amino acids were added thereto to give final concentrations of 5 mmol/l and 200 mmol/l each, respectively. The resulting mixture was subjected to reaction at 37° C. Fog 2 hours. As a control experiment, dipeptide-forming reaction was carried, out in the same manner as above using the wet cells without the heat treatment as the enzyme source. The results are shown in Table 12.

TABLE 12

| | | Substrate amino acid | |
|---|---|---|---|
| | | L-Ala L-Met | L-Ala L-Leu |
| | | Dipeptide formed | |
| | | L-Ala-L-Met | L-Ala-L-Leu |
| Amount of dipeptide formed (g/l) | No heat treatment | 2.8 | 3.8 |
| | Heat treatment | 4.5 | 4.2 |

The results shown in Table 12 revealed that the dipeptide production is remarkably improved by using the heat-treated wet cells compared with that by using the non-heat-treated wet cells.

EXAMPLE 8

Production of Dipeptides Using Thermostabilized Dipeptide Synthetase

Wet cells of *Escherichia coli* DH5α/pBTS2 obtained in Example 1, which produces thermostabilized mutant dipeptide synthetase, were prepared in the same manner as in Example 4. The obtained wet cells and the wet cells of *Escherichia coli* BL21-Gold(DE3)/pPK-Rs2-1 prepared in Example 5 were added to a 100 mmol/l phosphate buffer (pH 8.0) containing 50 g/l polyphosphoric acid and 100 mmol/l magnesium sulfate to give concentrations of 30 g/l and 20 g/l, respectively, followed by heat treatment at 52° C. Fog 30 minutes. After the resulting solution was cooled to 37° C., ATP and substrate amino acids were added thereto to give final concentrations of 5 mmol/l and 200 mmol/l each, respectively. The resulting mixture was subjected to reaction. During the reaction, the pH was adjusted to 7.5 to 8.0 by appropriately adding 2 mol/l sodium hydroxide. The results are shown in Table 13.

TABLE 13

| Substrate amino acid | Dipeptide formed | Amount of dipeptide formed (g/l) | Reaction time (hour) |
|---|---|---|---|
| L-Ala, L-Met | L-Ala-L-Met | 28.6 | 27 |
| L-Ala, L-Phe | L-Ala-L-Phe | 8.1 | 27 |
| L-Ala, L-Leu | L-Ala-L-Leu | 16.0 | 27 |

TABLE 13-continued

| Substrate amino acid | Dipeptide formed | Amount of dipeptide formed (g/l) | Reaction time (hour) |
|---|---|---|---|
| L-Ala, L-Val | L-Ala-L-Val | 15.8 | 27 |
| L-Ala, I-Ile | L-Ala-L-Ile | 13.2 | 27 |
| L-Thr, L-Met | L-Thr-L-Met | 8.7 | 19 |
| L-Thr, L-Phe | L-Thr-L-Phe | 8.5 | 24 |
| Gly, L-Met | Gly-L-Met | 13.2 | 27 |
| Gly, L-Phe | Gly-L-Phe | 10.6 | 24 |

The results shown in Table 13 revealed that the dipeptide production is further remarkably improved by using the heat-treated cells producing thermostabilized mutant dipeptide synthetase as the enzyme source.

All references cited herein are incorporated herein in their entirety by reference

What is claimed is:

1. A process for producing a dipeptide, which comprises:
allowing (i) polyphosphoric acid, (ii) a substance selected from the group consisting of adenosine-5'-monophosphate, adenosine-5'-diphosphate and adenosine-5'-triphosphate, (iii) a protein having polyphosphate kinase activity, or a culture of cells having the ability to produce the protein or a treated matter of the culture, (iv) a protein having the activity to adenosine-5'-triphosphate-dependently form said dipeptide from one or more kinds of amino acids, or a culture of cells having the ability to produce the protein or a treated matter of the culture and (v) one or more kinds of amino acids to be present in an aqueous medium;
allowing said dipeptide to form and accumulate in the aqueous medium; and
recovering said dipeptide from the aqueous medium,
wherein the cells having the ability to produce the protein having the activity to adenosine-5'-triphosphate-dependently form said dipeptide from one or more kinds of amino acids are cells of a prokaryote carrying DNA selected from the group consisting of the following [1] and [2]:
[1] DNA having the nucleotide sequence shown in any of SEQ ID NOs: 14 to 26 and 46;
[2] DNA comprising a nucleic acid sequence which hybridizes with DNA comprising the complement of a nucleic acid sequence shown in any of SEQ ID NOs: 14 to 26 and 46 at 65° C. in the presence of 0.7 to 1.0 mol/l followed by washing at 65° C. with 0.1 to 2×SSC solution and which encodes a protein having the activity to adenosine-5'-triphosphate-dependently form said dipeptide from one or more kinds of amino acids;
wherein the one or more kinds of amino acids are a combination of (i) L-Ala and L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit or L-theanine; (ii) Gly and L-Gln, Gly, L-Phe, L-Trp, L-Met, L-Ser, L-Thr, L-Cys, L-Tyr, L-Lys, L-Arg, L-α-AB or L-Cit; (iii) L-Met and L-Phe, L-Met, L-Ser, L-Thr, L-Cys, L-Tyr, L-Lys or L-His; (iv) L-Ser and L-Gln, L-Phe, L-Ser, L-Thr, L-Tyr, L-His or L-α-AB; (v) L-Thr and L-Gln, L-Phe, L-Leu, L-Thr or L-α-AB; (vi) L-Gln and L-Phe; (vii) β-Ala and L-Phe, L-Met, L-His or L-Cit; or (viii) L-α-AB, and L-Gln, L-Arg or L-α-AB, and the procaryote is a microorganism in which the activities of three or more kinds of peptidases and one or more kinds of proteins having peptide-permeating/transporting activity (hereinafter referred to also as peptide-permeating/transporting proteins) are reduced or lost.

2. A process for producing a dipeptide, which comprises:
allowing (i) polyphosphoric acid, (ii) a substance selected from the group consisting of adenosine-5'-monophosphate, adenosine-5'-disphosphate and adenosine 5'-triphosphate, (iii) a protein having polyphosphate kinase activity, or a culture of cells having the ability to produce the protein or a treated matter of the culture, (iv) a protein having the activity to adenosine-5'-triphosphate-dependently form said dipeptide from one or more kinds of amino acids, or a culture of cells having the ability to produce the protein or a treated matter of the culture and (v) one or more kinds of amino acids to be present in an aqueous medium;
allowing said dipeptide to form and accumulate in the aqueous medium;
modifying said dipeptide in the aqueous medium, or recovering said dipeptide from the aqueous medium, and then modifying thereof to form a modified dipeptide; and
recovering said modified dipeptide,
wherein the cells having the ability to produce the protein having the activity to adenosine-5'-triphosphate-dependently form said dipeptide from one or more kinds of amino acids are cells of a prokaryote carrying DNA selected from the group consisting of the following [1] and [2]:
[1] DNA having the nucleotide sequence shown in any of SEQ ID NOs: 14 to 26 and 46;
[2] DNA comprising a nucleic acid sequence which hybridizes with DNA comprising the complement of a nucleic acid sequence shown in any of SEQ ID NOs: 14 to 26 and 46 at 65° C. in the presence of 0.7 to 1.0 mol/l followed by washing at 65° C. with 0.1 to 2×SSC solution and which encodes a protein having the activity to adenosine-5'-triphosphate-dependently form said dipeptide from one or more kinds of amino acids;
wherein the one or more kinds of amino acids are a combination of (i) L-Ala and L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit or L-theanine; (ii) Gly and L-Gln, Gly, L-Phe, L-Trp, L-Met, L-Ser, L-Thr, L-Cys, L-Tyr, L-Lys, L-Arg, L-α-AB or L-Cit; (iii) L-Met and L-Phe, L-Met, L-Ser, L-Thr, L-Cys, L-Tyr, L-Lys or L-His; (iv) L-Ser and L-Gln, L-Phe, L-Ser, L-Thr, L-Tyr, L-His or L-α-AB; (v) L-Thr and L-Gln, L-Phe, L-Leu, L-Thr or L-α-AB; (vi) L-Gln and L-Phe; (vii) β-Ala and L-Phe, L-Met, L-His or L-Cit; or (viii) L-α-AB and L-Gln, L-Arg or L-α-AB, and the procaryote is a microorganism in which the activities of three or more kinds of peptidases and one or more kinds of proteins having peptide-permeating/transporting activity (hereinafter referred to also as peptide-permeating/transporting proteins) are reduced or lost.

3. A process for producing a dipeptide, which comprises:
allowing (i) polyphosphoric acid, (ii) a substance selected from the group consisting of adenosine-5'-monophosphate, adenosine-5'-diphosphate and adenosine-5'-triphosphate, (iii) a protein having polyphosphate kinase activity, or a culture of cells having the ability to produce the protein or a treated matter of the culture, (iv) a protein having the activity to adenosine-5'-triphosphate-dependently form said dipeptide from one or more kinds of amino acids, or a culture of cells having the ability to produce the protein or a treated matter of the culture and (v) one or more kinds of amino acids to be present in an aqueous medium;
allowing said dipeptide to form and accumulate in the aqueous medium; and
recovering said dipeptide from the aqueous medium,
wherein the cells having the ability to produce the protein having the activity to adenosine-5'-triphosphate-dependently form said dipeptide from one or more kinds of amino acids are cells of a prokaryote carrying DNA selected from the group consisting of the following [1] and [2]:
[1] DNA having the nucleotide sequence shown in any of SEQ ID NOs: 14 to 26 and 46;
[2] DNA comprising a nucleic acid sequence which hybridizes with DNA comprising the complement of a nucleic acid sequence shown in any of SEQ ID NOs: 14 to 26 and 46 at 65° C. in the presence of 0.7 to 1.0 mol/l followed by washing at 65° C. with 0.1 to 2×SSC solution and which encodes a protein having the activity to adenosine-5'-triphosphate-dependently form said dipeptide from one or more kinds of amino acids;
wherein the one or more kinds of amino acids are a combination of (i) L-Ala and L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit or L-theanine; (ii) Gly and L-Gln, Gly, L-Phe, L-Trp, L-Met, L-Ser, L-Thr, L-Cys, L-Tyr, L-Lys, L-Arg, L-α-AB or L-Cit; (iii) L-Met and L-Phe, L-Met, L-Ser, L-Thr, L-Cys, L-Tyr, L-Lys or L-His; (iv) L-Ser and L-Gln, L-Phe, L-Ser, L-Thr, L-Tyr, L-His or L-α-AB; (v) L-Thr and L-Gln, L-Phe, L-Leu, L-Thr or L-α-AB; (vi) L-Gln and L-Phe; (vii) β-Ala and L-Phe, L-Met, L-His or L-Cit; or (viii) L-α-AB, and L-Gln, L-Arg or L-α-AB, and the procaryote is a microorganism in which the activities of three or more kinds of peptidases are reduced or lost.

4. A process for producing a dipeptide, which comprises:
allowing (i) polyphosphoric acid, (ii) a substance selected from the group consisting of adenosine-5'-monophosphate, adenosine-5'-disphosphate and adenosine 5'-triphosphate, (iii) a protein having polyphosphate kinase activity, or a culture of cells having the ability to produce the protein or a treated matter of the culture, (iv) a protein having the activity to adenosine-5'-triphosphate-dependently form said dipeptide from one or more kinds of amino acids, or a culture of cells having the ability to produce the protein or a treated matter of the culture and (v) one or more kinds of amino acids to be present in an aqueous medium;
allowing said dipeptide to form and accumulate in the aqueous medium;
modifying said dipeptide in the aqueous medium, or recovering said dipeptide from the aqueous medium, and then modifying thereof to form a modified dipeptide; and
recovering said modified dipeptide,
wherein the cells having the ability to produce the protein having the activity to adenosine-5'-triphosphate-dependently form said dipeptide from one or more kinds of amino acids are cells of a prokaryote carrying DNA selected from the group consisting of the following [1] and [2]:
[1] DNA having the nucleotide sequence shown in any of SEQ ID NOs: 14 to 26 and 46;
[2] DNA comprising a nucleic acid sequence which hybridizes with DNA comprising the complement of a nucleic acid sequence shown in any of SEQ ID NOs: 14 to 26 and 46 at 65° C. in the presence of 0.7 to 1.0 mol/l followed by washing at 65° C. with 0.1 to 2×SSC solution and which encodes a protein having the activity to adenosine-5'-triphosphate-dependently form said dipeptide from one or more kinds of amino acids;
wherein the one or more kinds of amino acids are a combination of (i) L-Ala and L-Gln, Gly, L-Val, L-Leu, L-Ile, L-Phe, L-Trp, L-Met, L-Ser, L-Thr, L-Cys, L-Asn, L-Tyr, L-Lys, L-Arg, L-His, L-α-AB, L-azaserine, L-Cit or L-theanine; (ii) Gly and L-Gln, Gly, L-Phe, L-Trp, L-Met, L-Ser, L-Thr, L-Cys, L-Tyr, L-Lys, L-Arg, L-α-AB or L-Cit; (iii) L-Met and L-Phe, L-Met, L-Ser, L-Thr, L-Cys, L-Tyr, L-Lys or L-His; (iv) L-Ser and L-Gln, L-Phe, L-Ser, L-Thr, L-Tyr, L-His or L-α-AB; (v) L-Thr and L-Gln, L-Phe, L-Leu, L-Thr or L-α-AB; (vi) L-Gln and L-Phe; (vii) β-Ala and L-Phe, L-Met, L-His or L-Cit; or (viii) L-α-AB and L-Gln, L-Arg or L-α-AB, and the procaryote is a microorganism in which the activities of three or more kinds of peptidases are reduced or lost.

5. The process according to claim 1, 2, 3 or 4, wherein the cells having the ability to produce the protein having polyphosphate kinase activity are cells carrying DNA according to the following [1] or [2]:
[1] DNA having the nucleotide sequence shown in any of SEQ ID NOs: 116 to 123;
[2] DNA comprising a nucleic acid sequence which hybridizes with DNA comprising the complement of a nucleic acid sequence shown in any of SEQ ID NOs: 116 to 123 at 65° C. in the presence of 0.7 to 1.0 mol/l followed by washing at 65° C. with 0.1 to 2-fold concentrated SSC solution and which encodes a protein having polyphosphate kinase activity.

6. The process according to claim 1, 2, 3 or 4, wherein the one or more peptidases is a protein having the amino acid sequence shown in any of SEQ ID NOs: 55 to 58, or a protein having an amino acid sequence which has 80% or more homology to the amino acid sequence shown in any of SEQ ID NOs: 55 to 58 and having peptidase activity.

7. The process according to claim 1 or 2, wherein the one or more peptide-permeating/transporting proteins is a protein having the amino acid sequence shown in any of SEQ ID NOs: 59 to 63, or a protein having an amino acid sequence which has 80% or more homology to the amino acid sequence shown in any of SEQ ID NOs: 59 to 63 and having peptide-permeating/transporting activity.

8. The process according to claim 1, 2, 3 or 4, wherein the procaryote is a microorganism belonging to the genus *Escherichia*, *Bacillus* or *Corynebacterium*.

9. The process according to claim 8, wherein the microorganism belonging to the genus *Escherichia*, *Bacillus* or *Corynebacterium* is *Escherichia coli*, *Corynebacterium glutamicum*, *Corynebacterium ammoniagenes*, *Corynebacterium lactofermentum*, *Corynebacterium flavum*, *Corynebacterium efficiens*, *Bacillus subtilis* or *Bacillus megaterium*.

10. The process according to claim 1, 2, 3 or 4, wherein the treated matter of the culture is a treated matter 1) which is selected from the group consisting of heat-treated culture, concentrated culture, dried culture, cells obtained by centrifuging the culture, products obtained by subjecting the cells to heat treatment, drying, freeze-drying, treatment with a surfactant, ultrasonication, mechanical friction, treatment with a solvent, enzymatic treatment, protein fractionation and immobilization, and an enzyme preparation obtained by extracting the cells, and 2) which has the activity to ATP-dependently form dipeptide from one or more kinds of amino acids or polyphosphate kinase activity.

11. The process according to claim 10, wherein the heat-treated culture or cells are those in which the dipeptide-hydrolyzing enzyme activity of the culture or cells is reduced or lost.

\* \* \* \* \*